(12) United States Patent
Song et al.

(10) Patent No.: US 10,837,026 B2
(45) Date of Patent: Nov. 17, 2020

(54) DROUGHT AND SALT TOLERANT PLANTS

(71) Applicant: University of Florida Research Foundation, Inc., Gainesville, FL (US)

(72) Inventors: Wen-Yuan Song, Gainesville, FL (US); Xiuhua Chen, Gainesville, FL (US); Xiaoen Huang, Gainesville, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 502 days.

(21) Appl. No.: 15/157,965

(22) Filed: May 18, 2016

(65) Prior Publication Data

US 2016/0326542 A1 Nov. 10, 2016

Related U.S. Application Data

(63) Continuation-in-part of application No. PCT/US2014/067279, filed on Nov. 25, 2014.

(60) Provisional application No. 61/909,358, filed on Nov. 26, 2013.

(51) Int. Cl.
*C12N 15/82* (2006.01)
*C07K 14/415* (2006.01)

(52) U.S. Cl.
CPC ........ *C12N 15/8273* (2013.01); *C07K 14/415* (2013.01); *C12N 15/8241* (2013.01)

(58) Field of Classification Search
None
See application file for complete search history.

(56) References Cited

U.S. PATENT DOCUMENTS

2004/0123343 A1 6/2004 La Rosa et al.

FOREIGN PATENT DOCUMENTS

CN 200510002009.7 1/2005

OTHER PUBLICATIONS

Huang et al. PloS one 8.5 (2013): e63868 (Year: 2013).*
Yuan, et al. PloS one 8.3 (2013): e58003 (Year: 2013).*
Xu et al. (Journal of Experimental Botany, vol. 58, No. 13, pp. 3623-3630, 2007) (Year: 2007).*
Guo et al (2004, Proc. Natl. Acad. Sci. USA 101: 9205-9210) (Year: 2004).*
Wang et al. (The Plant Cell, vol. 18, 3635-3646, Dec. 2006). (Year: 2006).*
GenBank Accession AF272860, dated Aug. 26, 2002. (Year: 2002).*
Mendes, et al. (Plant Pathology 59.1 (2010): 68-75). (Year: 2010).*
GenBank Accession DQ086863, dated Jul. 20, 2005. (Year: 2005).*
Wang et al. Supplemental Table 1. (2006) (Year: 2006).*
Yamaguchi-Shinozaki et al. (Trends in plant science 10.2 (2005): 88-94). (Year: 2005).*
Datta et al. (Plant biotechnology journal 10.5 (2012):579-586). (Year: 2012).*
Wroblewski et al. (Plant Biotechnology Journal 3.2 (2005): 259-273). (Year: 2005).*
Bendahmane et al. (The Plant Journal 21.1 (2000):73-81). (Year: 2000).*
Chen et al., "Plasma membrane localization and potential endocytosis of constitutively expressed XA21 proteins in transgenic rice," *Mol Plant* 3:917-926, 2010.
Chen et al., "An ATPase promotes autophosphorylation of the pattern recognition receptor XA21 and inhibits XA21-mediated immunity," *Proc Natl Aced Sci U S A* 107: 8029-8034, 2010.
Ding et al., "A rice kinase-protein interaction map," *Plant Physiol* 149: 1478-1492, 2009.
GenBank AAY17949.1, ring zinc finger protein [*Artemisia desertorum*], Available at https://www.ncbi.nlm.nih.gov/protein/AAY17949.1, Retrieved Dec. 14, 2016.
GenBank AAZ14079.1, At2g28840 [*Arabidopsis thaliana*], Available at https://www.ncbi.nlm.nih.gov/protein/AAZ14079.1, Retrieved Dec. 14, 2016.
GenBank ABF95250.1, ankyrin repeat family protein, putative, expressed [*Oryza sativa Japonica* Group], Available at https://www.ncbi.nlm.nih.gov/protein/108707455, Retrieved Dec. 14, 2016.
GenBank ACF87653.1, unknown [*Zea mays*], Available at https://www.ncbi.nlm.nih.gov/protein/ACF87653.1, Retrieved Dec. 14, 2016.
GenBank ACG42929.1, XBAT32 [*Zea mays*], Available at https://www.ncbi.nlm.nih.gov/protein/ACG42929.1, Retrieved Dec. 14, 2016.
GenBank ACN25763.1, unknown [*Zea mays*], Available at https://www.ncbi.nlm.nih.gov/protein/ACN25763.1, Retrieved Dec. 14, 2016.
GenBank ACN27394.1, unknown [*Zea mays*], Available at https://www.ncbi.nlm.nih.gov/protein/ACN27394.1, Retrieved Dec. 14, 2016.
GenBank ACN35883.1, unknown [*Zea mays*], Available at https://www.ncbi.nlm.nih.gov/protein/ACN35883, Retrieved Dec. 14, 2016.
GenBank ACR36016.1, unknown [*Zea mays*], Available at https://www.ncbi.nlm.nih.gov/protein/ACR36016.1, Retrieved Dec. 14, 2016.
GenBank AEW69785.1, Hop-interacting protein THI012 [*Solanum lycopersicum*], Available at https://www.ncbi.nlm.nih.gov/protein/AEW69785, Retrieved Dec. 14, 2016.
GenBank AEW69787.1, Hop-interacting protein THI015 [*Solanum lycopersicum*], Available at https://www.ncbi.nlm.nih.gov/protein/AEW69787, Retrieved Dec. 14, 2016.
GenBank AEW69796.1, Hop-interacting protein THI033 [*Solanum lycopersicum*], Available at https://www.ncbi.nlm.nih.gov/protein/AEW69796, Retrieved Dec. 14, 2016.
GenBank AFW74956.1, hypothetical protein ZEAMMB73_503567 [*Zea mays*], Available at https://www.ncbi.nlm.nih.gov/protein/AFW74956, Retrieved Dec. 14, 2016.

(Continued)

*Primary Examiner* — Charles Logsdon
(74) *Attorney, Agent, or Firm* — Alston & Bird LLP

(57) ABSTRACT

The invention provides methods and compositions for enhancing drought and/or salt tolerance in plants. Nucleic acid constructs therefore are also described. Transgenic plants are also provided that exhibit enhanced agronomic properties. The inventors have demonstrated increased drought and salt tolerance in connection with increased expression of the Xb3 gene.

18 Claims, 15 Drawing Sheets

Specification includes a Sequence Listing.

(56) References Cited

OTHER PUBLICATIONS

GenBank BAJ88534.1, predicted protein [*Hordeum vulgare* subsp. *vulgare*], Available at https://www.ncbi.nlm.nih.gov/protein/BAJ88534, Retrieved Dec. 14, 2016.
GenBank BAJ95620.1, predicted protein [*Hordeum vulgare* subsp. *vulgare*], Available at https://www.ncbi.nlm.nih.gov/protein/BAJ95620.1, Retrieved Dec. 14, 2016.
GenBank BAJ97722.1, predicted protein [*Hordeum vulgare* subsp. *vulgare*], Available at https://www.ncbi.nlm.nih.gov/protein/BAJ97722.1, Retrieved Dec. 14, 2016.
GenBank BT061066, *Zea mays* full-length cDNA clone ZM_BFb0093J16 mRNA, complete cds, Available at https://www.ncbi.nlm.nih.gov/nuccore/BT061066, Retrieved Dec. 14, 2016.
GenBank BT085663, *Zea mays* full-length cDNA clone ZM_BFc0045M02 mRNA, complete cds, Available at https://www.ncbi.nlm.nih.gov/nuccore/238009961/, Retrieved Dec. 14, 2016.
GenBank CAN65557.1, hypothetical protein VITISV_034981 [*Vitis vinifera*], Available at https://www.ncbi.nlm.nih.gov/protein/CAN65557.1, Retrieved Dec. 14, 2016.
GenBank CBI16150.3, unnamed protein product, partial [*Vitis vinifera*], Available at https://www.ncbi.nlm.nih.gov/protein/CBI16150.3, Retrieved Dec. 14, 2016.
GenBank EF470290.1, *Mirabilis jalapa* ubiquitin ligase (XB3) mRNA, complete cds, Available at https://www.ncbi.nlm.nih.gov/nuccore/EF470290, Retrieved Dec. 14, 2016.
Gómez-Gómez et al., "Both the extracellular leucine-rich repeat domain and the kinase activity of FSL2 are required for flagellin binding and signaling in *Arabidopsis*," *Plant Cell* 13:1155-1163, 2001.
Huang et al., "Members of the XB3 family from diverse plant species induce programmed cell death in *Nicotiana benthamiana*," *PLOS ONE.* 8:e63868, 2013.
International Search Report and Written Opinion for PCT/US14/67279 dated May 18, 2015.
Jiang et al., "The XA21 binding protein XB25 is required for maintaining XA21-mediated disease resistance," *Plant J* 73:814-823, 2013.
Lee et al., "Genetic dissection of the biotic stress response using a genome-scale gene network for rice," *Proc Natl Acad Sci U S A* 108:18548-18553, 2011.
Lee et al., "Retraction. A type I-secreted, sulfated peptide triggers XA21-mediated innate immunity," *Science* 342:191, 2013.
NCBI Reference Sequence NP_001152540.1, ring zinc finger protein [*Zea mays*], Available at https://www.ncbi.nlm.nih.gov/protein/NP_001152540.1, Retrieved Dec. 14, 2016.
NCBI Reference Sequence XP_002283974.1, PREDICTED: putative E3 ubiquitin-protein ligase XBAT31 isoform 2 [*Vitis vinifera*], Available at https://www.ncbi.nlm.nih.gov/protein/XP_002283974.1?report=genpept, Retrieved Dec. 14, 2016.
NCBI Reference Sequence XP_002299878.1, ankyrin repeat family protein [*Populus trichocarpa*], Available at https://www.ncbi.nlm.nih.gov/protein/XP_002299878.1, Retrieved Dec. 14, 2016.
NCBI Reference Sequence XP_002314186.1, ankyrin repeat family protein [*Populus trichocarpa*], Available at https://www.ncbi.nlm.nih.gov/protein/XP_002314186.1, Retrieved Dec. 14, 2016.
NCBI Reference Sequence XP_002440462.1, hypothetical protein SORBIDRAFT_09g001370 [*Sorghum bicolor*], Available at https://www.ncbi.nlm.nih.gov/protein/242089259/, Retrieved Dec. 14, 2016.
NCBI Reference Sequence XP_002457030.1, hypothetical protein SORBIDRAFT_03g047430 [*Sorghum bicolor*], Available at https://www.ncbi.nlm.nih.gov/protein/242055769/, Retrieved Dec. 14, 2016.
NCBI Reference Sequence XP_002465483.1, hypothetical protein SORBIDRAFT_01g039610 [*Sorghum bicolor*], Available at https://www.ncbi.nlm.nih.gov/protein/XP_002465483, Retrieved Dec. 14, 2016.
NCBI Reference Sequence XP_003532313.1, PREDICTED: putative E3 ubiquitin-protein ligase XBAT31 [*Glycine max*], Available at https://www.ncbi.nlm.nih.gov/protein/XP_003532313, Retrieved Dec. 14, 2016.
NCBI Reference Sequence XP_003543511.1, PREDICTED: putative E3 ubiquitin-protein ligase XBAT31 [*Glycine max*], Available at https://www.ncbi.nlm.nih.gov/protein/XP_003543511, Retrieved Dec. 14, 2016.
NCBI Reference Sequence XP_003547367.1, PREDICTED: putative E3 ubiquitin-protein ligase XBAT31 [*Glycine max*], Available at https://www.ncbi.nlm.nih.gov/protein/XP_003547367, Retrieved Dec. 14, 2016.
NCBI Reference Sequence XP_003552156.1, PREDICTED: putative E3 ubiquitin-protein ligase XBAT31 [*Glycine max*], Available at https://www.ncbi.nlm.nih.gov/protein/XP_003552156, Retrieved Dec. 14, 2016.
NCBI Reference Sequence XP_003558233.1, PREDICTED: E3 ubiquitin-protein ligase XB3-like isoform X4 [*Brachypodium distachyon*], Available at https://www.ncbi.nlm.nih.gov/protein/XP_003558233.1, Retrieved Dec. 14, 2016.
NCBI Reference Sequence XP_003565178.1, PREDICTED: probable E3 ubiquitin-protein ligase XBOS31 [*Brachypodium distachyon*], Available at https://www.ncbi.nlm.nih.gov/protein/XP_003565178.1, Retrieved Dec. 14, 2016.
NCBI Reference Sequence XP_003568996.1, PREDICTED: E3 ubiquitin-protein ligase XB3 [*Brachypodium distachyon*], Available at https://www.ncbi.nlm.nih.gov/protein/357134785/, Retrieved Dec. 14, 2016.
Nodzon et al., "The ubiquitin ligase XBAT32 regulates lateral root development in *Arabidopsis*," *Plant J* 40:996-1006, 2004.
Park et al., "Rice XB15, a protein phosphatase 2C, negatively regulates cell death and XA21-mediated innate immunity," *PLOS Biol* 6:e231, 2008.
Park et al., "Overexpression of the endoplasmic reticulum chaperone BiP3 regulates XA21-mediated innate immunity in rice," *PLOS ONE* 5:e9262, 2010.
Park et al., "Cleavage and nuclear localization of the rice XA21 immune receptor," *Nat Commun* 3:920, 2012.
Peng et al., "OsWRKY62 is a negative regulator of basal and Xa21-mediated defense against *Xanthomonas oryzae* pv. oryzae in rice," *Mol Plant* 1:446-458, 2008.
Song et al., "A receptor kinase-like protein encoded by the rice disease resistance gene, Xa21," *Science* 270:1804-1806, 1995.
Uga et al., "Control of root system architecture by DEEPER ROOTING 1 increases rice yield under drought conditions," *Nat Genet* 45:1097-1102, 2013.
UniProtKB/Swiss-Prot Q65XV2.1, RecName: Full=E3 ubiquitin-protein ligase XB3; AltName: Full=Ankyrin repeat domain and RING finger-containing protein XB3; AltName: Full=XA21-binding protein 3, Available at https://www.ncbi.nlm.nih.gov/protein/75322407, Retrieved Dec. 14, 2016.
UniProtKB A0A067DWL1 (A0A067DWL1_CITSI), Uncharacterized protein, Available at http://www.uniprot.org/uniprot/A0A067DWL1, Retrieved Dec. 14, 2016.
UniProtKB A0A067FZQ8 (A0A067FZQ8_CITSI), Uncharacterized protein, Available at http://www.uniprot.org/uniprot/A0A067FZQ8, Retrieved Dec. 14, 2016.
UniProtKB/Swiss-Prot Q94CT7.1, RecName: Full=Probable E3 ubiquitin-protein ligase XBOS31; AltName: Full=Ankyrin repeat domain and RING finger-containing protein XBOS31; AltName: Full=XB3 protein homolog 1, Available at https://www.ncbi.nlm.nih.gov/protein/75332121, Retrieved Dec. 14, 2016.
Wang et al., "The cloned gene, *Xa21*, confers resistance to multiple *Xanthomonas oryzae* pv. *oryzae* isolates in transgenic plants," *Mol Plant Microbe Interact* 9:850-855, 1996.
Wang et al., "Rice XA21 binding protein 3 is a ubiquitin ligase required for full Xa21-mediated disease resistance," *Plant Cell* 18:3635-3646, 2006.
Xu et al., "The autophosphorylated Ser686, Thr688, and Ser689 residues in the intracellular juxtamembrane domain of XA21 are implicated in stability control of rice receptor-like kinase," *Plant J* 45:740-751, 2006.
Yang et al., "Molecular cloning and characterization of a gene encoding RING zinc finger ankyrin protein from drought-tolerant *Artemisia desertorum*," *J Biosci* 33:103-112, 2008.

(56) References Cited

OTHER PUBLICATIONS

Yuan et al., "Global analysis of ankyrin repeat domain C3HC4-type RING finger gene family in plants," *PLOS ONE* 8:e58003, 2013.

* cited by examiner

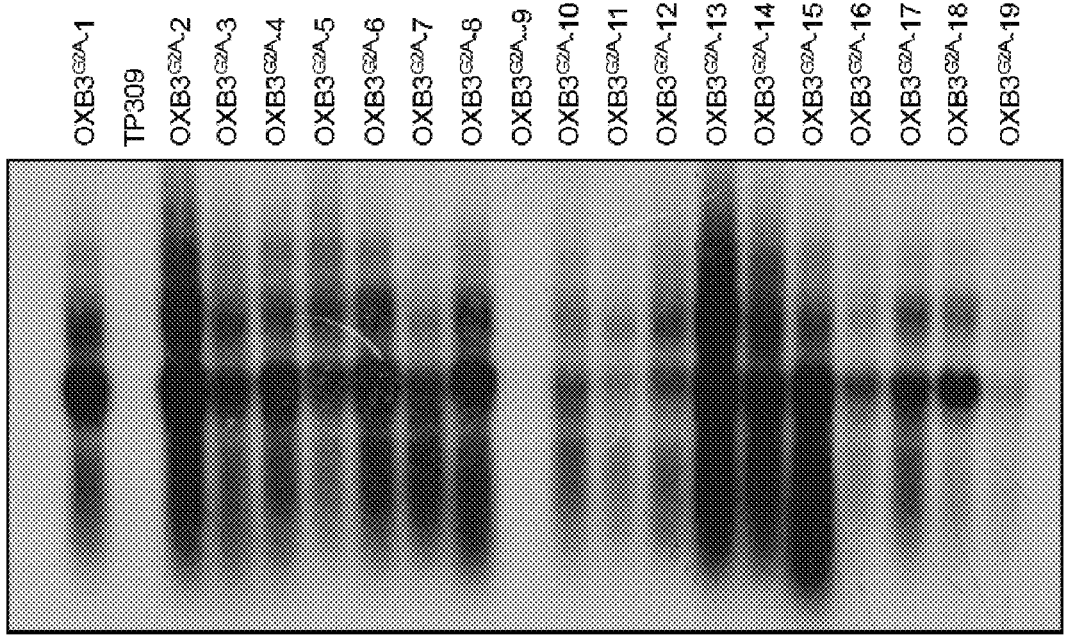
FIG. 8

| Plant Species | Accession number/Name | Sequence |
|---|---|---|
| | | 1         10 |
| Rice | (Os05g02130, XB3) | MGHCVSCART |
| Rice | (Os01g74320, XBOS31) | MGHGLSCSRD |
| Rice | (Os03g16780) | MGQGASCGRP |
| Barley | (BAJ95620) | MGHGVSCART |
| Barley | (BAJ97722) | MGHGLSCSRD |
| Barley | (BAJ88534) | MGHGASCGRP |
| Brachypodium distachyon | (XP_003565179.1) | MGHGLSCGRD |
| Brachypodium distachyon | (XP_003568996.1) | MGHGVSCART |
| Brachypodium distachyon | (XP_003558233.1) | MGHGASCGRP |
| Maize | (ACN35883) | MGHGVSCART |
| Maize | (AFW74956) | MGHGVSCART |
| Maize | (LOC100286180) | MGHVLSCSRD |
| Maize | (ACN27394) | MGHGASCGRP |
| Maize | (ACN25763) | MGHGASCSRP |
| Sorghum | (XP_002440462) | MGHGVSCART |
| Sorghum | (XP_002457030) | MGHGLSCSRD |
| Sorghum | (XP_002465483) | MGHGASCGRP |
| Sugarcane* | | MGHGVSCART |
| Switchgrass* | | MGHGVSCART |
| Wheat* | | MGHGVSCART |
| Artemisia desertorum | (AAY17949.1, AdZFP1) | MGQNLSCCVK |
| Arabidopsis | (At2g23840, XBAT31) | MGQSMSCGSR |
| Citrus | (orange1.1g012618m, XBCT31) | MGQPMSCRFR |
| Citrus | (Orange1.1g041054m, XBCT32) | MGQGLSCGAS |
| Cotton* | | MGQGLSCGAS |
| Grape | (XP_002283974.1) | MGQGLSCGVS |
| Grape | (CBI16150.3) | MGQGLSCGVS |
| Grape | (CAN65557.1) | MGQGLSCGEG |
| Mirabilis jalapa | (EF470290, MjXB3) | MGQALSSGDG |
| Populus trichocarpa | (XP_002299878.1) | MGQGLSCAAS |
| Populus trichocarpa | (XP_002314186.1) | MGQGLSCAAS |
| Potato* | | MGQCLSCCTS |
| Soybean | (XP_003552156) | MGQTLSCVQQ |
| Soybean | (XP_003547367) | MGQSLSCSGN |
| Soybean | (XP_003543511) | MGQSLSCSGN |
| Soybean | (XP_003532313) | MGQRLSCVQQ |
| Tomato | (AEW69796) | MGQCFSCCTS |
| Tomato | (AEW69785) | MGQGLSCGTS |
| Tomato | (AEW69787) | MGQKLSCGQQ |

FIG. 9

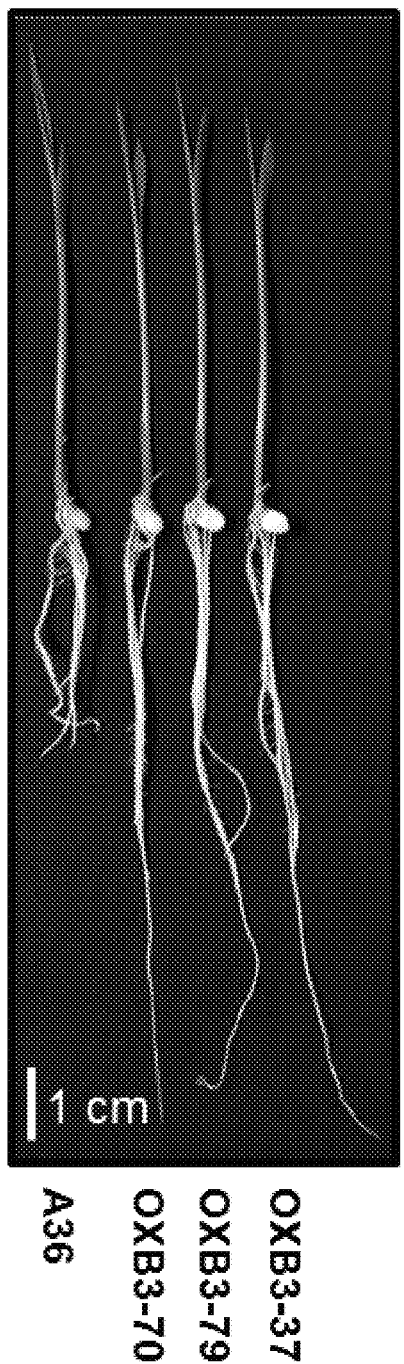
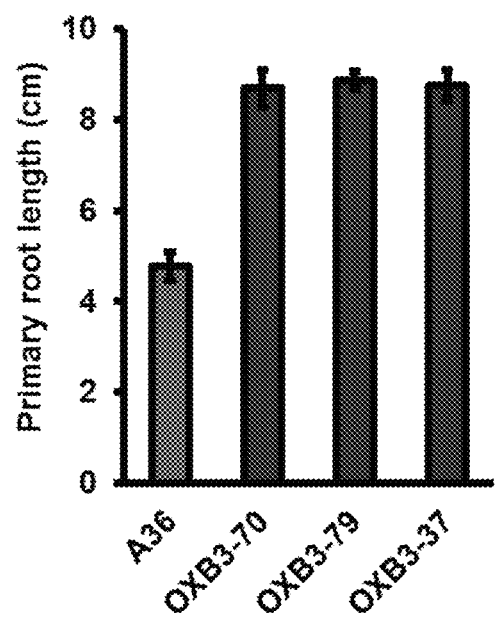
FIG. 12A
FIG. 12B

DROUGHT AND SALT TOLERANT PLANTS

CROSS-REFERENCE TO RELATED APPLICATIONS

This application is a National Stage of International Patent Application Number PCT/US2014/067279, filed Nov. 25, 2014, which claims the benefit of U.S. Provisional Appl. No. 61/909,358, filed Nov. 26, 2013, the entire disclosures of which are incorporated herein by reference.

FIELD OF THE INVENTION

The present invention relates generally to the field of molecular biology. More specifically, the invention relates to plant genes involved in plant physiology and methods of use thereof.

INCORPORATION OF SEQUENCE LISTING

This application includes an electronic sequence listing in a file named 2018-09-12_515610_SequenceListing_ST25.txt, created Sep. 12, 2018 and containing 282 kilobytes, which is incorporated herein by reference.

BACKGROUND OF THE INVENTION

Drought and high salinity water are major constraints to crop production worldwide. The greenhouse effect is predicted to raise temperatures and to prolong droughts, increasing the demands for water, and in particular low salinity water. Human-induced climate change is predicted to put pressure on the supply of water for agriculture. At the same time the world population is estimated to exceed 9.5 billion by the year 2050. Therefore, central to long-term agricultural security is implementing a sustainable system that is more resilient and productive, while at the same time requires less of the increasingly costly inputs such as water, and in particular water with low levels of salt.

SUMMARY OF THE INVENTION

In one aspect, the invention provides a method of increasing drought and/or salt tolerance comprising increasing expression of an Xb3 gene in a plant, wherein the drought and/or salt tolerance of the plant is increased when compared to a plant that lacks the increased expression. In one embodiment, the plant is a monocotyledonous plant. In a further embodiment, the monocotyledonous plant is selected from the group consisting of maize, wheat, rice, sorghum (*Sorghum bicolor*), oats, barley, sugar cane, African oil palm (*Elaeis guineensis*), or switchgrass. In another embodiment, the plant is a dicotyledonous plant. In a further embodiment, the dicotyledonous plant is selected from the group consisting of *Arabidopsis*, peanut (*Arachis hypogaea*), barrel medic (*Medicago truncatula*), carrot, soybean (*Glycine max*), cotton, *Brassica*, canola, tomato, potato, alfalfa, grape, clover, poplar, willow, *eucalyptus*, hemp, a *Lotus* sp., a *Vinca* sp., a *Nicotiana* sp., a *Vitis* sp., or a *Ricinus* sp.

In another aspect, a method of the invention is provided comprising increasing expression of a heterologous coding sequence in a plant selected from the group consisting of: (a) a polynucleotide sequence with at least 85% identity to SEQ ID NO: 4 or SEQ ID NO: 6; and (b) a polynucleotide sequence encoding a polypeptide with at least 85% identity to SEQ ID NO: 5 or SEQ ID NO: 7. In one embodiment, expressing in the plant comprises transforming the plant or a progenitor thereof with said heterologous coding sequence. In another embodiment, the plant comprises a heterologous coding sequence operably linked to a promoter, wherein the heterologous coding sequence is selected from the group consisting of: (a) a polynucleotide sequence with at least 85% identity to SEQ ID NO: 4 or SEQ ID NO: 6; and (b) a polynucleotide sequence encoding a polypeptide with at least 85% identity to SEQ ID NO: 5 or SEQ ID NO:7. In another embodiment, the promoter is a constitutive or inducible promoter.

In yet another aspect, the invention provides a plant comprising increased expression of the rice Xb3 gene, wherein the drought and/or salt tolerance of the plant is increased when compared to a plant that lacks the increased expression. In one embodiment, the plant is defined as a monocot plant. In another embodiment, the plant is a rice plant. In another embodiment, the plant is defined as a dicot plant. In another embodiment, the invention provides a seed that produces the plant. In yet another embodiment, the invention provides a DNA-containing plant part of the plant. In still yet another embodiment, the plant part is further defined as a protoplast, cell, meristem, root, leaf, node, pistil, anther, flower, seed, embryo, stalk or petiole.

In still yet another aspect, the invention provides a method of producing food for human or animal consumption comprising: a) obtaining a plant of the invention or a part thereof; and b) preparing food for human or animal consumption from said plant or part thereof. In one embodiment, the food is starch, protein, meal, flour or grain.

In still yet another aspect, the invention provides a method wherein increasing expression comprises expressing in the plant a heterologous coding sequence selected from the group consisting of: (a) a polynucleotide sequence with at least 85% identity to SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98 or SEQ ID NO: 100; and (b) a polynucleotide sequence encoding a polypeptide with at least 85% identity to SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99 or SEQ ID NO: 101. In specific embodiments, expressing in the plant comprises transforming the plant or a progenitor thereof with said heterologous coding sequence.

In still yet another aspect, the invention provides a plant comprising increased expression of a heterologous coding sequence operably linked to a promoter, wherein the heterologous coding sequence is selected from the group consisting of: (a) a polynucleotide sequence with at least 85% identity to SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98 or SEQ ID NO: 100; and (b) a polynucleotide sequence encoding a polypeptide with at least 85% identity to SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99 or SEQ ID NO: 101. In one embodiment, the plant is defined as a monocot plant. In another embodiment, the plant is a rice plant. In yet another embodiment, the plant is defined as a dicot plant. In still yet another embodiment, the promoter is a constitutive or inducible promoter. In one aspect, the invention provides a seed that produces the plant. In one embodiment, the invention provides a DNA-containing plant part of the plant. In another embodiment, the plant part is further defined as a protoplast, cell, meristem, root, leaf, node, pistil, anther, flower, seed, embryo, stalk or petiole.

In yet another aspect the invention provides a method of producing food for human or animal consumption comprising: (a) obtaining a plant according to the invention or a part thereof; and (b) preparing food for human or animal consumption from said plant or part thereof. In one embodiment, the food is starch, protein, meal, flour or grain.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 8 Overexpression of XB3$^{G2A}$ enhances the tolerance to drought stress at the T0 generation. (Panel A) RNA blot analysis of XB3$^{G2A}$ over-expression lines. Total RNA isolated from leaf tissues of indicated lines at the T0 generation was probed with the same Xb3-specific sequence described in FIG. 3 legend. (Panel B) Drought treatment of selected Xb3$^{G2A}$ overexpression lines, wild-type TP309 and the control plants A36. One month-old plants were subjected to drought treatment for 10 days and then recovered for four days by re-watering.

FIG. 9 A putative N-myristoylation site is highly conserved among members of the XB3 family. Amino acid sequence alignment of the N-terminal region of XB3 family members from diverse plant species. The putative myristoylation site is underlined. The invariable glycine and serine residues in the myristoylation site are highlighted in bold red. Accession numbers and names for the proteins used are indicated. The asterisk denotes the members annotated based on EST sequences in this study. Amino acid positions are indicated by numbers above the sequence.

FIGS. 12A-12B Over-expression of Xb3 promotes primary root development. (FIG. 12A) Empty-vector control (A36) and three Xb3 over-expression lines were grown on half strength MS medium supplemented with 50 μg/ml hygromycine to select transgenic plants. Photographs were taken from 7-day-old seedlings. (FIG. 12B) Primary root lengths of indicated lines (n=10).

BRIEF DESCRIPTION OF THE SEQUENCE LISTING

Figure 1:
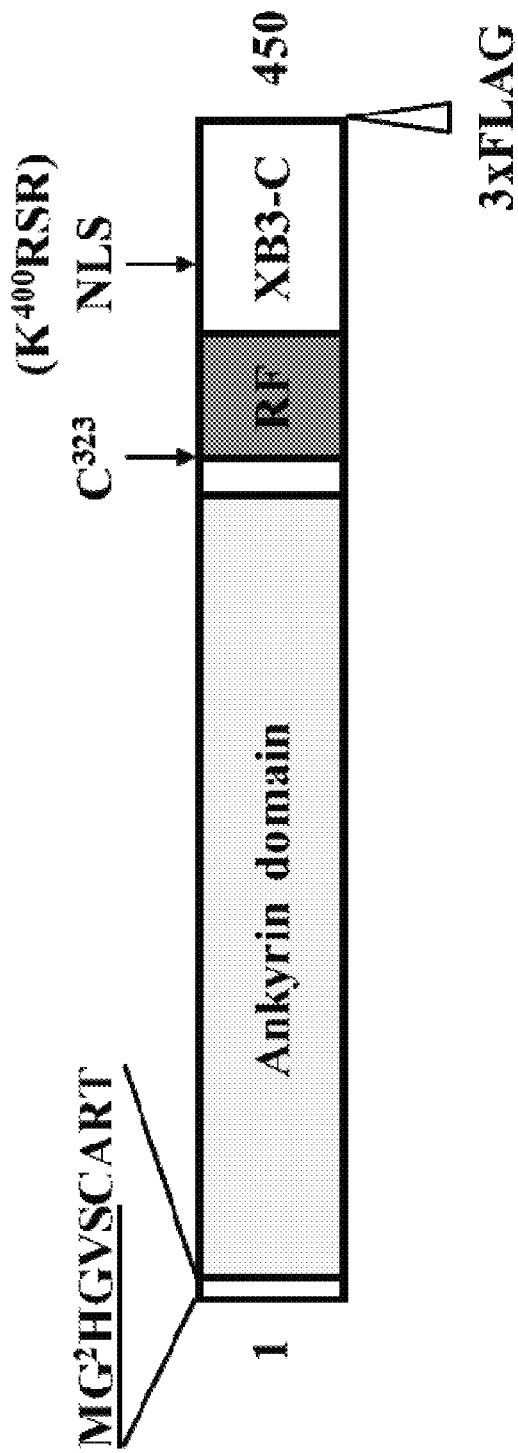
FIG. 1 Schematic diagram showing structure of XB3. Domains are indicated. The putative myristoylation site is underlined. The first conserved cysteine residue (C323) in the RING finger (RF) motif and the putative nuclear localization (NLS) site are shown. The position used for the insertion of 3xFLAG is shown. Amino acid positions are indicated by numbers above the sequence or on both sides of the diagram.

SEQ ID NO: 1 Sequence of primerXB3NEW-3.
SEQ ID NO: 2 Sequence of primerXB3CT-3.
SEQ ID NO: 3 Sequence of primerXB3NEW-4.
SEQ ID NO: 4 Xb3 (Os05g02130, *Oryza sativa*) full-length cDNA sequence
SEQ ID NO: 5 XB3 (Os05g02130, *Oryza sativa*) protein sequence
SEQ ID NO: 6 Xb3$^{G2A}$ full-length cDNA sequence
SEQ ID NO: 7 XB3$^{G2A}$ protein sequence
SEQ ID NO: 8 Cassava4.1_007655 m (Cassava, *Manihot esculenta*) full-length cDNA
SEQ ID NO: 9 Cassava4.1_007655 m (Cassava, *Manihot esculenta*) protein sequence
SEQ ID NO: 10 Cassava4.1_007651m (Cassava, *Manihot esculenta*) full-length cDNA
SEQ ID NO: 11 Cassava4.1_007651m (Cassava, *Manihot esculenta*) protein sequence
SEQ ID NO: 12 Potri.001G238800.1 (*Populus trichocarpa*) full-length cDNA sequence
SEQ ID NO: 13 Potri.001G238800.1 (*Populus trichocarpa*) protein sequence
SEQ ID NO: 14 Potri.009G030000.2 (*Populus trichocarpa*) full-length cDNA sequence
SEQ ID NO: 15 Potri.009G030000.2 (*Populus trichocarpa*) protein sequence
SEQ ID NO: 16 Gorai.003G132700.1 (Cotton, *Gossypium raimondii*) full-length cDNA sequence
SEQ ID NO: 17 Gorai.003G132700.1 (Cotton, *Gossypium raimondii*) protein sequence
SEQ ID NO: 18 Gorai.009G099800.1 (Cotton, *Gossypium raimondii*) full-length cDNA sequence
SEQ ID NO: 19 Gorai.009G099800.1 (Cotton, *Gossypium raimondii*) protein sequence
SEQ ID NO: 20 Gorai.001G110100.1 (Cotton, *Gossypium raimondii*) full-length cDNA sequence
SEQ ID NO: 21 Gorai.001G110100.1 (Cotton, *Gossypium raimondii*) protein sequence
SEQ ID NO: 22 Gorai.006G173500.1 (Cotton, *Gossypium raimondii*) full-length cDNA sequence
SEQ ID NO: 23 Gorai.006G173500.1 (Cotton, *Gossypium raimondii*) protein sequence
SEQ ID NO: 24 Orange1.1g041054m (Citrus) full-length cDNA sequence
SEQ ID NO: 25 Orange1.1g041054m (Citrus) protein sequence
SEQ ID NO: 26 Orange1.1g012618m (Citrus) full-length cDNA sequence
SEQ ID NO: 27 Orange1.1g012618m (Citrus) protein sequence
SEQ ID NO: 28 XBAT31 (At2g28840) (*Arabidopsis thaliana*) full-length cDNA sequence
SEQ ID NO: 29 XBAT31 (At2g28840) (*Arabidopsis thaliana*) protein sequence
SEQ ID NO: 30 XP_003552156 (Soybean, *Glycine max*) full-length cDNA sequence
SEQ ID NO: 31 XP_003552156 (Soybean, *Glycine max*) protein sequence
SEQ ID NO: 32 XP_003547367 (Soybean, *Glycine max*) full-length cDNA sequence
SEQ ID NO: 33 XP_003547367 (Soybean, *Glycine max*) protein sequence
SEQ ID NO: 34 XP_003543511 (Soybean, *Glycine max*) full-length cDNA sequence
SEQ ID NO: 35 XP_003543511 (Soybean, *Glycine max*) protein sequence
SEQ ID NO: 36 XP_003532313 (Soybean, *Glycine max*) full-length cDNA sequence
SEQ ID NO: 37 XP_003532313 (Soybean, *Glycine max*) protein sequence
SEQ ID NO: 38 XM_002283938 (Grape, *Vitis vinifera*) full-length cDNA sequence
SEQ ID NO: 39 XP_002283974 (Grape, *Vitis vinifera*) protein sequence
SEQ ID NO: 40 GSVIVT01024983001 (Grape, *Vitis vinifera*) full-length cDNA sequence
SEQ ID NO: 41 GSVIVT01024983001 (Grape, *Vitis vinifera*) protein sequence
SEQ ID NO: 42 GSVIVT01034187001 (Grape, *Vitis vinifera*) full-length cDNA sequence
SEQ ID NO: 43 GSVIVT01034187001 (Grape, *Vitis vinifera*) protein sequence
SEQ ID NO: 44 EF470290 (Four-o'clock, *Mirabilis jalapa*) full-length cDNA sequence
SEQ ID NO: 45 EF470290 (Four-o'clock, *Mirabilis jalapa*) protein sequence
SEQ ID NO: 46 GQ261229 (Tomato, *Solanum lycopersicum*) full-length cDNA sequence SEQ ID NO: 47 AEW69785.1 (Tomato, *Solanum lycopersicum*) protein sequence
SEQ ID NO: 48 GQ261231 (Tomato, *Solanum lycopersicum*) full-length cDNA sequence
SEQ ID NO: 49 AEW69787.1 (Tomato, *Solanum lycopersicum*) protein sequence
SEQ ID NO: 50 GQ261240 (Tomato, *Solanum lycopersicum*) full-length cDNA sequence
SEQ ID NO: 51 AEW69796.1 (Tomato, *Solanum lycopersicum*) protein sequence
SEQ ID NO: 52 PGSC0003DMT400001171 (Potato, *Solanum tuberosum*) full-length cDNA sequence
SEQ ID NO: 53 PGSC0003DMP400000870 (Potato, *Solanum tuberosum*) protein sequence
SEQ ID NO: 54 PGSC0003DMT400077953 (Potato, *Solanum tuberosum*) full-length cDNA sequence
SEQ ID NO: 55 PGSC0003DMP400052765 (Potato, *Solanum tuberosum*) protein sequence
SEQ ID NO: 56 PGSC0003DMT400023029 (Potato, *Solanum tuberosum*) full-length cDNA sequence
SEQ ID NO: 57 PGSC0003DMP400015686 (Potato, *Solanum tuberosum*) Protein sequence
SEQ ID NO: 58 XM_002440417 (Sorghum, *Sorghum bicolor*) full-length cDNA sequence
SEQ ID NO: 59 XP_002440462.1 (Sorghum, *Sorghum bicolor*) protein sequence
SEQ ID NO: 60 XM_002456985 (Sorghum, *Sorghum bicolor*) full-length cDNA sequence
SEQ ID NO: 61 XP_002457030.1 (Sorghum, *Sorghum bicolor*) protein sequence
SEQ ID NO: 62 XM_002465438 (Sorghum, *Sorghum bicolor*) full-length cDNA sequence
SEQ ID NO: 63 XP_002465483.1 (Sorghum, *Sorghum bicolor*) protein sequence
SEQ ID NO: 64 BT042648 (Maize, *Zea may*) full-length cDNA sequence
SEQ ID NO: 65 ACF87653.1 (Maize, *Zea may*) protein sequence
SEQ ID NO: 66 BT085663 (Maize, *Zea may*) full-length cDNA sequence
SEQ ID NO: 67 ACR36016.1 (Maize, *Zea may*) protein sequence
SEQ ID NO: 68 NM_001159068 (Maize, *Zea may*) full-length cDNA sequence
SEQ ID NO: 69 NP_001152540.1 (Maize, *Zea may*) protein sequence
SEQ ID NO: 70 BT062697 (Maize, *Zea may*) full-length cDNA sequence
SEQ ID NO: 71 ACN27394.1 (Maize, *Zea may*) protein sequence
SEQ ID NO: 72 BT061066 (Maize, *Zea may*) full-length cDNA sequence
SEQ ID NO: 73 ACN25763.1 (Maize, *Zea may*) protein sequence
SEQ ID NO: 74 XBOS31 (Os01g74320, *Oryza sativa*) full-length cDNA sequence
SEQ ID NO: 75 XBOS31 (Os01g74320, *Oryza sativa*) protein sequence
SEQ ID NO: 76 XBOS37 (Os03g16780, *Oryza sativa*) full-length cDNA sequence
SEQ ID NO: 77 XBOS37 (Os03g16780, *Oryza sativa*) protein sequence
SEQ ID NO: 78 AK364417 (Barley, *Hordeum vulgare*) full-length cDNA sequence
SEQ ID NO: 79 BAJ95620.1 (Barley, *Hordeum vulgare*) protein sequence
SEQ ID NO: 80 AK366519 (Barley, *Hordeum vulgare*) full-length cDNA sequence
SEQ ID NO: 81 BAJ97722.1 (Barley, *Hordeum vulgare*) protein sequence
SEQ ID NO: 82 AK357320 (Barley, *Hordeum vulgare*) full-length cDNA sequence
SEQ ID NO: 83 BAJ88534.1 (Barley, *Hordeum vulgare*) protein sequence
SEQ ID NO: 84 XM_003565130 (Purple false brome, *Brachypodium distachyon*) full-length cDNA sequence
SEQ ID NO: 85 XP_003565178.1 (Purple false brome, *Brachypodium distachyon*) protein sequence
SEQ ID NO: 86 XM_003568948 (Purple false brome, *Brachypodium distachyon*) full-length cDNA sequence
SEQ ID NO: 87 XP_003568996.1 (Purple false brome, *Brachypodium distachyon*) protein sequence
SEQ ID NO: 88 XM_003558185.1 (Purple false brome, *Brachypodium distachyon*) full-length cDNA sequence
SEQ ID NO: 89 XP_003558233.1 (Purple false brome, *Brachypodium distachyon*) protein sequence
SEQ ID NO: 90 XBTA31 (Wheat, *Triticum aestivum*) full-length cDNA sequence
SEQ ID NO: 91 XBTA31 (Wheat, *Triticum aestivum*) protein sequence
SEQ ID NO: 92 XBSC31 (Sugarcane) full-length cDNA sequence
SEQ ID NO: 93 XBSC31 (Sugarcane) protein sequence
SEQ ID NO: 94 Pavirv00039060m (Switchgrass, *Panicum virgatum*) full-length cDNA sequence
SEQ ID NO: 95 Pavirv00039060m (Switchgrass, *Panicum virgatum*) protein sequence
SEQ ID NO: 96 Pavirv00008792m (Switchgrass, *Panicum virgatum*) full-length cDNA sequence
SEQ ID NO: 97 Pavirv00008792m (Switchgrass, *Panicum virgatum*) protein sequence
SEQ ID NO: 98 Pavirv00044808m (Switchgrass, *Panicum virgatum*) full-length cDNA sequence
SEQ ID NO: 99 Pavirv00044808m (Switchgrass, *Panicum virgatum*) protein sequence
SEQ ID NO: 100 Pavirv00066820m (Switchgrass, *Panicum virgatum*) full-length cDNA sequence
SEQ ID NO: 101 Pavirv00066820m (Switchgrass, *Panicum virgatum*) protein sequence
SEQ ID NO: 102 AY928808 (Sand sagebrush, *Artemisia desertorum*) full-length cDNA sequence
SEQ ID NO: 103 AAY17949.1 (Sand sagebrush, *Artemisia desertorum*) protein sequence

DETAILED DESCRIPTION OF THE INVENTION

The following detailed description is provided to better define the present invention and to guide those of ordinary skill in the art in the practice of the present invention. Unless otherwise noted, terms are to be understood according to conventional usage by those of ordinary skill in the relevant art.

It has surprisingly been shown that transgenic plants over-expressing the wild-type Xb3 gene displayed strong drought tolerance. The invention thus represents a significant advance in the art by providing methods and compositions that permit engineering of plants for drought tolerance. In this manner, agronomic performance of crop plants may be increased, particularly when plants are subject to osmotic stress at any given stage of growth. This is particularly important in avoiding crop loss and also in increasing water use efficiency.

The invention thus provides methods and compositions for obtaining improvements in osmotic stress tolerance. In specific embodiments, expression cassettes comprising a nucleotide sequence that up-regulates the Xb3 gene are provided operably linked to a promoter that directs expression of the nucleotide sequence in the plant cell. In some aspects, the Xb3 gene may be mutated to achieve up-regulation, including where the mutation may be made by deletion, a point mutation, an insertion, or is alternatively produced by irradiation or chemical mutagenesis. In other embodiments, the promoter may be a constitutive promoter or may, for example, be an inducible promoter, such as an osmotic stress-induced promoter.

In one embodiment of the invention, a plant conferred with osmotic stress tolerance in accordance with the disclosed methods and compositions may be a monocot plant, for example maize, wheat, rice, sorghum (*Sorghum bicolor*), oats, barley, sugarcane, or switchgrass. In other embodiments, the plant may be a dicot, for example *Arabidopsis*, peanut (*Arachis hypogaea*), barrel medic (*Medicago truncatula*), carrot, soybean (*Glycine max*), cotton, *Brassica*, canola, tomato, potato, alfalfa, grape, clover, poplar, willow, eucalyptus, hemp, a *Lotus* sp., a *Vinca* sp., a *Nicotiana* sp., a *Vitis* sp., or a *Ricinus* sp.

I. Nucleic Acids, Polypeptides and Plant Transformation Constructs

Certain embodiments of the current invention concern recombinant nucleic acid sequences comprising an Xb3 coding sequence. Complements to any nucleic acid sequences described herein are also provided.

In further embodiments, nucleic acids and polypeptides are provided having a specified degree of identity to a reference sequence. "Identity," as is well understood in the art, is a relationship between two or more polypeptide sequences or two or more polynucleotide sequences, as determined by comparing the sequences. In the art, "identity" also means the degree of sequence relatedness between polypeptide or polynucleotide sequences, as determined by the match between strings of such sequences. Methods to determine "identity" are designed to give the largest match between the sequences tested. Moreover, methods to determine identity are codified in publicly available programs. "Identity" can be readily calculated by known methods including, but not limited to, those described in Lesk, ed., (1988); Smith, ed., (1993); Griffin, and Griffin, eds., (1994); von Heinje, (1987); Gribskov and Devereux, eds., (1991); and Carillo and Lipman, (1988). Computer programs can be used to determine "identity" between two sequences these programs include but are not limited to, GCG (Devereux, 1984); suite of five BLAST programs, three designed for nucleotide sequences queries (BLASTN, BLASTX, and TBLASTX) and two designed for protein sequence queries (BLASTP and TBLASTN) (Coulson, 1994; Birren, et al., 1997). The BLASTX program is publicly available from NCBI and other sources (BLAST Manual, Altschul, S., et al., NCBI NLM NIH, Bethesda, Md. 20894; Altschul, S., et al., 1990). The well known Smith Waterman algorithm can also be used to determine identity.

Parameters for polypeptide sequence comparison include the following: Algorithm: Needleman and Wunsch (1970); Comparison matrix: BLOSUM62 from Hentikoff and Hentikoff, (1992); Gap Penalty: 12; and Gap Length Penalty: 4. A program which can be used with these parameters is publicly available as the "gap" program from Genetics Computer Group, Madison Wis. The above parameters along with no penalty for end gap may serve as default parameters for peptide comparisons.

Parameters for nucleic acid sequence comparison include the following: Algorithm: Needleman and Wunsch (1970); Comparison matrix: matches=+10; mismatches=0; Gap Penalty: 50; and Gap Length Penalty: 3. A program which can be used with these parameters is publicly available as the "gap" program from Genetics Computer Group, Madison Wis. The above parameters may serve as the default parameters for nucleic acid comparisons.

As used herein, "hybridization," "hybridizes" or "capable of hybridizing" is understood to mean the forming of a double- or triple-stranded molecule or a molecule with partial double- or triple-stranded nature. Such hybridization may take place under relatively high-stringency conditions, including low salt and/or high temperature conditions, such as provided by a wash in about 0.02 M to about 0.15 M NaCl at temperatures of about 50° C. to about 70° C. for 10 min. In one embodiment of the invention, the conditions are 0.15 M NaCl and 70° C. Stringent conditions tolerate little mismatch between a nucleic acid and a target strand. Such conditions are well known to those of ordinary skill in the art, and are preferred for applications requiring high selectivity. Non-limiting applications include isolating a nucleic acid, such as a gene or a nucleic acid segment thereof, or detecting at least one specific mRNA transcript or a nucleic acid segment thereof, and the like.

The nucleic acids provided herein may be from any source, e.g., identified as naturally occurring in a plant, or synthesized, e.g., by mutagenesis. In an embodiment, the naturally occurring sequence may be from any plant. In some embodiments, the plant may be a dicotyledonous plant, for example, *Arabidopsis*, peanut (*Arachis hypogaea*), barrel medic (*Medicago truncatula*), carrot, soybean (*Glycine max*), cotton, *Brassica*, canola, tomato, potato, alfalfa, grape, clover, poplar, willow, eucalyptus, hemp, a *Lotus* sp., a *Vinca* sp., a *Nicotiana* sp., a *Vitis* sp., or a *Ricinus* sp. In other embodiments, a plant useful for the present invention may be a monocotyledonous plant, for example maize, wheat, rice, sorghum (*Sorghum bicolor*), oats, barley, sugar cane, African oil palm (*Elaeis guineensis*), or switchgrass.

Coding sequences may be provided in a recombinant vector operably linked to a heterologous promoter functional in plants, in either sense or antisense orientation. Expression constructs may also be provided comprising these sequences, including antisense oligonucleotides thereof. In other embodiments, plants and plant cells transformed with the sequences may be provided. The construction of vectors which may be employed in conjunction with plant transformation techniques using these or other sequences according to the invention will be known to those of skill of the art in light of the present disclosure (see, for example, Sambrook et al., 1989; Gelvin et al., 1990). The techniques of the current invention are thus not limited to any particular nucleic acid sequences.

The choice of any additional elements used in conjunction with the Xb3 coding sequences may depend on the purpose of the transformation. One of the major purposes of transformation of crop plants is to add commercially desirable, agronomically important traits to the plant, as described above.

Vectors used for plant transformation may include, for example, plasmids, cosmids, YACs (yeast artificial chromosomes), BACs (bacterial artificial chromosomes) or any other suitable cloning system, as well as fragments of DNA therefrom. Thus when the term "vector" or "expression vector" is used, all of the foregoing types of vectors, as well as nucleic acid sequences obtained therefrom, are included. It is contemplated that utilization of cloning systems with large insert capacities will allow introduction of large DNA sequences comprising more than one selected gene. In accordance with the invention, this could be used to introduce genes corresponding to, e.g., an entire biosynthetic pathway, into a plant.

Particularly useful for transformation are expression cassettes which have been derived from such vectors. DNA segments used for transforming plant cells will generally comprise the cDNA, gene or genes which one desires to introduce into and have expressed in the host cells. These DNA segments can further include structures such as promoters, enhancers, polylinkers, or even regulatory genes as desired. The DNA segment or gene chosen for cellular introduction will often encode a protein which will be expressed in the resultant recombinant cells resulting in a screenable or selectable trait and/or which will impart an improved phenotype to the resulting transgenic plant. Preferred components likely to be included with vectors used in the current invention are as follows.

A. Regulatory Elements

Exemplary promoters for expression of a nucleic acid sequence include plant promoters such as the CaMV 35S promoter (Odell et al., 1985), or others such as CaMV 19S (Lawton et al., 1987), nos (Ebert et al., 1987), Adh (Walker et al., 1987), sucrose synthase (Yang and Russell, 1990), α-tubulin, actin (Wang et al., 1992), cab (Sullivan et al., 1989), PEPCase (Hudspeth and Grula, 1989) or those promoters associated with the R gene complex (Chandler et al., 1989). Tissue-specific promoters such as leaf specific promoters, or tissue selective promoters and tissue-specific enhancers (Fromm et al., 1986) are also contemplated to be useful, as are inducible promoters such as ABA- and turgor-inducible promoters. Any suitable promoters known in the art may be used to express XB3 coding sequences in a plant. In an embodiment of the invention, an actin or CaMV35S promoter may be used to express Xb3 coding sequences in a plant. In another embodiment of the invention, an osmotic stress-inducible promoter may be used to express Xb3 coding sequences in a plant.

The DNA sequence between the transcription initiation site and the start of the coding sequence, i.e., the untranslated leader sequence, can also influence gene expression. One may thus wish to employ a particular leader sequence with a transformation construct of the invention. In an embodiment, leader sequences are contemplated to include those which comprise sequences predicted to direct optimum expression of the attached gene, i.e., to include a consensus leader sequence which may increase or maintain mRNA stability and prevent inappropriate initiation of translation. The choice of such sequences will be known to those of skill in the art in light of the present disclosure. In some embodiments, sequences that are derived from genes that are highly expressed in plants may be used for expression of Xb3 coding sequences.

It is envisioned that Xb3 coding sequences may be introduced under the control of novel promoters, enhancers, etc., or homologous or tissue-specific or tissue-selective promoters or control elements. Vectors for use in tissue-specific targeting of genes in transgenic plants will typically include tissue-specific or tissue-selective promoters and may also include other tissue-specific or tissue-selective control elements such as enhancer sequences. Promoters which direct specific or enhanced expression in certain plant tissues will be known to those of skill in the art in light of the present disclosure. These include, for example, the rbcS promoter, specific for green tissue; the ocs, nos and mas promoters which have higher activity in roots.

B. Terminators

Transformation constructs prepared in accordance with the invention may include a 3' end DNA sequence that acts as a signal to terminate transcription and allow for the polyadenylation of the mRNA produced by coding sequences operably linked to a promoter. In one embodiment of the invention, the native terminator of a Xb3 coding sequence may be used. Alternatively, a heterologous 3' end may enhance the expression of sense or antisense Xb3 coding sequences. Examples of terminators that may be used in this context include those from the nopaline synthase gene of *Agrobacterium tumefaciens* (nos 3' end) (Bevan et al., 1983), the terminator for the T7 transcript from the octopine synthase gene of *Agrobacterium tumefaciens*, and the 3' end of the protease inhibitor I or II gene from potato or tomato. Regulatory elements such as an Adh intron (Callis et al., 1987), sucrose synthase intron (Vasil et al., 1989) or TMV omega element (Gallie et al., 1989), may further be included where desired.

C. Transit or Signal Peptides

Sequences that are joined to the coding sequence of an expressed gene, which are removed post-translationally from the initial translation product and which facilitate the transport of the protein into or through intracellular or extracellular membranes, are termed transit (usually into vacuoles, vesicles, plastids and other intracellular organelles) and signal sequences (usually to the endoplasmic reticulum, Golgi apparatus and outside of the cellular membrane). By facilitating the transport of the protein into compartments inside and outside the cell, these sequences may increase the accumulation of gene products by protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It further is contemplated that targeting of certain proteins may be desirable in order to enhance the stability of the protein (U.S. Pat. No. 5,545,818, incorporated herein by reference in its entirety).

Additionally, vectors may be constructed and employed in the intracellular targeting of a specific gene product within the cells of a transgenic plant or in directing a protein to the extracellular environment. This generally will be achieved by joining a DNA sequence encoding a transit or signal peptide sequence to the coding sequence of a particular gene. The resultant transit or signal peptide will transport the protein to a particular intracellular or extracellular destination, respectively, and will then be post-translationally removed.

D. Marker Genes

By employing a selectable or screenable marker, one can provide or enhance the ability to identify transformants. “Marker genes” are genes that impart a distinct phenotype to cells expressing the marker protein and thus allow such transformed cells to be distinguished from cells that do not have the marker. Such genes may encode either a selectable or screenable marker, depending on whether the marker confers a trait which one can “select” for by chemical means, i.e., through the use of a selective agent (e.g., a herbicide, antibiotic, or the like), or whether it is simply a trait that one can identify through observation or testing, i.e., by "screening" (e.g., the green fluorescent protein). Of course, many examples of suitable marker proteins are known to the art and can be employed in the practice of the invention.

Many selectable marker coding regions are known and could be used with the present invention including, but not limited to, neo (Potrykus et al., 1985), which provides kanamycin resistance and can be selected for using kanamycin, G418, paromomycin, etc.; bar, which confers bialaphos or phosphinothricin resistance; a mutant EPSP synthase protein (Hinchee et al., 1988) conferring glyphosate resistance; a nitrilase such as bxn from *Klebsiella ozaenae* which confers resistance to bromoxynil (Stalker et al., 1988); a mutant acetolactate synthase (ALS) which confers resistance to imidazolinone, sulfonylurea or other ALS inhibiting chemicals (European Patent Application 154, 204, 1985); a methotrexate resistant DHFR (Thillet et al., 1988), a dalapon dehalogenase that confers resistance to the herbicide dalapon; or a mutated anthranilate synthase that confers resistance to 5-methyl tryptophan.

An illustrative embodiment of selectable marker capable of being used in systems to select transformants are those that encode the enzyme phosphinothricin acetyltransferase, such as the bar gene from *Streptomyces hygroscopicus* or the pat gene from *Streptomyces viridochromogenes*. The enzyme phosphinothricin acetyl transferase (PAT) inactivates the active ingredient in the herbicide bialaphos, phosphinothricin (PPT). PPT inhibits glutamine synthetase, (Murakami et al., 1986; Twell et al., 1989) causing rapid accumulation of ammonia and cell death.

II. Genetic Transformation

Additionally provided herein are transgenic plants transformed with the above-identified recombinant vectors encoding a Xb3, or a sequence modulating up-regulation thereof.

Suitable methods for transformation of plant or other cells for use with the current invention are believed to include virtually any method by which DNA can be introduced into a cell, such as by direct delivery of DNA such as by PEG-mediated transformation of protoplasts (Omirulleh et al., 1993), by desiccation/inhibition-mediated DNA uptake (Potrykus et al., 1985), by electroporation (U.S. Pat. No. 5,384,253, specifically incorporated herein by reference in its entirety), by agitation with silicon carbide fibers (Kaeppler et al., 1990; U.S. Pat. No. 5,302,523, specifically incorporated herein by reference in its entirety; and U.S. Pat. No. 5,464,765, specifically incorporated herein by reference in its entirety), by *Agrobacterium*-mediated transformation (U.S. Pat. Nos. 5,591,616 and 5,563,055; both specifically incorporated herein by reference) and by acceleration of DNA coated particles (U.S. Pat. Nos. 5,550,318; 5,538,877; and 5,538,880; each specifically incorporated herein by reference in its entirety), etc. Through the application of techniques such as these, the cells of virtually any plant species may be stably transformed, and these cells developed into transgenic plants.

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example, the methods described by Fraley et al., (1985), Rogers et al., (1987) and U.S. Pat. No. 5,563,055, specifically incorporated herein by reference in its entirety.

*Agrobacterium*-mediated transformation is most efficient in dicotyledonous plants and is the preferable method for transformation of dicots, including *Arabidopsis*, tobacco, tomato, alfalfa and potato. Indeed, while *Agrobacterium*-mediated transformation has been routinely used with dicotyledonous plants for a number of years, including alfalfa (Thomas et al., 1990), it has only recently become applicable to monocotyledonous plants. Advances in *Agrobacterium*-mediated transformation techniques have now made the technique applicable to nearly all monocotyledonous plants. For example, *Agrobacterium*-mediated transformation techniques have now been applied to rice (Hiei et al., 1997; U.S. Pat. No. 5,591,616, specifically incorporated herein by reference in its entirety), wheat (McCormac et al., 1998), barley (Tingay et al., 1997; McCormac et al., 1998) and maize (Ishidia et al., 1996).

One also may employ protoplasts for electroporation transformation of plants (Bates, 1994; Lazzeri, 1995). Another method for delivering transforming DNA segments to plant cells in accordance with the invention is microprojectile bombardment (U.S. Pat. Nos. 5,550,318; 5,538,880; 5,610,042; and PCT Application WO 94/09699; each of which is specifically incorporated herein by reference in its entirety). In this method, particles may be coated with nucleic acids and delivered into cells by a propelling force.

The transgenic plants of the present invention expressing heterologous Xb3 can be of any species. The plants can be an $R_0$ transgenic plant (i.e., a plant derived from the original transformed tissue). The plants can also be a progeny plant of any generation of an $R_0$ transgenic plant, wherein the transgenic plant comprises the nucleic acid sequence from the $R_0$ transgenic plant.

Seeds of the any above-described transgenic plants may also be provided, particularly where the seed comprises the nucleic acid sequence. Additionally contemplated are host cells transformed with the above-identified recombinant vector. In some embodiments, the host cell is a plant cell.

Also contemplated herein is a plant genetically engineered to increase expression of Xb3, where the protein product (e.g. a polypeptide) increases drought tolerance. Such plants are described in the Examples, and may be useful, e.g., as commercial plants, due to their increased plant size and seed number.

The plants of these embodiments having increased or enhanced expression of Xb3 may be of any species. The species may be any monocotyledonous or dicotyledonous plant, such as those described herein. One of skill in the art will recognize that the present invention may be applied to plants of other species by employing methods described herein and others known in the art.

Tissue cultures may be used in certain transformation techniques for the preparation of cells for transformation and for the regeneration of plants therefrom. Maintenance of tissue cultures requires use of media and controlled environments. "Media" refers to the numerous nutrient mixtures that are used to grow cells in vitro, that is, outside of the intact living organism. A medium usually is a suspension of various categories of ingredients (salts, amino acids, growth regulators, sugars, buffers) that are required for growth of most cell types. However, each specific cell type requires a specific range of ingredient proportions for growth, and an even more specific range of formulas for optimum growth. The rate of cell growth also will vary among cultures initiated with the array of media that permit growth of that cell type.

III. Production and Characterization of Stably Transformed Plants

After effecting delivery of exogenous DNA to recipient cells, the next steps generally concern identifying the transformed cells for further culturing and plant regeneration. In order to improve the ability to identify transformants, one may desire to employ a selectable or screenable marker gene with a transformation vector prepared in accordance with the invention. In this case, one would then generally assay the potentially transformed cell population by exposing the cells to a selective agent or agents, or one would screen the cells for the desired marker gene trait. Potentially transformed cells then are exposed to the selective agent. In the population of surviving cells will be those cells where, generally, the resistance-conferring gene has been integrated and expressed at sufficient levels to permit cell survival. Cells may be tested further to confirm stable integration of the exogenous DNA.

One herbicide which constitutes a desirable selection agent is the broad-spectrum herbicide bialaphos. Another example of a herbicide which is useful for selection of transformed cell lines in the practice of the invention is the broad-spectrum herbicide glyphosate. Glyphosate inhibits the action of the enzyme EPSPS which is active in the aromatic amino acid biosynthetic pathway. Inhibition of this enzyme leads to starvation for the amino acids phenylalanine, tyrosine, and tryptophan and secondary metabolites derived therefrom. U.S. Pat. No. 4,535,060 describes the isolation of EPSPS mutations which confer glyphosate resistance on the EPSPS of *Salmonella typhimurium*, encoded by the gene aroA. The EPSPS gene from *Zea mays* was cloned and mutations similar to those found in a glyphosate resistant aroA gene were introduced in vitro. Mutant genes encoding glyphosate resistant EPSPS enzymes are described in, for example, International Patent WO 97/4103.

The transformed cells, identified by selection or screening and cultured in an appropriate medium that supports regeneration, will then be allowed to mature into plants. Developing plantlets can be transferred to soilless plant growth mix, and hardened, e.g., in an environmentally controlled chamber, for example, at about 85% relative humidity, 600 ppm $CO_2$, and 25-250 microeinsteins $m^{-2}$ $s^{-1}$ of light. Plants may be matured in a growth chamber or greenhouse. Plants can be regenerated after a transformant is identified, depending on the initial tissue. During regeneration, cells are grown on solid media in tissue culture vessels. Illustrative embodiments of such vessels are petri dishes and Plant Cons. Regenerating plants can be grown at about 19 to 28° C., for example. After the regenerating plants have reached the stage of shoot and root development, they may be transferred to a greenhouse for further growth and testing.

To confirm the presence of the exogenous DNA or "transgene(s)" in the regenerating plants, a variety of assays may be performed. Such assays include, for example, "molecular biological" assays, such as Southern and Northern blotting and PCR™; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced genes in high molecular weight DNA, i.e., confirm that the introduced gene has been integrated into the host cell genome. The technique of Southern hybridization provides information that is obtained using PCR™, e.g., the presence of a gene, but also demonstrates integration into the genome and characterizes each individual transformant.

The expression of a gene product is often determined by evaluating the phenotypic results of its expression. These assays also may take many forms including but not limited to analyzing changes in the chemical composition, morphology, or physiological properties of the plant. Chemical composition may be altered by expression of genes encoding enzymes or storage proteins which change amino acid composition and may be detected by amino acid analysis, or by enzymes that change starch quantity which may be analyzed by near infrared reflectance spectrometry. Morphological changes may include greater stature or thicker stalks. Most often changes in response of plants or plant parts to imposed treatments are evaluated under carefully controlled conditions termed bioassays.

IV. Breeding Plants of the Invention

In addition to direct transformation of a particular plant genotype with a construct prepared according to the current invention, transgenic plants may be made by crossing a plant having a selected DNA of the invention to a second plant lacking the construct. For example, a selected Xb3 coding sequence can be introduced into a particular plant variety by crossing, without the need for ever directly transforming a plant of that given variety. Therefore, the current invention not only encompasses a plant directly transformed or regenerated from cells which have been transformed in accordance with the current invention, but also the progeny of such plants. As used herein, the term "progeny" denotes the offspring of any generation of a parent plant prepared in accordance with the instant invention, wherein the progeny comprises a selected DNA construct prepared in accordance with the invention. "Crossing" a plant to provide a plant line having one or more added transgenes relative to a starting plant line, as disclosed herein, is defined as the techniques that result in a transgene of the invention being introduced into a plant line by crossing a plant of a starting line with a plant of a donor plant line that comprises a transgene of the invention. To achieve this one could, for example, perform the following steps:

(a) plant seeds of the first (starting line) and second (donor plant line that comprises a transgene of the invention) parent plants;

(b) grow the seeds of the first and second parent plants into plants that bear flowers;

(c) pollinate a flower from the first parent plant with pollen from the second parent plant; and (d) harvest seeds produced on the parent plant bearing the fertilized flower.

Backcrossing is herein defined as the process including the steps of:

(a) crossing a plant of a first genotype containing a desired gene, DNA sequence or element to a plant of a second genotype lacking the desired gene, DNA sequence or element;

(b) selecting one or more progeny plant containing the desired gene, DNA sequence or element;

(c) crossing the progeny plant to a plant of the second genotype; and (d) repeating steps (b) and (c) for the purpose of transferring a desired DNA sequence from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking the desired DNA sequence may be referred to as an unconverted genotype, line, inbred, or hybrid.

V. Definitions

Expression: The combination of intracellular processes, including transcription and translation, undergone by a coding DNA molecule such as a structural gene to produce a polypeptide.

Genetic Transformation: A process of introducing a DNA sequence or construct (e.g., a vector or expression cassette) into a cell or protoplast in which that exogenous DNA is incorporated into a chromosome or is capable of autonomous replication.

Heterologous: A sequence which is not normally present in a given host genome in the genetic context in which the sequence is currently found. In this respect, the sequence may be native to the host genome, but be rearranged with respect to other genetic sequences within the host sequence. For example, a regulatory sequence may be heterologous in that it is linked to a different coding sequence relative to the native regulatory sequence.

Obtaining: When used in conjunction with a transgenic plant cell or transgenic plant, obtaining means either transforming a non-transgenic plant cell or plant to create the transgenic plant cell or plant, or planting transgenic plant seed to produce the transgenic plant cell or plant. Such a transgenic plant seed may be from an $R_0$ transgenic plant or may be from a progeny of any generation thereof that inherits a given transgenic sequence from a starting transgenic parent plant.

Over-expression: The increase in the expression of a DNA or RNA transcript and/or the function or activity of a protein relative to a control or naturally-occurring counterpart.

Promoter: A recognition site on a DNA sequence or group of DNA sequences that provides an expression control element for a structural gene and to which RNA polymerase specifically binds and initiates RNA synthesis (transcription) of that gene.

$T_0$ transgenic plant: A plant that has been genetically transformed or has been regenerated from a plant cell or cells that have been genetically transformed.

Regeneration: The process of growing a plant from a plant cell (e.g., plant protoplast, callus or explant).

Selected DNA: A DNA segment which one desires to introduce or has introduced into a plant genome by genetic transformation.

Transformation construct: A chimeric DNA molecule which is designed for introduction into a host genome by genetic transformation. Preferred transformation constructs will comprise all of the genetic elements necessary to direct the expression of one or more exogenous genes. In particular embodiments of the instant invention, it may be desirable to introduce a transformation construct into a host cell in the form of an expression cassette.

Transformed cell: A cell in which the DNA complement has been altered by the introduction of an exogenous DNA molecule into that cell.

Transgene: A segment of DNA which has been incorporated into a host genome or is capable of autonomous replication in a host cell and is capable of causing the expression of one or more coding sequences. Exemplary transgenes will provide the host cell, or plants regenerated therefrom, with a novel phenotype relative to the corresponding non-transformed cell or plant. Transgenes may be directly introduced into a plant by genetic transformation, or may be inherited from a plant of any previous generation which was transformed with the DNA segment.

Transgenic plant: A plant or progeny plant of any subsequent generation derived therefrom, wherein the DNA of the plant or progeny thereof contains an introduced exogenous DNA segment not naturally present in a non-transgenic plant of the same strain. The transgenic plant may additionally contain sequences which are native to the plant being transformed, but wherein the "exogenous" gene has been altered in order to alter the level or pattern of expression of the gene, for example, by use of one or more heterologous regulatory or other elements.

Up-regulation: The increase in the expression of a DNA or RNA transcript and/or the function or activity of a protein relative to a control or naturally-occurring counterpart.

Vector: A DNA molecule designed for transformation into a host cell. Some vectors may be capable of replication in a host cell. A plasmid is an exemplary vector, as are expression cassettes obtained therefrom.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Over-expression of Wild-type Xb3 in Rice Confers Drought Tolerance

A full-length cDNA of Xb3 (SEQ ID NO: 4) under the control of the maize ubiquitin promoter was transformed into *O. sativa* ssp. *Japonica* var. Taipei309 (TP309). For protein detection, a 3xFLAG epitope tag was fused to the C-terminus of XB3 and this tag unlikely influences XB3 function as evidenced by the cell death assays in *N. benthamiana* (Huang et al., *PLoS One.* 8: e63868, 2013). A total of 69 transgenic lines were obtained, of which 57 were found to express the transgene. Among these, three lines (OXB3-69, OXB3-84, OXB3-79) were subjected to drought treatment and the results showed that they all displayed tolerance to drought and the levels of Xb3 transcripts in the lines correlated positively with enhanced drought response.

Figure 3:
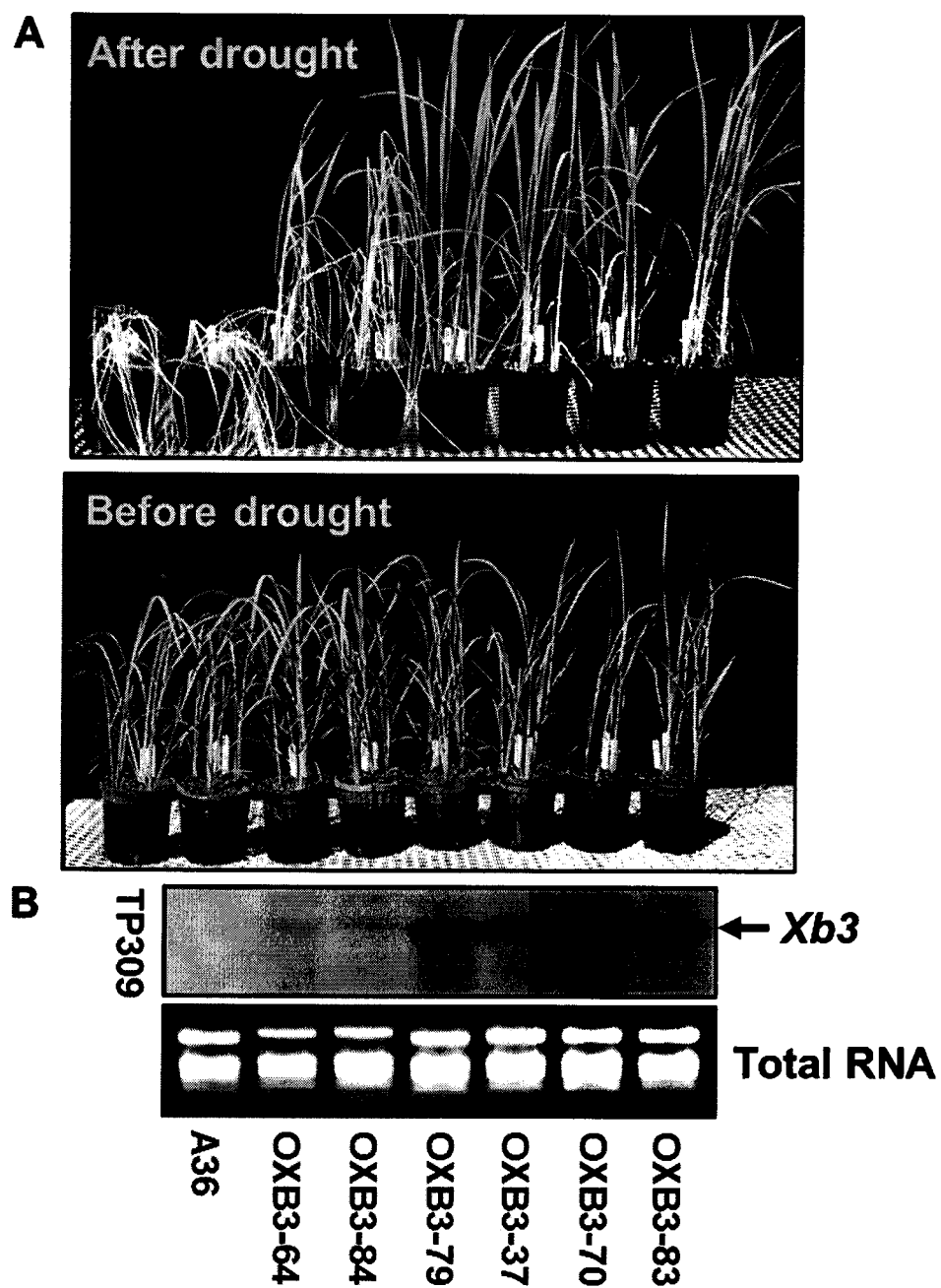
FIG. 3 Rice transgenic plants (OXB3s) over-expressing Xb3 survive drought stress. (Panel A) One-month-old T1 plants were subjected to drought stress treatment. Water was withheld 17 days and reapplied for 4 days of plant recovery. Wild-type (TP309) and the empty-vector line A36 are controls. Similar results were obtained when T0 plants of these lines were drought stressed. (Panel B) RNA gel blot analysis showing Xb3 transcripts in the indicated lines. Total RNA was probed with an Xb3-specific probe. Both autorad (upper panel) and agarose gel (lower panel) are shown. (Panel C) Survival rate of indicated lines (n=18 each line). Data sets in all figures with asterisks indicate statistically significant difference from the control A36 (*: $p<0.05$; **: $p<0.01$).
Figure 3:
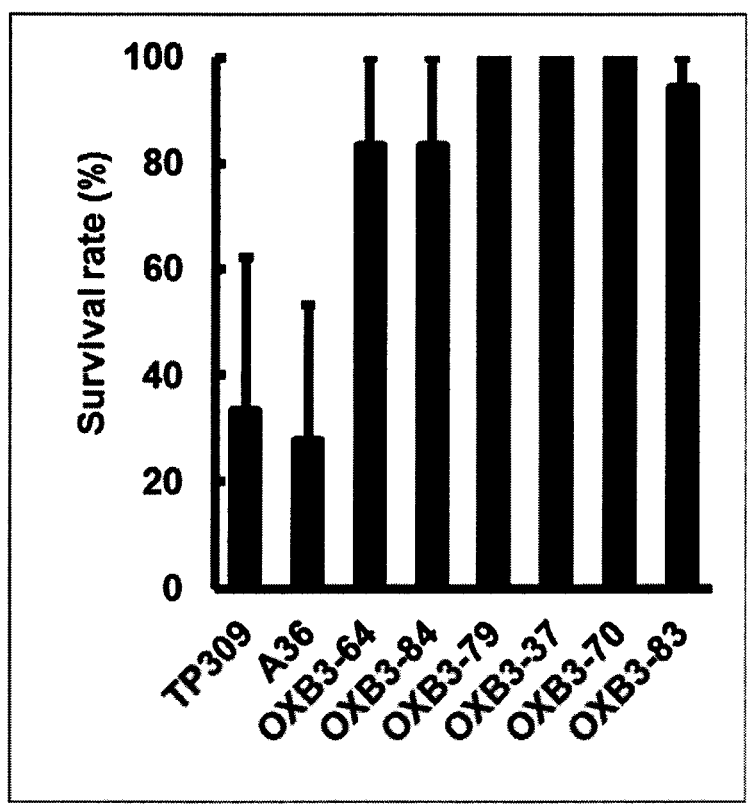

To verify these observations, the T1 generation of these lines together with additional four transgenic lines, except for OXB3-69 that expressed low levels of the Xb3 transgene but produced no seeds, were chosen for drought assays. The transgenic line A36 containing only empty vector and the recipient line TP309 was used as negative controls. To ensure that T1 plants carry the transgene, the seeds harvested from transgenic plants were germinated on half-strength Murashige and Skoog (½ MS) medium containing 50 µg/mL hygromycin. When the seedlings reached one month stage, water was withheld for 17 days followed by re-watering for 4 days. As shown in FIG. 3, the transgenic plants OXB3-79, OXB3-37, OXB3-70 and OXB3-83 with high levels of transgene largely survived the drought stress treatment, whereas OXB3-64 and OXB3-84 plants expressing relatively lower levels of the transgene were significantly damaged. In contrast, most A36 and TP309 plants were killed by the drought stress. Notably, the extent of damage caused by the stress was inversely correlated to the levels of Xb3 expression. Over-expression of Xb3, therefore, leads to drought tolerance.

Example 2

Down-regulation of Xb3 Increases Rice Sensitivity to Drought

Figure 4:
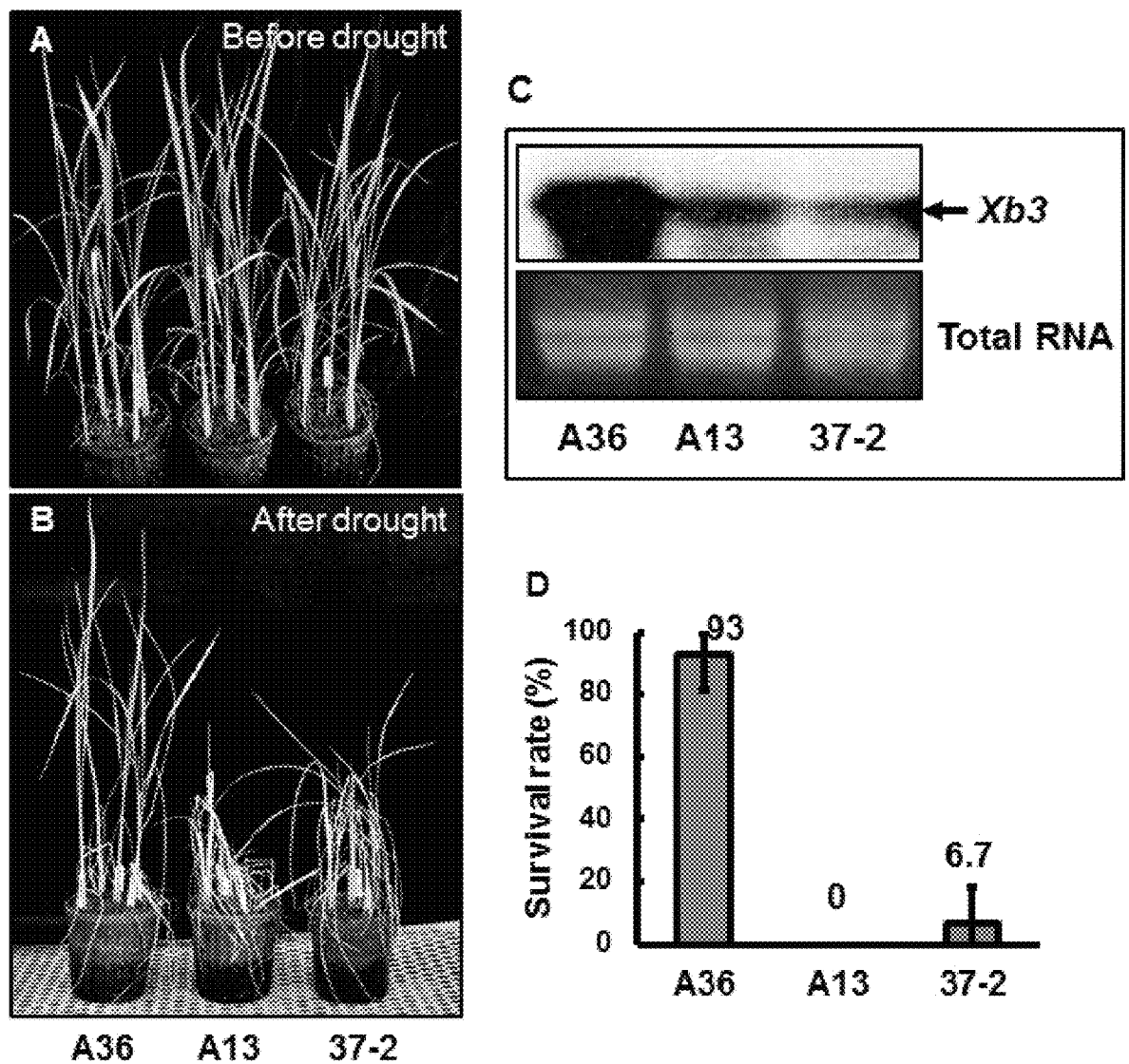
FIG. 4 Reduction of Xb3 transcripts RNAi causes an increased sensitivity to drought. One-month-old plants (Panel A) were subjected to drought stress treatment. Water was withheld 29 days and reapplied for 4 days of plant recovery (Panel B). Empty-vector control (A36) and two RNAi lines (A13 and 37-2) are shown. (Panel C) RNA gel blot analysis showing Xb3 transcripts in the indicated lines. Total RNA was probed with an Xb3-specific probe. Both autorad (upper panel) and agarose gel (lower panel) are shown. (Panel D) Survival rate of drought-treated plants (n=20 each line). Numbers indicate the survival rate of each line.

To confirm the role of Xb3 in drought response, RNA interference (RNAi) technology was used to down-regulate this gene in rice. An RNAiXb3 construct, driven by the maize ubiquitin promoter, was transformed into the rice cultivar TP309 using *Agrobacterium tumefaciens*-mediated transformation. Two transgenic lines, A13 and 37-2, were chosen for drought stress treatment. As shown in FIG. 4, the empty-vector control line A36 was able to survive the water stress that severely damaged or killed the RNAi lines. RNA blot analysis confirmed that Xb3 transcripts were significantly decreased in the RNAi lines compared to A36 (FIG. 4). These results indicate that Xb3 is required for rice tolerance to severe water deficit.

Example 3

Xb3 is Induced by Drought Treatment

Figure 5:
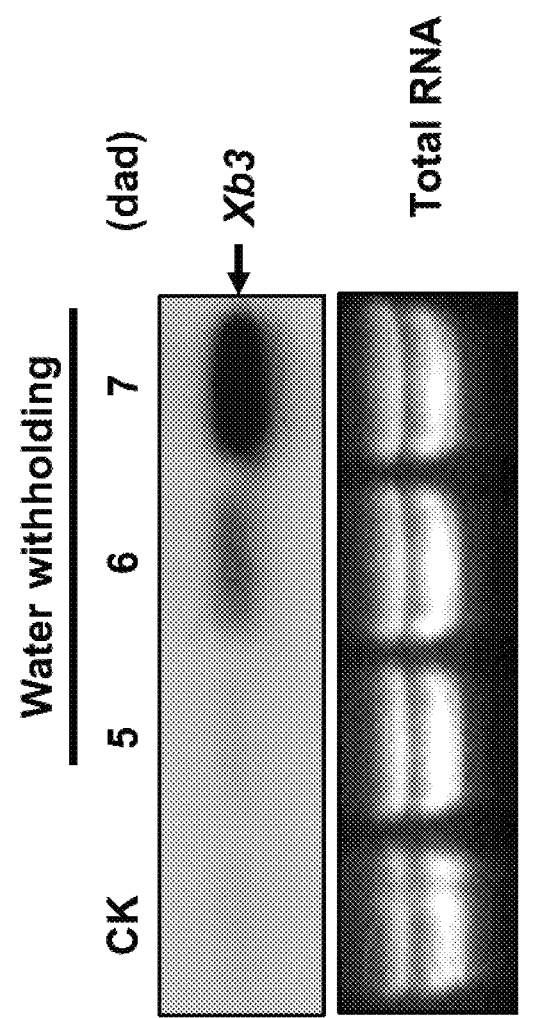
FIG. 5 RNA blot analysis showing induction of Xb3 by drought conditions. Wild-type rice plants TP309 were subjected to water withholding. Total RNA extracted from leaf samples collected at indicated days after drought (dad) was subjected to RNA blot probed with an Xb3-specific probe. Both autorad (upper panel) and agarose gel (lower panel) are shown. CK is the control well-watered plants at the same age.

To determine whether the Xb3 gene is induced by drought conditions, one-month old TP309 plants were subjected to drought treatment. Total RNA was isolated from leaf tissues harvested from treated plants and probed with an Xb3-specific probe using RNA blot analysis. Xb3 transcripts in wild-type plants were elevated 6 days after drought stress (FIG. 5). At day 7, its levels were further increased. These results are consistent with the data from transgenic studies and suggest that Xb3 may be an important regulator of drought response.

Example 4

Two Maize Orthologs of Xb3 are Drought-stress-responsive

Figure 2:
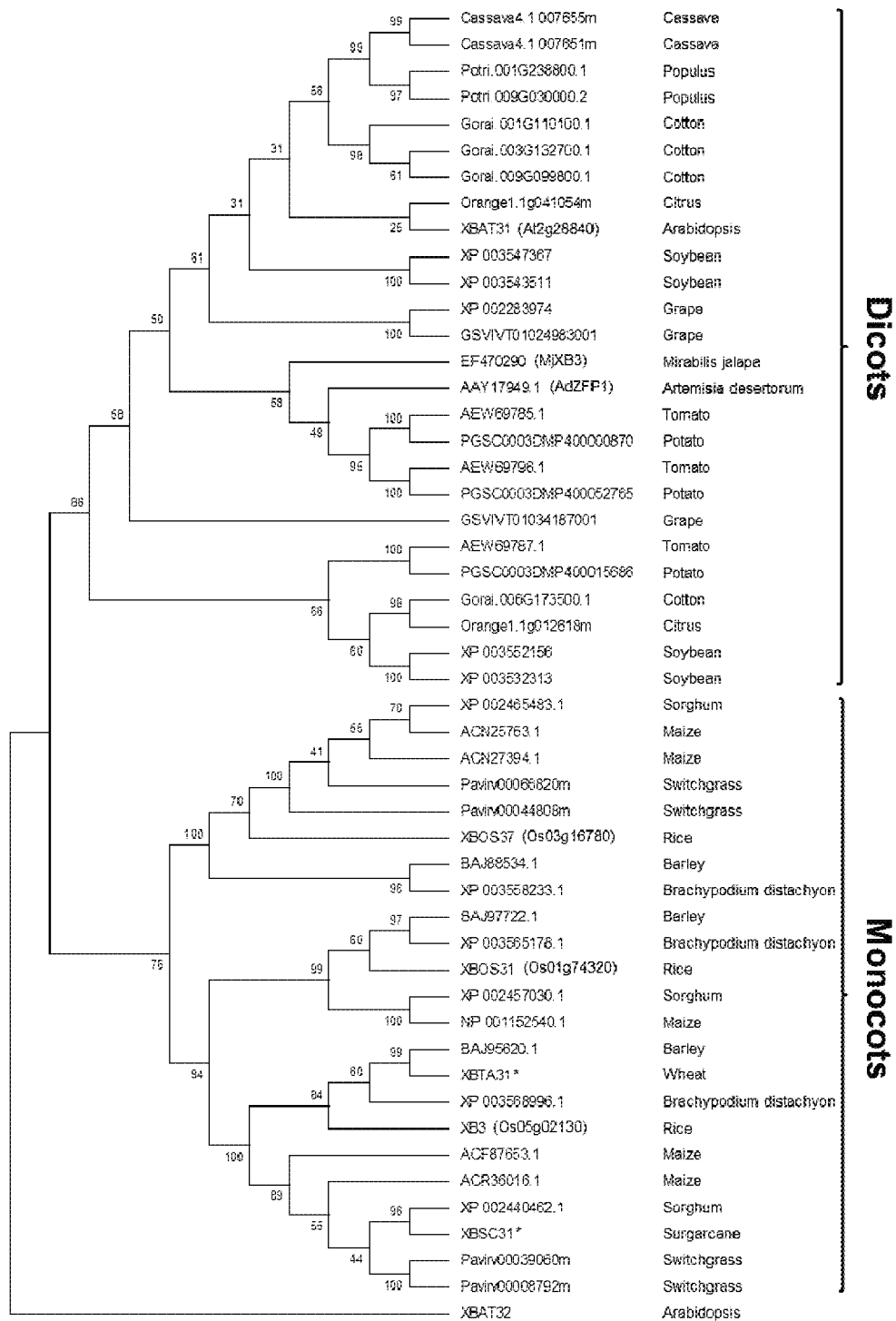
FIG. 2 Phylogenetic analysis of the XB3 family. A phylogenetic tree was generated with members of the XB3 family by the neighbor-joining method. The *Arabidopsis* ankyrin-RING protein XBAT32 was used as an out-family control. Accession numbers and names for the proteins used are indicated. The asterisk denotes the members annotated based on EST sequences in this study.
Figure 6:
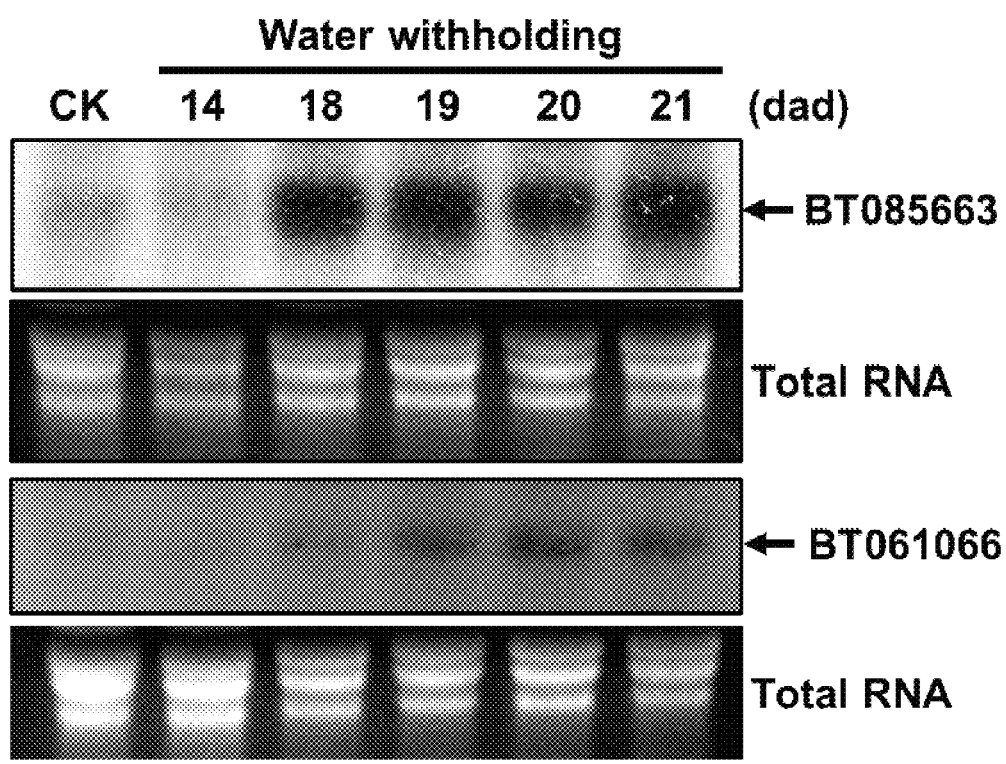
FIG. 6 RNA blot analysis showing induction of the maize orthologs (BT085663 and BT061066) of Xb3 by drought stress. Wild-type maize plants (B73) were subjected to water withholding. Total RNA extracted from leaf samples collected at indicated days after drought (dad) was probed with a BT085663- or BT061066-specific probe. Both autorad (upper panel) and agarose gel (lower panel, Total RNA) are shown. CK is well-watered plants at the same age.

Five maize predicted proteins (ACR36016.1, ACF87653.1, NP_001152540.1, ACN27394.1 and ACN25763.1) were found to be closely-related to XB3 (FIG. 2). Similar to Xb3, the maize gene BT085663 encoding ACR36016.1 is strongly induced by drought treatment, whereas the ACN25763.1 encoding gene BT061066 shows moderate response to the stress (FIG. 6). These results suggest that members of the Xb3 family may function conserved in drought response in grains and possibly other plant species.

Example 5

ABA Levels Rise in Lines Over-expressing Dt1

Figure 7:
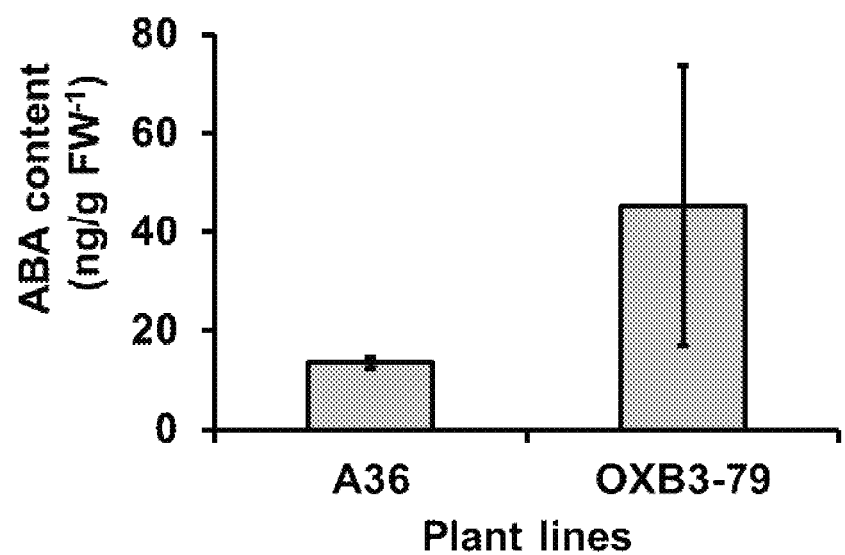
FIG. 7 Over-expression of Xb3 leads to increased ABA contents. ABA contents of A36 and the Xb3 over-expression line OXB3-79 were determined from leaf tissues of one-month-old plants using mass spectrometry. Each data point represents four replications. The standard deviations are indicated. FW: fresh weight.

Endogenous ABA levels regulate plant response to drought. ABA contents of the Xb3 over-expression line OXB3-79 was compared to that of the empty-vector control A36. The OXB3-79 showed higher levels of endogenous ABA than A36 in the absence of stress (FIG. 7).

Example 6

Over-Expression of the $Xb3^{G2A}$ Mutant in Rice Confers Drought Tolerance the T0 Generation A total of 30 transgenic rice lines carrying $Xb3^{G2A}$-3xFLAG (SEQ ID NO: 6) driven by the maize ubiquitin promoter were generated. $Xb3^{G2A}$ transcripts were detected in 29 of the 30 transgenic lines (FIG. 8A), and there were significant more lines with high levels of $Xb3^{G2A}$ expression than those with high levels of wild-type Xb3. Three $Xb3^{G2A}$ over-expression lines [$OXB3^{G2A}$-2, $OXB3^{G2A}$-6 and $OXB3^{G2A}$-16] were chosen for further functional characterization. Ten days after drought treatment followed by four days re-watering, $OXB3^{G2A}$-2 and $OXB3^{G2A}$-6 plants exhibited a strong tolerant response that is comparable to OXB3-79 (FIG. 8B). $OXB3^{G2A}$-16 plants were severely damaged by the stress. Therefore, Gly2 might be dispensable for Xb3 drought function and negatively influences Xb3 accumulation.

Example 7

Figure 10:
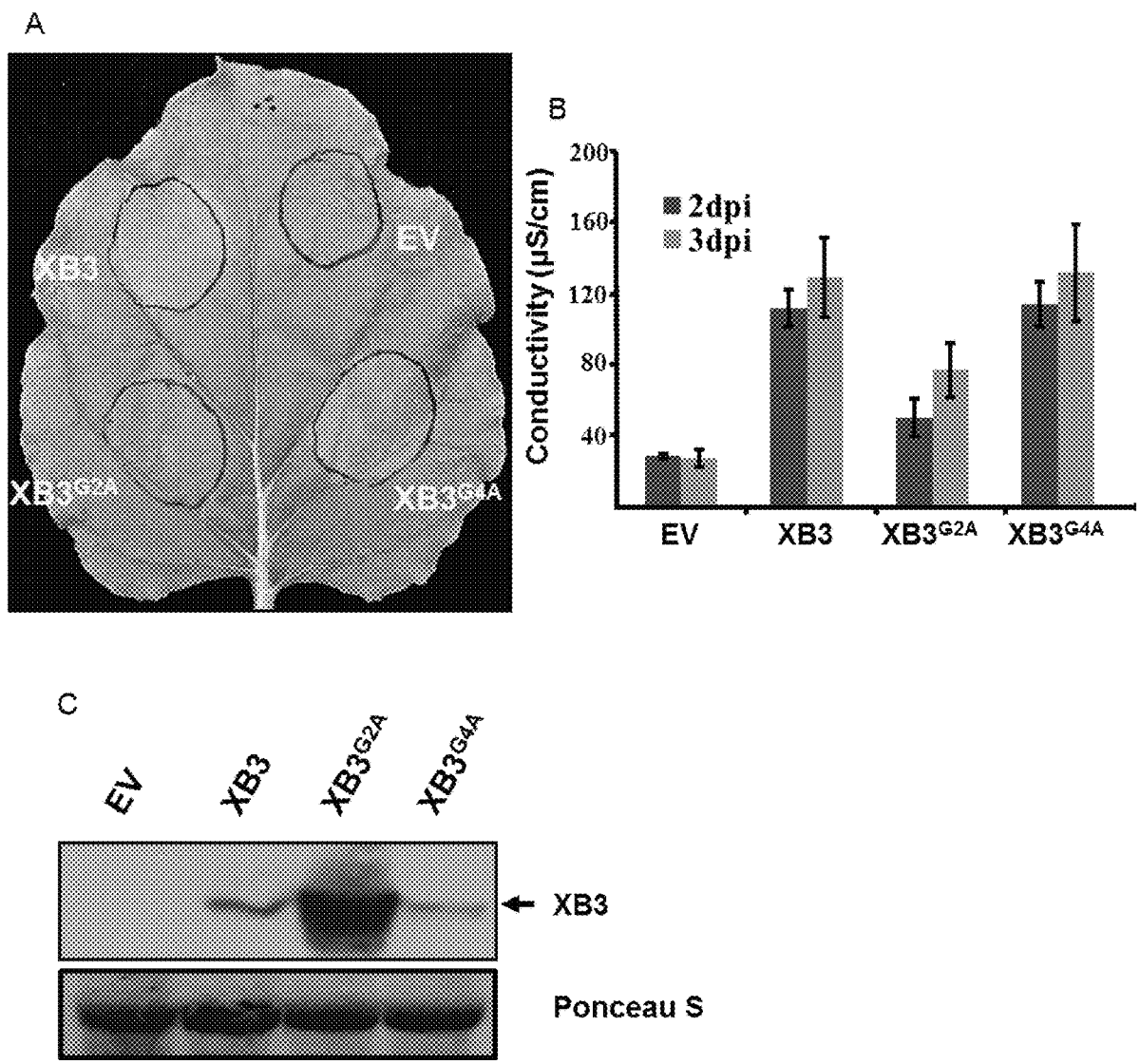
FIG. 10 Mutation of the invariable Gly2 residue significantly compromises XB3 cell death activity. (Panel A) *Nicotiana benthamiana* leaves were infiltrated with *Agrobacterium* (agroinfiltration) carrying constructs for the expression of the indicated proteins. Photograph was taken 3 days post infiltration (dpi). Infiltrated areas are circled. EV: empty vector. (Panel B) Quantification of cell death in *N. benthamiana* leaves by measuring electrolyte leakage at the indicated time points after agroinfiltration. Each data point represents the mean+SD from 3 infiltrated leaves. (Panel C) Protein blot analysis showing the level of XB3 in the infiltrated leaves. Total protein extracts were sampled 40 hours post infiltration and immunoblotted with anti-FLAG M2 antibody (Top). The same blot stained with Ponceau S to show sample loading (Bottom).

Mutation of the Invariable Gly2 Residue Significantly Compromises XB3 Cell Death Activity Lipidation of the second glycine residue through post-translational myristoylation is a well-known mechanism to regulate localization and function of many proteins (Sorek et al., *Curr Opin Plant Biol.* 12: 714-20, 2009). A glycine at position 2 is highly conserved among members of the XB3 family (FIG. 9). To examine a role for this residue in XB3 functions, an XB3 mutant in which Gly2 was mutated to alanine was generated. Wild-type Xb3-3xFLAG and the $Xb3^{G2A}$-3xFLAG genes, under the control of the cauliflower mosaic virus (CaMV) 35S promoter, were expressed in 4-week-old *N. benthamiana* leaves by agroinfiltration. It has been shown previously that the 3xFLAG epitope tag allows detection of the XB3 protein in the infiltrated leaves, but has no effects on XB3 cell death activity (Huang et al., *PLoS One.* 8: e63868, 2013). Transient expression of $XB3^{G2A}$-3xFLAG induced no obvious tissue collapse three days after agroinfiltration (FIG. 10A). However, results from the more quantitative ion leakage assays indicated that cell death occurred weakly in the leaves infiltrated with the $Xb3^{G2A}$-3xFLAG construct (FIG. 10B). The reduced cell death activity did not result from lower expression of $XB3^{G2A}$, because a higher accumulation of the mutant protein was detected using anti-FLAG M2 antibody as compared with that of wild-type XB3 in the infiltrated leaves (FIG. 10C). By contrast, expression of wild-type XB3 triggered a strong cell death response three days after agroinfiltration, whereas expression of the empty vector (pCAMBIA1300S) failed to cause cell death (FIGS. 10A and 10B). To test specificity of Gly2 function in XB3-mediated cell death, the glycine residue at position 4 was mutated. Similar to wild-type XB3, the XB3$^{G4A}$ mutant was able to induce a strong cell death response (FIGS. 10A and 10B). These results indicate that Gly2 is crucial for XB3 cell death activity.

Example 8

Bacteria and Plant Growth Conditions

*Agrobacterium tumefaciens* strains LBA4404 and EHA105 were cultured at 29° C. in YM and Luria-Bertani medium with appropriate antibiotics, respectively. Dehusked rice seeds were surface sterilized for 2 min using 70% ethanol followed by 30 min in commercial bleach (8.25% Sodium Hypochlotite). After extensive washing with sterile water, the seeds were germinated on ½ MS medium supplemented with 3% sucrose. For transgenic seeds, ½ MS medium with 50 µg/ml hygromycin B (Roche, Indianapolis, Ind.) was supplemented to the medium. Seedlings were transplanted to soil in the pots that contains drainage holes on the bottom. The pots were then maintained in a large tank filled with water in a greenhouse under natural light conditions. For drought treatment, the pots with plants were moved out of the water tank and kept on a bench without watering. To recover from drought stress, the treated plants were re-watered and the pots were placed back to the water tank. *N. benthamiana* plants were grown at 24-26° C. with a 16 hour photoperiod under florescent light.

Example 9

Rice Transformation

An Xb3 over-expression construct (pCmHU-Xb3-3xFLAG) was made by cloning the Xb3-3xFLAG fragment from pCR8GW-Xb3-3xFLAG (Huang et al., *PLoS One.* 8: e63868, 2013) into the BamHI-SpeI sites of pCmHU-1, a binary vector with the maize ubiquitin promoter for over-expressing the gene of interest (Wang et al., *Plant Cell* 18: 3635-3646, 2006). To generate pCmHU-Xb3$^{G2A}$-3xFLAG, the Xb3 gene was PCR amplified with the primer pair XB3NEW-3 (5' GTTCTAGAGGATCCATGGCTCACGGT-GTCAGCTGCGCCCG 3') (SEQ ID NO: 1) and XB3CT-3 (5' TTTCTAGAAATCAACTAGTTAGATCGTGCTCAG-GCTTGTCCA 3') (SEQ ID NO: 2). After digestion with BamHI-SpeI, the PCR product carrying a G to C mutation at nucleotide 5 of Xb3 was used to replace the wild-type gene in pCmHU-Xb3-3xFLAG. Both pCmHU-Xb3-3xFLAG and pCmHU-Xb3$^{G2A}$-3xFLAG were sequenced and individually transformed into *Agrobacterium tumefaciens* strain LBA4404. Rice transformation was performed using calli induced from immature embryos of TP309 as described by Hiei et al. (*Plant Mol. Biol.* 35: 205-218, 1997).

Example 10

RNA Blot Analysis

RNA blot analysis was performed according to standard methods. Total RNA was isolated from rice leaves using TRIZOL Reagent (Life Technologies, Grand Island, N.Y.) according to the manufacturer's instruction. Ten micrograms of RNA from each sample were analyzed on a 1.0% formaldehyde agarose gel followed by transferring to IMMO-BILON-NY$^+$ membrane (Millipore, Billerica, Mass.). Probes were labeled by [$\alpha^{32}$P]dCTP using the Prime-It II Random Primer Labeling kit (Stratagene, La Jolla, Calif.) following the manufacturer's instruction. Hybridization was carried out at 42° C. overnight in hybridization buffer (5xSSPE, 50% formammide, 5xDenhardt's solution, 1% SDS, and 10% Detran Sulphate). For detection of Xb3-3xFLAG and Xb3$^{G2A}$-3xFLAG in the Xb3 over-expression lines, a 336 by probe including a sequence of 234 by from the 3' end of the Xb3 coding region and a sequence of 102 by from 3xFLAG.

Example 11

*Agrobacterium*-mediated Transient Assay in *N. benthamiana* pCAMBIA1300S-Xb3-3xFLAG was described previously (Huang et al., *PLoS One.* 8: e63868, 2013). pCAMBIA1300S-Xb3$^{G2A}$-3xFLAG and pCAMBIA1300S-Xb3$^{G4A}$-3xFLAG, were generated using a similar strategy as for pCmHU-Xb3$^{G2A}$-3xFLAG described above, except for the binary construct pCAMBIA1300S-Xb3-3xFLAG that contains the 35S promoter for over-expressing the gene of interest. PCR primers used include: XB3NEW-3 (5' GTTCTAGAGGATCCATGGCTCACGGTGTCAGCT-GCGCCCG 3') (SEQ ID NO: 1) and XB3CT-3 (5' TTTCTA-GAAATCAACTAGTTAGATCGTGCTCAGGCTT-GTCCA 3') (SEQ ID NO: 2) for pCAMBIA1300S-Xb3$^{G2A}$-3xFLAG; primer pair XB3NEW-4 (5' GTTCTAGAGGATCCATGGGTCACGCTGTCAGCT-GCGCCCGCA 3') (SEQ ID NO: 3) and XB3CT-3 (5' TTTCTAGAAATCAACTAGTTAGATCGTGCTCAG-GCTTGTCCA 3') (SEQ ID NO: 2) for pCAMBIA1300S-Xb3$^{G4A}$-3xFLAG. The constructs were sequenced and individually transformed into *Agrobacterium tumefaciens* strain EHA105.

*Agrobacterium*-mediated transformation of *N. benthamiana* was performed according to the procedure the constructs described previous (Huang et al., *PLoS One.* 8: e63868, 2013). Briefly, bacterial cells containing the above constructs were grown overnight. The propagated cells were harvested by centrifugation at 4,000 g for ten minutes and resuspended to an optical density (OD) of 0.5 at 600 nm in buffer (10 mM MES, pH 5.6, 10 mM MgCl2 and 150 µM acetosyringone). After incubation at room temperature for three hours, the bacterial cultures were infiltrated into 4-week-old *N. benthamiana* leaves using a 1-ml needleless syringe. Tissue collapse was scored at 2 and 3 dpi (days post infiltration), unless indicated otherwise. Protein was extracted from infiltrated tissues at 40 hpi (hours post infiltration) for further analyses.

Example 12

Protein Blot Analysis

Harvested tissues were ground to a fine powder in liquid nitrogen and thawed in an equal volume of extraction buffer [50m M Tris-HCl, pH 7.4, 150m M NaCl, 10% glycerol, 0.5% TritonX-100, 2 mM EDTA, 2 mM DTT, 1 mM phenylmethylsulfonyl fluoride]. For protein extraction from *N. benthamiana*, 2% polyvinylpolypyrrolidone (PVPP) was included in the buffer, whereas 5% β-mercaptoethanol was added when extracting rice proteins. After incubation with rocking for 1 hour at 4° C., cell debris was removed by centrifugation twice at 12,000 g for 15 min at 4° C. Protein concentration was determined with Bio-Rad protein assays (Hercules, Calif.). SDS polyacrylamide gel electrophoresis was used to resolve proteins. After transferring to IMMO-BILON-P PVDF membrane (Millipore, Billerica, Mass.), blots were blocked with Blotto [5% non-fat dried milk in TTBS (100 mM Tris-HCl, pH 7.9; 150 mM NaCl; 0.1% Tween 20)]. Incubation with the primary antibodies [anti-c-Myc (University of Florida Hybridoma lab), 1:5,000; anti-FLAG M2 (Sigma, St. Louis, Mo.), 1:10,000] was carried out in 3% bovine serum albumin in TTBS (anti-c-Myc) or in Blotto (anti-FLAG M2) overnight at 4° C. (anti-c-Myc) or for 1 hour at room temperature (anti-FLAG M2) followed by three 10 min washes in TTBS. Then blots were incubated with secondary antibodies for 1 hour at room temperature, followed by three 10 min washes in TTBS. The blot was developed using ECL Prime Western Blotting Detection Reagents (GE Healthcare, Piscataway, N.J.).

Example 13

Electrolyte Leakage Assays

Electrolyte leakage was performed as described previously (Huang et al., PLoS One. 8: e63868, 2013). Three leaf discs (~10 mm in diameter) harvested from the Agrobacterium-infiltrated area were immersed in 10 mL of non-ionic, double-distilled water and incubated at room temperature for two hours with shaking at 160 rpm. Conductivity of the solution was measured using a COND 6+ conductivity meter (EUTECH Instruments, Burlington, Vt.). Error bars represent three replicates at each time point.

Example 14

Phylogenic Analysis of the XB3 Family 34 members of the XB3 family were previously identified from the NCBI Entrez Protein database by using the XB3 protein sequence as a query (Huang et al., PLoS One. 8: e63868, 2013). To identify more family members, NCBI Expressed Sequence Tags (EST), NCBI Whole-genome Shotgun Contigs, and Phytozome databases were searched. Together with previous results, a total of 49 members were found from 18 plant species. A neighbor-joining phylogenetic tree was generated using the MEGA4 program (Saitou and Nei, Mol Biol Evol 4: 406-425, 1987; Tamura et al., Mol Biol Evol 24: 1596-1599, 2007). All newly identified members were found within the two major clades (dicotyledonous and monocotyledonous) of the XB3 family that are phylogenetically distinct from XBAT32 (FIG. 2). This family of proteins have not been observed to be absent in a well-annotated genome. In contrast, family expansion, ranging from one member in Arabidopsis to 3-5 members in tomato, soybean, rice and maize, is obvious in higher plant species (FIG. 2). Thus, XB3 members likely play critical role in plant function, and probably exist in all plant species.

Example 15

Xb3 Levels Influence Leaf Water Retention Under Drought Stress

Figure 11:
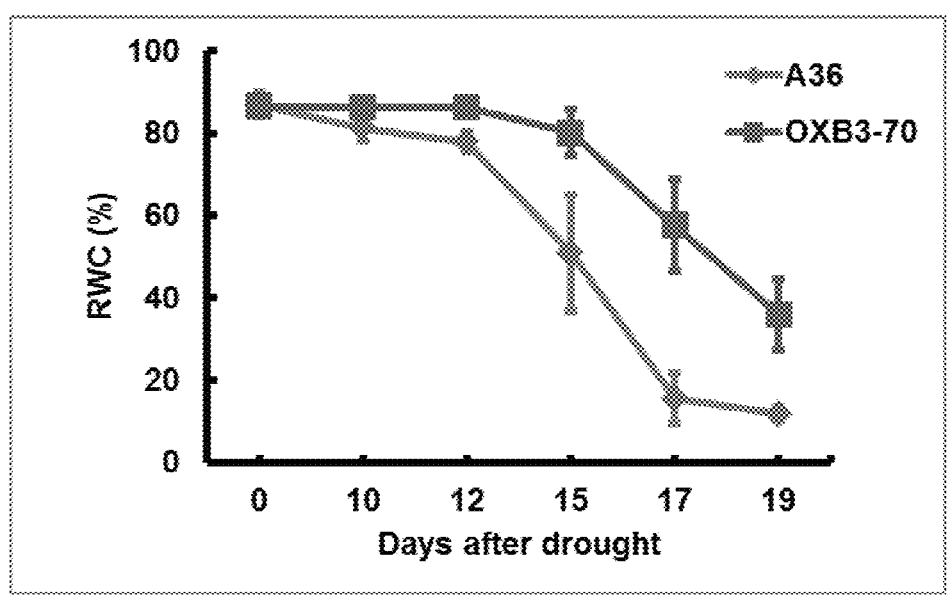
FIG. 11 Changes in relative water content (RWC) of the indicated lines during drought stress. Each data point represents the mean of three independent biological replicates.

Relative water content (RWC) is an indicator of plant leaf water status and has been used to determine physiological consequence of cellular water deficit (O'toole and Cruz, Plant Physiol. 65:428-432, 1980). The RWC of drought stressed leaves was determined using the equation: RWC= (FW−DW)/(TW−DW), where FW is the fresh weight of the leaves. Turgid weight (TW) was measured after floating the leaves on water for 24 hour at room temperature in dark. Dry weight (DW) was determined by weighing the leaves after drying at 65° C. for 3 days, which was adequate to assure complete drying of the biomass. Consistent with the phenotypes described above, the Xb3 over-expression line OXB3-70 was able to maintain markedly higher levels of RWC than A36 during drought treatment conditions (FIG. 11).

Example 16

Over-expression of Xb3 Promotes the Growth of Primary Roots

Root growth, particularly deep rooting, influences plant access to soil water, thereby contributing to tolerance to water deficit (Uga et al., Nat Genet. 45: 1097-1102, 2013). Interestingly, Xb3 over-expression plants showed significantly longer primary roots than the control when grown on half-strength MS media for 7 days (FIG. 12). This result suggests that Xb3 might be involved in primary root development in rice. However, no significant differences in root architecture were observed between Xb3 RNAi lines and the control, which could result from redundancy of root development signaling.

Example 17

Gene Expression Profile of Xb3 Over-expression Plants

To determine molecular mechanisms underlying Xb3-mediated drought response, RNA-seq analysis was performed. Total RNA was isolated from leaf tissues of one-month-old A36 (control) and the Xb3 over-expression line OXB3-70, respectively. More than 45,387,400 short sequence reads were generated from each sample. Among the 391 differentially expressed genes (DEGs, 272 up-regulated and 119 down-regulated in OXB3-70, cutoff: P<0.05, fold change >=2), 106 (72 up-regulated, Table 1; 34 down-regulated, Table 2) have been previously associated with the expression of drought regulators. These data suggest that over-expression of Xb3 in rice leads to an enhanced competent to drought stress.

TABLE 1

| Gene model | Annotation | Fold Change (XB3-70/A36) | p-value # | OXB3-70 (FPKM) | A36 (FPKM) |
|---|---|---|---|---|---|
| LOC_Os04g14690 | flavin-containing monooxygenase | 12.26 | 5.00E−05 | 20.6053 | 1.68112 |
| LOC_Os11g06980 | BURP domain containing protein, expressed | 8.795847446 | 0.00035 | 1.99956 | 0.22733 |

TABLE 1-continued

| Gene model | Annotation | Fold Change (XB3-70/A36) | p-value # | OXB3-70 (FPKM) | A36 (FPKM) |
|---|---|---|---|---|---|
| LOC_Os11g02240 | OsCIPK15 | 6.624943224 | 0.0012 | 1.5169 | 0.228968 |
| LOC_Os09g28340 | expressed protein | 6.18 | 5.00E−05 | 17.8988 | 2.8968 |
| LOC_Os01g52240 | chlorophyll A-B binding protein | 5.11 | 5.00E−05 | 297.676 | 58.227 |
| LOC_Os01g13690 | ligA | 4.57 | 5.00E−05 | 63.1367 | 13.8067 |
| LOC_Os11g19730 | expressed protein | 4.55 | 5.00E−05 | 3.25017 | 0.713541 |
| LOC_Os09g36680 | ribonuclease T2 family domain containing protein | 4.33 | 5.00E−05 | 117.769 | 27.212 |
| LOC_Os03g63330 | aspartokinase, chloroplast precursor | 4.16 | 5.00E−05 | 25.3122 | 6.08803 |
| LOC_Os09g27820 | 1-aminocyclopropane-1-carboxylate oxidase protein | 4.07 | 0.0002 | 3.96049 | 0.973778 |
| LOC_Os02g54920 | expressed protein | 3.759289339 | 0.0432 | 2.09224 | 0.556552 |
| LOC_Os03g60840 | BBTI13 - Bowman-Birk type bran trypsin inhibitor | 3.53 | 0.00015 | 10.479 | 2.96658 |
| LOC_Os09g26810 | chlorophyll A-B binding protein | 3.28 | 5.00E−05 | 101.487 | 30.9831 |
| LOC_Os09g26810 | chlorophyll A-B binding protein, putative, expressed | 3.275559902 | 0.00005 | 101.487 | 30.9831 |
| LOC_Os05g30500 | expressed protein | 3.09 | 0.0005 | 10.7895 | 3.49402 |
| LOC_Os10g25060 | expressed protein | 3.09 | 0.00275 | 3.23559 | 1.04825 |
| LOC_Os01g02080 | peptidyl-prolyl cis-trans isomerase | 3.05 | 0.00015 | 29.4436 | 9.663 |
| LOC_Os01g05080 | thylakoid lumenal protein | 3.04 | 5.00E−05 | 37.5569 | 12.3483 |
| LOC_Os08g40910 | expressed protein | 3.00 | 0.0016 | 7.00314 | 2.33249 |
| LOC_Os10g35810 | thylakoid lumenal protein | 2.97 | 0.0001 | 52.1767 | 17.5691 |
| LOC_Os04g49210 | naringenin, 2-oxoglutarate 3-dioxygenase | 2.96 | 0.0017 | 3.38667 | 1.14332 |
| LOC_Os05g12640 | BURP domain containing protein | 2.93 | 0.00025 | 8.28492 | 2.82536 |
| LOC_Os04g54380 | aluminum resistance protein | 2.84 | 0.00015 | 11.8199 | 4.16285 |
| LOC_Os06g50080 | DUF581 domain containing protein | 2.81 | 0.0052 | 2.89664 | 1.03138 |
| LOC_Os07g30670 | 2Fe—2S iron-sulfur cluster binding domain containing protein | 2.73 | 0.0003 | 201.852 | 73.8469 |
| LOC_Os03g31150 | expressed protein | 2.63 | 0.00055 | 35.2875 | 13.3935 |
| LOC_Os01g27140 | OsGrx_C7 - glutaredoxin subgroup III | 2.62 | 0.00025 | 27.5615 | 10.5166 |
| LOC_Os10g41410 | nucleoside diphosphate kinase | 2.59 | 0.00035 | 26.6869 | 10.2926 |
| LOC_Os02g52150 | heat shock 22 kDa protein | 2.59 | 0.0003 | 21.4531 | 8.29281 |
| LOC_Os01g61320 | thioredoxin | 2.51 | 0.0004 | 47.8919 | 19.0539 |
| LOC_Os05g46950 | expressed protein | 2.507187182 | 0.04315 | 1.46339 | 0.583678 |
| LOC_Os04g51300 | peroxidase precursor, putative | 2.47 | 0.0138 | 72.6325 | 29.3544 |
| LOC_Os10g38940 | fatty acid hydroxylase | 2.45 | 0.00525 | 6.22734 | 2.54148 |
| LOC_Os02g49230 | CCT/B-box zinc finger protein | 2.44 | 0.014 | 2.49824 | 1.02321 |
| LOC_Os09g10760 | RNA recognition motif containing protein | 2.43 | 0.0016 | 230.776 | 94.852 |
| LOC_Os10g30550 | tRNA methyltransferase | 2.39 | 0.00115 | 7.60386 | 3.18597 |
| LOC_Os06g39240 | endothelial differentiation-related factor 1, putative | 2.38 | 0.0407 | 2.47358 | 1.0378 |
| LOC_Os07g38150 | expressed protein | 2.35 | 0.0015 | 47.0388 | 20.0272 |
| LOC_Os11g37200 | transmembrane BAX inhibitor motif-containing protein | 2.33 | 0.01905 | 3.25122 | 1.39439 |
| LOC_Os06g35574 | mki67 protein | 2.33 | 0.0348 | 2.90719 | 1.24956 |
| LOC_Os03g45710 | 2Fe—2S iron-sulfur cluster binding domain containing protein | 2.32 | 0.0018 | 92.9664 | 40.0055 |
| LOC_Os04g46010 | PPR repeat domain containing protein | 2.32 | 0.0021 | 73.9307 | 31.8802 |
| LOC_Os05g27100 | expressed protein | 2.32 | 0.0021 | 148.731 | 64.2446 |

TABLE 1-continued

| Gene model | Annotation | Fold Change (XB3-70/A36) | p-value # | OXB3-70 (FPKM) | A36 (FPKM) |
|---|---|---|---|---|---|
| LOC_Os07g49110 | D-alanine--D-alanine ligase family | 2.31 | 0.0028 | 59.0987 | 25.5571 |
| LOC_Os06g48600 | macrophage migration inhibitory factor | 2.30 | 0.002 | 30.008 | 13.0265 |
| LOC_Os08g12780 | chloroplast envelope membrane protein, putative, expressed | 2.286432283 | 0.00225 | 14.1299 | 6.17989 |
| LOC_Os01g70820 | lumenal PsbP | 2.26 | 0.0461 | 2.94636 | 1.30236 |
| LOC_Os05g49060 | uncharacterized protein ycf23 | 2.24 | 0.0043 | 267.874 | 119.577 |
| LOC_Os03g44430 | ubiquitin carboxyl-terminal hydrolase | 2.22 | 0.0047 | 6.95281 | 3.13301 |
| LOC_Os03g21560 | photosystem II 11 kD protein, putative, expressed | 2.171595798 | 0.00745 | 497.176 | 228.945 |
| LOC_Os01g59090 | thylakoid lumenal 20 kDa protein, putative, expressed | 2.158055431 | 0.0048 | 182.289 | 84.4691 |
| LOC_Os09g38440 | ATXR, putative, expressed | 2.146846635 | 0.02595 | 1.12276 | 0.522981 |
| LOC_Os03g19200 | DNAJ heat shock N-terminal domain-containing protein, putative, expressed | 2.136353383 | 0.0382 | 0.984923 | 0.46103 |
| LOC_Os07g36570 | KI domain interacting kinase 1, putative, expressed | 2.130903177 | 0.0155 | 0.997105 | 0.467926 |
| LOC_Os07g44630 | thymidylate kinase | 2.13 | 0.0264 | 3.75987 | 1.76419 |
| LOC_Os05g44330 | DJ-1 family protein | 2.13 | 0.0036 | 13.1324 | 6.1767 |
| LOC_Os10g36860 | CRS1/YhbY domain | 2.13 | 0.0048 | 51.7424 | 24.3466 |
| LOC_Os01g55240 | gibberellin 2-beta-dioxygenase, putative, expressed | 2.127486796 | 0.0269 | 1.9125 | 0.898948 |
| LOC_Os07g12630 | transcription elongation factor protein | 2.12 | 0.0207 | 3.64885 | 1.7224 |
| LOC_Os07g13770 | UDP-glucoronosyl and UDP-glucosyl transferase domain | 2.11 | 0.02055 | 3.43461 | 1.62394 |
| LOC_Os02g51570 | peptidyl-prolyl cis-trans isomerase, FKBP-type | 2.11 | 0.0057 | 142.102 | 67.2697 |
| LOC_Os12g02200 | OsCIPK14 | 2.10 | 0.00485 | 8.29356 | 3.94924 |
| LOC_Os01g47350 | enoyl-CoA hydratase/isomerase family protein | 2.10 | 0.00465 | 25.1815 | 12.0002 |
| LOC_Os09g25060 | OsWRKY76 | 2.09 | 0.0244 | 2.72624 | 1.30734 |
| LOC_Os05g49220 | GTP-binding protein | 2.08 | 0.0047 | 37.6929 | 18.1331 |
| LOC_Os10g35460 | COBRA, putative, expressed | 2.070929018 | 0.04775 | 1.721 | 0.831028 |
| LOC_Os01g74170 | expressed protein | 2.06 | 0.0452 | 2.0753 | 1.00705 |
| LOC_Os03g16470 | expressed protein | 2.05 | 0.00465 | 77.6172 | 37.8469 |
| LOC_Os05g30700 | expressed protein | 2.052541039 | 0.04295 | 1.71935 | 0.837669 |
| LOC_Os04g32850 | basic proline-rich protein | 2.03 | 0.0115 | 9.05553 | 4.46234 |
| LOC_Os02g09940 | peroxiredoxin, ROS-related gene | 2.01 | 0.00995 | 135.978 | 67.5236 |
| LOC_Os02g14440 | peroxidase precursor, putative | 2.01 | 0.0257 | 4.21179 | 2.09554 |

TABLE 2

| Gene model | Annotation | Fold change (XB3-70/A36) | p-value | OXB3-70 (FPKM) | A36 (FPKM) |
|---|---|---|---|---|---|
| LOC_Os03g02470 | expressed protein | 0.004 | 5.00E−05 | 0.16466 | 45.3005 |
| LOC_Os10g28350 | 1,2-dihydroxy-3-keto-5-methylthiopentene dioxygenase protein | 0.011 | 0.00055 | 0.333126 | 31.7021 |
| LOC_Os07g03040 | expressed protein | 0.026 | 5.00E−05 | 0.166882 | 6.47662 |
| LOC_Os04g17660 | rhodanese-like domain | 0.093 | 5.00E−05 | 1.95248 | 20.9304 |
| LOC_Os10g09290, LOC_Os10g09300 | expressed protein | 0.163 | 5.00E−05 | 2.27822 | 13.9496 |

TABLE 2-continued

| Gene model | Annotation | Fold change (XB3-70/A36) | p-value | OXB3-70 (FPKM) | A36 (FPKM) |
|---|---|---|---|---|---|
| LOC_Os10g09990 | Cytokinin-O-glucosyltransferase 3 | 0.181 | 5.00E−05 | 5.45609 | 30.1608 |
| LOC_Os07g06834 | expressed protein | 0.213 | 5.00E−05 | 1.99993 | 9.39006 |
| LOC_Os04g30490 | MATE efflux | 0.239 | 0.0001 | 0.659933 | 2.76109 |
| LOC_Os07g48450 | NAC domain transcription factor, OsNAC103 | 0.246 | 0.0005 | 0.686722 | 2.7901 |
| LOC_Os04g47360 | OsPOP9 - Putative Prolyl Oligopeptidase homologue | 0.260 | 5.00E−05 | 96.5152 | 371.078 |
| LOC_Os09g04050 | dehydrogenase | 0.261 | 0.0019 | 0.600271 | 2.29938 |
| LOC_Os08g26230 | expressed protein | 0.268 | 0.00095 | 1.31515 | 4.9066 |
| LOC_Os07g05840, LOC_Os07g05850 | expressed protein | 0.287 | 0.00015 | 1.55485 | 5.40942 |
| LOC_Os03g01300 | LTPL114 - Protease inhibitor/seed storage/LTP family protein precursor | 0.289 | 0.00545 | 1.15929 | 4.00774 |
| LOC_Os01g07170 | HORMA domain containing protein | 0.368 | 0.0002 | 4.32225 | 11.7436 |
| LOC_Os06g38450 | vignain precursor | 0.397 | 0.0036 | 1.9338 | 4.87346 |
| LOC_Os03g14910 | expressed protein | 0.417 | 0.0009 | 11.2836 | 27.0414 |
| LOC_Os02g12890 | cytochrome P450, CYP711A1, OsMAX1e | 0.418 | 0.00085 | 11.2386 | 26.8764 |
| LOC_Os04g32920 | potassium transporter HAK1 | 0.423 | 0.00075 | 7.38541 | 17.4677 |
| LOC_Os08g39830 | Ethylene-insensitive 3 | 0.428 | 0.00135 | 3.31944 | 7.75403 |
| LOC_Os06g21570 | Os6bglu24 - beta-glucosidase homologue | 0.430 | 0.01635 | 1.14786 | 2.67093 |
| LOC_Os08g06170 | berberine and berberine like domain | 0.454 | 0.0059 | 3.01175 | 6.63279 |
| LOC_Os08g01940 | non-lysosomal glucosylceramidase | 0.460 | 0.0024 | 5.80537 | 12.6105 |
| LOC_Os03g56930 | app1, putative | 0.461 | 0.03395 | 0.949825 | 2.06046 |
| LOC_Os03g54130 | cysteine protease 1 | 0.476 | 0.0061 | 47.3195 | 99.3175 |
| LOC_Os09g26780 | zinc-finger protein | 0.483 | 0.0145 | 3.2161 | 6.65286 |
| LOC_Os03g08980 | expressed protein | 0.489 | 0.03285 | 3.18124 | 6.5019 |
| LOC_Os05g33900 | auxin-induced protein 5NG4 | 0.501 | 0.0089 | 21.8254 | 43.6045 |
| LOC_Os10g40360 | proline oxidase | 0.501 | 0.00855 | 15.0746 | 30.1002 |
| LOC_Os02g31860 | expressed protein | 0.228749792 | 0.0002 | 0.453087 | 1.98071 |
| LOC_Os09g10340 | cytochrome P450, putative, expressed | 0.342706768 | 0.02125 | 0.284095 | 0.828974 |
| LOC_Os10g17960 | DUF26 kinases | 0.379443649 | 0.0376 | 0.251666 | 0.66325 |
| LOC_Os09g29540 | OsWAK82 - OsWAK receptor-like cytoplasmic kinase OsWAK-RLCK, expressed | 0.411382931 | 0.0223 | 0.421577 | 1.02478 |
| LOC_Os01g36070 | nodulin MtN3 family protein, putative, expressed | 0.415362838 | 0.0302 | 0.711583 | 1.71316 |

Example 17

Figure 13:
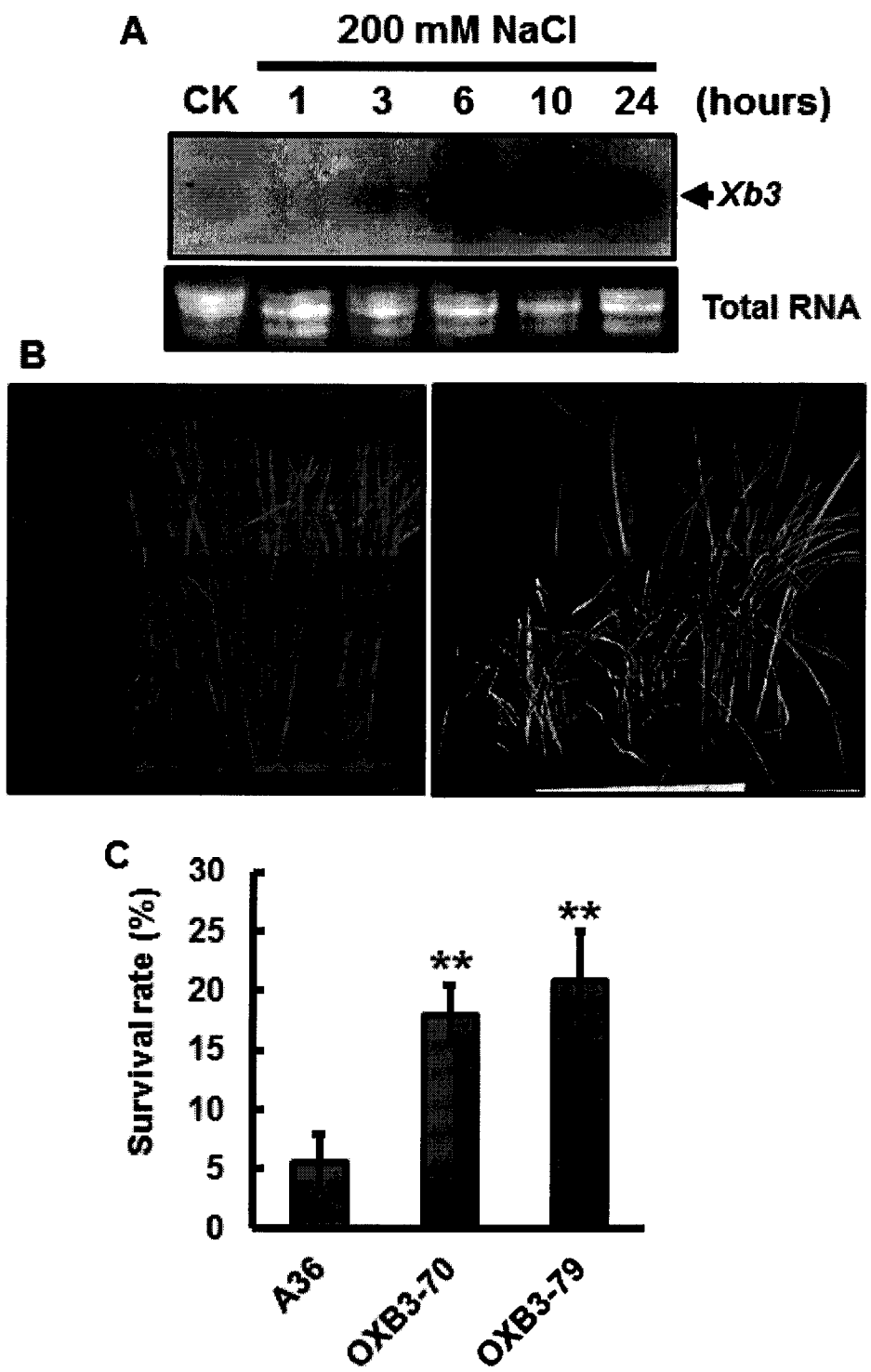
FIG. 13 Over-expression of Xb3 confers tolerance to salt stress. (Panel A) RNA gel blot analysis showing induction of Xb3 after salt treatment. (Panel B) Seedlings are grown in liquid medium for two weeks under normal conditions (left), and then treated with 100 mM NaCl for 10 days followed by 4 days of recovery in water (right). (Panel C) Survival rate of treated plants (3×24 each line). (Panel D) Seeds germinated on half MS medium supplemented with 150 mM NaCl. (Panel E) Shoot length of seedlings in D (n=10 each line).
Figure 13:
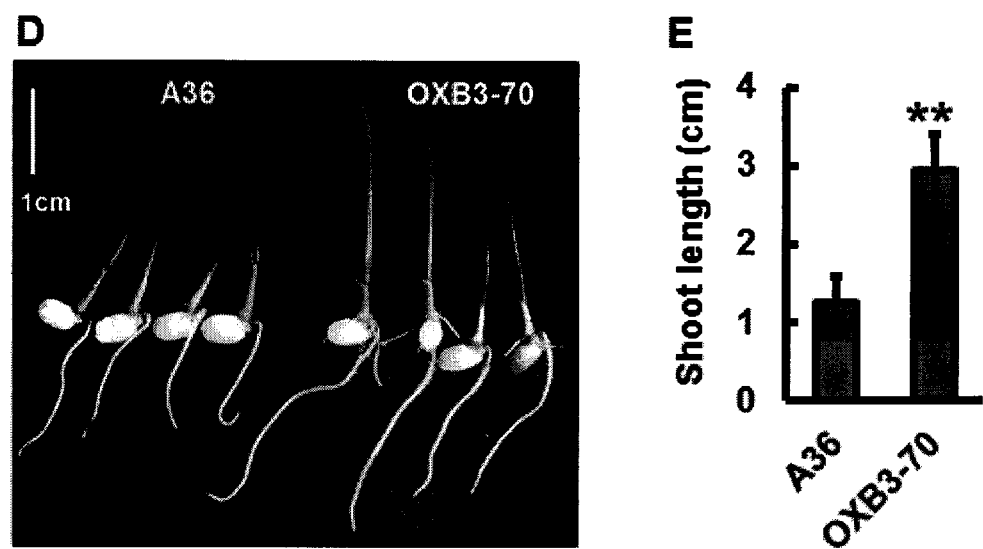

Xb3 is Salt-stress-responsive and Confers Tolerance to Salt Stress when Over-expressed Plants utilize closely-related mechanisms to cope with drought and salt stresses (Zhu et al., *Annu Rev Plant Biol.* 53:247-273, 2002). It was therefore determined whether Xb3 transcripts are also salt-stress-responsive in rice. Northern blot analysis indicated that Xb3 was indeed induced by the treatment of 200 mM NaCl (FIG. 13A).

Xb3 was then tested for the ability to confer salt tolerance. Two-week-old seedlings were stressed with 100 mM NaCl for 10 days followed by 4 days of recovery in half-strength MS medium. As shown in FIG. 13B and FIG. 13C, OXB3-70 and OXB3-79 displayed significantly higher levels of survival rates relative to the empty vector control A36. Moreover, Xb3 over-expression seedlings also showed increased growth in the salt solution than the control. Thus, Xb3 acts as a regulator in response to salinity stress.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method of increasing drought tolerance in a plant, comprising: (a) expressing in one or more plants a heterologous nucleic acid encoding an XA21 binding protein 3 (Xb3) polypeptide having a mutation of a glycine residue at position 2 of the amino acid sequence of the polypeptide; (b) subjecting the one or more plants to drought treatment; and (c) selecting a plant having increased drought tolerance when compared to a plant that lacks the heterologous nucleic acid.

2. The method of claim 1, wherein the plant having increased drought tolerance is a monocotyledonous plant.

3. The method of claim 2, wherein the monocotyledonous plant is selected from the group consisting of maize, wheat, rice, sorghum (*Sorghum bicolor*), oats, barley, sugar cane, African oil palm (*Elaeis guineensis*), or switchgrass.

4. The method of claim 1, wherein the plant having increased drought tolerance is a dicotyledonous plant.

5. The method of claim 4, wherein the dicotyledonous plant is selected from the group consisting of *Arabidopsis*, peanut (*Arachis hypogaea*), barrel medic (*Medicago truncatula*), carrot, soybean (*Glycine max*), cotton, *Brassica*, canola, tomato, potato, alfalfa, grape, clover, poplar, willow, *eucalyptus*, hemp, a *Lotus* sp., a *Vinca* sp., a *Nicotiana* sp., a *Vitis* sp., or a *Ricinus* sp.

6. The method of claim 1, wherein the heterologous nucleic acid comprises: (a) a polynucleotide sequence with at least 85% identity to SEQ ID NO: 4 wherein the polynucleotide encodes a mutation of a glycine residue at position 2 of the encoded polypeptide or (b) a polynucleotide sequence encoding a polypeptide with at least 85% identity to SEQ ID NO: 5 wherein the polypeptide has a mutation of a glycine residue at position 2.

7. The method of claim 6, wherein expressing in one or more plants comprises transforming the one or more plants with said heterologous nucleic acid.

8. The method of claim 1, wherein the heterologous nucleic acid is selected from the group consisting of:
   (a) a polynucleotide sequence comprising a nucleic acid sequence of: SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68, SEQ ID NO: 70, SEQ ID NO: 72, SEQ ID NO: 74, SEQ ID NO: 76, SEQ ID NO: 78, SEQ ID NO: 80, SEQ ID NO: 82, SEQ ID NO: 84, SEQ ID NO: 86, SEQ ID NO: 88, SEQ ID NO: 90, SEQ ID NO: 92, SEQ ID NO: 94, SEQ ID NO: 96, SEQ ID NO: 98, SEQ ID NO: 100, or SEQ ID NO: 102, wherein the polynucleotide encodes a mutation of a glycine residue at position 2 of the encoded polypeptide amino acid sequence; and
   (b) a polynucleotide sequence encoding a polypeptide comprising an amino acid sequence of SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO 93, SEQ ID NO: 95, SEQ ID NO: 97, SEQ ID NO: 99 SEQ ID NO: 101 or SEQ ID NO: 103, wherein the polypeptide has a mutation of a glycine residue at position 2.

9. A method of increasing salt tolerance in a plant, comprising: (a) expressing in one or more plants a heterologous nucleic acid encoding an XA21 binding protein 3 (Xb3) polypeptide having a mutation of a glycine residue at position 2 of the amino acid sequence of the polypeptide; (b) subjecting the one or more plants to salt stress; and (c) selecting a plant having increased salt tolerance when compared to a plant that lacks the heterologous nucleic acid.

10. A method of increasing drought and salt tolerance in a plant, comprising: (a) expressing in one or more plants a heterologous nucleic acid encoding an XA21 binding protein 3 (Xb3) polypeptide having a mutation of a glycine residue at position 2 of the amino acid sequence of the polypeptide; (b) subjecting the one or more plants to drought treatment and salt stress; and (c) selecting a plant having increasing drought and salt tolerance when compared to a plant that lacks the heterologous nucleic acid.

11. The method of claim 1, wherein the heterologous nucleic acid is operably linked a heterologous promoter.

12. The method of claim 11, wherein the promoter is a constitutive promoter or an inducible promoter.

13. The method of claim 12, wherein the constitutive promoter is selected from the group consisting of: cauliflower mosaic virus (CaMV) 35S promoter and maize ubiquitin promoter.

14. The method of claim 12, wherein the inducible promoter is selected from the group consisting of: osmotic stress-induced promoter and turgor-inducible promoter.

15. The method of claim 1, wherein the Xb3 polypeptide has an amino acid sequence having at least 85% identity to SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99 or SEQ ID NO: 101, wherein the polypeptide has a mutation of a glycine residue at position 2.

16. The method of claim 1, wherein the Xb3 polypeptide comprises the amino acid sequence of SEQ ID NO:7.

17. The method of claim 1, wherein the mutation is a glycine to alanine mutation.

18. The method of claim 1, wherein the heterologous nucleic acid comprises: a polynucleotide sequence of SEQ ID NO: 6.

* * * * *

SEQUENCE LISTING

<160> NUMBER OF SEQ ID NOS: 103

<210> SEQ ID NO 1
<211> LENGTH: 40
<212> TYPE: DNA
<213> ORGANISM: Artificial sequence
<220> FEATURE:
<223> OTHER INFORMATION: Primer

<400> SEQUENCE: 1
gttctagagg atccatggct cacggtgtca gctgcgcccg          40

<210> SEQ ID NO 2
<211> LENGTH: 42
<212> TYPE: DNA
<213> ORGANISM: Artificial sequence
<220> FEATURE:
<223> OTHER INFORMATION: Primer

<400> SEQUENCE: 2
tttctagaaa tcaactagtt agatcgtgct caggcttgtc ca       42

<210> SEQ ID NO 3
<211> LENGTH: 42
<212> TYPE: DNA
<213> ORGANISM: Artificial sequence
<220> FEATURE:
<223> OTHER INFORMATION: Primer

<400> SEQUENCE: 3
gttctagagg atccatgggt cacgctgtca gctgcgcccg ca       42

<210> SEQ ID NO 4
<211> LENGTH: 1353
<212> TYPE: DNA
<213> ORGANISM: Oryza sativa

<400> SEQUENCE: 4
atgggtcacg gtgtcagctg cgcccgcacc ggcgacgagc acgacttctt ccgggcggcg    60
cagctcggcg acctcgacgc cctggccgcc ctcctcgccg ccgaccctt cctcgctcgc   120 cgcgccaccc tctacgaccg cctctccgtc ctccacatcg ccgccgccaa tggccgcatc   180
gaggtgctct ccatgttctt ggatcgcggg gcgccgccgg acgcggtgaa tcggcacaag   240
cagacgccgc tgatgctcgc ggccatgcac ggcaagatcg actgcgtgct caagctcctc   300
caggccgacg caaatatctt gatgttcgac tcggtgcacg cgaggacctg cctccaccac   360
gcggcgtact acggccacgt cgactgcctg caggccatcc tcgccgccgc gcagaccacg   420
ccggtggccg actcatgggg tttcgcccgg ttcgtcaacg tcagggacga ccacggcgcc   480
actccgctgc atctcgcggc caggcagggg cggccggggt gcgtgcaggt gttgctggag   540
aacggcgcca ttgtgtcggc tttgacagga tcatatggct tccctggaag cacgtcgctt   600
catttggctg ctcgtagcgg gaacttggat tgcatcagga agctgcttgc ctggggagct   660
gatcggctcc aaagggattc ggctgggaga attccctatt ctgttgcgct gaaacggaac   720
catggagcat gtgcagcttt gctgaaccct acatcagcag agcccatggt gtggccatcc   780
ccacttaagt tcatcagtga gcttgaacca gaagctaagg ctctcctgga agcagctctg   840
atggaagcca acagggagag ggagaagaaa atcctgaatg cacaaagta ctccctgcca   900 tcccccttcgc ccggtgatga cagtgccgat gacgatgcat gctcagaggt gagcgacacg   960
gagctttgct gcatctgctt cgaccaggct tgcaccattg aggtgcaaga ctgtggacat  1020

-continued

```
caaatgtgtg caccgtgcac gctggcactg tgctgtcaca acaaacccaa tccgacgacc    1080
ctgacaccgc cctcaccggc ctgcccattc tgccggggca gcatctcacg ctggtggtg     1140 gcccaaacaa ggtctgcttg tgatcctgac aagccgtcat ccctgcagct cacccggaag    1200
cggtcgcgtc gatctcacaa cctcagtgag ggcagcagca gcttcaaagg ctaccttcg     1260 gccatgggct ccttctcaaa gcttggccgt ggctcgagcc gcatggcgga cagtgacagc    1320
agcaacctgg acaagcctga gcacgatcta tga                                 1353
```

<210> SEQ ID NO 5
<211> LENGTH: 450
<212> TYPE: PRT
<213> ORGANISM: Oryza sativa

<400> SEQUENCE: 5

```
Met Gly His Gly Val Ser Cys Ala Arg Thr Gly Asp Glu His Asp Phe
1               5                   10                  15

Phe Arg Ala Ala Gln Leu Gly Asp Leu Asp Ala Leu Ala Ala Leu Leu
            20                  25                  30

Ala Ala Asp Pro Ser Leu Ala Arg Arg Ala Thr Leu Tyr Asp Arg Leu
        35                  40                  45

Ser Val Leu His Ile Ala Ala Ala Asn Gly Arg Ile Glu Val Leu Ser
    50                  55                  60

Met Phe Leu Asp Arg Gly Ala Pro Pro Asp Ala Val Asn Arg His Lys
65                  70                  75                  80

Gln Thr Pro Leu Met Leu Ala Ala Met His Gly Lys Ile Asp Cys Val
                85                  90                  95

Leu Lys Leu Leu Gln Ala Asp Ala Asn Ile Leu Met Phe Asp Ser Val
            100                 105                 110

His Ala Arg Thr Cys Leu His His Ala Ala Tyr Tyr Gly His Val Asp
        115                 120                 125

Cys Leu Gln Ala Ile Leu Ala Ala Gln Thr Thr Pro Val Ala Asp
    130                 135                 140

Ser Trp Gly Phe Ala Arg Phe Val Asn Val Arg Asp Asp His Gly Ala
145                 150                 155                 160

Thr Pro Leu His Leu Ala Ala Arg Gln Gly Arg Pro Gly Cys Val Gln
                165                 170                 175

Val Leu Leu Glu Asn Gly Ala Ile Val Ser Ala Leu Thr Gly Ser Tyr
            180                 185                 190

Gly Phe Pro Gly Ser Thr Ser Leu His Leu Ala Ala Arg Ser Gly Asn
        195                 200                 205

Leu Asp Cys Ile Arg Lys Leu Leu Ala Trp Gly Ala Asp Arg Leu Gln
    210                 215                 220

Arg Asp Ser Ala Gly Arg Ile Pro Tyr Ser Val Ala Leu Lys Arg Asn
225                 230                 235                 240

His Gly Ala Cys Ala Ala Leu Leu Asn Pro Thr Ser Ala Glu Pro Met
                245                 250                 255

Val Trp Pro Ser Pro Leu Lys Phe Ile Ser Glu Leu Glu Pro Glu Ala
            260                 265                 270

Lys Ala Leu Leu Glu Ala Ala Leu Met Glu Ala Asn Arg Glu Arg Glu
        275                 280                 285

Lys Lys Ile Leu Asn Gly Thr Lys Tyr Ser Leu Pro Ser Pro Ser Pro
    290                 295                 300

Gly Asp Asp Ser Ala Asp Asp Ala Cys Ser Glu Val Ser Asp Thr
```

```
            305                 310                 315                 320
    Glu Leu Cys Cys Ile Cys Phe Asp Gln Ala Cys Thr Ile Glu Val Gln
                        325                 330                 335

Asp Cys Gly His Gln Met Cys Ala Pro Cys Thr Leu Ala Leu Cys Cys
                    340                 345                 350

His Asn Lys Pro Asn Pro Thr Thr Leu Thr Pro Ser Pro Ala Cys
                355                 360                 365

Pro Phe Cys Arg Gly Ser Ile Ser Arg Leu Val Val Ala Gln Thr Arg
            370                 375                 380

Ser Ala Cys Asp Pro Asp Lys Pro Ser Ser Leu Gln Leu Thr Arg Lys
    385                 390                 395                 400

Arg Ser Arg Arg Ser His Asn Leu Ser Glu Gly Ser Ser Phe Lys
                        405                 410                 415

Gly Leu Pro Ser Ala Met Gly Ser Phe Ser Lys Leu Gly Arg Gly Ser
                    420                 425                 430

Ser Arg Met Ala Asp Ser Asp Ser Ser Asn Leu Asp Lys Pro Glu His
                435                 440                 445

Asp Leu
        450
```

<210> SEQ ID NO 6
<211> LENGTH: 1353
<212> TYPE: DNA
<213> ORGANISM: Oryza sativa

<400> SEQUENCE: 6

```
atggctcacg gtgtcagctg cgcccgcacc ggcgacgagc acgacttctt ccgggcggcg    60
cagctcggcg acctcgacgc cctggccgcc ctcctcgccg ccgacccttc cctcgctcgc   120
cgcgccaccc tctacgaccg cctctccgtc ctccacatcg ccgccgccaa tggccgcatc   180
gaggtgctct ccatgttctt ggatcgcggg gcgccgccgg acgcggtgaa tcggcacaag   240
cagacgccgc tgatgctcgc ggccatgcac ggcaagatcg actgcgtgct caagctcctc   300
caggccgacg caaatatctt gatgttcgac tcggtgcacg cgaggacctg cctccaccac   360
gcggcgtact acgccacgt cgactgcctg caggccatcc tcgccgccgc gcagaccacg   420
ccggtggccg actcatgggg tttcgcccgg ttcgtcaacg tcagggacga ccacggcgcc   480
actccgctgc atctcgcggc caggcagggg cggccggggt gcgtgcaggt gttgctggag   540
aacggcgcca ttgtgtcggc tttgacagga tcatatggct tccctggaag cacgtcgctt   600
catttggctg ctcgtagcgg gaacttggat tgcatcagga agctgcttgc ctggggagct   660
gatcggctcc aaagggattc ggctgggaga attccctatt ctgttgcgct gaaacggaac   720
catggagcat gtgcagcttt gctgaaccct acatcagcag agcccatggt gtggccatcc   780
ccacttaagt tcatcagtga gcttgaacca aagctaagg ctctcctgga agcagctctg   840
atggaagcca cagggagag ggagaagaaa atcctgaatg cacaaagta ctccctgcca   900
tcccttcgc ccggtgatga cagtgccgat gacgatgcat gctcagaggt gagcgacacg   960
gagctttgct gcatctgctt cgaccaggct tgcaccattg aggtgcaaga ctgtggacat  1020
caaatgtgtg caccgtgcac gctggcactg tgctgtcaca caaacccaa tccgacgacc  1080
ctgacaccgc cctcaccggc tgcccattc tgccggggca gcatctcacg gctggtggtg  1140
gcccaaacaa ggtctgcttg tgatcctgac aagccgtcat ccctgcagct cacccggaag  1200
cggtcgcgtc gatctcacaa cctcagtgag ggcagcagca gcttcaaagg gctacccttg  1260
```

```
gccatgggct ccttctcaaa gcttggccgt ggctcgagcc gcatggcgga cagtgacagc    1320
agcaacctgg acaagcctga gcacgatcta tga                                 1353
```

<210> SEQ ID NO 7
<211> LENGTH: 450
<212> TYPE: PRT
<213> ORGANISM: Oryza sativa

<400> SEQUENCE: 7

```
Met Ala His Gly Val Ser Cys Ala Arg Thr Gly Asp Glu His Asp Phe
1               5                   10                  15

Phe Arg Ala Ala Gln Leu Gly Asp Leu Asp Ala Leu Ala Ala Leu Leu
            20                  25                  30

Ala Ala Asp Pro Ser Leu Ala Arg Arg Ala Thr Leu Tyr Asp Arg Leu
        35                  40                  45

Ser Val Leu His Ile Ala Ala Asn Gly Arg Ile Glu Val Leu Ser
    50                  55                  60

Met Phe Leu Asp Arg Gly Ala Pro Pro Asp Ala Val Asn Arg His Lys
65                  70                  75                  80

Gln Thr Pro Leu Met Leu Ala Ala Met His Gly Lys Ile Asp Cys Val
                85                  90                  95

Leu Lys Leu Leu Gln Ala Asp Ala Asn Ile Leu Met Phe Asp Ser Val
            100                 105                 110

His Ala Arg Thr Cys Leu His His Ala Ala Tyr Tyr Gly His Val Asp
        115                 120                 125

Cys Leu Gln Ala Ile Leu Ala Ala Gln Thr Thr Pro Val Ala Asp
    130                 135                 140

Ser Trp Gly Phe Ala Arg Phe Val Asn Val Arg Asp Asp His Gly Ala
145                 150                 155                 160

Thr Pro Leu His Leu Ala Ala Arg Gln Gly Arg Pro Gly Cys Val Gln
                165                 170                 175

Val Leu Leu Glu Asn Gly Ala Ile Val Ser Ala Leu Thr Gly Ser Tyr
            180                 185                 190

Gly Phe Pro Gly Ser Thr Ser Leu His Leu Ala Ala Arg Ser Gly Asn
        195                 200                 205

Leu Asp Cys Ile Arg Lys Leu Leu Ala Trp Gly Ala Asp Arg Leu Gln
    210                 215                 220

Arg Asp Ser Ala Gly Arg Ile Pro Tyr Ser Val Ala Leu Lys Arg Asn
225                 230                 235                 240

His Gly Ala Cys Ala Ala Leu Leu Asn Pro Thr Ser Ala Glu Pro Met
                245                 250                 255

Val Trp Pro Ser Pro Leu Lys Phe Ile Ser Glu Leu Glu Pro Glu Ala
            260                 265                 270

Lys Ala Leu Leu Glu Ala Ala Leu Met Glu Ala Asn Arg Glu Arg Glu
        275                 280                 285

Lys Lys Ile Leu Asn Gly Thr Lys Tyr Ser Leu Pro Ser Pro Ser Pro
    290                 295                 300

Gly Asp Asp Ser Ala Asp Asp Ala Cys Ser Glu Val Ser Asp Thr
305                 310                 315                 320

Glu Leu Cys Cys Ile Cys Phe Asp Gln Ala Cys Thr Ile Glu Val Gln
                325                 330                 335

Asp Cys Gly His Gln Met Cys Ala Pro Cys Thr Leu Ala Leu Cys Cys
            340                 345                 350

His Asn Lys Pro Asn Pro Thr Thr Leu Thr Pro Pro Ser Pro Ala Cys
```

```
                355                 360                 365
Pro Phe Cys Arg Gly Ser Ile Ser Arg Leu Val Val Ala Gln Thr Arg
    370                 375                 380

Ser Ala Cys Asp Pro Asp Lys Pro Ser Ser Leu Gln Leu Thr Arg Lys
385                 390                 395                 400

Arg Ser Arg Arg Ser His Asn Leu Ser Glu Gly Ser Ser Ser Phe Lys
                405                 410                 415

Gly Leu Pro Ser Ala Met Gly Ser Phe Ser Lys Leu Gly Arg Gly Ser
            420                 425                 430

Ser Arg Met Ala Asp Ser Asp Ser Ser Asn Leu Asp Lys Pro Glu His
            435                 440                 445

Asp Leu
    450

<210> SEQ ID NO 8
<211> LENGTH: 1341
<212> TYPE: DNA
<213> ORGANISM: Manihot esculenta

<400> SEQUENCE: 8
atgggacagg gactcagctg tgcagctact caagaacatg ggctcttcag tgccgtgcag      60
tctggtgact tggacactgt aaaggctatg ctcgagagag acccatctct cacgcaccaa     120
actacttctt atgatcgcca atctgcactc catattgctg ctgccaatgg ccggatcgag     180
attttgtcta tgcttttgga gcgatctgtg gatccagatg ttgtaaatcg tcacaaacag     240
actccgctta tgctggctgc aatgcatggc aaaatcggct gtttgaagaa gctaatcgaa     300
gcaggagcaa atattttgaa gtttgattca cttaatggaa gaacttgctt gcactatgct     360
gcttactatg ccattctga ttgccttcaa gctgtactct ctgctgctca atctagccct     420
gttgctgtct cttggggata tgcacggttc gtcaatatta gggatggcag aggagctgca     480
ccattgcatt tggcagctcg tcaaagacga cccgaatgtg tacgtatttt gttagacaat     540
ggagctcttg tctgtgcttc aacaggcgga tttggttgcc cggggagcac tcctcttcat     600
ttggcagcca gaggcggatc tattgattgc attcgcgaat tgctggcgtg gggtgcggat     660
cgccttcaaa gagattcatc tgggagaata ccctatttgg tcgccttgaa gcataagcat     720
ggagcttgtg cagccctact caatccttct tcagctgagc tcttgtctg ccatcacct      780 ttaaagttca tcagtgagct taatcaggag ctaaaactc ttcttgaaca tgctttaatg     840
gaggcaaaca gggagaggga gaagaacatc ttgaagggaa cttcttattc ccttccgtcc     900
ccatcacatt ctgatattgg ggcagacgac aatatatctg aggcgagcga tgcggagctg     960
tgctgcatat gttttgagca gtttgcaca attgaagtac aagactgtgg tcaccaaatg    1020
tgtgcacaat gcacactagc cctatgttgc cataataagc caaacccaac aaccgcatgc    1080
ctaaaccctc cagtttgccc gttctgccga agcaccattg tccgcctagt ggttgctaaa    1140
gtcaaggatt gtgatgatgc tgatcaagac attggcgata tcggttcacc aaagatgaga    1200
aaggcaagga agtcacgaaa cttcagcagc gagggaagca gcagcttcaa ggggttatca    1260
gcaatgagtc cattcggaaa aatgggtggc cggggttcag gaagaatcgc cgcagacaat    1320
gaatggatcg ataagcctta a                                              1341

<210> SEQ ID NO 9
<211> LENGTH: 446
<212> TYPE: PRT
<213> ORGANISM: Manihot esculenta
```

```
<400> SEQUENCE: 9

Met Gly Gln Gly Leu Ser Cys Ala Ala Thr Gln Glu His Gly Leu Phe
1               5                   10                  15

Ser Ala Val Gln Ser Gly Asp Leu Asp Thr Val Lys Ala Met Leu Glu
            20                  25                  30

Arg Asp Pro Ser Leu Thr His Gln Thr Thr Ser Tyr Asp Arg Gln Ser
        35                  40                  45

Ala Leu His Ile Ala Ala Asn Gly Arg Ile Glu Ile Leu Ser Met
    50                  55                  60

Leu Leu Glu Arg Ser Val Asp Pro Asp Val Val Asn Arg His Lys Gln
65              70                  75                  80

Thr Pro Leu Met Leu Ala Ala Met His Gly Lys Ile Gly Cys Leu Lys
                85                  90                  95

Lys Leu Ile Glu Ala Gly Ala Asn Ile Leu Lys Phe Asp Ser Leu Asn
                100                 105                 110

Gly Arg Thr Cys Leu His Tyr Ala Ala Tyr Tyr Gly His Ser Asp Cys
            115                 120                 125

Leu Gln Ala Val Leu Ser Ala Ala Gln Ser Ser Pro Val Ala Val Ser
130                 135                 140

Trp Gly Tyr Ala Arg Phe Val Asn Ile Arg Asp Gly Arg Gly Ala Ala
145                 150                 155                 160

Pro Leu His Leu Ala Ala Arg Gln Arg Arg Pro Glu Cys Val Arg Ile
                165                 170                 175

Leu Leu Asp Asn Gly Ala Leu Val Cys Ala Ser Thr Gly Gly Phe Gly
            180                 185                 190

Cys Pro Gly Ser Thr Pro Leu His Leu Ala Ala Arg Gly Gly Ser Ile
        195                 200                 205

Asp Cys Ile Arg Glu Leu Leu Ala Trp Gly Ala Asp Arg Leu Gln Arg
210                 215                 220

Asp Ser Ser Gly Arg Ile Pro Tyr Leu Val Ala Leu Lys His Lys His
225                 230                 235                 240

Gly Ala Cys Ala Ala Leu Leu Asn Pro Ser Ser Ala Glu Pro Leu Val
                245                 250                 255

Trp Pro Ser Pro Leu Lys Phe Ile Ser Glu Leu Asn Gln Glu Ala Lys
            260                 265                 270

Thr Leu Leu Glu His Ala Leu Met Glu Ala Asn Arg Glu Arg Glu Lys
        275                 280                 285

Asn Ile Leu Lys Gly Thr Ser Tyr Ser Leu Pro Ser Pro Ser His Ser
290                 295                 300

Asp Ile Gly Ala Asp Asn Ile Ser Glu Ala Ser Asp Ala Glu Leu
305                 310                 315                 320

Cys Cys Ile Cys Phe Glu Gln Val Cys Thr Ile Glu Val Gln Asp Cys
                325                 330                 335

Gly His Gln Met Cys Ala Gln Cys Thr Leu Ala Leu Cys Cys His Asn
            340                 345                 350

Lys Pro Asn Pro Thr Thr Ala Cys Leu Asn Pro Val Cys Pro Phe
                355                 360                 365

Cys Arg Ser Thr Ile Val Arg Leu Val Val Ala Lys Val Lys Asp Cys
        370                 375                 380

Asp Asp Ala Asp Gln Asp Ile Gly Asp Ile Gly Ser Pro Lys Met Arg
385                 390                 395                 400

Lys Ala Arg Lys Ser Arg Asn Phe Ser Ser Glu Gly Ser Ser Ser Phe
```

```
                    405                 410                 415
Lys Gly Leu Ser Ala Met Ser Pro Phe Gly Lys Met Gly Gly Arg Gly
            420                 425                 430

Ser Gly Arg Ile Ala Ala Asp Asn Glu Trp Ile Asp Lys Pro
            435                 440                 445
```

<210> SEQ ID NO 10
<211> LENGTH: 1341
<212> TYPE: DNA
<213> ORGANISM: Manihot esculenta

<400> SEQUENCE: 10

```
atgggtcagg gactcagttg tgcagcaact caagaacatg ggttcttcag tgcagtccag      60
tctggtgatt tggacgctgt aaaaactatg ctcgagagag acccatctct tattcaccaa     120
accactgctt atgatcgcca atctgcactc catattgctg ctgctaatgg ccggatcgag     180
attttatcta tgattttgga gcgatctgtg gatccagatg ttgtgaatcg tcacaaacag     240
actccgctta tgctggctgc aatgcatggc aagattgctt gtttgataaa gctaatcgaa     300
gcaggagcaa atatttaaa gtttgattca cttcatgaaa gaacttgctt gcactatgct     360
gcttactacg gccattctga ttgccttcaa gctgttctct ctgctgctca atctagccat     420
gttgctgtgt cttggggata tgcacggttt gtgaatatta gagatggtag gggagctgcg     480
ccattgcatt tagcagcccg tcaaagacgg ccgcaatgtg tacgcatctt gttagacaat     540
ggagctcttg tctgtgcttc aaccggcgga tatggttgcc agggagcac tcctcttcat     600
ctggcagcca ggggaggatc tcttgattgc atccgcgaat gctggcatg gggtgctgat     660
cgtattcaaa gagatgcgtc cgggagaata ccttatctag ttgccctgaa gcataagcat     720
ggagcttgtg cagccctact aaatccttct gcaaccgagc tcttgtctg gccatcacct     780
ttaaagttca ttagtgagct taatcaggag gctaaagctc tgctagaacg cgccttaatg     840
gacgcaaaca aggagaggga gaagaacatc ttgaagggaa ctgcttattc acttccatct     900
ccatcacatt ccgattctgg ggcagatgac aatatatctg aggcgagcga tacagaggtc     960
tgctgcatat gtttcgagca gtttgcaca attgaagtgc aagactgtgg tcaccagatg    1020
tgtgcacaat gcacactagc actatgctgc cacaacaaac caaacccaac aaccgcatgc    1080
ttaaaccctc cagtttgccc gttttgtcga agctccattg tccgcctagt ggttgctaaa    1140
gtcaaggaca gtgaggatgc ggatctggac attggagaca ttggttcgcc aaagatgaga    1200
aaggcaagga agtcacgaaa cttcagtagc gaggaaagta gcagcttcaa gggcttgtca    1260
gggatgagtc cgtttggaaa aatgggcggc cgaggctcag gaagaatcgc tgcagaaaac    1320
gaacgggtcg ataaaccttg a                                              1341
```

<210> SEQ ID NO 11
<211> LENGTH: 446
<212> TYPE: PRT
<213> ORGANISM: Manihot esculenta

<400> SEQUENCE: 11

```
Met Gly Gln Gly Leu Ser Cys Ala Ala Thr Gln Glu His Gly Phe Phe
1               5                   10                  15

Ser Ala Val Gln Ser Gly Asp Leu Asp Ala Val Lys Thr Met Leu Glu
            20                  25                  30

Arg Asp Pro Ser Leu Ile His Gln Thr Thr Ala Tyr Asp Arg Gln Ser
            35                  40                  45
```

```
Ala Leu His Ile Ala Ala Ala Asn Gly Arg Ile Glu Ile Leu Ser Met
 50                  55                  60
Ile Leu Glu Arg Ser Val Asp Pro Asp Val Val Asn Arg His Lys Gln
 65                  70                  75                  80
Thr Pro Leu Met Leu Ala Ala Met His Gly Lys Ile Ala Cys Leu Ile
                 85                  90                  95
Lys Leu Ile Glu Ala Gly Ala Asn Ile Leu Lys Phe Asp Ser Leu His
            100                 105                 110
Glu Arg Thr Cys Leu His Tyr Ala Ala Tyr Gly His Ser Asp Cys
        115                 120                 125
Leu Gln Ala Val Leu Ser Ala Ala Gln Ser Ser His Val Ala Val Ser
    130                 135                 140
Trp Gly Tyr Ala Arg Phe Val Asn Ile Arg Asp Gly Arg Gly Ala Ala
145                 150                 155                 160
Pro Leu His Leu Ala Ala Arg Gln Arg Pro Gln Cys Val Arg Ile
                165                 170                 175
Leu Leu Asp Asn Gly Ala Leu Val Cys Ala Ser Thr Gly Gly Tyr Gly
            180                 185                 190
Cys Pro Gly Ser Thr Pro Leu His Leu Ala Ala Arg Gly Gly Ser Leu
        195                 200                 205
Asp Cys Ile Arg Glu Leu Leu Ala Trp Gly Ala Asp Arg Ile Gln Arg
    210                 215                 220
Asp Ala Ser Gly Arg Ile Pro Tyr Leu Val Ala Leu Lys His Lys His
225                 230                 235                 240
Gly Ala Cys Ala Ala Leu Leu Asn Pro Ser Ala Thr Glu Pro Leu Val
                245                 250                 255
Trp Pro Ser Pro Leu Lys Phe Ile Ser Glu Leu Asn Gln Glu Ala Lys
            260                 265                 270
Ala Leu Leu Glu Arg Ala Leu Met Asp Ala Asn Lys Glu Arg Glu Lys
        275                 280                 285
Asn Ile Leu Lys Gly Thr Ala Tyr Ser Leu Pro Ser Pro Ser His Ser
    290                 295                 300
Asp Ser Gly Ala Asp Asn Ile Ser Glu Ala Ser Asp Thr Glu Val
305                 310                 315                 320
Cys Cys Ile Cys Phe Glu Gln Val Cys Thr Ile Glu Val Gln Asp Cys
                325                 330                 335
Gly His Gln Met Cys Ala Gln Cys Thr Leu Ala Leu Cys His Asn
            340                 345                 350
Lys Pro Asn Pro Thr Thr Ala Cys Leu Asn Pro Val Cys Pro Phe
        355                 360                 365
Cys Arg Ser Ser Ile Val Arg Leu Val Val Ala Lys Val Lys Asp Ser
    370                 375                 380
Glu Asp Ala Asp Leu Asp Ile Gly Asp Ile Gly Ser Pro Lys Met Arg
385                 390                 395                 400
Lys Ala Arg Lys Ser Arg Asn Phe Ser Ser Glu Glu Ser Ser Ser Phe
                405                 410                 415
Lys Gly Leu Ser Gly Met Ser Pro Phe Gly Lys Met Gly Gly Arg Gly
            420                 425                 430
Ser Gly Arg Ile Ala Ala Glu Asn Glu Arg Val Asp Lys Pro
        435                 440                 445
```

<210> SEQ ID NO 12
<211> LENGTH: 1329
<212> TYPE: DNA

<213> ORGANISM: Populus trichocarpa

<400> SEQUENCE: 12

```
atgggccagg gactgagttg tgcagcgagt caagatcata ggttcttctc tgctgtgcat    60
ttcggtgact tggacactgt aaatgctatg cttgagagag acccatctct gctttatcaa   120
actacttatg atcgccagta tccgcttcat attgctgctg ccaatggcca gatcgagatt   180
ttatcaatgc ttctggagcg atctgtggat cctgatatgg tgaatcgtca gaagcagact   240
ccgcttatgt tggctgcaat gcatggcaaa atctcatgtg tgaagaagct cgtcgaagca   300
ggagcaaata tgttgaagtt tgattcactt aatggaagaa cttgcttgca ctttgctgct   360
tactatggcc attctgattg ccttcaagct attctttctg ctgttcaatc cagccctgtt   420
gctgtttctt ggggatatac gcggtttgtc aatattagag acggtagagg agcaacacca   480
ttgcatttag cagcccgtca aaggcggcct gaatgtgtac atatcttgtt agacaatggt   540
gctcttgttt gttcttcaac aggcggatat ggctccccgg ggaccactcc tcttcatttg   600
gctgccagag aggatctctc tgattgtatt cgtgaattgc tggcatgggg tgcagatcgt   660
atgcaaagag atgcatctgg agaaatacct tatgtagttg ctttgaagta cagaaatgga   720
acatgtgcag ctcttctcaa tccttcgtca gcagagcctc ttgtctggcc gtcaccgttg   780
aagttcatca gtgagctgaa tcaagaggca aaagctctgc tagagtgtgc cttgatggag   840
gccaacaggg agagggaaaa gaacatcttg aagggaacgg ggtactctct ccatctcca    900
tcacattctg atgatgggac agatgacaat atatctgagg caagcgatac agagttgtgc   960
tgcatatgct ttgagcaggt ttgtacaatt gaagtcgaag actgtggcca tcagatgtgt  1020
gcacaatgca cactggccct ctgctgccat aacaaaccca accctacaac cgcatgcctt  1080
accccctcag tttgcccatt ctgtcgtagc accattgccc gcctagtggt tgctaagatg  1140
aaggattgca atgatgctga tcaggacatt ggggacgttg gttccccaaa gctgagaaag  1200
tccaggaggt cactgaactt cagtgaggga agcagcagct tcaagggctt atcagcaaca  1260
tttggaaaaa tgggtggccg tggctcagga aggattgctg cagaaaatga gtgggtggat  1320
aagccttga                                                          1329
```

<210> SEQ ID NO 13
<211> LENGTH: 442
<212> TYPE: PRT
<213> ORGANISM: Populus trichocarpa

<400> SEQUENCE: 13

```
Met Gly Gln Gly Leu Ser Cys Ala Ala Ser Gln Asp His Arg Phe Phe
1               5                   10                  15

Ser Ala Val His Phe Gly Asp Leu Asp Thr Val Asn Ala Met Leu Glu
            20                  25                  30

Arg Asp Pro Ser Leu Leu Tyr Gln Thr Thr Tyr Asp Arg Gln Tyr Pro
        35                  40                  45

Leu His Ile Ala Ala Ala Asn Gly Gln Ile Glu Ile Leu Ser Met Leu
    50                  55                  60

Leu Glu Arg Ser Val Asp Pro Asp Met Val Asn Arg Gln Lys Gln Thr
65                  70                  75                  80

Pro Leu Met Leu Ala Ala Met His Gly Lys Ile Ser Cys Val Lys Lys
                85                  90                  95

Leu Val Glu Ala Gly Ala Asn Met Leu Lys Phe Asp Ser Leu Asn Gly
            100                 105                 110
```

```
Arg Thr Cys Leu His Phe Ala Ala Tyr Tyr Gly His Ser Asp Cys Leu
            115                 120                 125

Gln Ala Ile Leu Ser Ala Val Gln Ser Ser Pro Val Ala Val Ser Trp
        130                 135                 140

Gly Tyr Thr Arg Phe Val Asn Ile Arg Asp Gly Arg Gly Ala Thr Pro
145                 150                 155                 160

Leu His Leu Ala Ala Arg Gln Arg Arg Pro Glu Cys Val His Ile Leu
                165                 170                 175

Leu Asp Asn Gly Ala Leu Val Cys Ser Ser Thr Gly Tyr Gly Tyr Ser
            180                 185                 190

Pro Gly Thr Thr Pro Leu His Leu Ala Ala Arg Gly Gly Ser Leu Asp
        195                 200                 205

Cys Ile Arg Glu Leu Leu Ala Trp Gly Ala Asp Arg Met Gln Arg Asp
210                 215                 220

Ala Ser Gly Arg Ile Pro Tyr Val Val Ala Leu Lys Tyr Arg Asn Gly
225                 230                 235                 240

Thr Cys Ala Ala Leu Leu Asn Pro Ser Ser Ala Glu Pro Leu Val Trp
                245                 250                 255

Pro Ser Pro Leu Lys Phe Ile Ser Glu Leu Asn Gln Glu Ala Lys Ala
            260                 265                 270

Leu Leu Glu Cys Ala Leu Met Glu Ala Asn Arg Glu Arg Glu Lys Asn
        275                 280                 285

Ile Leu Lys Gly Thr Gly Tyr Ser Leu Pro Ser Pro Ser His Ser Asp
        290                 295                 300

Asp Gly Thr Asp Asp Asn Ile Ser Glu Ala Ser Asp Thr Glu Leu Cys
305                 310                 315                 320

Cys Ile Cys Phe Glu Gln Val Cys Thr Ile Glu Val Glu Asp Cys Gly
                325                 330                 335

His Gln Met Cys Ala Gln Cys Thr Leu Ala Leu Cys Cys His Asn Lys
            340                 345                 350

Pro Asn Pro Thr Thr Ala Cys Leu Thr Pro Val Cys Pro Phe Cys
        355                 360                 365

Arg Ser Thr Ile Ala Arg Leu Val Val Ala Lys Met Lys Asp Cys Asn
370                 375                 380

Asp Ala Asp Gln Asp Ile Gly Asp Val Gly Ser Pro Lys Leu Arg Lys
385                 390                 395                 400

Ser Arg Arg Ser Leu Asn Phe Ser Glu Gly Ser Ser Phe Lys Gly
                405                 410                 415

Leu Ser Ala Thr Phe Gly Lys Met Gly Gly Arg Gly Ser Gly Arg Ile
            420                 425                 430

Ala Ala Glu Asn Glu Trp Val Asp Lys Pro
        435                 440

<210> SEQ ID NO 14
<211> LENGTH: 1365
<212> TYPE: DNA
<213> ORGANISM: Populus trichocarpa

<400> SEQUENCE: 14
atgggtcagg gactgagttg tgcagcgagt caagagcatg cgttcttcac tgctgtgcag     60
ttgggtgaat cgacaccgt aaatgctatg cttgagagag acccatctct ccttcatcaa    120
actacttatg atcgccagta tccgctacat attgctgctg ccaatggcca gatcgagatt    180
ttaacaatgc ttctggagcg atctgtggat cctgatatgg tgaatcgtca caagcagact    240
```

```
ccgcttatgt tggctgcaat gcatggcaaa atctcatgtt tgaaaaagct catcgaagca     300
ggggcaaata ttttgaagtt tgattcactt aatggaagaa cttgcttgca ctatgctgct     360
tactatggcc attcggattg ccttcaagct attatttctg ctgctcaatc aagccctgtt     420
gctgtttctt ggggatatgc acggtttgtc aatatcagag atggtagagg agcaacacca     480
ttgcatttag cagcccgtca agacggcct ggatgtgtac atatcttgtt aggcaatggt      540
gctcttgttt gttcttcgac aggaggatat ggttccccgg ggagcactcc tcttcatttg     600
gcagccagag ggggatctct tgattgtatc cgtgcattgc tggcgtgggg ggcagatcgt     660
cttcaaagag atgcatctgg gagaataccc tatgtagttg ctttgaagca caaaaatgga     720
atgtgtgcag cccttcttaa tccttcatca gcagagcctc ttgtctggcc atcaccattg     780
aagttcatca gtgagctgaa tcaagaggca aaagctctac tggagtgtgc cttgatggag     840
gccaacaggg agagggaaaa gaatatattg atggaggcca acagggagag ggaaaagaac     900
atattgaagg atctgggca ttcacttcca tctccatcac attctgctga tgggacagat      960
tacaatatat ctgaggcaag cgatacagag gtgtgctgca tatgctttga gcaggtttgt    1020
acaattgaag ttcaagactg tggccatcag atgtgtgcac aatgcacact agctctctgc    1080
tgccataaca aacccaaccc tacaaccgca tgccttaacc ctccagtttg tccattctgt    1140
cgaagcacca ttgtccgtct agtggttgct aaaatcaaga actgtaatga tgctgatcaa    1200
gacattgggg aaattggttc accaaaactg agaaagtcca ggaagtcacg gaacttcagc    1260
gagggaagca gtagtttcaa ggggttatca gcaacatttg gaaaaatggg tggccgtggc    1320
tcaggaagga ttgctgcaga aaatgagtgg atggataagc cttga                    1365
```

<210> SEQ ID NO 15
<211> LENGTH: 454
<212> TYPE: PRT
<213> ORGANISM: Populus trichocarpa

<400> SEQUENCE: 15

```
Met Gly Gln Gly Leu Ser Cys Ala Ala Ser Gln Glu His Ala Phe Phe
1               5                   10                  15

Thr Ala Val Gln Leu Gly Glu Phe Asp Thr Val Asn Ala Met Leu Glu
            20                  25                  30

Arg Asp Pro Ser Leu Leu His Gln Thr Thr Tyr Asp Arg Gln Tyr Pro
        35                  40                  45

Leu His Ile Ala Ala Ala Asn Gly Gln Ile Glu Ile Leu Thr Met Leu
    50                  55                  60

Leu Glu Arg Ser Val Asp Pro Asp Met Val Asn Arg His Lys Gln Thr
65                  70                  75                  80

Pro Leu Met Leu Ala Ala Met His Gly Lys Ile Ser Cys Leu Lys Lys
                85                  90                  95

Leu Ile Glu Ala Gly Ala Asn Ile Leu Lys Phe Asp Ser Leu Asn Gly
            100                 105                 110

Arg Thr Cys Leu His Tyr Ala Ala Tyr Tyr Gly His Ser Asp Cys Leu
        115                 120                 125

Gln Ala Ile Ile Ser Ala Ala Gln Ser Ser Pro Val Ala Val Ser Trp
    130                 135                 140

Gly Tyr Ala Arg Phe Val Asn Ile Arg Asp Gly Arg Gly Ala Thr Pro
145                 150                 155                 160

Leu His Leu Ala Ala Arg Gln Arg Arg Pro Gly Cys Val His Ile Leu
                165                 170                 175
```

```
Leu Gly Asn Gly Ala Leu Val Cys Ser Ser Thr Gly Tyr Gly Ser
            180                 185                 190

Pro Gly Ser Thr Pro Leu His Leu Ala Ala Arg Gly Gly Ser Leu Asp
        195                 200                 205

Cys Ile Arg Ala Leu Leu Ala Trp Gly Ala Asp Arg Leu Gln Arg Asp
    210                 215                 220

Ala Ser Gly Arg Ile Pro Tyr Val Val Ala Leu Lys His Lys Asn Gly
225                 230                 235                 240

Met Cys Ala Ala Leu Leu Asn Pro Ser Ser Ala Glu Pro Leu Val Trp
            245                 250                 255

Pro Ser Pro Leu Lys Phe Ile Ser Glu Leu Asn Gln Glu Ala Lys Ala
        260                 265                 270

Leu Leu Glu Cys Ala Leu Met Glu Ala Asn Arg Glu Arg Glu Lys Asn
    275                 280                 285

Ile Leu Met Glu Ala Asn Arg Glu Arg Glu Lys Asn Ile Leu Lys Gly
    290                 295                 300

Ser Gly His Ser Leu Pro Ser Pro Ser His Ser Ala Asp Gly Thr Asp
305                 310                 315                 320

Tyr Asn Ile Ser Glu Ala Ser Asp Thr Glu Val Cys Cys Ile Cys Phe
            325                 330                 335

Glu Gln Val Cys Thr Ile Glu Val Gln Asp Cys Gly His Gln Met Cys
        340                 345                 350

Ala Gln Cys Thr Leu Ala Leu Cys His Asn Lys Pro Asn Pro Thr
    355                 360                 365

Thr Ala Cys Leu Asn Pro Pro Val Cys Pro Phe Cys Arg Ser Thr Ile
    370                 375                 380

Val Arg Leu Val Val Ala Lys Ile Lys Asn Cys Asn Asp Ala Asp Gln
385                 390                 395                 400

Asp Ile Gly Glu Ile Gly Ser Pro Lys Leu Arg Lys Ser Arg Lys Ser
            405                 410                 415

Arg Asn Phe Ser Glu Gly Ser Ser Phe Lys Gly Leu Ser Ala Thr
        420                 425                 430

Phe Gly Lys Met Gly Gly Arg Gly Ser Gly Arg Ile Ala Ala Glu Asn
    435                 440                 445

Glu Trp Met Asp Lys Pro
    450

<210> SEQ ID NO 16
<211> LENGTH: 1323
<212> TYPE: DNA
<213> ORGANISM: Gossypium raimondii

<400> SEQUENCE: 16
atgggtcagg ggctgagttg tggggcgagt caagagaatg gattgtttag tgcagttaaa      60
gttggagact tgaaaccgt ggaagctttg ttaaagagag aacccagtct tttacatcat     120
accactgttt atgatcgcca ttctgctctt catatagctg ctgctaatgg ccagatcgag     180
attttggcca tgcttttgga taaatccatg aacccagatg cggtgaatcg taacaagcag     240
actccactta tgttggctgc aatgcatggg aagatctcct gtgtgaagaa gctcattgaa     300 gcggggggcca atatcttaat gtttgattcc ctccatggaa gaacttgctt gcactatgca     360
gcctattatg gccactttga ctgccttcaa gccatcctct ctgctgctca atctagccct     420
gttgctgttt catggggata tgcacggttt gtgaatataa agacgctag ggagccact     480 cctttgcact tagcagctcg tcaaagacgg cccgaatgcg ttcatatcct gttagataac     540
```

| | | | | |
|---|---|---|---|---|
| ggtgctcttg | tttgtgcttc | aaccggtgga | tacggttgtc | caggaagcac | ccctcttcat | 600 |
| ttggctgcta | gaggtggatc | tctcgattgt | atacgtaagt | tgttggcgtg | gggtgcggat | 660 |
| cgtcttcaaa | gagatgcaac | agggagaata | ccgtatattg | ttgctcttaa | gtacaaacat | 720 |
| ggagcatgtg | ccgctctgtt | aaatccgtca | tctgccgaac | ctcttgtctg | gccagcacct | 780 |
| ttaaagttca | ttagtgagct | caatgacgag | gcaaagttac | tattagaaca | ggccttaatg | 840 |
| gatgcaaaca | gggaaaggga | aagaacatc | ttgaaggaa | cagcttactc | acttctatca | 900 |
| ccgtcaccat | cccactctga | ttctgggtta | gacgacagta | tttctgaggt | tagtgatgcc | 960 |
| gaactatgct | gcatatgctt | cgagcagatc | tgcacgatcg | aagtccaaga | ctgtggtcac | 1020 |
| cagatgtgcg | cacaatgcac | attggcccct | tgctgccata | caagccgaa | ccccacaact | 1080 |
| gcaagcgtaa | cacccccggt | ctgccccttt | tgccgcagca | ccattgtccg | attggcagta | 1140 |
| gccaagataa | aagattgcga | cggcgatgtt | ggggaggatg | gtagttcccc | gaaggtgaga | 1200 |
| agacggagga | agtcaaggaa | tttcagcgag | gggagcagca | gtttcaagag | cttatctgca | 1260 |
| gttggatcat | ttaacaagat | ggggaggatt | gcagcagaaa | atgaatggat | tgataagcct | 1320 |
| tga | | | | | | 1323 |

<210> SEQ ID NO 17
<211> LENGTH: 440
<212> TYPE: PRT
<213> ORGANISM: Gossypium raimondii

<400> SEQUENCE: 17

Met Gly Gln Gly Leu Ser Cys Gly Ala Ser Gln Glu Asn Gly Leu Phe
1               5                   10                  15

Ser Ala Val Lys Val Gly Asp Phe Glu Thr Val Glu Ala Leu Leu Lys
            20                  25                  30

Arg Glu Pro Ser Leu Leu His His Thr Thr Val Tyr Asp Arg His Ser
        35                  40                  45

Ala Leu His Ile Ala Ala Ala Asn Gly Gln Ile Glu Ile Leu Ala Met
    50                  55                  60

Leu Leu Asp Lys Ser Met Asn Pro Asp Ala Val Asn Arg Asn Lys Gln
65                  70                  75                  80

Thr Pro Leu Met Leu Ala Ala Met His Gly Lys Ile Ser Cys Val Lys
                85                  90                  95

Lys Leu Ile Glu Ala Gly Ala Asn Ile Leu Met Phe Asp Ser Leu His
            100                 105                 110

Gly Arg Thr Cys Leu His Tyr Ala Ala Tyr Tyr Gly His Phe Asp Cys
        115                 120                 125

Leu Gln Ala Ile Leu Ser Ala Ala Gln Ser Ser Pro Val Ala Val Ser
    130                 135                 140

Trp Gly Tyr Ala Arg Phe Val Asn Ile Arg Asp Ala Arg Gly Ala Thr
145                 150                 155                 160

Pro Leu His Leu Ala Ala Arg Gln Arg Arg Pro Glu Cys Val His Ile
                165                 170                 175

Leu Leu Asp Asn Gly Ala Leu Val Cys Ala Ser Thr Gly Gly Tyr Gly
            180                 185                 190

Cys Pro Gly Ser Thr Pro Leu His Leu Ala Ala Arg Gly Gly Ser Leu
        195                 200                 205

Asp Cys Ile Arg Lys Leu Leu Ala Trp Gly Ala Asp Arg Leu Gln Arg
    210                 215                 220

Asp Ala Thr Gly Arg Ile Pro Tyr Ile Val Ala Leu Lys Tyr Lys His
225                 230                 235                 240

Gly Ala Cys Ala Ala Leu Leu Asn Pro Ser Ser Ala Glu Pro Leu Val
            245                 250                 255

Trp Pro Ala Pro Leu Lys Phe Ile Ser Glu Leu Asn Asp Glu Ala Lys
        260                 265                 270

Leu Leu Leu Glu Gln Ala Leu Met Asp Ala Asn Arg Glu Arg Glu Lys
    275                 280                 285

Asn Ile Leu Lys Gly Thr Ala Tyr Ser Leu Leu Ser Pro Ser Pro Ser
290                 295                 300

His Ser Asp Ser Gly Leu Asp Asp Ser Ile Ser Glu Val Ser Asp Ala
305                 310                 315                 320

Glu Leu Cys Cys Ile Cys Phe Glu Gln Ile Cys Thr Ile Glu Val Gln
                325                 330                 335

Asp Cys Gly His Gln Met Cys Ala Gln Cys Thr Leu Ala Leu Cys Cys
            340                 345                 350

His Asn Lys Pro Asn Pro Thr Thr Ala Ser Val Thr Pro Val Cys
        355                 360                 365

Pro Phe Cys Arg Ser Thr Ile Val Arg Leu Ala Val Ala Lys Ile Lys
    370                 375                 380

Asp Cys Asp Gly Asp Val Gly Glu Asp Gly Ser Ser Pro Lys Val Arg
385                 390                 395                 400

Arg Arg Arg Lys Ser Arg Asn Phe Ser Glu Gly Ser Ser Ser Phe Lys
                405                 410                 415

Ser Leu Ser Ala Val Gly Ser Phe Asn Lys Met Gly Arg Ile Ala Ala
            420                 425                 430

Glu Asn Glu Trp Ile Asp Lys Pro
435                 440

<210> SEQ ID NO 18
<211> LENGTH: 1338
<212> TYPE: DNA
<213> ORGANISM: Gossypium raimondii

<400> SEQUENCE: 18
atgggtcaag gctgagttg tggagcgagt caagagaatg tattgtttag tgcagttcaa      60
ggtggagacc ttgaaactgt ggaagcttta ttaaggagag aatccaatct tttacatcat     120
acgactgttt atgatcgcca ctctgctctt catatagctg ctgcttatgg ccagatcgag     180
attttggcta tgcttttgga gaaatccgtg aacccggacg tagtgaatcg tcaaaagcag     240 actccccctta tgttggctgc aatgcatggg aatatctcct gcgtgaagaa gctgattgaa     300
gccggggcaa atatcttaat gtttgattca attcatggaa gaacttgctt gcactatgca     360
gcctattatg gtcactctga ctgccttcag gctattctct ctgctgctca atctagccct     420
gttgctgttt catggggata tgcacgtttt gtgaatataa agatgccaa gggagctact      480 tccttacact tagcagctcg tcaaaggcgg cctgactgcg tacatatcct gttagacaat     540
ggtgctcttg tttgtgcttc aactggtgga tatggttgtc aggaagcac acctcttcat      600 ttggctgcta gaggtggatc tcttgattgc atccgcaagt tgttggcatg gggtgcggac     660
cgtcttcaaa gagatgcatc cgggagaata ccttatgtag ttgctctaaa gcacaaacat     720
ggggcatgtg cagctctgct aaatccttca tcagcagaac ctatcgtctg gccggcacct     780
ttaaagttca ttagtgagct taatgaggag gcaaaaacac tattagaaca agccttaatg     840
gatgcaaacc gggaaagaga aaagaacatc ctgaagggaa cagcttactc aattccatca     900

```
ccttcacaat ctgattctgg gttagatgac aatatctctg aggctagtga tactgaacta    960
tgctgcatat gctttgagca aatctgcaca attgaagttc aagactgtgg tcaccagatg   1020
tgtgcacaat gcacactggc attgtgctgc cacaacaagc caaaccctac aactgcaagt   1080
ctaacacccc ccgcatgccc cttttgccgg agccccattg tccgattggt ggtagccaag   1140
ataaagaatc atgatgacgt ggatcatgac attggggatg ttagttcctc gaagctgaga   1200
aaaacaagga agtcaaggaa tttagtgaa ggaagcagca gcttcaagag cttatctgca   1260
gttggttcat tcagcaagat cagtggccga ggctccggaa ggattgctgc agaaaatgaa   1320
tggattgata agccttga                                                  1338
```

```
<210> SEQ ID NO 19
<211> LENGTH: 445
<212> TYPE: PRT
<213> ORGANISM: Gossypium raimondii

<400> SEQUENCE: 19

Met Gly Gln Gly Leu Ser Cys Gly Ala Ser Gln Glu Asn Val Leu Phe
1               5                   10                  15

Ser Ala Val Gln Gly Gly Asp Leu Glu Thr Val Glu Ala Leu Leu Arg
            20                  25                  30

Arg Glu Ser Asn Leu Leu His His Thr Thr Val Tyr Asp Arg His Ser
        35                  40                  45

Ala Leu His Ile Ala Ala Ala Tyr Gly Gln Ile Glu Ile Leu Ala Met
    50                  55                  60

Leu Leu Glu Lys Ser Val Asn Pro Asp Val Val Asn Arg Gln Lys Gln
65                  70                  75                  80

Thr Pro Leu Met Leu Ala Ala Met His Gly Asn Ile Ser Cys Val Lys
                85                  90                  95

Lys Leu Ile Glu Ala Gly Ala Asn Ile Leu Met Phe Asp Ser Ile His
            100                 105                 110

Gly Arg Thr Cys Leu His Tyr Ala Ala Tyr Tyr Gly His Ser Asp Cys
        115                 120                 125

Leu Gln Ala Ile Leu Ser Ala Ala Gln Ser Ser Pro Val Ala Val Ser
    130                 135                 140

Trp Gly Tyr Ala Arg Phe Val Asn Ile Arg Asp Ala Lys Gly Ala Thr
145                 150                 155                 160

Ser Leu His Leu Ala Ala Arg Gln Arg Arg Pro Asp Cys Val His Ile
                165                 170                 175

Leu Leu Asp Asn Gly Ala Leu Val Cys Ala Ser Thr Gly Gly Tyr Gly
            180                 185                 190

Cys Pro Gly Ser Thr Pro Leu His Leu Ala Ala Arg Gly Gly Ser Leu
        195                 200                 205

Asp Cys Ile Arg Lys Leu Leu Ala Trp Gly Ala Asp Arg Leu Gln Arg
    210                 215                 220

Asp Ala Ser Gly Arg Ile Pro Tyr Val Val Ala Leu Lys His Lys His
225                 230                 235                 240

Gly Ala Cys Ala Ala Leu Leu Asn Pro Ser Ser Ala Glu Pro Ile Val
                245                 250                 255

Trp Pro Ala Pro Leu Lys Phe Ile Ser Glu Leu Asn Glu Glu Ala Lys
            260                 265                 270

Thr Leu Leu Glu Gln Ala Leu Met Asp Ala Asn Arg Glu Arg Glu Lys
        275                 280                 285
```

```
Asn Ile Leu Lys Gly Thr Ala Tyr Ser Ile Pro Ser Pro Ser Gln Ser
    290                 295                 300

Asp Ser Gly Leu Asp Asp Asn Ile Ser Glu Ala Ser Asp Thr Glu Leu
305                 310                 315                 320

Cys Cys Ile Cys Phe Glu Gln Ile Cys Thr Ile Glu Val Gln Asp Cys
                325                 330                 335

Gly His Gln Met Cys Ala Gln Cys Thr Leu Ala Leu Cys Cys His Asn
                340                 345                 350

Lys Pro Asn Pro Thr Thr Ala Ser Leu Thr Pro Pro Ala Cys Pro Phe
    355                 360                 365

Cys Arg Ser Pro Ile Val Arg Leu Val Val Ala Lys Ile Lys Asn His
370                 375                 380

Asp Asp Val Asp His Asp Ile Gly Asp Val Ser Ser Ser Lys Leu Arg
385                 390                 395                 400

Lys Thr Arg Lys Ser Arg Asn Phe Ser Glu Gly Ser Ser Ser Phe Lys
                405                 410                 415

Ser Leu Ser Ala Val Gly Ser Phe Ser Lys Ile Ser Gly Arg Gly Ser
                420                 425                 430

Gly Arg Ile Ala Ala Glu Asn Glu Trp Ile Asp Lys Pro
                435                 440                 445
```

```
<210> SEQ ID NO 20
<211> LENGTH: 1341
<212> TYPE: DNA
<213> ORGANISM: Gossypium raimondii

<400> SEQUENCE: 20
atgggtcagg ggctgagttg tgtagcgagt caagagaatg aattgtttac tgcagttcaa      60
gttggagact ttgaaactgt ggaaactttg ttagagagag aacccaatct ttcgcatcac     120
acaactgttt atgatcgcca ctctgctctt catatagcag ctgctaatgg tcagatcgag     180
attttggcca tgttttttgga gaaatccgtg aatccggatg tagtgaatcg tcacaagcag     240
actccactta tgttggctgc aatgcatggg aagacctcct gtgtgaagag gctcattgaa     300
gctagggcaa atatattaat gtttgattcc cttcatggaa gaacttgctt acactatgca     360
gcctattatg gtcactctga ctgccttcaa gccatcctct ctgctgctca atctagccct     420
gttgctgttt catggtgggg atatgcacgg tttgtgaata agagatgg taggggagcc     480
actcccttgc acttagcagc acgccggaag cagcctgaat gcgtacatat cctgttatac     540
aatggtgctc ttgtttgtgc atcaactggt cgatatggtt ccccaggaag cactcctctt     600
catttggctg ctagaggggg ctctcttgat tgcattcgta tgttgttggc ttggggtgca     660
gatcgtcttc aaagagatgc atctgggaga atatcatttg tcgttgcgct aaaacacaaa     720
catggagctt gtgcagctct tctaaatcct tcatcagcag aacctcttgt ctggccagca     780
actttaaagt tcattaccga gcttaatgaa gaggcaaaat cactattaga acaggcctta     840
atggaggcaa accgggaaag ggaaaagaac atcttaaagg gaacagctta ctcacttcca     900
tcaccctcac attctgactc agggttagat gacagtgttt ctgaggctag cgatactgaa     960
gtatgctgta tatgctttga gcagctctgc actattgaag ttcaagactg tggccaccag    1020
atgtgtgcac aatgcacagt tgccttgtgc tgtcacaaca agccaaaccc tgtgactgca    1080
agcctaacaa ccctggtatg ccccttttgc cggtgcacca ttgtccgact ggtggtagcc    1140
aagatgaaat gttatgacaa taccaatcgc tttactggag aagatagtac ttcaaagcca    1200
agaaaatcaa gaaagccaag gaatttcagt gagggaagca gcagctttaa aagtttatcc    1260
```

```
gcaataggtt cattcagcaa gattggtggc cgtagctcag gaaggattgc tgcagaaaat    1320
gaatggattg ataagacttg a                                              1341
```

<210> SEQ ID NO 21
<211> LENGTH: 446
<212> TYPE: PRT
<213> ORGANISM: Gossypium raimondii

<400> SEQUENCE: 21

```
Met Gly Gln Gly Leu Ser Cys Val Ala Ser Gln Glu Asn Glu Leu Phe
1               5                   10                  15

Thr Ala Val Gln Val Gly Asp Phe Glu Thr Val Glu Thr Leu Leu Glu
            20                  25                  30

Arg Glu Pro Asn Leu Ser His His Thr Thr Val Tyr Asp Arg His Ser
        35                  40                  45

Ala Leu His Ile Ala Ala Ala Asn Gly Gln Ile Glu Ile Leu Ala Met
    50                  55                  60

Phe Leu Glu Lys Ser Val Asn Pro Asp Val Val Asn Arg His Lys Gln
65                  70                  75                  80

Thr Pro Leu Met Leu Ala Ala Met His Gly Lys Thr Ser Cys Val Lys
                85                  90                  95

Arg Leu Ile Glu Ala Arg Ala Asn Ile Leu Met Phe Asp Ser Leu His
            100                 105                 110

Gly Arg Thr Cys Leu His Tyr Ala Ala Tyr Tyr Gly His Ser Asp Cys
        115                 120                 125

Leu Gln Ala Ile Leu Ser Ala Ala Gln Ser Ser Pro Val Ala Val Ser
    130                 135                 140

Trp Trp Gly Tyr Ala Arg Phe Val Asn Ile Arg Asp Gly Arg Gly Ala
145                 150                 155                 160

Thr Pro Leu His Leu Ala Ala Arg Arg Lys Gln Pro Glu Cys Val His
                165                 170                 175

Ile Leu Leu Tyr Asn Gly Ala Leu Val Cys Ala Ser Thr Gly Arg Tyr
            180                 185                 190

Gly Phe Pro Gly Ser Thr Pro Leu His Leu Ala Ala Arg Gly Gly Ser
        195                 200                 205

Leu Asp Cys Ile Arg Met Leu Leu Ala Trp Gly Ala Asp Arg Leu Gln
    210                 215                 220

Arg Asp Ala Ser Gly Arg Ile Ser Phe Val Val Ala Leu Lys His Lys
225                 230                 235                 240

His Gly Ala Cys Ala Ala Leu Leu Asn Pro Ser Ser Ala Glu Pro Leu
                245                 250                 255

Val Trp Pro Ala Thr Leu Lys Phe Ile Thr Glu Leu Asn Glu Glu Ala
            260                 265                 270

Lys Ser Leu Leu Glu Gln Ala Leu Met Glu Ala Asn Arg Glu Arg Glu
        275                 280                 285

Lys Asn Ile Leu Lys Gly Thr Ala Tyr Ser Leu Pro Ser Pro Ser His
    290                 295                 300

Ser Asp Ser Gly Leu Asp Asp Ser Val Ser Glu Ala Ser Asp Thr Glu
305                 310                 315                 320

Val Cys Cys Ile Cys Phe Glu Gln Leu Cys Thr Ile Glu Val Gln Asp
                325                 330                 335

Cys Gly His Gln Met Cys Ala Gln Cys Thr Val Ala Leu Cys Cys His
            340                 345                 350
```

```
Asn Lys Pro Asn Pro Val Thr Ala Ser Leu Thr Thr Leu Val Cys Pro
        355                 360                 365

Phe Cys Arg Cys Thr Ile Val Arg Leu Val Val Ala Lys Met Lys Cys
370                 375                 380

Tyr Asp Asn Thr Asn Arg Phe Thr Gly Glu Asp Ser Thr Ser Lys Pro
385                 390                 395                 400

Arg Lys Ser Arg Lys Pro Arg Asn Phe Ser Glu Gly Ser Ser Ser Phe
            405                 410                 415

Lys Ser Leu Ser Ala Ile Gly Ser Phe Ser Lys Ile Gly Gly Arg Ser
            420                 425                 430

Ser Gly Arg Ile Ala Ala Glu Asn Glu Trp Ile Asp Lys Thr
            435                 440                 445

<210> SEQ ID NO 22
<211> LENGTH: 1383
<212> TYPE: DNA
<213> ORGANISM: Gossypium raimondii

<400> SEQUENCE: 22
```

| | | | | | |
|---|---|---|---|---|---|
| atgggtcaaa | agcttagctg | cttggaaaac | catgagaatg | atttgctcag | tgctgttcag      60 |
| acaggtgacc | tggacatggt | taaggcaatg | gttgaagcag | acccagttac | cttaaaaagc     120 |
| accactcgat | atgggaagtt | gtctatactt | catgtggcag | ctatccatgg | tcagatcgag     180 |
| attctttcgt | tcctttaga  | tcggcatcca | aattcagaca | tcttgaatcg | tcacagacag     240 |
| accccattga | tgttggctgc | aatgcatggg | aagaccgatt | gtgtgaaaag | gcttatccag     300 |
| agtggatcat | atgtattgat | gtttgattca | cttcaaggaa | ggacttgctt | gcattatgct     360 |
| gcctactatg | ccattttga  | ttgccttcaa | gctcttcttt | ctgctgctca | cagcagcccc     420 |
| cttgcagatt | cttggggctt | tgcgagattt | gttaacataa | gagatgagaa | cggtgctacg     480 |
| cctctgcatt | tggcggctcg | tgaaggatgg | tctgattgtg | ttcatgcact | cttagataat     540 |
| ggggctcttg | tttgtgcttc | aactggtgga | aatggctacc | ctgggagcac | accccttcat     600 |
| tttgccgcgc | gcggggggttc | tatagagtgt | atccgggaat | tacttgcttg | gggagctgat     660 |
| aggcttcaac | cggattcata | tgggagaata | ccatatttga | ttgctttgaa | gcacaaacac     720 |
| gatgcatgtg | cagctttgtt | gaaccctgca | tctgcagaac | ctcttgtttg | gccattgcct     780 |
| ttaaggttca | taagcgagct | taatccagaa | gcaaaagagc | tcttggagaa | ggccttaatg     840 |
| gaggctaaca | gagagaggga | gagagccatt | ttgaaggata | cagtccatga | acttccatct     900 |
| gcttcacagt | acgaggtcga | agctgacgat | actgcctccg | aggcaagcga | catagatgta     960 |
| tgctgcatat | gctttgaccg | gctatgcaca | atagagatta | gacaatgtgg | tcaccggatg    1020 |
| tgtgctcatt | gcatcttagc | tctatgctgt | cacaagaagc | ccaacccact | gacagcatct    1080 |
| cctttagtcc | tagtttgtcc | cttctgccgt | aggggaatca | cccaactagt | tgtcgccaaa    1140 |
| attgacaaca | acgaatcaga | agcagatgct | agtcctttaa | ggctgagtag | tggaatgatg    1200 |
| accaacgtcg | atacaggagc | agaattcagt | ccctctaagc | caactaaatc | taggaagtcc    1260 |
| aatgtcagtg | aaggaagcag | cagtttcaaa | ggtttgtcgg | ccatcagctc | gttcgggaaa    1320 |
| atggctagcc | acagtcctgg | aaaagtgcct | gctgaatgta | gtgaagaaac | tgagaagttc    1380 |
| tga         |            |            |            |            |           1383 |

```
<210> SEQ ID NO 23
<211> LENGTH: 460
<212> TYPE: PRT
<213> ORGANISM: Gossypium raimondii
```

<400> SEQUENCE: 23

```
Met Gly Gln Lys Leu Ser Cys Leu Glu Asn His Glu Asn Asp Leu Leu
1               5                   10                  15

Ser Ala Val Gln Thr Gly Asp Leu Asp Met Val Lys Ala Met Val Glu
            20                  25                  30

Ala Asp Pro Val Thr Leu Lys Ser Thr Thr Arg Tyr Gly Lys Leu Ser
        35                  40                  45

Ile Leu His Val Ala Ala Ile His Gly Gln Ile Glu Ile Leu Ser Phe
    50                  55                  60

Leu Leu Asp Arg His Pro Asn Ser Asp Ile Leu Asn Arg His Arg Gln
65                  70                  75                  80

Thr Pro Leu Met Leu Ala Ala Met His Gly Lys Thr Asp Cys Val Lys
                85                  90                  95

Arg Leu Ile Gln Ser Gly Ser Tyr Val Leu Met Phe Asp Ser Leu Gln
            100                 105                 110

Gly Arg Thr Cys Leu His Tyr Ala Ala Tyr Tyr Gly His Phe Asp Cys
        115                 120                 125

Leu Gln Ala Leu Leu Ser Ala Ala His Ser Ser Pro Leu Ala Asp Ser
    130                 135                 140

Trp Gly Phe Ala Arg Phe Val Asn Ile Arg Asp Glu Asn Gly Ala Thr
145                 150                 155                 160

Pro Leu His Leu Ala Ala Arg Glu Gly Trp Ser Asp Cys Val His Ala
                165                 170                 175

Leu Leu Asp Asn Gly Ala Leu Val Cys Ala Ser Thr Gly Gly Asn Gly
            180                 185                 190

Tyr Pro Gly Ser Thr Pro Leu His Phe Ala Ala Arg Gly Gly Ser Ile
        195                 200                 205

Glu Cys Ile Arg Glu Leu Leu Ala Trp Gly Ala Asp Arg Leu Gln Pro
    210                 215                 220

Asp Ser Tyr Gly Arg Ile Pro Tyr Leu Ile Ala Leu Lys His Lys His
225                 230                 235                 240

Asp Ala Cys Ala Ala Leu Leu Asn Pro Ala Ser Ala Glu Pro Leu Val
                245                 250                 255

Trp Pro Leu Pro Leu Arg Phe Ile Ser Glu Leu Asn Pro Glu Ala Lys
            260                 265                 270

Glu Leu Leu Glu Lys Ala Leu Met Glu Ala Asn Arg Glu Arg Glu Arg
        275                 280                 285

Ala Ile Leu Lys Asp Thr Val His Glu Leu Pro Ser Ala Ser Gln Tyr
    290                 295                 300

Glu Val Glu Ala Asp Asp Thr Ala Ser Glu Ala Ser Asp Ile Asp Val
305                 310                 315                 320

Cys Cys Ile Cys Phe Asp Arg Leu Cys Thr Ile Glu Ile Arg Gln Cys
                325                 330                 335

Gly His Arg Met Cys Ala His Cys Ile Leu Ala Leu Cys Cys His Lys
            340                 345                 350

Lys Pro Asn Pro Leu Thr Ala Ser Pro Leu Val Leu Cys Pro Phe
        355                 360                 365

Cys Arg Arg Gly Ile Thr Gln Leu Val Val Ala Lys Ile Asp Asn Asn
    370                 375                 380

Glu Ser Glu Ala Asp Ala Ser Pro Leu Arg Leu Ser Ser Gly Met Met
385                 390                 395                 400

Thr Asn Val Asp Thr Gly Ala Glu Phe Ser Pro Ser Lys Pro Thr Lys
```

```
                    405                 410                 415
Ser Arg Lys Ser Asn Val Ser Glu Gly Ser Ser Ser Phe Lys Gly Leu
            420                 425                 430

Ser Ala Ile Ser Ser Phe Gly Lys Met Ala Ser His Ser Pro Gly Lys
        435                 440                 445

Val Pro Ala Glu Cys Ser Glu Glu Thr Glu Lys Phe
    450                 455                 460

<210> SEQ ID NO 24
<211> LENGTH: 1332
<212> TYPE: DNA
<213> ORGANISM: Citrus

<400> SEQUENCE: 24
atgggtcagg gactgagttg tggagcgagt tatgagcatg ctttgttcac cgctgtgcag      60
catggtgata tcgagtttgt taatgatttg ttagagaaag attcaagtct cttacatcaa     120
accactgttt atgatcgcca ctctgctctt catatttctg ctgccaatgg ccagatcgag     180
attttggaga ttttgctgaa ccgatctgtg aatcctgatg cggtgaatcg ttacaagcag     240
actccgctta tgctggctgc aatgcatggg aagatctatt gtgttaaaag ctgcttgaa      300 gctggagcta atatactgat gtttgattct ctcaatggaa gaacttgctt gcattatgct     360
gcttactacg ccacgccga ttgcgttcaa gccattctct ctgctgctca gtctagtcct      420
attgccgttt cttggggata tgcgaggttt gtgaacatta gagatggaag gggagcgacg     480
ccattacact tggctgcgcg tcaaagacgg cccgaatgtg tacatatttt gctagatagt     540
ggtgctcttg tttgtgcttc aaccggtgga tatggttgcc aggaagcac tcctcttcac      600 ttggcagcta gagggggatc tattgattgc atccgcgagc tgctggcatg gggtgcagat     660
cgccttcata gagatgtatc tgggaggatt ccgtatgcag ttgcgttgaa gcacaaacat     720
ggagcttgtg cagccttgtt aaatcctgca tctgcagagc tcttgtctg gccatcacct      780 ctaaagttca tcagtgagct taatcaggag gcaaaagctc tcttagaaaa tgccctgatg     840
gaggcaaaca aggagagaga gaagaacatt ttaaagggta ctgcatactc acttccatct     900
ccatcgcatt ctgatgtcgg agcagatgac aatatttctg aggctagtga taccgagtta     960
tgctgcatat gctttgagca ggtatgtaca attgaagtcc aagattgtgg ccatcagatg    1020
tgtgcacaat gcacactagc cctatgctgc acaacaagc caaaccctac aactgcatgc     1080
ctaacacctc cggtgtgtcc attttgccga agcaccattg cccatctagt tgttgtgaaa    1140
atcgagaacc aggaagatgc tgaccgtgac attggtgaca taagttcgcc aaagttgaga    1200
aaggcgagga agtcacgcaa cttcagcgag ggaagcagca gcttcaaagg attatccaca    1260
tcatttagca agatgggtgg ccgcggctca ggcaggattg ctgccgaaaa tgagtggatt    1320
gataagcgtt ga                                                       1332

<210> SEQ ID NO 25
<211> LENGTH: 443
<212> TYPE: PRT
<213> ORGANISM: Citrus

<400> SEQUENCE: 25

Met Gly Gln Gly Leu Ser Cys Gly Ala Ser Tyr Glu His Ala Leu Phe
1               5                   10                  15

Thr Ala Val Gln His Gly Asp Ile Glu Phe Val Asn Asp Leu Leu Glu
            20                  25                  30
```

-continued

```
Lys Asp Ser Ser Leu Leu His Gln Thr Thr Val Tyr Asp Arg His Ser
             35                  40                  45
Ala Leu His Ile Ser Ala Ala Asn Gly Gln Ile Glu Ile Leu Glu Ile
     50                  55                  60
Leu Leu Asn Arg Ser Val Asn Pro Asp Ala Val Asn Arg Tyr Lys Gln
 65                  70                  75                  80
Thr Pro Leu Met Leu Ala Ala Met His Gly Lys Ile Tyr Cys Val Lys
                 85                  90                  95
Arg Leu Leu Glu Ala Gly Ala Asn Ile Leu Met Phe Asp Ser Leu Asn
                100                 105                 110
Gly Arg Thr Cys Leu His Tyr Ala Ala Tyr Tyr Gly His Ala Asp Cys
             115                 120                 125
Val Gln Ala Ile Leu Ser Ala Ala Gln Ser Ser Pro Ile Ala Val Ser
         130                 135                 140
Trp Gly Tyr Ala Arg Phe Val Asn Ile Arg Asp Gly Arg Gly Ala Thr
145                 150                 155                 160
Pro Leu His Leu Ala Ala Arg Gln Arg Arg Pro Glu Cys Val His Ile
                165                 170                 175
Leu Leu Asp Ser Gly Ala Leu Val Cys Ala Ser Thr Gly Gly Tyr Gly
                180                 185                 190
Cys Pro Gly Ser Thr Pro Leu His Leu Ala Ala Arg Gly Gly Ser Ile
             195                 200                 205
Asp Cys Ile Arg Glu Leu Leu Ala Trp Gly Ala Asp Arg Leu His Arg
         210                 215                 220
Asp Val Ser Gly Arg Ile Pro Tyr Ala Val Ala Leu Lys His Lys His
225                 230                 235                 240
Gly Ala Cys Ala Ala Leu Leu Asn Pro Ala Ser Ala Glu Pro Leu Val
                245                 250                 255
Trp Pro Ser Pro Leu Lys Phe Ile Ser Glu Leu Asn Gln Glu Ala Lys
                260                 265                 270
Ala Leu Leu Glu Asn Ala Leu Met Glu Ala Asn Lys Glu Arg Glu Lys
             275                 280                 285
Asn Ile Leu Lys Gly Thr Ala Tyr Ser Leu Pro Ser Pro Ser His Ser
         290                 295                 300
Asp Val Gly Ala Asp Asp Asn Ile Ser Glu Ala Ser Asp Thr Glu Leu
305                 310                 315                 320
Cys Cys Ile Cys Phe Glu Gln Val Cys Thr Ile Glu Val Gln Asp Cys
                325                 330                 335
Gly His Gln Met Cys Ala Gln Cys Thr Leu Ala Leu Cys Cys His Asn
             340                 345                 350
Lys Pro Asn Pro Thr Thr Ala Cys Leu Thr Pro Val Cys Pro Phe
         355                 360                 365
Cys Arg Ser Thr Ile Ala His Leu Val Val Lys Ile Glu Asn Gln
         370                 375                 380
Glu Asp Ala Asp Arg Asp Ile Gly Asp Ile Ser Ser Pro Lys Leu Arg
385                 390                 395                 400
Lys Ala Arg Lys Ser Arg Asn Phe Ser Glu Gly Ser Ser Phe Lys
             405                 410                 415
Gly Leu Ser Thr Ser Phe Ser Lys Met Gly Gly Arg Gly Ser Gly Arg
         420                 425                 430
Ile Ala Ala Glu Asn Glu Trp Ile Asp Lys Arg
         435                 440
```

<210> SEQ ID NO 26
<211> LENGTH: 1383
<212> TYPE: DNA
<213> ORGANISM: Citrus

<400> SEQUENCE: 26

```
atgggtcaga gaatgagttg tagggaacga agtgaaagtg cattgtttgt tgccgtggag        60
aatggggact tgcagatgat tgaggctatg gtggaagctg atccaactgt cttgggaatg       120
actagtggat atggaaagca atctgcgttg catttggccg ctgcttatgg ccagatcgag       180
gttctgtcaa tgctgttgga tcagttcttt ttatatacca atacagatgc cttgaatcgc       240
tataaacaga ccccattaat ggtggctgca atgaatggga agttatcttg tgtgaaaaag       300
ctcattgaaa gtggagcatt tattctgaat tttgattctc ttcaaggaag aacttgtcta       360
cactatgctg cctactatgg ccattcagat tgcctgcaag cattacttac tgctgcccgg       420
acaagccctg tagcaaatac ttggggattt tcaagatttg ttaacataag agacgaaagt       480
ggtgctaccc cactgcactt ggctgcccgt caaggatggt ctgaatgtgt tcataccctc       540
ttagacaatg gagctcttgc ttgttcatca actggtggaa atggatatcc agggagcaca       600
ccacttcatt tgctgctcg gggaggttca ttggagtgta cgggaatt gcttgcttgg        660
ggagctgata gggttcagcc agatgcattt gggagaatac catatgcaat gctctcaag       720
tacaaacatc aagcgtgtgc agccttgctg aacccttcat ctgcagagcc tcttgtctgg       780
ccattgcaat acggaacat gactgatctt aatccagagg ccaagagct gctggagaag       840
gccttaatgg agagtaatga ggagagggag aaagccattt tgaatgagac aatctgctca       900
gttccatcaa cttcaccttc tgatgctgag gtcgatgaca atacctctga ggcaagtgac       960
gttgagctat gctgcatatg ctttgaaaat ctctgcacaa ttgagataaa gccatgtggg      1020
catcaaatgt gtgctcattg caccctagcc ctgtgttgcc acaagaagcc tgacatcata      1080
acagctgtcc cagaggtccc tgcttgcccc ttctgccgct gcagcattgc caacctagtt      1140
gctgccagaa ttatcaactc tgctaccgaa ctggacatta gtccctcaaa acccaggata      1200
tcaaggaagt cctggaattc cagcgaagga agcagcagca gcttcaaggg tttgtcagcc      1260
atgggctcat ttgtgaagat agctggcaga agttcaggaa gggtcacagc tgaatgcaat      1320
gaagcaagtg ataagctttt acacatggat gctagggatt ctccttcttg ccatgttagt      1380
tga                                                                   1383
```

<210> SEQ ID NO 27
<211> LENGTH: 460
<212> TYPE: PRT
<213> ORGANISM: Citrus

<400> SEQUENCE: 27

```
Met Gly Gln Arg Met Ser Cys Arg Glu Arg Ser Glu Ser Ala Leu Phe
1               5                   10                  15

Val Ala Val Glu Asn Gly Asp Leu Gln Met Ile Glu Ala Met Val Glu
            20                  25                  30

Ala Asp Pro Thr Val Leu Gly Met Thr Ser Gly Tyr Gly Lys Gln Ser
        35                  40                  45

Ala Leu His Leu Ala Ala Ala Tyr Gly Gln Ile Glu Val Leu Ser Met
    50                  55                  60

Leu Leu Asp Gln Phe Phe Leu Tyr Thr Asn Thr Asp Ala Leu Asn Arg
65                  70                  75                  80

Tyr Lys Gln Thr Pro Leu Met Val Ala Ala Met Asn Gly Lys Leu Ser
```

```
                85                  90                  95
Cys Val Lys Lys Leu Ile Glu Ser Gly Ala Phe Ile Leu Asn Phe Asp
            100                 105                 110

Ser Leu Gln Gly Arg Thr Cys Leu His Tyr Ala Ala Tyr Tyr Gly His
            115                 120                 125

Ser Asp Cys Leu Gln Ala Leu Leu Thr Ala Ala Arg Thr Ser Pro Val
130                 135                 140

Ala Asn Thr Trp Gly Phe Ser Arg Phe Val Asn Ile Arg Asp Glu Ser
145                 150                 155                 160

Gly Ala Thr Pro Leu His Leu Ala Ala Arg Gln Gly Trp Ser Glu Cys
                165                 170                 175

Val His Thr Leu Leu Asp Asn Gly Ala Leu Ala Cys Ser Ser Thr Gly
            180                 185                 190

Gly Asn Gly Tyr Pro Gly Ser Thr Pro Leu His Phe Ala Ala Arg Gly
            195                 200                 205

Gly Ser Leu Glu Cys Ile Arg Glu Leu Leu Ala Trp Gly Ala Asp Arg
        210                 215                 220

Val Gln Pro Asp Ala Phe Gly Arg Ile Pro Tyr Ala Ile Ala Leu Lys
225                 230                 235                 240

Tyr Lys His Gln Ala Cys Ala Leu Leu Asn Pro Ser Ser Ala Glu
                245                 250                 255

Pro Leu Val Trp Pro Leu Gln Leu Arg Asn Met Thr Asp Leu Asn Pro
            260                 265                 270

Glu Ala Lys Glu Leu Leu Glu Lys Ala Leu Met Glu Ser Asn Glu Glu
        275                 280                 285

Arg Glu Lys Ala Ile Leu Asn Glu Thr Ile Cys Ser Val Pro Ser Thr
290                 295                 300

Ser Pro Ser Asp Ala Glu Val Asp Asn Thr Ser Glu Ala Ser Asp
305                 310                 315                 320

Val Glu Leu Cys Cys Ile Cys Phe Glu Asn Leu Cys Thr Ile Glu Ile
                325                 330                 335

Lys Pro Cys Gly His Gln Met Cys Ala His Cys Thr Leu Ala Leu Cys
            340                 345                 350

Cys His Lys Lys Pro Asp Ile Ile Thr Ala Val Pro Glu Val Pro Ala
        355                 360                 365

Cys Pro Phe Cys Arg Cys Ser Ile Ala Asn Leu Val Ala Ala Arg Ile
        370                 375                 380

Ile Asn Ser Ala Thr Glu Leu Asp Ile Ser Pro Ser Lys Pro Arg Ile
385                 390                 395                 400

Ser Arg Lys Ser Trp Asn Ser Ser Glu Gly Ser Ser Ser Phe Lys
                405                 410                 415

Gly Leu Ser Ala Met Gly Ser Phe Val Lys Ile Ala Gly Arg Ser Ser
            420                 425                 430

Gly Arg Val Thr Ala Glu Cys Asn Glu Ala Ser Asp Lys Leu Leu His
        435                 440                 445

Met Asp Ala Arg Asp Ser Pro Ser Cys His Val Ser
450                 455                 460

<210> SEQ ID NO 28
<211> LENGTH: 1371
<212> TYPE: DNA
<213> ORGANISM: Arabidopsis thaliana

<400> SEQUENCE: 28
```

```
atggggcaga gtatgagctg tggaagtcga ccggagcacg gaatattcgc ctctgtacag      60
tgcggcgata tcatcactat ccgtcgtgtg atggcgacgg agcctagtct gttgaatcaa     120
actactcctt atgatcgtca ctctgttctt catgtcgctg ctgctaatgg tcagatcgag     180
attttgtcat tgcttttgga acgatttacg aatccagatt tgttgaatcg tcacaagcag     240
actccgttaa tgttggctgc gatgtatgga agaatctctt gtgtgaagaa gctagctgaa     300
gttggagcta atattttgat gtttgattct gtgaatcgaa gaacatgttt gcattacgct     360
gcttattatg gacatgctaa ttgtgttcaa gctattctct ctgctgctca atcaagtcct     420
gttgctgtcc attggggata tgcgagattt gtgaacataa gagatgataa aggagcgact     480
ccgttgcatt tagctgctcg acagagacga cctgaatgtg tgaatgtttt gttggatagt     540
ggttctcttg tttgtgcatc tactagtgta tatggttctc caggaagcac acctcttcat     600
ttagcagcta gaagtggatc tatagattgt gtcagaaagt tgcttgcttg gggtgctgat     660
cgtcttcaac gagacgcttc tgggagaata ccttatgtgg ttgcgatgaa gcataagcat     720
ggagcatgtg gagccttact taatccgtcc tctgcagagc cacttgtttg gccatcacca     780
ttaaagttca tcagtgagct taatgacgag gcgaaacttc tcttagagca ggctttaatg     840
gaggctaaca gggagagaga gaaaaccatc ctcaaaggaa cagcttattc cttaccatca     900 ccctcttttct ctgacacgga tgataacatg tccgaggtga gtgatacgga actgtgctgc     960
atttgctttg agcaagtatg tacaattgaa gttaaagact gtggtcacca atgtgtgca    1020 caatgcacac ttgcactgtg ctgtcacaac aaaccaaacc caacgacctc aaccgtgact    1080
ccaccggtct gtccgttctg tagaagcacc attgcatgtt tagtcgtcgc ccagaacaac    1140
aacaacaaca acgaaaagag caaaagccta gatgatgttg ttgttgttga tcgtgaggca    1200
ggtgatgtta gctcctccaa attcagaaaa catagaagat caataaacct tggcgaagaa    1260
agcagcagct tcatgggact atcaactatt ggatcattcg gtaggataac cggccgtggc    1320
tcgggaagga tcgcagccga aaacgagctg atggacaaac caatattgtg a             1371
```

<210> SEQ ID NO 29
<211> LENGTH: 456
<212> TYPE: PRT
<213> ORGANISM: Arabidopsis thaliana

<400> SEQUENCE: 29

```
Met Gly Gln Ser Met Ser Cys Gly Ser Arg Pro Glu His Gly Ile Phe
1               5                   10                  15

Ala Ser Val Gln Cys Gly Asp Ile Ile Thr Ile Arg Arg Val Met Ala
            20                  25                  30

Thr Glu Pro Ser Leu Leu Asn Gln Thr Thr Pro Tyr Asp Arg His Ser
        35                  40                  45

Val Leu His Val Ala Ala Ala Asn Gly Gln Ile Glu Ile Leu Ser Leu
    50                  55                  60

Leu Leu Glu Arg Phe Thr Asn Pro Asp Leu Leu Asn Arg His Lys Gln
65                  70                  75                  80

Thr Pro Leu Met Leu Ala Ala Met Tyr Gly Arg Ile Ser Cys Val Lys
                85                  90                  95

Lys Leu Ala Glu Val Gly Ala Asn Ile Leu Met Phe Asp Ser Val Asn
            100                 105                 110

Arg Arg Thr Cys Leu His Tyr Ala Ala Tyr Tyr Gly His Ala Asn Cys
        115                 120                 125

Val Gln Ala Ile Leu Ser Ala Ala Gln Ser Ser Pro Val Ala Val His
```

```
                   130                 135                 140
Trp Gly Tyr Ala Arg Phe Val Asn Ile Arg Asp Asp Lys Gly Ala Thr
145                 150                 155                 160

Pro Leu His Leu Ala Ala Arg Gln Arg Arg Pro Glu Cys Val Asn Val
                165                 170                 175

Leu Leu Asp Ser Gly Ser Leu Val Cys Ala Ser Thr Ser Val Tyr Gly
            180                 185                 190

Ser Pro Gly Ser Thr Pro Leu His Leu Ala Ala Arg Ser Gly Ser Ile
        195                 200                 205

Asp Cys Val Arg Lys Leu Leu Ala Trp Gly Ala Asp Arg Leu Gln Arg
210                 215                 220

Asp Ala Ser Gly Arg Ile Pro Tyr Val Val Ala Met Lys His Lys His
225                 230                 235                 240

Gly Ala Cys Gly Ala Leu Leu Asn Pro Ser Ser Ala Glu Pro Leu Val
                245                 250                 255

Trp Pro Ser Pro Leu Lys Phe Ile Ser Glu Leu Asn Asp Glu Ala Lys
            260                 265                 270

Leu Leu Leu Glu Gln Ala Leu Met Glu Ala Asn Arg Glu Arg Glu Lys
        275                 280                 285

Thr Ile Leu Lys Gly Thr Ala Tyr Ser Leu Pro Ser Pro Ser Phe Ser
290                 295                 300

Asp Thr Asp Asn Met Ser Glu Val Ser Asp Thr Glu Leu Cys Cys
305                 310                 315                 320

Ile Cys Phe Glu Gln Val Cys Thr Ile Glu Val Lys Asp Cys Gly His
                325                 330                 335

Gln Met Cys Ala Gln Cys Thr Leu Ala Leu Cys Cys His Asn Lys Pro
            340                 345                 350

Asn Pro Thr Thr Ser Thr Val Thr Pro Val Cys Pro Phe Cys Arg
        355                 360                 365

Ser Thr Ile Ala Cys Leu Val Val Ala Gln Asn Asn Asn Asn Asn
370                 375                 380

Glu Lys Ser Lys Ser Leu Asp Asp Val Val Val Asp Arg Glu Ala
385                 390                 395                 400

Gly Asp Val Ser Ser Ser Lys Phe Arg Lys His Arg Arg Ser Ile Asn
                405                 410                 415

Leu Gly Glu Glu Ser Ser Phe Met Gly Leu Ser Thr Ile Gly Ser
            420                 425                 430

Phe Gly Arg Ile Thr Gly Arg Gly Ser Gly Arg Ile Ala Ala Glu Asn
        435                 440                 445

Glu Leu Met Asp Lys Pro Ile Leu
450                 455

<210> SEQ ID NO 30
<211> LENGTH: 1326
<212> TYPE: DNA
<213> ORGANISM: Glycine max

<400> SEQUENCE: 30
atgggtcaga cgctgagttg cgtgcaacag cacgaggacc atggtgtgct cttccctgca      60
cttgcaagtg gagaattgga ggttgttgag gccatggtgg aggaagaccc cactgtgttg     120
gaacacacca ttggctgtga caggcttttct cctctgcatg tcgctgctgc caatggtcgg    180
atcgaggttc tttccatgtt gttggatagg tctttcaatg ttgacgtatt gaatcgacat    240
aaacagaccc cgttgatgtt ggctgtgatg catggaaaga ctggttgtgt tgagaagctt    300
```

```
attcatgccg gagcgaatat attgatgttt gattctatac gtcgaagaac ttgcttgcac    360
tacgctgctt attatgggca tatagactgc cttaaggcca ttctttctgc tgctcattcc    420
acacctgttg ctgattcttg gggatttgca agatttgtca acataagaga tggaaacggt    480
gccacccctc tgcatcttgc agctcgccat agacggtcgg aatgtcttca tgcccttta    540 gacaatggtg ctcttgtttg tgcttcaacc ggtggatatg gttaccctgg aagcacgcca    600
cttcatatgg ctgcacgtgg tggttctttg gactgtgtcc ggatgctgct tgcttgggga    660
gcggatagac ttcaattaga ttcttctggg aaaataccgt tctcagttgc tctgaagcac    720
aagcataagg catgtgctgc cctgctggat ccgtcgtcag cagcaccgct tgtttggcca    780
tccccattaa agttcatcag tgagctcaat caggaagcaa aagccttact ggaaaaggcc    840
ttactagaag ctaacaggga gagggagaag accatactaa aggagactga catgcctcca    900
tccccactgc attcagagag tgaagatgat aacattgcct ctgaggctag cgatatggag    960
ttatgttgca tatgctttga ccaagcatgc acaattgagg tcagaccctg tggccatcaa   1020
atgtgtgctc attgcaccct agcactatgc tgtcacaaaa agcctgatcc tgctactgcc   1080 ggccttctg gaccagtttg tccattttgc cgtggcacca ttcttcaatt actggttgct   1140
aagattaaca aaatcagtga tacagaagtg gaatctggcc ctatgaagcc aaggagatca   1200
cggaaatcaa atttcagtga aggaagcagc agcttcaaga gcttgtcggc catgggctca   1260
tttggaagga ttgctggccg caattccggg aagattacag atgaaaagca atgggaggtt   1320
tcttga                                                              1326
```

<210> SEQ ID NO 31
<211> LENGTH: 441
<212> TYPE: PRT
<213> ORGANISM: Glycine max

<400> SEQUENCE: 31

```
Met Gly Gln Thr Leu Ser Cys Val Gln Gln His Glu Asp His Gly Val
1               5                   10                  15

Leu Phe Pro Ala Leu Ala Ser Gly Glu Leu Glu Val Val Glu Ala Met
            20                  25                  30

Val Glu Glu Asp Pro Thr Val Leu Glu His Thr Ile Gly Cys Asp Arg
        35                  40                  45

Leu Ser Pro Leu His Val Ala Ala Ala Asn Gly Arg Ile Glu Val Leu
    50                  55                  60

Ser Met Leu Leu Asp Arg Ser Phe Asn Val Asp Val Leu Asn Arg His
65                  70                  75                  80

Lys Gln Thr Pro Leu Met Leu Ala Val Met His Gly Lys Thr Gly Cys
                85                  90                  95

Val Glu Lys Leu Ile His Ala Gly Ala Asn Ile Leu Met Phe Asp Ser
            100                 105                 110

Ile Arg Arg Arg Thr Cys Leu His Tyr Ala Ala Tyr Tyr Gly His Ile
        115                 120                 125

Asp Cys Leu Lys Ala Ile Leu Ser Ala Ala His Ser Thr Pro Val Ala
    130                 135                 140

Asp Ser Trp Gly Phe Ala Arg Phe Val Asn Ile Arg Asp Gly Asn Gly
145                 150                 155                 160

Ala Thr Pro Leu His Leu Ala Ala Arg His Arg Arg Ser Glu Cys Leu
                165                 170                 175

His Ala Leu Leu Asp Asn Gly Ala Leu Val Cys Ala Ser Thr Gly Gly
```

|     |     |     | 180 |     |     |     | 185 |     |     |     | 190 |     |
Tyr | Gly | Tyr | Pro | Gly | Ser | Thr | Pro | Leu | His | Met | Ala | Ala | Arg | Gly | Gly
        195                          200                          205

Ser | Leu | Asp | Cys | Val | Arg | Met | Leu | Leu | Ala | Trp | Gly | Ala | Asp | Arg | Leu
        210                          215                          220

Gln | Leu | Asp | Ser | Ser | Gly | Lys | Ile | Pro | Phe | Ser | Val | Ala | Leu | Lys | His
225                          230                          235                          240

Lys | His | Lys | Ala | Cys | Ala | Ala | Leu | Leu | Asp | Pro | Ser | Ser | Ala | Ala | Pro
                        245                          250                          255

Leu | Val | Trp | Pro | Ser | Pro | Leu | Lys | Phe | Ile | Ser | Glu | Leu | Asn | Gln | Glu
                260                          265                          270

Ala | Lys | Ala | Leu | Leu | Glu | Lys | Ala | Leu | Leu | Glu | Ala | Asn | Arg | Glu | Arg
            275                          280                          285

Glu | Lys | Thr | Ile | Leu | Lys | Glu | Thr | Asp | Met | Pro | Ser | Pro | Leu | His
        290                          295                          300

Ser | Glu | Ser | Glu | Asp | Asp | Asn | Ile | Ala | Ser | Glu | Ala | Ser | Asp | Met | Glu
305                          310                          315                          320

Leu | Cys | Cys | Ile | Cys | Phe | Asp | Gln | Ala | Cys | Thr | Ile | Glu | Val | Arg | Pro
                        325                          330                          335

Cys | Gly | His | Gln | Met | Cys | Ala | His | Cys | Thr | Leu | Ala | Leu | Cys | Cys | His
                    340                          345                          350

Lys | Lys | Pro | Asp | Pro | Ala | Thr | Ala | Gly | Leu | Ser | Gly | Pro | Val | Cys | Pro
                355                          360                          365

Phe | Cys | Arg | Gly | Thr | Ile | Leu | Gln | Leu | Leu | Val | Ala | Lys | Ile | Asn | Lys
        370                          375                          380

Ile | Ser | Asp | Thr | Glu | Val | Glu | Ser | Gly | Pro | Met | Lys | Pro | Arg | Arg | Ser
385                          390                          395                          400

Arg | Lys | Ser | Asn | Phe | Ser | Glu | Gly | Ser | Ser | Phe | Lys | Ser | Leu | Ser
                        405                          410                          415

Ala | Met | Gly | Ser | Phe | Gly | Arg | Ile | Ala | Gly | Arg | Asn | Ser | Gly | Lys | Ile
                420                          425                          430

Thr | Asp | Glu | Lys | Gln | Trp | Glu | Val | Ser
            435                          440

<210> SEQ ID NO 32
<211> LENGTH: 1335
<212> TYPE: DNA
<213> ORGANISM: Glycine max

<400> SEQUENCE: 32

```
atgggtcaga gcctaagttg cagtggcaac tatgaccacg gcctcttcac cgccgtgcag      60
cacggtgacc ttgaaattgt cacaactctc ttggactccg accctctctc ttgcaccaa     120 accactctct acgatcgcca ctctcctctt catattgccg ctaccaatga ccagatcgag     180
attctgtcta agctcttaga tggatctctc aacccagatg ttttaaatcg ccacaaacag     240
actccgctta tgctggcagc aatgcatggg aacatcgcgt gtgtggagaa gcttcttcaa     300
gccggagcta atgttttgat gtttgatact agttacggga gaacctgctt acactatgcc     360
gcatactacg ccattcttc ttgccttaag gctattcttt cttctgctca atctagtcca      420
gtatctgctt cttgggggtt ttctcggttt gtgaatatta gagatggaaa aggtgcaacg     480
ccattgcact ggcagctcg tcagagacgg tctgaatgtg tacatattct attagacagt      540
ggtgctcttg tttgtgcttc aactggtgga tatggctgtc ctgggagcac tcctctacat     600
ctagcagcta gagggggatc tatagattgc attcgtgaat tgttggcatg gggtgctgat     660
```

```
cgtcttcaac gcgatgcatc tgggcggata ccatatatgg ttgctctgaa acacaaacat    720
ggagcctgtg catcattgct aaatcctaca tctgcagaac ctcttgtctg ccgtctcca     780 ttgaagttca tcagtgagct taatcctgaa gccaaagctt tattagagca ggcattgatg    840
gatgcaaaca gagaaagaga gaaaaacata ttgaaaggga gttcttactc tctgccatct    900
ccatcacatt ctgatggggt agctgataat atgtctgagg ttagtgagtc cgaattatgt    960
tgcatctgct ttgagcaggt gtgcacaatt gaagttcaga actgtggcca ccagatgtgt   1020
gcacaatgca cactagccct gtgttgccac aacaagccca accctgccac tgcctgtctt   1080
actccaccag tttgtccatt ttgtcggagc acgataacaa gactcgttgt tgtgaagaca   1140
gaatgccacg atgaaactga tcaagacagt gctgatatca actgttccaa gctgagcaag   1200
tcatcaagga aactcagaca cttgaatgac agtggtagca gcagcttcaa gggactatct   1260
agtgttagtt cattcgggaa gttgggtagc cgcagctctg gaaggattgc tgctgagtgg   1320
cttgataaac agtga                                                    1335

<210> SEQ ID NO 33
<211> LENGTH: 444
<212> TYPE: PRT
<213> ORGANISM: Glycine max

<400> SEQUENCE: 33

Met Gly Gln Ser Leu Ser Cys Ser Gly Asn Tyr Asp His Gly Leu Phe
1               5                   10                  15

Thr Ala Val Gln His Gly Asp Leu Glu Ile Val Thr Thr Leu Leu Asp
            20                  25                  30

Ser Asp Pro Ser Leu Leu His Gln Thr Thr Leu Tyr Asp Arg His Ser
        35                  40                  45

Pro Leu His Ile Ala Ala Thr Asn Asp Gln Ile Glu Ile Leu Ser Lys
    50                  55                  60

Leu Leu Asp Gly Ser Leu Asn Pro Asp Val Leu Asn Arg His Lys Gln
65                  70                  75                  80

Thr Pro Leu Met Leu Ala Ala Met His Gly Asn Ile Ala Cys Val Glu
                85                  90                  95

Lys Leu Leu Gln Ala Gly Ala Asn Val Leu Met Phe Asp Thr Ser Tyr
            100                 105                 110

Gly Arg Thr Cys Leu His Tyr Ala Ala Tyr Tyr Gly His Ser Ser Cys
        115                 120                 125

Leu Lys Ala Ile Leu Ser Ser Ala Gln Ser Ser Pro Val Ser Ala Ser
    130                 135                 140

Trp Gly Phe Ser Arg Phe Val Asn Ile Arg Asp Gly Lys Gly Ala Thr
145                 150                 155                 160

Pro Leu His Leu Ala Ala Arg Gln Arg Arg Ser Glu Cys Val His Ile
                165                 170                 175

Leu Leu Asp Ser Gly Ala Leu Val Cys Ala Ser Thr Gly Gly Tyr Gly
            180                 185                 190

Cys Pro Gly Ser Thr Pro Leu His Leu Ala Ala Arg Gly Ser Ile
        195                 200                 205

Asp Cys Ile Arg Glu Leu Leu Ala Trp Gly Ala Asp Arg Leu Gln Arg
    210                 215                 220

Asp Ala Ser Gly Arg Ile Pro Tyr Met Val Ala Leu Lys His Lys His
225                 230                 235                 240

Gly Ala Cys Ala Ser Leu Leu Asn Pro Thr Ser Ala Glu Pro Leu Val
```

245                 250                 255
Trp Pro Ser Pro Leu Lys Phe Ile Ser Glu Leu Asn Pro Glu Ala Lys
            260                 265                 270

Ala Leu Leu Glu Gln Ala Leu Met Asp Ala Asn Arg Glu Arg Glu Lys
        275                 280                 285

Asn Ile Leu Lys Gly Ser Ser Tyr Ser Leu Pro Ser Pro Ser His Ser
    290                 295                 300

Asp Gly Val Ala Asp Asn Met Ser Glu Val Ser Glu Ser Glu Leu Cys
305                 310                 315                 320

Cys Ile Cys Phe Glu Gln Val Cys Thr Ile Glu Val Gln Asn Cys Gly
                325                 330                 335

His Gln Met Cys Ala Gln Cys Thr Leu Ala Leu Cys Cys His Asn Lys
            340                 345                 350

Pro Asn Pro Ala Thr Ala Cys Leu Thr Pro Val Cys Pro Phe Cys
        355                 360                 365

Arg Ser Thr Ile Thr Arg Leu Val Val Val Lys Thr Glu Cys His Asp
    370                 375                 380

Glu Thr Asp Gln Asp Ser Ala Asp Ile Asn Cys Ser Lys Leu Ser Lys
385                 390                 395                 400

Ser Ser Arg Lys Leu Arg His Leu Asn Asp Ser Gly Ser Ser Ser Phe
                405                 410                 415

Lys Gly Leu Ser Ser Val Ser Ser Phe Gly Lys Leu Gly Ser Arg Ser
            420                 425                 430

Ser Gly Arg Ile Ala Ala Glu Trp Leu Asp Lys Gln
        435                 440

<210> SEQ ID NO 34
<211> LENGTH: 1335
<212> TYPE: DNA
<213> ORGANISM: Glycine max

<400> SEQUENCE: 34
atgggtcaga gcctgagttg cagtggcaac catgaccacg gcctcttcac cgccgtgctg      60
cacggcgacc ttcaaattgt cacaactctc ttggattccg acccttctct cttgcaccaa     120
acaactctct acgatcgcca ctctcctctt catattgctg cagccaatgg ccagatcgag     180
attctgtcta ggctcttaga tggatctctt aacccagatg ttttaaatcg ccacaaacag     240
actccgctta tgttggcagc aatgcacggg aacatcgcct gtgtggagaa gcttcttcaa     300
gccggagcta atgttttgat gtttgatact atttacggga gaacctgctt acactattcc     360
gcttactacg gccattcttc ttgccttaag gctattcttt ccgctgctca atctagtcca     420
gtggctgctt cttggggggtt tgctcggttt gtgaatatta gagatggaaa aggtgcaacg     480
ccattgcact tggcggctcg tcagaggcgg tctgaatgtg tacatattct attagacagt     540
ggagctcttg tttgtgcttc aactggtgga tatggctgtc ctgggagcac tcctcttcat     600
ctagcagcta gaggaggatc tctggattgc attcgtgaat tgttggcatg ggtgcagatt     660
cgtcttcaac gcgatgcatc tgggcgtata ccatatatgg ttgcccttaa acacaaacat     720
ggagcctgtg catcattgct aaatcctaca tctgcagaac tcttgtctg gccgtctcca     780 ttgaagttca tcagtgagct aatcctgaa gccaaagctt attagagca ggccttgatg     840 gatgcaaaca gagaaagaga gaaaaacata ttgaaaggga gttcttactc tctgccatct     900
ccatctcatt ctgatggggt agctgataat acgtctgagg ttagtgaatc cgaattatgt     960
tgcatctgct ttgagcaggt gtgcacaatt gaagttcaga actgtggcca ccagatgtgt    1020

```
gcacaatgca cactagccct gtgttgccac aacaagccca accctgccac tgcctgtctt    1080
actccaccag tttgtccatt ttgtcgaagc accataacaa gacttgttgt tgtgaagacg    1140
gaatgccacg atgaaactga tcaagacagt gttgatatca actgttccaa gctgagcaag    1200
tcatcaagga aactcagaaa cttgaatgac attggtagca gcagcttcaa gggactatct    1260
agtgttagtt cattcgggaa attgggtagc cgcagctctg aaggattgc tgcagagtgg    1320 cttgataaac agtga                                                    1335
```

<210> SEQ ID NO 35
<211> LENGTH: 444
<212> TYPE: PRT
<213> ORGANISM: Glycine max

<400> SEQUENCE: 35

```
Met Gly Gln Ser Leu Ser Cys Ser Gly Asn His Asp His Gly Leu Phe
1               5                   10                  15

Thr Ala Val Leu His Gly Asp Leu Gln Ile Val Thr Thr Leu Leu Asp
            20                  25                  30

Ser Asp Pro Ser Leu Leu His Gln Thr Thr Leu Tyr Asp Arg His Ser
        35                  40                  45

Pro Leu His Ile Ala Ala Ala Asn Gly Gln Ile Glu Ile Leu Ser Arg
    50                  55                  60

Leu Leu Asp Gly Ser Leu Asn Pro Asp Val Leu Asn Arg His Lys Gln
65                  70                  75                  80

Thr Pro Leu Met Leu Ala Ala Met His Gly Asn Ile Ala Cys Val Glu
                85                  90                  95

Lys Leu Leu Gln Ala Gly Ala Asn Val Leu Met Phe Asp Thr Ile Tyr
            100                 105                 110

Gly Arg Thr Cys Leu His Tyr Ser Ala Tyr Tyr Gly His Ser Ser Cys
        115                 120                 125

Leu Lys Ala Ile Leu Ser Ala Ala Gln Ser Ser Pro Val Ala Ala Ser
    130                 135                 140

Trp Gly Phe Ala Arg Phe Val Asn Ile Arg Asp Gly Lys Gly Ala Thr
145                 150                 155                 160

Pro Leu His Leu Ala Ala Arg Gln Arg Arg Ser Glu Cys Val His Ile
                165                 170                 175

Leu Leu Asp Ser Gly Ala Leu Val Cys Ala Ser Thr Gly Gly Tyr Gly
            180                 185                 190

Cys Pro Gly Ser Thr Pro Leu His Leu Ala Ala Arg Gly Gly Ser Leu
        195                 200                 205

Asp Cys Ile Arg Glu Leu Leu Ala Trp Gly Ala Asp Arg Leu Gln Arg
    210                 215                 220

Asp Ala Ser Gly Arg Ile Pro Tyr Met Val Ala Leu Lys His Lys His
225                 230                 235                 240

Gly Ala Cys Ala Ser Leu Leu Asn Pro Thr Ser Ala Glu Pro Leu Val
                245                 250                 255

Trp Pro Ser Pro Leu Lys Phe Ile Ser Glu Leu Asn Pro Glu Ala Lys
            260                 265                 270

Ala Leu Leu Glu Gln Ala Leu Met Asp Ala Asn Arg Glu Arg Glu Lys
        275                 280                 285

Asn Ile Leu Lys Gly Ser Ser Tyr Ser Leu Pro Ser Pro Ser His Ser
    290                 295                 300

Asp Gly Val Ala Asp Asn Thr Ser Glu Val Ser Glu Ser Glu Leu Cys
```

```
                305                 310                 315                 320
            Cys Ile Cys Phe Glu Gln Val Cys Thr Ile Glu Val Gln Asn Cys Gly
                            325                 330                 335

His Gln Met Cys Ala Gln Cys Thr Leu Ala Leu Cys Cys His Asn Lys
                            340                 345                 350

Pro Asn Pro Ala Thr Ala Cys Leu Thr Pro Val Cys Pro Phe Cys
                            355                 360                 365

Arg Ser Thr Ile Thr Arg Leu Val Val Val Lys Thr Glu Cys His Asp
                370                 375                 380

Glu Thr Asp Gln Asp Ser Val Asp Ile Asn Cys Ser Lys Leu Ser Lys
            385                 390                 395                 400

Ser Ser Arg Lys Leu Arg Asn Leu Asn Asp Ile Gly Ser Ser Phe
                            405                 410                 415

Lys Gly Leu Ser Ser Val Ser Ser Phe Gly Lys Leu Gly Ser Arg Ser
                            420                 425                 430

Ser Gly Arg Ile Ala Ala Glu Trp Leu Asp Lys Gln
                            435                 440

<210> SEQ ID NO 36
<211> LENGTH: 1317
<212> TYPE: DNA
<213> ORGANISM: Glycine max

<400> SEQUENCE: 36
atgggtcaga ggctaagctg cgtgcaacag cagcacgagg agcatggtgt gctcttccca      60
gcacttgcaa gtggagaatt ggaggttgtt gaggccatgg tggaggaaga ccccactgtg     120
ttggaacaca ccactggctg tgaccgcctt tctcctctgc atgtagctgc tgccaatggt     180
cggatcgagg ttctttccat gttgttggat aggtctttca atgttgacgt attgaatcgc     240
cataaacaga ccccgttgat gttggctgtg atgcatggaa agactggttg tgttgagaag     300
cttattcatg ccggagcaag tatattgatg tttgattcta tacgtcggag aacttgcttg     360
cactatgccg cttattatgg aaatatagac tgccttaagg tcattctttc tgctgctcat     420
tccacacctg ttgcagattc ttggggattt gcaagatttg tcaacataag agatggaaac     480
ggtgccaccc ctctgcatct tgcagctcgc catagatggc cggaatgtct tcatgccctt     540
ctagacaatg tgctcttgt ttgtgcttca actggtggat atggttaccc tggaagcacg     600
ccacttcata tggctgcccg tggtggttct ttggactgtg tccggatgtt gcttgcttgg     660
ggagcagata gacttcaatt agattcttct gggaaaatac cattctcagt tgccctgaag     720
cacaagcata aggcatgtgc tgccctgctg gatccctcgt ctgcagcacc gcttgtttgg     780
ccatccccat taaagttcat cagcgagctc aatcaagaag caaaggcctt actggaaaag     840
gccttgcaag aagctaacag agagagggag aagaccatac taaggagac tgacatgcct     900 ccatccccac tgaattctga gagtgaagat gataacattg cctctgaggc tagcgatatg     960
gagttatgtt gcatatgctt tgaccaagca tgcacaattg aggtaagacc ctgtggccat    1020
caaatgtgtg ctcattgcac cctagcgcta tgctgtcaca aaaagcttga tcctgctact    1080
accggccttt ctggaccagt tgtccattt gccgtggat ccattcttca attactggtt    1140
gctaagatta acaaaatcag tgatacagaa gtggaatcta gccctatgaa gccaaggaga    1200
tcacggaaat caaatttcag tgaagggagc agcagcttca agagcttgtc ggccatgggc    1260
tcatttggaa ggattgccgg ccgcaattca gggaaaatta cagatgaaaa gcaatga      1317
```

```
<210> SEQ ID NO 37
<211> LENGTH: 438
<212> TYPE: PRT
<213> ORGANISM: Glycine max

<400> SEQUENCE: 37

Met Gly Gln Arg Leu Ser Cys Val Gln Gln His Glu His Gly
1               5                   10                  15

Val Leu Phe Pro Ala Leu Ala Ser Gly Glu Leu Glu Val Val Glu Ala
            20                  25                  30

Met Val Glu Glu Asp Pro Thr Val Leu Glu His Thr Thr Gly Cys Asp
        35                  40                  45

Arg Leu Ser Pro Leu His Val Ala Ala Asn Gly Arg Ile Glu Val
50                  55                  60

Leu Ser Met Leu Leu Asp Arg Ser Phe Asn Val Asp Val Leu Asn Arg
65                  70                  75                  80

His Lys Gln Thr Pro Leu Met Leu Ala Val Met His Gly Lys Thr Gly
                85                  90                  95

Cys Val Glu Lys Leu Ile His Ala Gly Ala Ser Ile Leu Met Phe Asp
            100                 105                 110

Ser Ile Arg Arg Thr Cys Leu His Tyr Ala Ala Tyr Tyr Gly Asn
        115                 120                 125

Ile Asp Cys Leu Lys Val Ile Leu Ser Ala Ala His Ser Thr Pro Val
130                 135                 140

Ala Asp Ser Trp Gly Phe Ala Arg Phe Val Asn Ile Arg Asp Gly Asn
145                 150                 155                 160

Gly Ala Thr Pro Leu His Leu Ala Ala Arg His Arg Trp Pro Glu Cys
                165                 170                 175

Leu His Ala Leu Leu Asp Asn Gly Ala Leu Val Cys Ala Ser Thr Gly
            180                 185                 190

Gly Tyr Gly Tyr Pro Gly Ser Thr Pro Leu His Met Ala Ala Arg Gly
        195                 200                 205

Gly Ser Leu Asp Cys Val Arg Met Leu Leu Ala Trp Gly Ala Asp Arg
210                 215                 220

Leu Gln Leu Asp Ser Ser Gly Lys Ile Pro Phe Ser Val Ala Leu Lys
225                 230                 235                 240

His Lys His Lys Ala Cys Ala Ala Leu Leu Asp Pro Ser Ser Ala Ala
                245                 250                 255

Pro Leu Val Trp Pro Ser Pro Leu Lys Phe Ile Ser Glu Leu Asn Gln
            260                 265                 270

Glu Ala Lys Ala Leu Leu Glu Lys Ala Leu Gln Glu Ala Asn Arg Glu
        275                 280                 285

Arg Glu Lys Thr Ile Leu Lys Glu Thr Asp Met Pro Pro Ser Pro Leu
290                 295                 300

Asn Ser Glu Ser Glu Asp Asp Asn Ile Ala Ser Glu Ala Ser Asp Met
305                 310                 315                 320

Glu Leu Cys Cys Ile Cys Phe Asp Gln Ala Cys Thr Ile Glu Val Arg
                325                 330                 335

Pro Cys Gly His Gln Met Cys His Cys Thr Leu Ala Leu Cys Cys
            340                 345                 350

His Lys Lys Leu Asp Pro Ala Thr Thr Gly Leu Ser Gly Pro Val Cys
        355                 360                 365

Pro Phe Cys Arg Gly Ser Ile Leu Gln Leu Leu Val Ala Lys Ile Asn
370                 375                 380
```

Lys Ile Ser Asp Thr Glu Val Glu Ser Ser Pro Met Lys Pro Arg Arg
385                 390                 395                 400

Ser Arg Lys Ser Asn Phe Ser Glu Gly Ser Ser Phe Lys Ser Leu
            405                 410                 415

Ser Ala Met Gly Ser Phe Gly Arg Ile Ala Gly Arg Asn Ser Gly Lys
            420                 425                 430

Ile Thr Asp Glu Lys Gln
        435

<210> SEQ ID NO 38
<211> LENGTH: 1317
<212> TYPE: DNA
<213> ORGANISM: Vitis vinifera

<400> SEQUENCE: 38

```
atgggtcagg ggctgagctg tggagtgagt catgagcatg gcttgttcag tgcggttcag      60
gttggggact tggagtctgt tgagtcattg ttggcgagag accccagtct cttgcatcag     120
actactgtct acgatcgcca ctctgctctt catatcgccg ctgctaatgg tcagatcgag     180
attctttcca tgattttgga tcgatctatt agtcccgatt tgttgaatcg caacaagcaa     240
actccgctta tgcttgctgc aatgcacgga aagatttcat gtgtccaaaa gctccttcaa     300
gcaggcgcca atgttttgat gtttgattcg atgcatggta gaacctgctt gcactacgcg     360
gcctattacg gccattccga ttgccttcaa gccatacttt ctgctgccca ttcaaaccct     420
gtggctgatt cgtggggatt tgcaaggttt gtaaatataa agatggcag gggagcaaca     480
cctttgcatt tagcagcccg tcaaagacgg cccgattgcg ttcatattct gttagataat     540
ggagctcttg tttgtgcttc cactggtgga tacggttgcc cagggagcac tccacttcat     600
ttggcagcca aggagggtc tctggattgc atcaggaat tgctggcttg gggtgctgat      660
cgtcttcaga gagattcatc agggagaata ccgtacgtgg ttgctcttaa gcacaagcat     720
ggagcatgtg cagccttact gaatcccaca tcagcagagc ctcttgtttg gccatctccc     780
ttgaagttca tcagtgagct taaccaggat gcaaaagctc tgctagaaca ggccttaatg     840
gaggcaaaca gggagaggga aagagcatc ttaaagggaa catcttactc gcttccatct     900
ccatctcatt ctgatgtcgc tgccagtgaa acagagcttt gctgcatatg cttcgatcag     960
gtgtgcacaa ttgaagtcca agactgcggt caccagatgt gcgctcaatg cacactagcc    1020
ctgtgttgcc acaacaagcc gaatcccacg accgcatgcc taactgcccc agtttgcccc    1080
ttctgtagaa gcggcattgc acgactggca gttgccaaga tcaagaccaa caatgaagct    1140
gacagtgacg ttggcgatgt cagctcctcc aagctgagaa gatcaagaaa gtccagaaac    1200
ttaagtgagg gaagcagcag cttcaagggc ttatcagcag tgggctcctt cagcaaaatg    1260
ggtggccggg gctctggtag aattgctgca gaaaatgagt ggatcgataa gccttga       1317
```

<210> SEQ ID NO 39
<211> LENGTH: 438
<212> TYPE: PRT
<213> ORGANISM: Vitis vinifera

<400> SEQUENCE: 39

Met Gly Gln Gly Leu Ser Cys Gly Val Ser His Glu His Gly Leu Phe
1               5                   10                  15

Ser Ala Val Gln Val Gly Asp Leu Glu Ser Val Glu Ser Leu Leu Ala
            20                  25                  30

Arg Asp Pro Ser Leu Leu His Gln Thr Thr Val Tyr Asp Arg His Ser

```
                      35                  40                  45
Ala Leu His Ile Ala Ala Asn Gly Gln Ile Glu Ile Leu Ser Met
             50                  55                  60
Ile Leu Asp Arg Ser Ile Ser Pro Asp Leu Leu Asn Arg Asn Lys Gln
65                      70                  75                  80
Thr Pro Leu Met Leu Ala Ala Met His Gly Lys Ile Ser Cys Val Gln
                     85                  90                  95
Lys Leu Leu Gln Ala Gly Ala Asn Val Leu Met Phe Asp Ser Met His
                 100                 105                 110
Gly Arg Thr Cys Leu His Tyr Ala Ala Tyr Tyr Gly His Ser Asp Cys
                 115                 120                 125
Leu Gln Ala Ile Leu Ser Ala Ala His Ser Asn Pro Val Ala Asp Ser
             130                 135                 140
Trp Gly Phe Ala Arg Phe Val Asn Ile Arg Asp Gly Arg Gly Ala Thr
145                 150                 155                 160
Pro Leu His Leu Ala Ala Arg Gln Arg Arg Pro Asp Cys Val His Ile
                 165                 170                 175
Leu Leu Asp Asn Gly Ala Leu Val Cys Ala Ser Thr Gly Tyr Gly
             180                 185                 190
Cys Pro Gly Ser Thr Pro Leu His Leu Ala Ala Arg Gly Gly Ser Leu
             195                 200                 205
Asp Cys Ile Arg Glu Leu Leu Ala Trp Gly Ala Asp Arg Leu Gln Arg
             210                 215                 220
Asp Ser Ser Gly Arg Ile Pro Tyr Val Val Ala Leu Lys His Lys His
225                 230                 235                 240
Gly Ala Cys Ala Ala Leu Leu Asn Pro Thr Ser Ala Glu Pro Leu Val
                 245                 250                 255
Trp Pro Ser Pro Leu Lys Phe Ile Ser Glu Leu Asn Gln Asp Ala Lys
             260                 265                 270
Ala Leu Leu Glu Gln Ala Leu Met Glu Ala Asn Arg Glu Arg Glu Lys
             275                 280                 285
Ser Ile Leu Lys Gly Thr Ser Tyr Ser Leu Pro Ser Pro Ser His Ser
290                 295                 300
Asp Val Ala Ala Ser Glu Thr Glu Leu Cys Cys Ile Cys Phe Asp Gln
305                 310                 315                 320
Val Cys Thr Ile Glu Val Gln Asp Cys Gly His Gln Met Cys Ala Gln
                 325                 330                 335
Cys Thr Leu Ala Leu Cys Cys His Asn Lys Pro Asn Pro Thr Thr Ala
             340                 345                 350
Cys Leu Thr Ala Pro Val Cys Pro Phe Cys Arg Ser Gly Ile Ala Arg
             355                 360                 365
Leu Ala Val Ala Lys Ile Lys Thr Asn Asn Glu Ala Asp Ser Asp Val
             370                 375                 380
Gly Asp Val Ser Ser Lys Leu Arg Arg Ser Arg Lys Ser Arg Asn
385                 390                 395                 400
Leu Ser Glu Gly Ser Ser Ser Phe Lys Gly Leu Ser Ala Val Gly Ser
                 405                 410                 415
Phe Ser Lys Met Gly Gly Arg Gly Ser Gly Arg Ile Ala Ala Glu Asn
             420                 425                 430
Glu Trp Ile Asp Lys Pro
             435

<210> SEQ ID NO 40
```

<211> LENGTH: 1317
<212> TYPE: DNA
<213> ORGANISM: Vitis vinifera

<400> SEQUENCE: 40

```
atgggtcagg ggctgagctg tggagtgagt catgagcatg gcttgttcag tgcggttcag      60
gttggggact tggagtctgt tgagtcattg ttggcgagag accccagtct cttgcatcag     120
actactgtct acgatcgcca ctctgctctt catatcgccg ctgctaatgg tcagatcgag     180
attctttcca tgattttgga tcgatctatt agtcccgatt tgttgaatcg caacaagcaa     240
actccgctta tgcttgctgc aatgcacgga aagatttcat gtgtccaaaa gctccttcaa     300
gcaggcgcca atgttttgat gtttgattcg atgcatggta gaacctgctt gcactacgcg     360
gcctattacg gccattccga ttgccttcaa gccatacttt ctgctgccca ttcaaaccct     420
gtggctgatt cgtggggatt tgcaaggttt gtaaatataa gagatggcag gggagcaaca     480
cctttgcatt tagcagcccg tcaaagacgg cccgattgcg ttcatattct gttagataat     540
ggagctcttg tttgtgcttc cactggtgga tacggttgcc cagggagcac tccacttcat     600
ttggcagcca aggagggtc tctggattgc atcaggaat tgctggcttg ggtgctgat     660
cgtcttcaga gagattcatc agggagaata ccgtacgtgg ttgctcttaa gcacaagcat     720
ggagcatgtg cagccttact gaatcccaca tcagcagagc tcttgttttg gccatctccc     780
ttgaagttca tcagtgagct taaccaggat gcaaaagctc tgctagaaca ggccttaatg     840
gaggcaaaca gggagaggga agagcatc ttaaagggaa catcttactc gcttccatct     900
ccatctcatt ctgatgtcgc tgccagtgaa acagagcttt gctgcatatg cttcgatcag     960
gtgtgcacaa ttgaagtcca agactgcggt caccagatgt gcgctcaatg cacactagcc    1020
ctgtgttgcc acaacaagcc gaatcccacg accgcatgcc taactgcccc agtttgccc     1080
ttctgtagaa gcggcattgc acgactggca gttgccaaga tcaagaccaa caatgaagct    1140
gacagtgacg ttggcgatgt cagctcctcc aagctgagaa gatcaagaaa gtccagaaac    1200
ttaagtgagg gaagcagcag cttcaagggc ttatcagcag tgggctcctt cagcaaaatg    1260
ggtggccggg gctctggtag aattgctgca gaaaatgagt ggatcgataa gccttga       1317
```

<210> SEQ ID NO 41
<211> LENGTH: 438
<212> TYPE: PRT
<213> ORGANISM: Vitis vinifera

<400> SEQUENCE: 41

```
Met Gly Gln Gly Leu Ser Cys Gly Val Ser His Glu His Gly Leu Phe
1               5                   10                  15

Ser Ala Val Gln Val Gly Asp Leu Glu Ser Val Glu Ser Leu Leu Ala
            20                  25                  30

Arg Asp Pro Ser Leu Leu His Gln Thr Thr Val Tyr Asp Arg His Ser
        35                  40                  45

Ala Leu His Ile Ala Ala Ala Asn Gly Gln Ile Glu Ile Leu Ser Met
    50                  55                  60

Ile Leu Asp Arg Ser Ile Ser Pro Asp Leu Leu Asn Arg Asn Lys Gln
65                  70                  75                  80

Thr Pro Leu Met Leu Ala Ala Met His Gly Lys Ile Ser Cys Val Gln
                85                  90                  95

Lys Leu Leu Gln Ala Gly Ala Asn Val Leu Met Phe Asp Ser Met His
            100                 105                 110
```

```
Gly Arg Thr Cys Leu His Tyr Ala Ala Tyr Gly His Ser Asp Cys
            115                 120                 125

Leu Gln Ala Ile Leu Ser Ala Ala His Ser Asn Pro Val Ala Asp Ser
130                 135                 140

Trp Gly Phe Ala Arg Phe Val Asn Ile Arg Asp Gly Arg Gly Ala Thr
145                 150                 155                 160

Pro Leu His Leu Ala Ala Arg Gln Arg Arg Pro Asp Cys Val His Ile
                165                 170                 175

Leu Leu Asp Asn Gly Ala Leu Val Cys Ala Ser Thr Gly Gly Tyr Gly
                180                 185                 190

Cys Pro Gly Ser Thr Pro Leu His Leu Ala Ala Arg Gly Gly Ser Leu
                195                 200                 205

Asp Cys Ile Arg Glu Leu Leu Ala Trp Gly Ala Asp Arg Leu Gln Arg
            210                 215                 220

Asp Ser Ser Gly Arg Ile Pro Tyr Val Val Ala Leu Lys His Lys His
225                 230                 235                 240

Gly Ala Cys Ala Ala Leu Leu Asn Pro Thr Ser Ala Glu Pro Leu Val
                245                 250                 255

Trp Pro Ser Pro Leu Lys Phe Ile Ser Glu Leu Asn Gln Asp Ala Lys
                260                 265                 270

Ala Leu Leu Glu Gln Ala Leu Met Glu Ala Asn Arg Glu Arg Glu Lys
            275                 280                 285

Ser Ile Leu Lys Gly Thr Ser Tyr Ser Leu Pro Ser Pro Ser His Ser
            290                 295                 300

Asp Val Ala Ala Ser Glu Thr Glu Leu Cys Cys Ile Cys Phe Asp Gln
305                 310                 315                 320

Val Cys Thr Ile Glu Val Gln Asp Cys Gly His Gln Met Cys Ala Gln
                325                 330                 335

Cys Thr Leu Ala Leu Cys Cys His Asn Lys Pro Asn Pro Thr Thr Ala
                340                 345                 350

Cys Leu Thr Ala Pro Val Cys Pro Phe Cys Arg Ser Gly Ile Ala Arg
            355                 360                 365

Leu Ala Val Ala Lys Ile Lys Thr Asn Asn Glu Ala Asp Ser Asp Val
370                 375                 380

Gly Asp Val Ser Ser Ser Lys Leu Arg Arg Ser Arg Lys Ser Arg Asn
385                 390                 395                 400

Leu Ser Glu Gly Ser Ser Ser Phe Lys Gly Leu Ser Ala Val Gly Ser
                405                 410                 415

Phe Ser Lys Met Gly Gly Arg Gly Ser Gly Arg Ile Ala Ala Glu Asn
            420                 425                 430

Glu Trp Ile Asp Lys Pro
            435

<210> SEQ ID NO 42
<211> LENGTH: 1335
<212> TYPE: DNA
<213> ORGANISM: Vitis vinifera

<400> SEQUENCE: 42
atgggtcagg gattgagttg tggtgaaggc gctgattaca ggttttttgg tgccgttgag      60
gatggggacg tggatttggt ggaagctatg ctggaggagg aacctagtct tttggaacag     120 agggtggca atggaggct cctgcgctt catttggcag ctgccaaagg tcggatcgag      180
gtgctttctt tgattttggc tcggtctgtc aatccggatg tcttgaatgg gcagaaacag     240
```

```
acgcctctta tgttggctgc aatgcatgga aagatatatt gcgtgcaaaa gcttcttgaa        300
gcaggagcga atattttgat gtttgattct cgtcatggaa gaacctgctt gcattatgct        360
gcttactatg gccattctga ttgcctccaa gctattcttt ctgctgccca ttccacccct        420
attgcagttt cttggggatt ttcaagattt gtgaatataa gagatggaaa gggagcaact        480
ccgttacatt tagcagcccg ccaaaggagg tctgattgtg ttcatatcct cctaagccgt        540
ggcgcattag tctgtgcttc aaccagtgga tactgctacc cgggaagtac accccttcat        600
ttggcagctc gtggagggtc cttagatact gttcgggaat gcttgcatg gggagcagat         660 cgacttcacc gagattcatc tgggagaata ccatatacag ttgccatgaa acacaagcat        720
ggagcatgtg cagccttgct gaacccttca gcagcagggc cccttgtctg gccatcacct        780
ttgaagttca tcagcacact taacccagag gcaaaagccc tgttagagag ggccctaata        840
gaggcaaaca aggagaggga aaggccata ttgaaggggaa caatctacta tcttccatcc         900
cctttgcatt ctgatggtgg gcttgatgat gatgcctctg aggccagcga agccgagcta        960
tgctgcatat gctttgacca agtctgtacg attgaagtcc aagaatgtgg tcaccagatg       1020
tgtgcccatt gcaccctggc gctatgttgc cacaacaagc ccaatcctac aacggcctgt       1080
catacagttc cagtttgttg cccttctgc cgaagtgtca ttaccagatt agttgtggcc        1140
cagatcaaga ccaacgatga cacagaattg gaattagtc ccacaaagcc aagaaaatcg        1200
agagaaggtc gaaatttcag cgaaggaagc agcagcttca agagtttatc tgcaatgggc      1260
tcatttggga agatgggtgg gcgcaatcca agaaaggttg ccaccgaatg cagcgaggaa      1320
gttgataagc cttga                                                       1335
```

<210> SEQ ID NO 43
<211> LENGTH: 444
<212> TYPE: PRT
<213> ORGANISM: Vitis vinifera

<400> SEQUENCE: 43

```
Met Gly Gln Gly Leu Ser Cys Gly Glu Gly Ala Asp Tyr Arg Phe Leu
1               5                   10                  15

Gly Ala Val Glu Asp Gly Asp Val Asp Leu Val Glu Ala Met Leu Glu
            20                  25                  30

Glu Glu Pro Ser Leu Leu Glu Gln Arg Gly Gly Asn Gly Arg Leu Pro
        35                  40                  45

Ala Leu His Leu Ala Ala Ala Lys Gly Arg Ile Glu Val Leu Ser Leu
    50                  55                  60

Ile Leu Ala Arg Ser Val Asn Pro Asp Val Leu Asn Gly Gln Lys Gln
65                  70                  75                  80

Thr Pro Leu Met Leu Ala Ala Met His Gly Lys Ile Tyr Cys Val Gln
                85                  90                  95

Lys Leu Leu Glu Ala Gly Ala Asn Ile Leu Met Phe Asp Ser Arg His
            100                 105                 110

Gly Arg Thr Cys Leu His Tyr Ala Ala Tyr Tyr Gly His Ser Asp Cys
        115                 120                 125

Leu Gln Ala Ile Leu Ser Ala Ala His Ser Thr Pro Ile Ala Val Ser
    130                 135                 140

Trp Gly Phe Ser Arg Phe Val Asn Ile Arg Asp Gly Lys Gly Ala Thr
145                 150                 155                 160

Pro Leu His Leu Ala Ala Arg Gln Arg Arg Ser Asp Cys Val His Ile
                165                 170                 175
```

```
Leu Leu Ser Arg Gly Ala Leu Val Cys Ala Ser Thr Ser Gly Tyr Cys
            180                 185                 190

Tyr Pro Gly Ser Thr Pro Leu His Leu Ala Ala Arg Gly Gly Ser Leu
        195                 200                 205

Asp Thr Val Arg Glu Leu Leu Ala Trp Gly Ala Asp Arg Leu His Arg
    210                 215                 220

Asp Ser Ser Gly Arg Ile Pro Tyr Thr Val Ala Met Lys His Lys His
225                 230                 235                 240

Gly Ala Cys Ala Ala Leu Leu Asn Pro Ser Ala Gly Pro Leu Val
                245                 250                 255

Trp Pro Ser Pro Leu Lys Phe Ile Ser Thr Leu Asn Pro Glu Ala Lys
            260                 265                 270

Ala Leu Leu Glu Arg Ala Leu Ile Glu Ala Asn Lys Glu Arg Glu Lys
        275                 280                 285

Ala Ile Leu Lys Gly Thr Ile Tyr Tyr Leu Pro Ser Pro Leu His Ser
    290                 295                 300

Asp Gly Gly Leu Asp Asp Ala Ser Glu Ala Ser Glu Ala Glu Leu
305                 310                 315                 320

Cys Cys Ile Cys Phe Asp Gln Val Cys Thr Ile Glu Val Gln Glu Cys
                325                 330                 335

Gly His Gln Met Cys Ala His Cys Thr Leu Ala Leu Cys Cys His Asn
            340                 345                 350

Lys Pro Asn Pro Thr Thr Ala Cys His Thr Val Pro Val Cys Cys Pro
        355                 360                 365

Phe Cys Arg Ser Val Ile Thr Arg Leu Val Val Ala Gln Ile Lys Thr
    370                 375                 380

Asn Asp Asp Thr Glu Leu Glu Ile Ser Pro Thr Lys Pro Arg Lys Ser
385                 390                 395                 400

Arg Glu Gly Arg Asn Phe Ser Glu Gly Ser Ser Phe Lys Ser Leu
                405                 410                 415

Ser Ala Met Gly Ser Phe Gly Lys Met Gly Gly Arg Asn Pro Arg Lys
            420                 425                 430

Val Ala Thr Glu Cys Ser Glu Glu Val Asp Lys Pro
        435                 440
```

<210> SEQ ID NO 44
<211> LENGTH: 1335
<212> TYPE: DNA
<213> ORGANISM: Mirabilis jalapa

<400> SEQUENCE: 44

```
atgggtcagg gattgagttg tggtgaaggc gctgattaca ggttttttggg tgccgttgag    60
gatgggacg tggatttggt ggaagctatg ctggaggagg aacctagtct tttggaacag   120
aggggtggca atgggaggct ccctgcgctt catttggcag ctgccaaagg tcggatcgag   180
gtgctttctt tgattttggc tcggtctgtc aatccggatg tcttgaatgg cagaaacag    240
acgcctctta tgttggctgc aatgcatgga agatatatt gcgtgcaaaa gcttcttgaa    300
gcaggagcga atattttgat gtttgattct cgtcatggaa gaacctgctt gcattatgct    360
gcttactatg gccattctga ttgcctccaa gctattcttt ctgctgccca ttccacccct    420
attgcagttt cttggggatt ttcaagattt gtgaatataa gagatggaaa gggagcaact    480
ccgttacatt tagcagcccg ccaaaggagg tctgattgtg ttcatatcct cctaagccgt    540
ggcgcattag tctgtgcttc aaccagtgga tactgctacc cgggaagtac accccttcat    600
```

```
ttggcagctc gtggagggtc cttagatact gttcgggaat tgcttgcatg gggagcagat    660
cgacttcacc gagattcatc tgggagaata ccatatacag ttgccatgaa acacaagcat    720
ggagcatgtg cagccttgct gaacccttca gcagcagggc cccttgtctg gccatcacct    780
ttgaagttca tcagcacact aacccagag  gcaaaagccc tgttagagag ggccctaata    840
gaggcaaaca aggagaggga aaggccata  ttgaagggaa caatctacta tcttccatcc    900
cctttgcatt ctgatggtgg gcttgatgat gatgcctctg aggccagcga agccgagcta    960
tgctgcatat gctttgacca agtctgtacg attgaagtcc aagaatgtgg tcaccagatg   1020
tgtgcccatt gcaccctggc gctatgttgc acaacaagc  ccaatcctac aacggcctgt   1080
catacagttc cagtttgttg ccccttctgc cgaagtgtca ttaccagatt agttgtggcc   1140
cagatcaaga ccaacgatga cacagaattg gaattagtc  ccacaaagcc aagaaaatcg   1200
agagaaggtc gaaatttcag cgaaggaagc agcagcttca agagtttatc tgcaatgggc   1260
tcatttggga agatgggtgg gcgcaatcca agaaaggttg ccaccgaatg cagcgaggaa   1320
gttgataagc cttga                                                    1335
```

<210> SEQ ID NO 45
<211> LENGTH: 446
<212> TYPE: PRT
<213> ORGANISM: Mirabilis jalapa

<400> SEQUENCE: 45

```
Met Gly Gln Ala Leu Ser Ser Gly Asp Gly Gly Gly Ser Gln His
1               5                   10                  15

Lys Met Met Gly Val Phe Gly Leu Ala Gln Lys Gly Glu Leu Lys Met
            20                  25                  30

Leu Lys Cys Glu Ile Lys Met Asp Pro Ser Leu Leu Tyr Gln Thr Cys
        35                  40                  45

Leu Tyr His Arg Gln Ser Leu Leu His Ile Ala Ala Ile Tyr Gly Gln
    50                  55                  60

Ile His Val Leu Thr Trp Leu Leu Asp Gln Ser Met Lys Pro Asp Val
65                  70                  75                  80

Leu Asn Arg Asn Lys Gln Thr Pro Leu Met Leu Ala Ala Met His Gly
                85                  90                  95

Lys Ile Ser Cys Val Glu Lys Leu Leu His Ala Gly Ala Asn Ile Leu
            100                 105                 110

Met Phe Asp Ser Leu Arg Gly Arg Thr Cys Leu His Tyr Ala Ala Tyr
        115                 120                 125

Tyr Gly His Ser Asp Cys Leu Gln Ala Ile Leu Ser Ser Ala Arg Thr
    130                 135                 140

Ser His Val Ala Leu Ser Trp Gly Phe Thr Arg Phe Val Asn Ile Arg
145                 150                 155                 160

Asp Gly Lys Gly Glu Thr Pro Leu His Leu Ala Ala Arg Gln Arg Arg
                165                 170                 175

Ala Asp Cys Val His Ile Leu Leu Asp Asn Gly Ala Leu Val Cys Ala
            180                 185                 190

Ser Thr Gly Gly Tyr Gly Tyr Ala Gly Ser Thr Pro Leu His Leu Ala
        195                 200                 205

Ala Arg Gly Gly Ser Leu Asp Cys Ile Arg Glu Leu Leu Ala Trp Gly
    210                 215                 220

Ala Asp Arg Leu Gln Arg Asp Ala Ser Gly Arg Ile Pro Tyr Thr Val
225                 230                 235                 240
```

```
Ala Leu Lys His Lys His Gly Ala Cys Ala Ala Leu Leu Asn Pro Leu
            245                 250                 255

Ser Ala Glu Pro Leu Val Trp Pro Ser Pro Leu Lys Phe Ile Ser Glu
        260                 265                 270

Leu Asn Pro Asp Ala Lys Leu Leu Glu Arg Ala Leu Leu Glu Ala
    275                 280                 285

Asn Arg Glu Arg Glu Lys Ser Ile Leu Lys Gly Thr Ala Tyr Ser Ile
290                 295                 300

Glu Ser Leu Ser Gln Ser Asp Ser Gly Asp Asp Asp Thr Ile Ser
305                 310                 315                 320

Glu Ala Ser Asp Thr Glu Val Cys Cys Ile Cys Phe Asp Gln Val Cys
                325                 330                 335

Thr Ile Glu Val Gln Asp Cys Thr His Arg Met Cys Ala His Cys Thr
            340                 345                 350

Leu Ala Leu Cys Cys His Asn Lys Pro Asn Pro Thr Thr Ala Ser Ile
        355                 360                 365

Asn Pro Pro Val Cys Pro Phe Cys Arg Ser Asn Ile Ser His Leu Val
370                 375                 380

Val Ala Lys Leu Asn Ser Glu Met Asp Asp Ile Asp Asn Asn Ser Pro
385                 390                 395                 400

Lys Leu Arg Leu Thr Arg Arg Ser Trp Asn Cys His Glu Gly Ser Ser
                405                 410                 415

Ser Phe Lys Gly Leu Ser Thr Leu Gly Lys Met Gly Gly Arg Gly Ser
            420                 425                 430

Gly Arg Ile Ser Leu Asp Glu Leu Ile Asp Lys Pro Ser Glu
        435                 440                 445

<210> SEQ ID NO 46
<211> LENGTH: 1341
<212> TYPE: DNA
<213> ORGANISM: Solanum lycopersicum

<400> SEQUENCE: 46
atgggtcagg gactgagttg tggaacgagt gatgaacatg gtttattcag tgctgttcag      60
tgtggtgatt tagacacatt aaaatctgtt ttagacaaaa acccatctct tattcatcat     120
tctactgtat atgatcgaca atctcctctt catattgctg ctgccaatgg ccagatcgag     180
attgttacta tgctgttaaa caatctatc aacccagatt tgttgaatcg ctataaacag     240
actccattga tgttagcagc aatgcatggg aagatctctt gtgtggaaaa gctaattgaa     300
gcaggagcta atattttgaa gtttgattca cttaatggaa gaacatgttt gcactatgct     360
gcatactatg gacattttga atcacttaaa gctattctat ccacagctcg tacatctcat     420
gttgcagcat cttggggata tgcaaggttt gtgaatgtta gagatggtaa aggagcaaca     480
cctttgcatt tagcagcccg tcaaagacgg cctgaatgtg ttcacatttt gctcgacaat     540
ggcgctctgg tctgcgcatc aaccggtgga tatggatttc ctggtagtac tccgcttcat     600
ttggctgcaa gaggtggttc tcttgattgc atccgtgaat gttggcgtg gggagcagat     660
cgattacata gagattccac cgggagaata ccatcacgg ttgctttaag gtaccaccat     720
ggtgcttgtg cagctttgtt gaatccttca tcggcagagc ctctcgtgtg ccatcgccg     780
ttgaagttca ttagtcagct caatgatgag gcgaaagcct tgctagaacg tgcgttaatg     840
gaagcgaata aggagaggga aaaaaatatc ttaaagggta cagattactc tccaccttcc     900
ccatcacaat ctgatgcagg gatggatgac aacatgtctg aggtcagtga tacggaagta     960
```

-continued

```
tgttgcatct gttttgatca attatgcaca attgaagtcc aggactgtgg gcaccagatg      1020
tgtgcacatt gtgtactggc cttatgctgc cacaacaagc caaacccgac cacgactagt      1080
ccaccagaac ccgtgtgccc attctgcaga agcaacattg tacagttaca agctatcaag      1140
gtcacaaaga acaatgacac agattctgat ctccactcct caaaacttcg aaagactagg      1200
agatcacgaa acttcagcga gggcagcagt agtttcaagg ggttatcagc agtaagttct      1260
tttggcaaaa tgactggtcg tggctccggt aggattgctg ctgataacga atggatcgat      1320
aagccaataa cccttgattg a                                                1341
```

<210> SEQ ID NO 47
<211> LENGTH: 446
<212> TYPE: PRT
<213> ORGANISM: Solanum lycopersicum

<400> SEQUENCE: 47

```
Met Gly Gln Gly Leu Ser Cys Gly Thr Ser Asp Glu His Gly Leu Phe
1               5                   10                  15

Ser Ala Val Gln Cys Gly Asp Leu Asp Thr Leu Lys Ser Val Leu Asp
            20                  25                  30

Lys Asn Pro Ser Leu Ile His His Ser Thr Val Tyr Asp Arg Gln Ser
        35                  40                  45

Pro Leu His Ile Ala Ala Ala Asn Gly Gln Ile Glu Ile Val Thr Met
    50                  55                  60

Leu Leu Asn Lys Ser Ile Asn Pro Asp Leu Leu Asn Arg Tyr Lys Gln
65                  70                  75                  80

Thr Pro Leu Met Leu Ala Ala Met His Gly Lys Ile Ser Cys Val Glu
                85                  90                  95

Lys Leu Ile Glu Ala Gly Ala Asn Ile Leu Lys Phe Asp Ser Leu Asn
            100                 105                 110

Gly Arg Thr Cys Leu His Tyr Ala Ala Tyr Gly His Phe Glu Ser
        115                 120                 125

Leu Lys Ala Ile Leu Ser Thr Ala Arg Thr Ser His Val Ala Ala Ser
    130                 135                 140

Trp Gly Tyr Ala Arg Phe Val Asn Val Arg Asp Gly Lys Gly Ala Thr
145                 150                 155                 160

Pro Leu His Leu Ala Ala Arg Gln Arg Arg Pro Glu Cys Val His Ile
                165                 170                 175

Leu Leu Asp Asn Gly Ala Leu Val Cys Ala Ser Thr Gly Gly Tyr Gly
            180                 185                 190

Phe Pro Gly Ser Thr Pro Leu His Leu Ala Ala Arg Gly Gly Ser Leu
        195                 200                 205

Asp Cys Ile Arg Glu Leu Leu Ala Trp Gly Ala Asp Arg Leu His Arg
    210                 215                 220

Asp Ser Thr Gly Arg Ile Pro Tyr Thr Val Ala Leu Arg Tyr His His
225                 230                 235                 240

Gly Ala Cys Ala Ala Leu Leu Asn Pro Ser Ser Ala Glu Pro Leu Val
                245                 250                 255

Trp Pro Ser Pro Leu Lys Phe Ile Ser Gln Leu Asn Asp Glu Ala Lys
            260                 265                 270

Ala Leu Leu Glu Arg Ala Leu Met Glu Ala Asn Lys Glu Arg Glu Lys
        275                 280                 285

Asn Ile Leu Lys Gly Thr Asp Tyr Ser Pro Pro Ser Pro Ser Gln Ser
    290                 295                 300
```

```
Asp Ala Gly Met Asp Asp Asn Met Ser Glu Val Ser Asp Thr Glu Val
305                 310                 315                 320

Cys Cys Ile Cys Phe Asp Gln Leu Cys Thr Ile Glu Val Gln Asp Cys
            325                 330                 335

Gly His Gln Met Cys Ala His Cys Val Leu Ala Leu Cys Cys His Asn
                340                 345                 350

Lys Pro Asn Pro Thr Thr Thr Ser Pro Pro Glu Pro Val Cys Pro Phe
            355                 360                 365

Cys Arg Ser Asn Ile Val Gln Leu Gln Ala Ile Lys Val Thr Lys Asn
        370                 375                 380

Asn Asp Thr Asp Ser Asp Leu His Ser Ser Lys Leu Arg Lys Thr Arg
385                 390                 395                 400

Arg Ser Arg Asn Phe Ser Glu Gly Ser Ser Ser Phe Lys Gly Leu Ser
                405                 410                 415

Ala Val Ser Ser Phe Gly Lys Met Thr Gly Arg Gly Ser Gly Arg Ile
            420                 425                 430

Ala Ala Asp Asn Glu Trp Ile Asp Lys Pro Ile Thr Leu Asp
        435                 440                 445
```

<210> SEQ ID NO 48
<211> LENGTH: 1356
<212> TYPE: DNA
<213> ORGANISM: Solanum lycopersicum

<400> SEQUENCE: 48

```
atggggcaga aattgagctg tggacagcaa tctaatgaac atggattgtt tattgcagtc    60
caaaatggtg aggttgaaaa agttgaagct atggttgatg aaaatccaaa tgtgattaga   120
ctgaaaactc ttcgtgggaa gctttctgca cttcatgtag ctgctgttaa tggccagatc   180
gaggttctgt gtatgctttt ggatcgcgga gttaatccag acatcttgaa tcgccacaaa   240
cagaccccat taatgttagc tgctatgcat ggaaatgtgt cctgcgtgga gaggctaatt   300
cagctaggtg ctaatatttt aatgtttgat tcactacatg gaagaacttg tttgcattac   360
gctgcttacc atggccactc tgactgccta caatctattc ttgcatccgc tcattcggct   420
cctgttgctc aatcttgggg atttgcgaga tttgtgaaca taagagatgg aagtggtgca   480
accccattgc atttagcagc acgtcatggt agaccaggat gtgtccggat tcttctaagc   540
aatgaggctc ttgtctgtgc ttctagtggt ggctatggcc gtccaggaag tacaccactg   600
catttagcag ctcgagaagg ctcttttgga ctgtgtacgtg agttacttgc ttggggtgca   660
gatcgacttt atagagattc ttctgggcga attccataca tagttgcttt gaagaacaag   720
catgaagcat gtgctgctct tttaaatcca tcatctccag agcctttaac ctggccagca   780
cctttaaagt tcattactga gcttgatgct gaggcaaaag ctttactaga aaatgctctg   840
atcgaggcca acaaagatag agagaagttg atattggaaa aacagctgt ctcacaaata    900
tcactttcgc attgtgattc tggcctcgag agtgatgact tgaggccag tgatttcgag    960
ctatgttgca tctgctttga gcaagcttgc acgattgaga tacaaaagtg cggtcatcag   1020
atgtgtgctc attgcactct ggccttatgc tgccacaata acccaatcc agctagcaat    1080
agtgagaagg ttccttatg ccccttttgc cggagtgata tcactcattt agtcgttgtc    1140
cagaataaaa tcgacactta tgaagaggta ttaagtccct cgaggccaag aaaatcaaga   1200
acgtctttca gtcatgctga aggcgacagc agcagcagca gcagcagcaa caccagcttg   1260
aaagttttgt caccccttaac ctcatttggt aagttgggtt gtcgccattc aggcaaaatc   1320
```
agtgctgaac gcattgaagt atttgctaag ccttaa                                    1356

<210> SEQ ID NO 49
<211> LENGTH: 451
<212> TYPE: PRT
<213> ORGANISM: Solanum lycopersicum

<400> SEQUENCE: 49

Met Gly Gln Lys Leu Ser Cys Gly Gln Gln Ser Asn Glu His Gly Leu
1               5                   10                  15

Phe Ile Ala Val Gln Asn Gly Glu Val Lys Val Glu Ala Met Val
            20                  25                  30

Asp Glu Asn Pro Asn Val Ile Arg Leu Lys Thr Leu Arg Gly Lys Leu
        35                  40                  45

Ser Ala Leu His Val Ala Ala Val Asn Gly Gln Ile Glu Val Leu Cys
    50                  55                  60

Met Leu Leu Asp Arg Gly Val Asn Pro Asp Ile Leu Asn Arg His Lys
65                  70                  75                  80

Gln Thr Pro Leu Met Leu Ala Ala Met His Gly Asn Val Ser Cys Val
                85                  90                  95

Glu Arg Leu Ile Gln Leu Gly Ala Asn Ile Leu Met Phe Asp Ser Leu
            100                 105                 110

His Gly Arg Thr Cys Leu His Tyr Ala Ala Tyr His Gly His Ser Asp
        115                 120                 125

Cys Leu Gln Ser Ile Leu Ala Ser Ala His Ser Ala Pro Val Ala Gln
    130                 135                 140

Ser Trp Gly Phe Ala Arg Phe Val Asn Ile Arg Asp Gly Ser Gly Ala
145                 150                 155                 160

Thr Pro Leu His Leu Ala Ala Arg His Gly Arg Pro Gly Cys Val Arg
                165                 170                 175

Ile Leu Leu Ser Asn Glu Ala Leu Val Cys Ala Ser Ser Gly Gly Tyr
            180                 185                 190

Gly Arg Pro Gly Ser Thr Pro Leu His Leu Ala Ala Arg Glu Gly Ser
        195                 200                 205

Leu Asp Cys Val Arg Glu Leu Leu Ala Trp Gly Ala Asp Arg Leu Tyr
    210                 215                 220

Arg Asp Ser Ser Gly Arg Ile Pro Tyr Ile Val Ala Leu Lys Asn Lys
225                 230                 235                 240

His Glu Ala Cys Ala Ala Leu Leu Asn Pro Ser Ser Pro Glu Pro Leu
                245                 250                 255

Thr Trp Pro Ala Pro Leu Lys Phe Ile Thr Glu Leu Asp Ala Glu Ala
            260                 265                 270

Lys Ala Leu Leu Glu Asn Ala Leu Ile Glu Ala Asn Lys Asp Arg Glu
        275                 280                 285

Lys Leu Ile Leu Glu Lys Thr Ala Val Ser Gln Ile Ser Leu Ser His
    290                 295                 300

Cys Asp Ser Gly Leu Glu Ser Asp Asp Phe Glu Ala Ser Asp Phe Glu
305                 310                 315                 320

Leu Cys Cys Ile Cys Phe Glu Gln Ala Cys Thr Ile Glu Ile Gln Lys
                325                 330                 335

Cys Gly His Gln Met Cys Ala His Cys Thr Leu Ala Leu Cys Cys His
            340                 345                 350

Asn Lys Pro Asn Pro Ala Ser Asn Ser Glu Lys Val Pro Leu Cys Pro
        355                 360                 365

```
Phe Cys Arg Ser Asp Ile Thr His Leu Val Val Gln Asn Lys Ile
        370                 375                 380
Asp Thr Tyr Glu Glu Val Leu Ser Pro Ser Arg Pro Arg Lys Ser Arg
385                 390                 395                 400
Thr Ser Phe Ser His Ala Glu Gly Asp Ser Ser Ser Ser Ser Ser
                405                 410                 415
Asn Thr Ser Leu Lys Val Leu Ser Pro Leu Thr Ser Phe Gly Lys Leu
        420                 425                 430
Gly Cys Arg His Ser Gly Lys Ile Ser Ala Glu Arg Ile Glu Val Phe
        435                 440                 445
Ala Lys Pro
    450
```

<210> SEQ ID NO 50
<211> LENGTH: 1344
<212> TYPE: DNA
<213> ORGANISM: Solanum lycopersicum

<400> SEQUENCE: 50

```
atgggtcagg ggttcagttg tggaacaagt gatgaacacg gattgtttac tgctgttcag      60
tgtggtgatt tggagactgt aaaggctctg tttgagagaa acccaagtct tgttcatcat     120
tctacagttt atgatcgaca gtctgcttta catattgctg ctgccaatgg ccaaattgag     180
gttgtttcta tgcttttaga catgtctgtt aagcctgatt tattgaatcg gtataagcag     240
actccattga tgctagcagc aatgcacggg aagatctctt gtgtgcaaaa gcttattgaa     300
gccggggcca atattttgat gtttgattca ttgaatggga ggacatgctt gcactatgcg     360
gcctattatg ggtactctga ttgtctcaaa acaattcttt ttgctgctcg gacatcacac     420
attgcgtctt cttggggata tgcccggttt gtgaacgtta atgatggtaa aggagcaaca     480
cctttgcact tagcagctcg tcaaagacgg gctgattgtg ttcatatttt actagacaat     540
ggtgctcttg cttgtgcttc taccgatgga tatggtttcc caggtagtac accacttcat     600
ttggctgcaa gagctggttc tcttgattgt atccgtgaat tgttagcatg gggagcagag     660
cgattacaaa gagatgattt ggggagaata ccatacacaa ttgctttaag atacaaacat     720
ggtgcatgtg cagcgttgct gaatccttca tctgcagagc ctcttgtctg gccatcgcca     780
ttgaagttta tcagtgagct gaataaagag gcaaaacatt tgctagaatg tgcattgatg     840
gaggctaaca aggagaggga aaagaacatc ctgaaaggaa caacttattc gccaccatcg     900
ccaaccaatt ccgataatga gatggatgac aatatctctg aggtcaatga acagaaaatt     960
tgttgtatat gcttcgatca agtatgcaca attcaggtcc aggactgcgg gcaccagatg    1020
tgtgcacatt gtgtactggc gttatgctgt cataaaaagc ctaatcctac tactaccagt    1080
cctattgtac ctgtgtgccc attctgtcgt agcaacattg ttcaattaga tgttatcaag    1140
ctggaaaagg acgatgggac tagccacgat attgtttccc cttcaaagct taggaagtct    1200
aggcgatcaa gaaacttcag cgaggggagt agcagttttta agggcttatc tgcagtaagc    1260
tctttttggaa gaatggttgg tcgtggctct ggtagaattg ctgctgaaaa cgaatacatt    1320
gataagccaa taatccttga ctaa                                            1344
```

<210> SEQ ID NO 51
<211> LENGTH: 447
<212> TYPE: PRT
<213> ORGANISM: Solanum lycopersicum

<400> SEQUENCE: 51

```
Met Gly Gln Gly Phe Ser Cys Gly Thr Ser Asp Glu His Gly Leu Phe
1               5                   10                  15

Thr Ala Val Gln Cys Gly Asp Leu Glu Thr Val Lys Ala Leu Phe Glu
            20                  25                  30

Arg Asn Pro Ser Leu Val His His Ser Thr Val Tyr Asp Arg Gln Ser
            35                  40                  45

Ala Leu His Ile Ala Ala Ala Asn Gly Gln Ile Glu Val Val Ser Met
50                      55                  60

Leu Leu Asp Met Ser Val Lys Pro Asp Leu Leu Asn Arg Tyr Lys Gln
65                      70                  75                  80

Thr Pro Leu Met Leu Ala Ala Met His Gly Lys Ile Ser Cys Val Gln
                85                  90                  95

Lys Leu Ile Glu Ala Gly Ala Asn Ile Leu Met Phe Asp Ser Leu Asn
                100                 105                 110

Gly Arg Thr Cys Leu His Tyr Ala Ala Tyr Tyr Gly Tyr Ser Asp Cys
            115                 120                 125

Leu Lys Thr Ile Leu Phe Ala Ala Arg Thr Ser His Ile Ala Ser Ser
    130                 135                 140

Trp Gly Tyr Ala Arg Phe Val Asn Val Asn Asp Gly Lys Gly Ala Thr
145                 150                 155                 160

Pro Leu His Leu Ala Ala Arg Gln Arg Arg Ala Asp Cys Val His Ile
                165                 170                 175

Leu Leu Asp Asn Gly Ala Leu Ala Cys Ala Ser Thr Asp Gly Tyr Gly
            180                 185                 190

Phe Pro Gly Ser Thr Pro Leu His Leu Ala Ala Arg Ala Gly Ser Leu
            195                 200                 205

Asp Cys Ile Arg Glu Leu Leu Ala Trp Gly Ala Glu Arg Leu Gln Arg
210                 215                 220

Asp Asp Leu Gly Arg Ile Pro Tyr Thr Ile Ala Leu Arg Tyr Lys His
225                 230                 235                 240

Gly Ala Cys Ala Ala Leu Leu Asn Pro Ser Ser Ala Glu Pro Leu Val
                245                 250                 255

Trp Pro Ser Pro Leu Lys Phe Ile Ser Glu Leu Asn Lys Glu Ala Lys
                260                 265                 270

His Leu Leu Glu Cys Ala Leu Met Glu Ala Asn Lys Glu Arg Glu Lys
            275                 280                 285

Asn Ile Leu Lys Gly Thr Thr Tyr Ser Pro Pro Ser Pro Thr Asn Ser
            290                 295                 300

Asp Asn Glu Met Asp Asp Asn Ile Ser Glu Val Asn Glu Thr Glu Ile
305                 310                 315                 320

Cys Cys Ile Cys Phe Asp Gln Val Cys Thr Ile Gln Val Gln Asp Cys
                325                 330                 335

Gly His Gln Met Cys Ala His Cys Val Leu Ala Leu Cys Cys His Lys
            340                 345                 350

Lys Pro Asn Pro Thr Thr Thr Ser Pro Ile Val Pro Val Cys Pro Phe
            355                 360                 365

Cys Arg Ser Asn Ile Val Gln Leu Asp Val Ile Lys Leu Glu Lys Asp
            370                 375                 380

Asp Gly Thr Ser His Asp Ile Val Ser Pro Ser Lys Leu Arg Lys Ser
385                 390                 395                 400

Arg Arg Ser Arg Asn Phe Ser Glu Gly Ser Ser Phe Lys Gly Leu
                405                 410                 415
```

Ser Ala Val Ser Ser Phe Gly Arg Met Val Gly Arg Gly Ser Gly Arg
            420                 425                 430

Ile Ala Ala Glu Asn Glu Tyr Ile Asp Lys Pro Ile Ile Leu Asp
        435                 440                 445

<210> SEQ ID NO 52
<211> LENGTH: 1341
<212> TYPE: DNA
<213> ORGANISM: Solanum tuberosum

<400> SEQUENCE: 52

| | |
|---|---|
| atgggtcagg gactgagttg tggaacgagt gatgaacatg ggttattctg tgctgttcag | 60 |
| ttgggtgatt tagacacatt aaaatctgtt ttagagaaaa acccatctct tattcatcat | 120 |
| tctactgtat atgatcgaca atctcctctt catattgctg ctgccaatgg ccagatcgag | 180 |
| gttgttacta tgctgttgaa caaatctatc aacccagatt tgttgaatcg ctctaagcag | 240 |
| actccattga tgttagcagc aatgcatggg aagatctctt gtgtggaaaa gctaattgaa | 300 |
| gcaggagcta atattttgaa gtttgattca cttaaaggaa gaacatgttt gcactatgct | 360 |
| gcatactatg acattttga atcacttaaa gctattctat ccacagctcg tacatctcat | 420 |
| gttgcagcat cttggggata tgcaaggttt gtgaatgtta gagatggtaa aggagcaaca | 480 |
| cctttgcatt tagcagcccg tcaaagacgg tctgaatgtg ttcacatttt gcttgacaat | 540 |
| ggcgctctgg tttgcgcgtc aactggtgga tatggatttc ctggtagcac tccacttcat | 600 |
| ttggctgcaa gaggtggctc tcttgattgc atccgtgaat tgttggcgtg gggagcagat | 660 |
| cgactacata gagattccac cgggagaata ccatacatgg ttgctttaag gtaccaccat | 720 |
| ggtgcttgtg cagctttgtt gaatccttca tcggcagagc tcttgtgtg gccatcgccg | 780 |
| ttgaagttca ttagtcagct caatgatgag gcgaaagctt tactagaacg tgcattaatg | 840 |
| gaagcgaata aggagaggga aaaaaatatc ttaaagggga cagattactc tccaccttcc | 900 |
| ccatcccaat ctgatgcagg gatggatgac aacatgtctg aggtcagtga tacagaagta | 960 |
| tgttgtatct gttttgatca attatgcaca attgaagtcc aggactgtgg gcaccagatg | 1020 |
| tgtgcacatt gtgtactggc cttatgctgc acaacaagc caaatccaac cacgactagt | 1080 |
| ccaccagaac ccgtgtgccc attctgcaga agcaacattg tacagttaca agctattaag | 1140 |
| gccacaaaga acgatgacac agattctgat ttccactcct caaagcttcg aaagactagg | 1200 |
| agatcacgaa acgtcagcga gggcagcagt agctttaagg ggttatcagc agtaaattct | 1260 |
| tttggcaaaa tgactggtcg tggctccggt aggattgctg ctgataacga atggatcgat | 1320 |
| aagccaataa cccttgattg a | 1341 |

<210> SEQ ID NO 53
<211> LENGTH: 446
<212> TYPE: PRT
<213> ORGANISM: Solanum tuberosum

<400> SEQUENCE: 53

Met Gly Gln Gly Leu Ser Cys Gly Thr Ser Asp Glu His Gly Leu Phe
1               5                   10                  15

Cys Ala Val Gln Leu Gly Asp Leu Asp Thr Leu Lys Ser Val Leu Glu
            20                  25                  30

Lys Asn Pro Ser Leu Ile His His Ser Thr Val Tyr Asp Arg Gln Ser
        35                  40                  45

Pro Leu His Ile Ala Ala Ala Asn Gly Gln Ile Glu Val Val Thr Met
    50                  55                  60

Leu Leu Asn Lys Ser Ile Asn Pro Asp Leu Leu Asn Arg Ser Lys Gln
 65                  70                  75                  80

Thr Pro Leu Met Leu Ala Ala Met His Gly Lys Ile Ser Cys Val Glu
             85                  90                  95

Lys Leu Ile Glu Ala Gly Ala Asn Ile Leu Lys Phe Asp Ser Leu Lys
            100                 105                 110

Gly Arg Thr Cys Leu His Tyr Ala Ala Tyr Gly His Phe Glu Ser
            115                 120                 125

Leu Lys Ala Ile Leu Ser Thr Ala Arg Thr Ser His Val Ala Ala Ser
        130                 135                 140

Trp Gly Tyr Ala Arg Phe Val Asn Val Arg Asp Gly Lys Gly Ala Thr
145                 150                 155                 160

Pro Leu His Leu Ala Ala Arg Gln Arg Ser Glu Cys Val His Ile
            165                 170                 175

Leu Leu Asp Asn Gly Ala Leu Val Cys Ala Ser Thr Gly Gly Tyr Gly
            180                 185                 190

Phe Pro Gly Ser Thr Pro Leu His Leu Ala Ala Arg Gly Gly Ser Leu
            195                 200                 205

Asp Cys Ile Arg Glu Leu Leu Ala Trp Gly Ala Asp Arg Leu His Arg
210                 215                 220

Asp Ser Thr Gly Arg Ile Pro Tyr Met Val Ala Leu Arg Tyr His His
225                 230                 235                 240

Gly Ala Cys Ala Ala Leu Leu Asn Pro Ser Ser Ala Glu Pro Leu Val
            245                 250                 255

Trp Pro Ser Pro Leu Lys Phe Ile Ser Gln Leu Asn Asp Glu Ala Lys
            260                 265                 270

Ala Leu Leu Glu Arg Ala Leu Met Glu Ala Asn Lys Glu Arg Glu Lys
            275                 280                 285

Asn Ile Leu Lys Gly Thr Asp Tyr Ser Pro Pro Ser Pro Gln Ser
        290                 295                 300

Asp Ala Gly Met Asp Asp Asn Met Ser Glu Val Ser Asp Thr Glu Val
305                 310                 315                 320

Cys Cys Ile Cys Phe Asp Gln Leu Cys Thr Ile Glu Val Gln Asp Cys
            325                 330                 335

Gly His Gln Met Cys Ala His Cys Val Leu Ala Leu Cys Cys His Asn
            340                 345                 350

Lys Pro Asn Pro Thr Thr Thr Ser Pro Pro Glu Pro Val Cys Pro Phe
            355                 360                 365

Cys Arg Ser Asn Ile Val Gln Leu Gln Ala Ile Lys Ala Thr Lys Asn
            370                 375                 380

Asp Asp Thr Asp Ser Asp Phe His Ser Ser Lys Leu Arg Lys Thr Arg
385                 390                 395                 400

Arg Ser Arg Asn Val Ser Glu Gly Ser Ser Phe Lys Gly Leu Ser
            405                 410                 415

Ala Val Asn Ser Phe Gly Lys Met Thr Gly Arg Gly Ser Gly Arg Ile
            420                 425                 430

Ala Ala Asp Asn Glu Trp Ile Asp Lys Pro Ile Thr Leu Asp
            435                 440                 445

<210> SEQ ID NO 54
<211> LENGTH: 1332
<212> TYPE: DNA
<213> ORGANISM: Solanum tuberosum

<400> SEQUENCE: 54

```
atgggtcagg ggctcagttg tggaacaagt gatgaacatg gattgtttac tgctgttcag      60
tgtggtgatt tggagactgt gaaggctctg tttgagagaa acccaagtct tgttcatcat     120
tgtacagttt atgatcgaca gtctgcttta catattgctg ctgccaatgg ccaaattgag     180
gttctttcta tgcttttaga caagtctgtc aagcctgatt tattgaatcg atataagcag     240
actccattga tgctagcagc aatgcacggg aagatctcct gtgtgcaaaa gcttatcgaa     300
gccggggcca atattttgat gtttgattcg ctgaatggga gaacatgctt gcactatgcg     360
gcctattatg ggcactctga ttgtctcaaa acaattcttt ttgctgctcg acatcacac     420
attgcgtctt cttggggata tgcccggttt gtgaacgtta atgatggtaa aggagcaaca     480
cctttgcact agcagctcg tcaaagacgg gctgattgtg ttcatatttt actagacaat     540
ggtgctcttg cttgtgcttc tacagatgga tatggtttcc caggtagtac accacttcat     600
ttggctgcaa gagctggttc tcttgattgt atccgtgaat tgttagcatg gggagcagag     660
cgattacaaa gagatgattt ggggagaata ccatacacaa ttgctttaag acacaaacat     720
ggtgcatgtg cagcattgct gaatccttca tctgcagagc tcttgtctg gccatcgcca     780
ttgaaattca tcagtgagct gaatgaagag caaaacatt tgctagaatg tgccctgatg     840
gaggctaaca aggagaggga aaagaacatc ctgaaggaa caacttattc gccaaccaat     900
tctgataatg ggctggatga caacatctct gaggtcaatg atacagaaat ttgttgtata     960
tgcttcgatc aagtatgcac gattcaggtc caggactgcg gcaccagat gtgtgcacat    1020
tgcgtactgg ccttatgctg tcataaaaag cctaatccta ctacaaccag tcctattgca    1080
cctgtgtgcc cattctgtcg tagcaacatt gttcaattag atgttatcaa gcttgaaaag    1140
gatgatggct cgagccacga tgtttcctcc acaaagctta ggaagtctag gcgatcaaga    1200
aacttcagcg gggggagtag tagttttaag ggcctatctg cagtaagttc tttcggaaga    1260
atggttggtc gtggctctgg tagaattgct gctgaaaacg aatacattga taagccaata    1320
atccttgact aa                                                        1332
```

<210> SEQ ID NO 55
<211> LENGTH: 443
<212> TYPE: PRT
<213> ORGANISM: Solanum tuberosum

<400> SEQUENCE: 55

```
Met Gly Gln Gly Leu Ser Cys Gly Thr Ser Asp Glu His Gly Leu Phe
1               5                   10                  15

Thr Ala Val Gln Cys Gly Asp Leu Glu Thr Val Lys Ala Leu Phe Glu
            20                  25                  30

Arg Asn Pro Ser Leu Val His His Cys Thr Val Tyr Asp Arg Gln Ser
        35                  40                  45

Ala Leu His Ile Ala Ala Ala Asn Gly Gln Ile Glu Val Leu Ser Met
    50                  55                  60

Leu Leu Asp Lys Ser Val Lys Pro Asp Leu Leu Asn Arg Tyr Lys Gln
65                  70                  75                  80

Thr Pro Leu Met Leu Ala Ala Met His Gly Lys Ile Ser Cys Val Gln
                85                  90                  95

Lys Leu Ile Glu Ala Gly Ala Asn Ile Leu Met Phe Asp Ser Leu Asn
            100                 105                 110

Gly Arg Thr Cys Leu His Tyr Ala Ala Tyr Tyr Gly His Ser Asp Cys
        115                 120                 125
```

| | | | | | | | | | | | |
|---|---|---|---|---|---|---|---|---|---|---|---|
| Leu | Lys | Thr | Ile | Leu | Phe | Ala | Ala | Arg | Thr | Ser | His | Ile | Ala | Ser | Ser |
| | 130 | | | | 135 | | | | | 140 | | | | | |

Leu Lys Thr Ile Leu Phe Ala Ala Arg Thr Ser His Ile Ala Ser Ser
    130                 135                 140

Trp Gly Tyr Ala Arg Phe Val Asn Val Asn Asp Gly Lys Gly Ala Thr
145                 150                 155                 160

Pro Leu His Leu Ala Ala Arg Gln Arg Ala Asp Cys Val His Ile
            165                 170                 175

Leu Leu Asp Asn Gly Ala Leu Ala Cys Ala Ser Thr Asp Gly Tyr Gly
            180                 185                 190

Phe Pro Gly Ser Thr Pro Leu His Leu Ala Ala Arg Ala Gly Ser Leu
        195                 200                 205

Asp Cys Ile Arg Glu Leu Leu Ala Trp Gly Ala Glu Arg Leu Gln Arg
        210                 215                 220

Asp Asp Leu Gly Arg Ile Pro Tyr Thr Ile Ala Leu Arg His Lys His
225                 230                 235                 240

Gly Ala Cys Ala Ala Leu Leu Asn Pro Ser Ser Ala Glu Pro Leu Val
            245                 250                 255

Trp Pro Ser Pro Leu Lys Phe Ile Ser Glu Leu Asn Glu Glu Ala Lys
        260                 265                 270

His Leu Leu Glu Cys Ala Leu Met Glu Ala Asn Lys Glu Arg Glu Lys
    275                 280                 285

Asn Ile Leu Lys Gly Thr Thr Tyr Ser Pro Thr Asn Ser Asp Asn Gly
290                 295                 300

Leu Asp Asp Asn Ile Ser Glu Val Asn Asp Thr Glu Ile Cys Cys Ile
305                 310                 315                 320

Cys Phe Asp Gln Val Cys Thr Ile Gln Val Asp Cys Gly His Gln
            325                 330                 335

Met Cys Ala His Cys Val Leu Ala Leu Cys Cys His Lys Lys Pro Asn
            340                 345                 350

Pro Thr Thr Thr Ser Pro Ile Ala Pro Val Cys Pro Phe Cys Arg Ser
            355                 360                 365

Asn Ile Val Gln Leu Asp Val Ile Lys Leu Glu Lys Asp Asp Gly Ser
        370                 375                 380

Ser His Asp Val Ser Ser Thr Lys Leu Arg Lys Ser Arg Arg Ser Arg
385                 390                 395                 400

Asn Phe Ser Gly Gly Ser Ser Ser Phe Lys Gly Leu Ser Ala Val Ser
            405                 410                 415

Ser Phe Gly Arg Met Val Gly Arg Gly Ser Gly Arg Ile Ala Ala Glu
        420                 425                 430

Asn Glu Tyr Ile Asp Lys Pro Ile Ile Leu Asp
    435                 440

<210> SEQ ID NO 56
<211> LENGTH: 1353
<212> TYPE: DNA
<213> ORGANISM: Solanum tuberosum

<400> SEQUENCE: 56

```
atggggcaga aattgagctg tggacaacaa tccaatgaac atggattgtt tattgcagtc      60
caaaatggtg aggttgaaaa agttgaagct atggttgatg aaaatccaaa tgtgattcga     120
cttacaactg ttcgtgggaa gttctctgca cttcatgtag ctgctattaa tggccagatc     180
gaggttctgt gtatgctttt ggatcgtggg gttaatccag acatcttgaa tcgccacaaa     240
cagactccat taatgttagc tgctatgcat ggaaatgtgt cctgcgtgga gaggctaatt     300
```

```
cagctaggtg ctaatatttt aatgtttgat tcacttcatg gaagaacttg tctgcattat    360
gctgcttacc atggccactc tgactgccta caatcgatcc ttgcatccgc tcattcggct    420
cctgttgctc aatcttgggg atttgcgaga ttcgtgaaca taagagatgg gagtggtgca    480
accccattgc atttagcagc ccgtcatggt agaccagcat gtgtccggat cttctaagc     540
aatgaggctc ttgtctgtgc ttctagtggt ggctatggcc gtccaggaag tacaccactg    600
catttagcag ctcgagaagg ttcttttgga ctgtgtacgtg agttacttgc ttggggtgca   660
gatcgacttt atagagattc ttctgggcga attccataca tagttgcatt gaagaacaag    720
catgaagcat gtgctgctct tttgaatcca tcatctccgg agcctttgac atggccatcg    780
tctttgaagt tcattactga gcttgatgcc gaggcaaaag ctttactaga aaatgctctg    840
atcgaggcca acaaagatag agagaagttg atattggaga aaacagctgt ctcacaaata    900
tcactttcgc attgtgattc tggccttgag agtgatgact ttgagggcag tgatcttgag    960
ctatgttgca tctgctttga gcaggcttgc acgattgaga tacaaaagtg cggtcatcag   1020
atgtgtgctc attgcactct ggccttatgc tgccacaata aacccaatcc agctagcaat   1080
agtgagaagg ttcctttatg cccctttgc cggagtgata tcactcattt agtcgttgtc    1140
cagaataaaa tcgacactta tgaagaggta tcgagtccct caaggccaag aaaatcaaga   1200
acgtctttca gtcatgctga aggcgacagc agcagcagca gcagtagcac cagcttgaaa   1260
gttttgtcac ccttagcctc atttgggaag ttgggttgtc gccattcagg caaaatcagt   1320
gctgaatgca ttgaagcgtt tgctaagcct taa                                1353

<210> SEQ ID NO 57
<211> LENGTH: 450
<212> TYPE: PRT
<213> ORGANISM: Solanum tuberosum

<400> SEQUENCE: 57

Met Gly Gln Lys Leu Ser Cys Gly Gln Gln Ser Asn Glu His Gly Leu
1               5                   10                  15

Phe Ile Ala Val Gln Asn Gly Glu Val Glu Lys Val Glu Ala Met Val
            20                  25                  30

Asp Glu Asn Pro Asn Val Ile Arg Leu Thr Thr Val Arg Gly Lys Phe
        35                  40                  45

Ser Ala Leu His Val Ala Ala Ile Asn Gly Gln Ile Glu Val Leu Cys
    50                  55                  60

Met Leu Leu Asp Arg Gly Val Asn Pro Asp Ile Leu Asn Arg His Lys
65                  70                  75                  80

Gln Thr Pro Leu Met Leu Ala Ala Met His Gly Asn Val Ser Cys Val
                85                  90                  95

Glu Arg Leu Ile Gln Leu Gly Ala Asn Ile Leu Met Phe Asp Ser Leu
            100                 105                 110

His Gly Arg Thr Cys Leu His Tyr Ala Ala Tyr His Gly His Ser Asp
        115                 120                 125

Cys Leu Gln Ser Ile Leu Ala Ser Ala His Ser Ala Pro Val Ala Gln
    130                 135                 140

Ser Trp Gly Phe Ala Arg Phe Val Asn Ile Arg Asp Gly Ser Gly Ala
145                 150                 155                 160

Thr Pro Leu His Leu Ala Ala Arg His Gly Arg Pro Ala Cys Val Arg
                165                 170                 175

Ile Leu Leu Ser Asn Glu Ala Leu Val Cys Ala Ser Ser Gly Gly Tyr
            180                 185                 190
```

```
Gly Arg Pro Gly Ser Thr Pro Leu His Leu Ala Ala Arg Glu Gly Ser
            195                 200                 205
Leu Asp Cys Val Arg Glu Leu Leu Ala Trp Gly Ala Asp Arg Leu Tyr
    210                 215                 220
Arg Asp Ser Ser Gly Arg Ile Pro Tyr Ile Val Ala Leu Lys Asn Lys
225                 230                 235                 240
His Glu Ala Cys Ala Ala Leu Leu Asn Pro Ser Ser Pro Glu Pro Leu
                245                 250                 255
Thr Trp Pro Ser Ser Leu Lys Phe Ile Thr Glu Leu Asp Ala Glu Ala
            260                 265                 270
Lys Ala Leu Leu Glu Asn Ala Leu Ile Glu Ala Asn Lys Asp Arg Glu
        275                 280                 285
Lys Leu Ile Leu Glu Lys Thr Ala Val Ser Gln Ile Ser Leu Ser His
    290                 295                 300
Cys Asp Ser Gly Leu Glu Ser Asp Asp Phe Glu Gly Ser Asp Leu Glu
305                 310                 315                 320
Leu Cys Cys Ile Cys Phe Glu Gln Ala Cys Thr Ile Glu Ile Gln Lys
                325                 330                 335
Cys Gly His Gln Met Cys Ala His Cys Thr Leu Ala Leu Cys Cys His
            340                 345                 350
Asn Lys Pro Asn Pro Ala Ser Asn Ser Glu Lys Val Pro Leu Cys Pro
        355                 360                 365
Phe Cys Arg Ser Asp Ile Thr His Leu Val Val Gln Asn Lys Ile
    370                 375                 380
Asp Thr Tyr Glu Glu Val Ser Pro Ser Arg Pro Arg Lys Ser Arg
385                 390                 395                 400
Thr Ser Phe Ser His Ala Glu Gly Asp Ser Ser Ser Ser Ser Ser
                405                 410                 415
Thr Ser Leu Lys Val Leu Ser Pro Leu Ala Ser Phe Gly Lys Leu Gly
            420                 425                 430
Cys Arg His Ser Gly Lys Ile Ser Ala Glu Cys Ile Glu Ala Phe Ala
        435                 440                 445
Lys Pro
    450

<210> SEQ ID NO 58
<211> LENGTH: 1398
<212> TYPE: DNA
<213> ORGANISM: Sorghum bicolor

<400> SEQUENCE: 58
atggggcacg gcgtcagctg cgcccgcacc ggcgacgagc acgactactt ccgcgcggcg      60
caggtcgggg acctcgacgc cctgggcgcg ctcctcgccg ctgacccctc cctcgcccgc     120
cgcgccaccc tctacgaccg cctctccgcg ctccacatcg ccgccgcgaa tggccgcctc     180
gaggtgctgt ccatggtcct ggatcacggg gtgccgccgg acgcggtgaa tcggcacaag     240
cagactccgc tgatgcttgc ggcgatgcac ggcaagatcg actgcgtgct caagctcctg     300
caggccggcg ccaatatcct gatgttcgac tccctgcacg gcggtcctg cctgcaccac     360 gcgtcctact tcggcaacgt cgactgcctg caggccatcc tcacggcggc gcggaccacg     420
ccggtggccg actcatgggg tttcgcccgg ttcgtcaacg tcaggacga ccacggcgcc     480 acgccgctgc acctcgccgc caggcagggc cgacccggct gcgtgcaggt gctgctggag     540
aacggcgcca ttgtctccgc cctcaccggc tcctacgggt tccccggcag cacgtcgctg     600
```

```
catctggccg ctcgcagcgg gaacctggat tgcatccgga agctgctcgc ctggggcgca      660
gatcgtctcc agagggactc agcagggagg attccatatg ccgttgcgct gaagcgcaat      720
cacgaggcgt gtgcggcgct gctgaaccct tcgtcggcag agcccatggt gtggccttcc      780
ccgctcaagt tcatcagcga gctagacccg gaggcgaagg ctctcctgga agcggcactg      840
atggaagcca acaggagag ggagaagaag atcctgaagg cacaaagta ttctccgcca        900 tcatcgccac cttccacttg cgagcatgag attgatgccg atgccattga tgatgtgtcg      960
tcagagacga gcgacacgga gctgtgctgc atctgcttcg accaggcgtg cacgatcgag     1020
gtgcaagact gcggtcacca gatgtgcgcg ccatgcacac tagccctgtg ctgccacagc     1080
aagcccaacc cgacgacgct gacactgccg tcgccggcct gcccattctg ccgcggcaac     1140
atctcacggc tactggtggc ccgagcaagc accgcgtcgt tggacgccga caccgacaag     1200
gctgctgcgg cggcggcctc ctcacctcag ctggtccggc ggcggtcccg gcggtctcac     1260
aacctcagtg acggcgggag cagcagcttc aagggctgt cgtccgccgt ggccgggtcc      1320
ttctccaaga tcgggcgcgg gtcgagccgg atggccgaca gcgacaatgg catggacaag     1380
cccgagcacg acctgtga                                                   1398
```

<210> SEQ ID NO 59
<211> LENGTH: 465
<212> TYPE: PRT
<213> ORGANISM: Sorghum bicolor

<400> SEQUENCE: 59

```
Met Gly His Gly Val Ser Cys Ala Arg Thr Gly Asp Glu His Asp Tyr
1               5                   10                  15

Phe Arg Ala Ala Gln Val Gly Asp Leu Asp Ala Leu Gly Ala Leu Leu
            20                  25                  30

Ala Ala Asp Pro Ser Leu Ala Arg Arg Ala Thr Leu Tyr Asp Arg Leu
        35                  40                  45

Ser Ala Leu His Ile Ala Ala Asn Gly Arg Leu Glu Val Leu Ser
    50                  55                  60

Met Val Leu Asp His Gly Val Pro Pro Asp Ala Val Asn Arg His Lys
65                  70                  75                  80

Gln Thr Pro Leu Met Leu Ala Ala Met His Gly Lys Ile Asp Cys Val
                85                  90                  95

Leu Lys Leu Leu Gln Ala Gly Ala Asn Ile Leu Met Phe Asp Ser Leu
            100                 105                 110

His Gly Arg Ser Cys Leu His His Ala Ser Tyr Phe Gly Asn Val Asp
        115                 120                 125

Cys Leu Gln Ala Ile Leu Thr Ala Arg Thr Thr Pro Val Ala Asp
    130                 135                 140

Ser Trp Gly Phe Ala Arg Phe Val Asn Val Arg Asp His Gly Ala
145                 150                 155                 160

Thr Pro Leu His Leu Ala Ala Arg Gln Gly Arg Pro Gly Cys Val Gln
                165                 170                 175

Val Leu Leu Glu Asn Gly Ala Ile Val Ser Ala Leu Thr Gly Ser Tyr
            180                 185                 190

Gly Phe Pro Gly Ser Thr Ser Leu His Leu Ala Ala Arg Ser Gly Asn
        195                 200                 205

Leu Asp Cys Ile Arg Lys Leu Leu Ala Trp Gly Ala Asp Arg Leu Gln
    210                 215                 220
```

```
Arg Asp Ser Ala Gly Arg Ile Pro Tyr Ala Val Ala Leu Lys Arg Asn
225                 230                 235                 240

His Glu Ala Cys Ala Ala Leu Leu Asn Pro Ser Ser Ala Glu Pro Met
                245                 250                 255

Val Trp Pro Ser Pro Leu Lys Phe Ile Ser Glu Leu Asp Pro Glu Ala
                260                 265                 270

Lys Ala Leu Leu Glu Ala Ala Leu Met Glu Ala Asn Arg Glu Arg Glu
            275                 280                 285

Lys Lys Ile Leu Lys Gly Thr Lys Tyr Ser Pro Ser Ser Pro Pro
290                 295                 300

Ser Thr Cys Glu His Glu Ile Asp Ala Asp Ala Ile Asp Asp Val Ser
305                 310                 315                 320

Ser Glu Thr Ser Asp Thr Glu Leu Cys Cys Ile Cys Phe Asp Gln Ala
                325                 330                 335

Cys Thr Ile Glu Val Gln Asp Cys Gly His Gln Met Cys Ala Pro Cys
                340                 345                 350

Thr Leu Ala Leu Cys Cys His Ser Lys Pro Asn Pro Thr Thr Leu Thr
                355                 360                 365

Leu Pro Ser Pro Ala Cys Pro Phe Cys Arg Gly Asn Ile Ser Arg Leu
370                 375                 380

Leu Val Ala Arg Ala Ser Thr Ala Ser Leu Asp Ala Asp Thr Asp Lys
385                 390                 395                 400

Ala Ala Ala Ala Ala Ser Ser Pro Gln Leu Val Arg Arg Ser
                405                 410                 415

Arg Arg Ser His Asn Leu Ser Asp Gly Gly Ser Ser Ser Phe Lys Gly
                420                 425                 430

Leu Ser Ser Ala Val Ala Gly Ser Phe Ser Lys Ile Gly Arg Gly Ser
                435                 440                 445

Ser Arg Met Ala Asp Ser Asp Asn Gly Met Asp Lys Pro Glu His Asp
            450                 455                 460

Leu
465

<210> SEQ ID NO 60
<211> LENGTH: 1455
<212> TYPE: DNA
<213> ORGANISM: Sorghum bicolor

<400> SEQUENCE: 60
atgggccacg gcctcagctg cagccgcgac ggcggcgagg agcacgactt gttccgcgcg      60
gtgcagctcg gcgacctgga cgccctcctc gccgccgacc cggagctcgc ccgccacgcc     120
accaccatat acgaccgtct gtccctgctc cacatcgccg ccgctaatgg ccagctgcag     180
gtgctctcca tgttgttgga tgacgatggc gccggcgggg cacacgcacc ggcacgcccc     240
gacgtggacg tgctcaaccg gaagaagcag accccgttga tgctggcggc catgcacggc     300
aggacggact gcgtgctcag gctgctagaa gcgggagcaa atatcctgat gttcgactcg     360
gtacacgcgc ggacatgcct ccaccacgcg gcctactacg ccatgccga ctgtctccaa     420 gccatcctct cggctgccaa ggcctccccg gtggccgact catggggctt cgcgcgcttc     480
gtgaacgtca gggacgagca cggcgccacg ccgctgcacc tggcggccag gcaggggcgg     540
ccgcagtgcg tccaccacct gctccacgcc ggcgccatcg tctccgctcc aacagcctcc     600
tacggcttcc ccggcagcac ggcgctgcac ctggctgcac gccgcggcaa cctggactgc     660 gtccggggagc tcctcgccctg gggcgctgat cgcctccaca gggactcggc ggggaggatc     720
```

```
gcctacgcgg tggccctcag gcgcagccac cgagcgtgcg ccgcgctgct gaacccggcg      780
gcggcggagc ccatggtgtg gccttccccg ctcaagctca tcagcgagct caacccggag      840
gccaaggccc tcctggaggc ggccctgatg gaagccaaca gggagcggga gaagcagatc      900
attgtcaacc tcaagggcgg caccacaacc aaaaccaagt cgtcatactc gtcgtcgtct      960
gctcatgatg atgatggcac cgccgtcgcc agcagaagcc agcttgacga cgacgacgac     1020
gccaccgagc tgtgcggcat ctgcctggag caggcgtgca gcatggagat gcaggactgt     1080
gggcaccaga tgtgtgctgc ctgcacgctg gcgctgtgct gccacagcaa gcccaacccg     1140
acgaccctgg ctctgcagcc gccggcctgc ccgttctgcc gcgccaccat cacccggctg     1200
ctggtggcca acaacaagac tagcaacagc agtgatgagg cagccctagg cggcggcgtt     1260
aggtcccatt cccatggtag cagcagcttc agggggctca cctcggccat caggtccttg     1320
tccttgtcca ggattggtcg tcgtggctcc gggagggtag ccgacagcga cggcatatgc     1380
catggacaag cctccacacc atgtggtgtc aacagcttat tacccgcaca agcaataatc     1440
cagtcattct tttga                                                      1455
```

<210> SEQ ID NO 61
<211> LENGTH: 484
<212> TYPE: PRT
<213> ORGANISM: Sorghum bicolor

<400> SEQUENCE: 61

```
Met Gly His Gly Leu Ser Cys Ser Arg Asp Gly Gly Glu Glu His Asp
1               5                   10                  15

Leu Phe Arg Ala Val Gln Leu Gly Asp Leu Asp Ala Leu Leu Ala Ala
                20                  25                  30

Asp Pro Glu Leu Ala Arg His Ala Thr Thr Ile Tyr Asp Arg Leu Ser
            35                  40                  45

Leu Leu His Ile Ala Ala Ala Asn Gly Gln Leu Gln Val Leu Ser Met
        50                  55                  60

Leu Leu Asp Asp Asp Gly Ala Gly Gly Ala His Ala Pro Ala Arg Pro
65                  70                  75                  80

Asp Val Asp Val Leu Asn Arg Lys Lys Gln Thr Pro Leu Met Leu Ala
                85                  90                  95

Ala Met His Gly Arg Thr Asp Cys Val Leu Arg Leu Leu Glu Ala Gly
            100                 105                 110

Ala Asn Ile Leu Met Phe Asp Ser Val His Ala Arg Thr Cys Leu His
        115                 120                 125

His Ala Ala Tyr Tyr Gly His Ala Asp Cys Leu Gln Ala Ile Leu Ser
    130                 135                 140

Ala Ala Lys Ala Ser Pro Val Ala Asp Ser Trp Gly Phe Ala Arg Phe
145                 150                 155                 160

Val Asn Val Arg Asp Glu His Gly Ala Thr Pro Leu His Leu Ala Ala
                165                 170                 175

Arg Gln Gly Arg Pro Gln Cys Val His His Leu Leu His Ala Gly Ala
            180                 185                 190

Ile Val Ser Ala Pro Thr Ala Ser Tyr Gly Phe Pro Gly Ser Thr Ala
        195                 200                 205

Leu His Leu Ala Ala Arg Arg Gly Asn Leu Asp Cys Val Arg Glu Leu
    210                 215                 220

Leu Ala Trp Gly Ala Asp Arg Leu His Arg Asp Ser Ala Gly Arg Ile
225                 230                 235                 240
```

```
Ala Tyr Ala Val Ala Leu Arg Arg Ser His Arg Ala Cys Ala Ala Leu
            245                 250                 255

Leu Asn Pro Ala Ala Glu Pro Met Val Trp Pro Ser Pro Leu Lys
        260                 265                 270

Leu Ile Ser Glu Leu Asn Pro Glu Ala Lys Ala Leu Leu Glu Ala Ala
        275                 280                 285

Leu Met Glu Ala Asn Arg Glu Arg Glu Lys Gln Ile Ile Val Asn Leu
        290                 295                 300

Lys Gly Gly Thr Thr Lys Thr Lys Ser Ser Tyr Ser Ser Ser Ser
305                 310                 315                 320

Ala His Asp Asp Asp Gly Thr Ala Val Ala Ser Arg Ser Gln Leu Asp
            325                 330                 335

Asp Asp Asp Ala Thr Glu Leu Cys Gly Ile Cys Leu Glu Gln Ala
            340                 345                 350

Cys Ser Met Glu Met Gln Asp Cys Gly His Gln Met Cys Ala Ala Cys
        355                 360                 365

Thr Leu Ala Leu Cys Cys His Ser Lys Pro Asn Pro Thr Thr Leu Ala
        370                 375                 380

Leu Gln Pro Pro Ala Cys Pro Phe Cys Arg Ala Thr Ile Thr Arg Leu
385                 390                 395                 400

Leu Val Ala Asn Asn Lys Thr Ser Asn Ser Ser Asp Glu Ala Ala Leu
                405                 410                 415

Gly Gly Gly Val Arg Ser His Ser His Gly Ser Ser Ser Phe Arg Gly
                420                 425                 430

Leu Thr Ser Ala Ile Arg Ser Leu Ser Leu Ser Arg Ile Gly Arg Arg
        435                 440                 445

Gly Ser Gly Arg Val Ala Asp Ser Asp Gly Ile Cys His Gly Gln Ala
450                 455                 460

Ser Thr Pro Cys Gly Val Asn Ser Leu Leu Pro Ala Gln Ala Ile Ile
465                 470                 475                 480

Gln Ser Phe Phe

<210> SEQ ID NO 62
<211> LENGTH: 1347
<212> TYPE: DNA
<213> ORGANISM: Sorghum bicolor

<400> SEQUENCE: 62
atggggcacg gcgctagctg cggccgccca agcgacgagg tagacttctt cggcgcggcg      60
caggccgggg acacggcccg cctcgccgcc gcgcttcgct cccgcccac cttgctcacc      120 cgcaccacgc tcttcgaccg cctctccgcg ctccacatcg ccgccgcgca cggccacctc      180
caggtggtct ctctggcatt ggatctttgc gtgcaccccg acgtcgttaa ccgccacaag      240
cagacggcgt tgatgctcgc ggcgatgcac gggaagaccg actgcgtccg gcggctgctc      300
gacgccggcg ccaatatcgt gatgttcgat tcctcgcacg gcggacgtg cctgcactac      360 gcggcgtact acgggcacgc ggactgcctc cggaccatcc tctcggcggc caagtccgcg      420
ccggtctcgg aatcctgggg gttcgcgcgc ttcgtgaacg tgcgggacga caccggggcg      480
acgccgctgc accttgcggc gaggcagggc tggcggcgct gtgtccacgt cctgctcgag      540
aacggcgcca tcgtgtccgc ctcaagtggc gccttcggat ccccgggag cacgccgctg      600 catttggccg cgcgcggcgg caacctggac tgcgtccggc aactcctctc ctggggcgcc      660
gaccgcctcc agcgagactc cgtcgggaga attccgtatg aggtcgcagt gaagcgaggc      720
```

-continued

```
cacgtcgcgt gcgcggcgct gctgaacccg tcatcggcgg agcccctggt ctggccgtcc    780
gctctcaagt tcatcagcga gctggaaccc aacgccaagt ccctgctcga agcagcgctg    840
atggaggcca atagagagag ggagaggagg atcctcaaag ggactaagaa tgcactgccg    900
tcgccatcgc accccgatga cggcgctcat gacacggcca tagccgaggc tagcgacgcg    960
gaggtgtgca gcatctgctt cgagcaggcg tgcagcatcg aggtccggga gtgcgggcac   1020
cagatgtgct cggcgtgcac gctggcgctg tgctgccacg ccaagcccaa cccggcgacg   1080
cagtcccagc cgcagccgac ctgcccgttc tgccgcggcg catcgcgcg ctggtggtg    1140 gcgacgcgga cgagggccgg cgacgacgaa gacgacgagg agcggggcag gctggagtcg   1200
cccaggcacc ggcggtcccg ccggtccatg aacctcagcg cgacgcggg cagcaccagc   1260 acactcatgg gcagcatcgc ctcctccatc ggcaagatgg gccgccggcg aacagatagc   1320
agcgagcagg tcgacgtcaa gccgtag                                      1347
```

<210> SEQ ID NO 63
<211> LENGTH: 448
<212> TYPE: PRT
<213> ORGANISM: Sorghum bicolor

<400> SEQUENCE: 63

```
Met Gly His Gly Ala Ser Cys Gly Arg Pro Ser Asp Glu Val Asp Phe
1               5                   10                  15

Phe Gly Ala Ala Gln Ala Gly Asp Thr Ala Arg Leu Ala Ala Ala Leu
                20                  25                  30

Arg Ser Arg Pro Thr Leu Leu Thr Arg Thr Thr Leu Phe Asp Arg Leu
            35                  40                  45

Ser Ala Leu His Ile Ala Ala Ala His Gly His Leu Gln Val Val Ser
        50                  55                  60

Leu Ala Leu Asp Leu Cys Val His Pro Asp Val Val Asn Arg His Lys
65                  70                  75                  80

Gln Thr Ala Leu Met Leu Ala Ala Met His Gly Lys Thr Asp Cys Val
                85                  90                  95

Arg Arg Leu Leu Asp Ala Gly Ala Asn Ile Val Met Phe Asp Ser Ser
            100                 105                 110

His Gly Arg Thr Cys Leu His Tyr Ala Ala Tyr Tyr Gly His Ala Asp
        115                 120                 125

Cys Leu Arg Thr Ile Leu Ser Ala Ala Lys Ser Ala Pro Val Ser Glu
    130                 135                 140

Ser Trp Gly Phe Ala Arg Phe Val Asn Val Arg Asp Asp Thr Gly Ala
145                 150                 155                 160

Thr Pro Leu His Leu Ala Ala Arg Gln Gly Trp Arg Arg Cys Val His
                165                 170                 175

Val Leu Leu Glu Asn Gly Ala Ile Val Ser Ala Ser Gly Ala Phe
            180                 185                 190

Gly Phe Pro Gly Ser Thr Pro Leu His Leu Ala Ala Arg Gly Gly Asn
        195                 200                 205

Leu Asp Cys Val Arg Gln Leu Leu Ser Trp Gly Ala Asp Arg Leu Gln
    210                 215                 220

Arg Asp Ser Val Gly Arg Ile Pro Tyr Glu Val Ala Val Lys Arg Gly
225                 230                 235                 240

His Val Ala Cys Ala Ala Leu Leu Asn Pro Ser Ser Ala Glu Pro Leu
                245                 250                 255
```

```
Val Trp Pro Ser Ala Leu Lys Phe Ile Ser Glu Leu Glu Pro Asn Ala
            260                 265                 270

Lys Ser Leu Leu Glu Ala Ala Leu Met Glu Ala Asn Arg Glu Arg Glu
        275                 280                 285

Arg Arg Ile Leu Lys Gly Thr Lys Asn Ala Leu Pro Ser Pro Ser His
    290                 295                 300

Pro Asp Asp Gly Ala His Asp Thr Ala Ile Ala Glu Ala Ser Asp Ala
305                 310                 315                 320

Glu Val Cys Ser Ile Cys Phe Glu Gln Ala Cys Ser Ile Glu Val Arg
                325                 330                 335

Glu Cys Gly His Gln Met Cys Ser Ala Cys Thr Leu Ala Leu Cys Cys
            340                 345                 350

His Ala Lys Pro Asn Pro Ala Thr Gln Ser Gln Pro Gln Pro Thr Cys
        355                 360                 365

Pro Phe Cys Arg Gly Gly Ile Ala Arg Leu Val Val Ala Thr Arg Thr
370                 375                 380

Arg Ala Gly Asp Asp Glu Asp Glu Glu Arg Gly Arg Leu Glu Ser
385                 390                 395                 400

Pro Arg His Arg Arg Ser Arg Arg Ser Met Asn Leu Ser Gly Asp Ala
                405                 410                 415

Gly Ser Thr Ser Thr Leu Met Gly Ser Ile Ala Ser Ile Gly Lys
            420                 425                 430

Met Gly Arg Arg Arg Thr Asp Ser Ser Glu Gln Val Asp Val Lys Pro
                435                 440                 445
```

```
<210> SEQ ID NO 64
<211> LENGTH: 1341
<212> TYPE: DNA
<213> ORGANISM: Zea mays

<400> SEQUENCE: 64
atggggcacg gcgtcagctg cgctcgcacg ggcgacgagc acaactactt ccgcgcggcg      60
caggtcgggg acctcgacgc cctggacgcg ctcctcgccg ccgacccctc cctcgcccgc     120
cgcgccacgc tctacgaccg cctctccgcg ctgcacatca ccgccgcgaa tggccacctc     180
gaggtgatgt ccatgatctt ggatcacggg gtgccgccgg acgccgtgaa ccggcacaag     240
cagacgccgc tgatgctcgc ggcgatgcac ggcaagatcg actgcgcgcg gaagctcctg     300
gaggccggcg ccaatatcct gatgttcgac tccctgcacg gcggacctg  cctgcaccac     360 gcgtcctact tcggccacgt cgactgcctg cgggccatcc tcgcggcggc gcggaccacg     420
ccggtggccg actcatgggg tttcgcccgg ttcgtcaacg tcagggacga ccgcggcgcc     480
acgccgctgc acctcgccgc caggcagggc cgctccgcct gcgtgcaggt gctgctggag     540
aacggcgcca ttgtctccgc cctcaccggc tcctacgggt tccccggcag cacgtcgctg     600
catctggccg ctcgaagcgg gaacctggac tgcatccgga aactgctcgc ctggggcgcg     660
gatcgtctcc agagggactc agcagggagg attccttacg ccgtggcgct gaagcgcaac     720
cacgcggcgt gcgcggcgct gctgaacccg tcggcggcgg agcccatggt gtggccttcc     780
ccgctcaagt tcatcagcga gctggacccg gaggcgaagg ctctcctgga agcggcactg     840
atggacgcca ataggagag  ggaggagaag atcctcaagg gcatcaccaa gtattcgcag     900
ccatcgccta cttcgccttg cgagcacgat gccattgacg aagcgtcctt ggaggccagc     960
gacggggagc tgtgctgcat ctgcttcgag caggcgtgca gcatcgaggt gcaggactgc    1020
gggcaccaga tgtgcgcggc gtgcacactg gcgctgtgct gccacagcaa gccgaacccg    1080
```

```
gcgacgctga cgccgccgtc gccggcctgc ccgttctgcc gcggcagcat ctcgaggctg    1140
ctggtggccc gggcgagccc cgacgccgat gacgacgaca aggccgccgc cgcctcgtcc    1200
ccgcagctcg tccggcggcg gtcgcacaac ctcagatggg cggcggcgac ggcgtggaca    1260
agcccgagca cgacctgtga tcggcatttg atgctgtgcg tggctgagca gacagcagag    1320
cacgaccatt ttaaaagctg a                                              1341
```

<210> SEQ ID NO 65
<211> LENGTH: 446
<212> TYPE: PRT
<213> ORGANISM: Zea mays

<400> SEQUENCE: 65

```
Met Gly His Gly Val Ser Cys Ala Arg Thr Gly Asp Glu His Asn Tyr
1               5                   10                  15

Phe Arg Ala Ala Gln Val Gly Asp Leu Asp Ala Leu Asp Ala Leu Leu
            20                  25                  30

Ala Ala Asp Pro Ser Leu Ala Arg Ala Thr Leu Tyr Asp Arg Leu
        35                  40                  45

Ser Ala Leu His Ile Thr Ala Ala Asn Gly His Leu Glu Val Met Ser
    50                  55                  60

Met Ile Leu Asp His Gly Val Pro Pro Asp Ala Val Asn Arg His Lys
65                  70                  75                  80

Gln Thr Pro Leu Met Leu Ala Ala Met His Gly Lys Ile Asp Cys Ala
                85                  90                  95

Arg Lys Leu Leu Glu Ala Gly Ala Asn Ile Leu Met Phe Asp Ser Leu
            100                 105                 110

His Gly Arg Thr Cys Leu His His Ala Ser Tyr Phe Gly His Val Asp
        115                 120                 125

Cys Leu Arg Ala Ile Leu Ala Ala Ala Arg Thr Thr Pro Val Ala Asp
    130                 135                 140

Ser Trp Gly Phe Ala Arg Phe Val Asn Val Arg Asp Asp Arg Gly Ala
145                 150                 155                 160

Thr Pro Leu His Leu Ala Ala Arg Gln Gly Arg Ser Ala Cys Val Gln
                165                 170                 175

Val Leu Leu Glu Asn Gly Ala Ile Val Ser Ala Leu Thr Gly Ser Tyr
            180                 185                 190

Gly Phe Pro Gly Ser Thr Ser Leu His Leu Ala Ala Arg Ser Gly Asn
        195                 200                 205

Leu Asp Cys Ile Arg Lys Leu Leu Ala Trp Gly Ala Asp Arg Leu Gln
    210                 215                 220

Arg Asp Ser Ala Gly Arg Ile Pro Tyr Ala Val Ala Leu Lys Arg Asn
225                 230                 235                 240

His Ala Ala Cys Ala Ala Leu Leu Asn Pro Ser Ala Ala Glu Pro Met
                245                 250                 255

Val Trp Pro Ser Pro Leu Lys Phe Ile Ser Glu Leu Asp Pro Glu Ala
            260                 265                 270

Lys Ala Leu Leu Glu Ala Ala Leu Met Asp Ala Asn Arg Glu Arg Glu
        275                 280                 285

Glu Lys Ile Leu Lys Gly Ile Thr Lys Tyr Ser Gln Pro Ser Pro Thr
    290                 295                 300

Ser Pro Cys Glu His Asp Ala Ile Asp Glu Ala Ser Leu Glu Ala Ser
305                 310                 315                 320
```

| | | | | | | | | | | | |
|---|---|---|---|---|---|---|---|---|---|---|---|
|Asp|Gly|Glu|Leu|Cys|Cys|Ile|Cys|Phe|Glu|Gln|Ala|Cys|Ser|Ile|Glu|
| | | | |325| | | |330| | | |335|

Asp Gly Glu Leu Cys Cys Ile Cys Phe Glu Gln Ala Cys Ser Ile Glu
            325                 330                 335

Val Gln Asp Cys Gly His Gln Met Cys Ala Ala Cys Thr Leu Ala Leu
        340                 345                 350

Cys Cys His Ser Lys Pro Asn Pro Ala Thr Leu Thr Pro Pro Ser Pro
        355                 360                 365

Ala Cys Pro Phe Cys Arg Gly Ser Ile Ser Arg Leu Leu Val Ala Arg
    370                 375                 380

Ala Ser Pro Asp Ala Asp Asp Asp Lys Ala Ala Ala Ser Ser
385                 390                 395                 400

Pro Gln Leu Val Arg Arg Ser His Asn Leu Arg Trp Ala Ala Ala
                405                 410                 415

Thr Ala Trp Thr Ser Pro Ser Thr Thr Cys Asp Arg His Leu Met Leu
            420                 425                 430

Cys Val Ala Glu Gln Thr Ala Glu His Asp His Phe Lys Ser
        435                 440                 445

<210> SEQ ID NO 66
<211> LENGTH: 1419
<212> TYPE: DNA
<213> ORGANISM: Zea mays

<400> SEQUENCE: 66

```
atggggcacg gcgtcagctg cgcccgcacc ggtgacgagc acgactactt ccgcgcggcg      60
caggtcgggg acctcgaggc cctggaagcg ctcctcgacg ctgacccctc ccttgcccgc     120
cgcgccacgc tctacgaccg cctctccgcg ctccacatcg ccgccgcgaa tggccgcctc     180
gaggtgctgt caatggtctt ggatcacggg gtgccgccgg acgtggtgaa tcggcacaag     240
cagacgccgc tgatgctcgc ggcgatgcac ggcaagaccg actgcgtgct gaagctcctg     300
caggccggcg ccaatatcct catgttcgac tcccagcacg gcggacctg cctgcaccac      360
gcgtcctact tcggccacgt cggctgcctg caggccatcc tcacggcggc gcggaccacg     420
ccggtggcca actcatgggg tttcgctcgg ttcgtcaacg tgagagacga ccacggcgcc     480
acgccgctcc acctcgccgc caggcagggc cgccccggct gcgtgcaggc gctgctggag     540
aacggtgcca tcgtctccgc tttgaccggc tcatacgggt tcctggtag cacgtcgctg      600
cacctcgccg ctcgcagcgg gagcctggat tgcacccgga agctgctcgc ctggggagcg     660
gatcgtctcc ggagggattc agcagggagg atcccttacg ccgtggcgct gaagcgcaac     720
cacgaggcgt cgcggcggct gctgaacccg tcggcggcgg agcccatggt gtggccgtcc     780
ccgttcaagt tcatcagcga gctggagccg gaggccaagg cgctccttga gcggcgctg      840
acggaagcca acagggagag ggaggagaag atcctcaggg gcaccaagca ctctccgcat     900
cctcccacct gggaccacgc gagcgacgcc gccgacgccg acgccatcga cgacgcgtcc     960
tcagatgcca cgccagcga cgcggagctg tgctgcatct gcttcgacca ggcgtgcacg    1020
atggaggtgc aggactgcgg gcaccagatg tgcgcgccgt gcacgctcgc gctgctgc     1080
cacagcaagc ccgacccggt gacgctagcg ctgccgtcgc cagcctgccc gttctgccgc    1140
ggcagcatct cgcggctgct gctggtggcc cgggcaagca gcgacgacgc agacaccgag    1200
aagtcggcgg cagcggctgc ggcagcggct gcctcctccc cgcagctcgt ccggcggcgg    1260
tcccggcggt cgcacaacct cagcgacggc ggcagcagca gcttcaaggg gctgtcgtcc    1320
gccgtggccg ttccttctc caagatcggg cgcgggtcga ccggacgat ggccgacagc     1380
gacggctgcg gcgtggacaa gcccgagcac gacccgtga                          1419
```

<210> SEQ ID NO 67
<211> LENGTH: 472
<212> TYPE: PRT
<213> ORGANISM: Zea mays

<400> SEQUENCE: 67

```
Met Gly His Gly Val Ser Cys Ala Arg Thr Gly Asp Glu His Asp Tyr
1               5                   10                  15

Phe Arg Ala Ala Gln Val Gly Asp Leu Glu Ala Leu Glu Ala Leu Leu
            20                  25                  30

Asp Ala Asp Pro Ser Leu Ala Arg Arg Ala Thr Leu Tyr Asp Arg Leu
        35                  40                  45

Ser Ala Leu His Ile Ala Ala Asn Gly Arg Leu Glu Val Leu Ser
    50                  55                  60

Met Val Leu Asp His Gly Val Pro Pro Asp Val Val Asn Arg His Lys
65                  70                  75                  80

Gln Thr Pro Leu Met Leu Ala Ala Met His Gly Lys Thr Asp Cys Val
                85                  90                  95

Leu Lys Leu Leu Gln Ala Gly Ala Asn Ile Leu Met Phe Asp Ser Gln
            100                 105                 110

His Gly Arg Thr Cys Leu His His Ala Ser Tyr Phe Gly His Val Gly
        115                 120                 125

Cys Leu Gln Ala Ile Leu Thr Ala Ala Arg Thr Thr Pro Val Ala Asn
    130                 135                 140

Ser Trp Gly Phe Ala Arg Phe Val Asn Val Arg Asp Asp His Gly Ala
145                 150                 155                 160

Thr Pro Leu His Leu Ala Ala Arg Gln Gly Arg Pro Gly Cys Val Gln
                165                 170                 175

Ala Leu Leu Glu Asn Gly Ala Ile Val Ser Ala Leu Thr Gly Ser Tyr
            180                 185                 190

Gly Phe Pro Gly Ser Thr Ser Leu His Leu Ala Ala Arg Ser Gly Ser
        195                 200                 205

Leu Asp Cys Thr Arg Lys Leu Leu Ala Trp Gly Ala Asp Arg Leu Arg
    210                 215                 220

Arg Asp Ser Ala Gly Arg Ile Pro Tyr Ala Val Ala Leu Lys Arg Asn
225                 230                 235                 240

His Glu Ala Cys Ala Ala Leu Leu Asn Pro Ser Ala Ala Glu Pro Met
                245                 250                 255

Val Trp Pro Ser Pro Phe Lys Phe Ile Ser Glu Leu Glu Pro Glu Ala
            260                 265                 270

Lys Ala Leu Leu Glu Ala Ala Leu Thr Glu Ala Asn Arg Glu Arg Glu
        275                 280                 285

Glu Lys Ile Leu Arg Gly Thr Lys His Ser Pro His Pro Pro Thr Trp
    290                 295                 300

Asp His Ala Ser Asp Ala Ala Asp Ala Asp Ile Asp Asp Ala Ser
305                 310                 315                 320

Ser Asp Ala Ser Ala Ser Asp Ala Glu Leu Cys Cys Ile Cys Phe Asp
                325                 330                 335

Gln Ala Cys Thr Met Glu Val Gln Asp Cys Gly His Gln Met Cys Ala
            340                 345                 350

Pro Cys Thr Leu Ala Leu Cys Cys His Ser Lys Pro Asp Pro Val Thr
        355                 360                 365

Leu Ala Leu Pro Ser Pro Ala Cys Pro Phe Cys Arg Gly Ser Ile Ser
```

```
             370                 375                 380
Arg Leu Leu Leu Val Ala Arg Ala Ser Ser Asp Asp Ala Asp Thr Glu
385                 390                 395                 400

Lys Ser Ala Ala Ala Ala Ala Ala Ala Ala Ser Ser Pro Gln Leu
            405                 410                 415

Val Arg Arg Arg Ser Arg Arg Ser His Asn Leu Ser Asp Gly Gly Ser
                420                 425                 430

Ser Ser Phe Lys Gly Leu Ser Ser Ala Val Ala Gly Ser Phe Ser Lys
            435                 440                 445

Ile Gly Arg Gly Ser Ser Arg Thr Met Ala Asp Ser Asp Gly Cys Gly
            450                 455                 460

Val Asp Lys Pro Glu His Asp Pro
465                 470
```

<210> SEQ ID NO 68
<211> LENGTH: 1260
<212> TYPE: DNA
<213> ORGANISM: Zea mays

<400> SEQUENCE: 68

```
atgggccacg tcctcagctg cagccgcgac ggcgctgact tgttccgcgc ggtgcagcac      60
ggcgacctgg acgccctcct cgccgtcgac ccggagctcg cccgccgcgc caccaccata     120
tacgaccgtc tgtccctgct ccacatcgcc gccgccaatg ccagctgca ggtgctctcc      180
atgttgttgt tcgatgacgg tggcgccggc gggaacgtgg acgtgctgaa ccggaagaag     240
cagacccccgt tgatgctggc ggccatgcac ggcaggacgg actgcgtgct cagcctgcta    300
gacgccggag caaatatcct catgttcgac tcggtacacg cgcggacatg cctccaccac    360
gcggcctact acgccatgc ccactgcctc caagccatcc tctcggccgc caagaccacg      420
ccggtggccg actcatgggg cttcgcgcgc ttcgtgaacg tgagggacga gcacggcgcc    480
acgccgctgc acctggcggc aaggcagggg cggccgcagt gcgtccgcca cctgctccac    540
gccggcgcca tcgtctccgc cccaacagcc tcctacggct tccccggcag cacggcgttg    600
cacctggctg cacgccgcgg caacctggac tgcgtccggg agctcctcgc ctggggcgct    660
gaccgcctcc acagggactc ggcggggagg atcgcctacg cggtggccct caagcacagc    720
caccgagagt gcgccgcgct gctgaacccg cggcggcgg aaccaatggt gtggccgtcc     780
ccgctcaagt tcatcagcga gctcagcccg gaggccaagg cgctcctgga gggggctctc    840
atggaagcca cagggagcg cgagaagcgc atcacggaca ccacaaccaa acaaacaac     900
gacggcggcc ttgacgacga cgacgagcag ctgtgcggca tctgcctgga gcaggcgtgc   960
accatggagg tgcaggactg cgggcaccag atgtgcgccg cgtgcacgct ggcgctgtgc  1020
tgccacagca agcccaaccc gacgaccctg gcactgcagc acccgcctg cccttctgc    1080
cgcgccacca tcacccggct gctggtggcc aacagcaaga ctactgctac ctccaacagc  1140
ttcaggggac tcacctcggc catcaggtcc ttgtccttgt ccaggattgc tcgtggctcc  1200
gggagggtag ccgacagctc attccccag tcattctttg aggaacaagg atccaaatga  1260
```

<210> SEQ ID NO 69
<211> LENGTH: 419
<212> TYPE: PRT
<213> ORGANISM: Zea mays

<400> SEQUENCE: 69

Met Gly His Val Leu Ser Cys Ser Arg Asp Gly Ala Asp Leu Phe Arg

-continued

```
1               5                   10                  15
Ala Val Gln His Gly Asp Leu Asp Ala Leu Leu Ala Val Asp Pro Glu
            20                  25                  30
Leu Ala Arg Arg Ala Thr Thr Ile Tyr Asp Arg Leu Ser Leu Leu His
            35                  40                  45
Ile Ala Ala Ala Asn Gly Gln Leu Gln Val Leu Ser Met Leu Leu Phe
            50                  55                  60
Asp Asp Gly Gly Ala Gly Gly Asn Val Asp Val Leu Asn Arg Lys Lys
65                  70                  75                  80
Gln Thr Pro Leu Met Leu Ala Ala Met His Gly Arg Thr Asp Cys Val
                85                  90                  95
Leu Ser Leu Leu Asp Ala Gly Ala Asn Ile Leu Met Phe Asp Ser Val
            100                 105                 110
His Ala Arg Thr Cys Leu His His Ala Ala Tyr Tyr Gly His Ala His
            115                 120                 125
Cys Leu Gln Ala Ile Leu Ser Ala Ala Lys Thr Thr Pro Val Ala Asp
            130                 135                 140
Ser Trp Gly Phe Ala Arg Phe Val Asn Val Arg Asp Glu His Gly Ala
145                 150                 155                 160
Thr Pro Leu His His Leu Ala Ala Arg Gln Gly Arg Pro Gln Cys Val Arg
            165                 170                 175
His Leu Leu His Ala Gly Ala Ile Val Ser Ala Pro Thr Ala Ser Tyr
            180                 185                 190
Gly Phe Pro Gly Ser Thr Ala Leu His Leu Ala Ala Arg Arg Gly Asn
            195                 200                 205
Leu Asp Cys Val Arg Glu Leu Leu Ala Trp Gly Ala Asp Arg Leu His
210                 215                 220
Arg Asp Ser Ala Gly Arg Ile Ala Tyr Ala Val Ala Leu Lys His Ser
225                 230                 235                 240
His Arg Glu Cys Ala Ala Leu Leu Asn Pro Ala Ala Ala Glu Pro Met
                245                 250                 255
Val Trp Pro Ser Pro Leu Lys Phe Ile Ser Glu Leu Ser Pro Glu Ala
            260                 265                 270
Lys Ala Leu Leu Glu Gly Ala Leu Met Glu Ala Asn Arg Glu Arg Glu
            275                 280                 285
Lys Arg Ile Thr Asp Thr Thr Lys Thr Asn Asn Asp Gly Gly Leu
            290                 295                 300
Asp Asp Asp Asp Glu Gln Leu Cys Gly Ile Cys Leu Glu Gln Ala Cys
305                 310                 315                 320
Thr Met Glu Val Gln Asp Cys Gly His Gln Met Cys Ala Ala Cys Thr
                325                 330                 335
Leu Ala Leu Cys Cys His Ser Lys Pro Asn Pro Thr Thr Leu Ala Leu
            340                 345                 350
Gln Pro Pro Ala Cys Pro Phe Cys Arg Ala Thr Ile Thr Arg Leu Leu
            355                 360                 365
Val Ala Asn Ser Lys Thr Thr Ala Thr Ser Asn Ser Phe Arg Gly Leu
            370                 375                 380
Thr Ser Ala Ile Arg Ser Leu Ser Leu Ser Arg Ile Ala Arg Gly Ser
385                 390                 395                 400
Gly Arg Val Ala Asp Ser Ser Leu Pro Gln Ser Phe Phe Glu Glu Gln
                405                 410                 415
Gly Ser Lys
```

<210> SEQ ID NO 70
<211> LENGTH: 1260
<212> TYPE: DNA
<213> ORGANISM: Zea mays

<400> SEQUENCE: 70

```
atgggccacg tcctcagctg cagccgcgac ggcgctgact tgttccgcgc ggtgcagcac      60
ggcgacctgg acgccctcct cgccgtcgac ccggagctcg cccgccgcgc caccaccata     120
tacgaccgtc tgtccctgct ccacatcgcc gccgccaatg ccagctgca ggtgctctcc      180
atgttgttgt cgatgacggt ggcgccggc gggaacgtgg acgtgctgaa ccggaagaag      240
cagaccccgt tgatgctggc ggccatgcac ggcaggacgg actgcgtgct cagcctgcta     300
gacgccggag caaatatcct catgttcgac tcggtacacg cgcggacatg cctccaccac     360
gcggcctact acggccatgc ccactgcctc caagccatcc tctcggccgc caagaccacg     420
ccggtggccg actcatgggg cttcgcgcgc ttcgtgaacg tgaggacga gcacggcgcc      480
acgccgctgc acctggcggc aaggcagggg cggccgcagt gcgtccgcca cctgctccac     540
gccggcgcca tcgtctccgc cccaacagcc tcctacggct ccccggcag cacggcgttg      600
cacctggctg cacgccgcgg caacctggac tgcgtccggg agctcctcgc ctggggcgct     660
gaccgcctcc acagggactc ggcggggagg atcgcctacg cggtggccct caagcacagc     720
caccgagagt gcgccgcgct gctgaacccg gcggcggcgg aaccaatggt gtggccgtcc     780
ccgctcaagt tcatcagcga gctcagcccg gaggccaagg cgctcctgga ggggctctc      840
atggaagcca cagggagcg cgagaagcgc atcacggaca ccacaaccaa acaaacaac      900
gacggcggcc ttgacgacga cgacgagcag ctgtgcggca tctgcctgga gcaggcgtgc     960
accatggagg tgcaggactg cgggcaccag atgtgcgccg cgtgcacgct ggcgctgtgc    1020
tgccacagca agcccaaccc gacgaccctg gcactgcagc caccgcctg cccttctgc     1080
cgcgccacca tcacccggct gctggtggcc aacagcaaga ctactgctac ctccaacagc    1140
ttcaggggac tcacctcggc catcaggtcc ttgtccttgt ccaggattgc tcgtggctcc    1200
gggagggtag ccgacagctc attaccccag tcattctttg aggaacaagg atccaaatga    1260
```

<210> SEQ ID NO 71
<211> LENGTH: 446
<212> TYPE: PRT
<213> ORGANISM: Zea mays

<400> SEQUENCE: 71

```
Met Gly His Gly Ala Ser Cys Gly Arg Pro Ser Glu Glu Val Asp Phe
1               5                   10                  15

Phe Gly Ala Ala Gln Ser Gly Asp Met Ala Arg Leu Ala Ala Ala Leu
            20                  25                  30

Arg Ser Arg Pro Thr Leu Leu Ser Arg Thr Thr Leu Phe Asp Arg Leu
        35                  40                  45

Ser Ala Leu His Ile Ala Ala Ala His Gly His Leu Gln Val Val Ser
    50                  55                  60

Leu Ala Leu Asp Leu Cys Val His Pro Asp Val Val Asn Arg His Lys
65                  70                  75                  80

Gln Thr Ala Leu Met Leu Ser Ala Met His Gly Lys Thr Asp Cys Val
                85                  90                  95

Arg Arg Leu Leu Asp Ala Gly Ala Asn Ile Val Met Phe Asp Ser Ser
            100                 105                 110
```

His Gly Arg Thr Cys Leu His Tyr Ala Ala Tyr Gly His Ala Asp
            115                 120                 125

Cys Leu Arg Thr Ile Leu Ser Ala Ala Lys Ser Ala Pro Val Ser
        130                 135                 140

Glu Ser Trp Gly Phe Ala Arg Phe Val Asn Val Arg Asp Asp Thr Gly
145                 150                 155                 160

Ala Thr Pro Leu His Leu Ala Ala Arg Gln Gly Trp Arg Arg Cys Val
            165                 170                 175

His Val Leu Leu Glu Asn Gly Ala Ile Val Ser Ala Ser Ser Gly Ala
        180                 185                 190

Phe Gly Phe Pro Gly Ser Thr Pro Leu His Leu Ala Ala Arg Gly Gly
    195                 200                 205

Asn Leu Asp Cys Val Arg Gln Leu Leu Ser Trp Gly Ala Asp Arg Leu
210                 215                 220

Gln Arg Asp Ser Val Gly Arg Ile Pro Tyr Glu Val Ala Ala Lys Arg
225                 230                 235                 240

Gly His Val Ala Cys Ala Ala Leu Leu Asn Pro Ser Ser Ala Glu Pro
            245                 250                 255

Leu Val Trp Pro Ser Ala Leu Lys Phe Ile Ser Glu Leu Glu Pro Asp
        260                 265                 270

Ala Lys Ser Leu Leu Glu Ala Ala Leu Met Glu Ala Asn Arg Glu Arg
    275                 280                 285

Glu Arg Arg Ile Leu Lys Gly Ala Lys Asn Ala Leu Pro Ser Pro Ser
290                 295                 300

His Pro Asp Asp Gly Ala His Asp Thr Ala Ile Ala Glu Ala Ser Asp
305                 310                 315                 320

Ala Glu Val Cys Ser Ile Cys Phe Glu Gln Ala Cys Ser Ile Glu Val
            325                 330                 335

Arg Glu Cys Gly His Gln Met Cys Ala Ala Cys Thr Leu Ala Leu Cys
        340                 345                 350

Cys His Ala Lys Pro Asn Pro Ala Thr Gln Ser Gln Pro Leu Pro Thr
    355                 360                 365

Cys Pro Phe Cys Arg Gly Gly Ile Ala Arg Leu Val Val Ala Thr Arg
370                 375                 380

Thr Arg Ala Gly Asp Asp Glu Glu Arg Cys Lys Leu Glu Ser Pro Arg
385                 390                 395                 400

His Cys Arg Ala Arg Arg Ser Met Ser Leu Ser Gly Asp Ala Gly Ser
            405                 410                 415

Thr Ser Thr Leu Met Gly Ser Ile Ala Ser Ser Ile Gly Lys Met Gly
        420                 425                 430

Arg Arg Arg Thr Glu Ser Ser Glu Gln Val Asp Asp Lys Pro
    435                 440                 445

<210> SEQ ID NO 72
<211> LENGTH: 1341
<212> TYPE: DNA
<213> ORGANISM: Zea mays

<400> SEQUENCE: 72
atggggcacg gcgcgagctg cagccgccca agcgaggagg tggacttctt cggcgcggcg      60
cagtgcgggg acacggcccg cctcgccgcc gctcttcgct cccgccccac cttgctcgcc     120
cgcaccacgc tcttcgaccg cctctccgcg ctccacatcg ccgccgcaca cggccacctc     180
caggtggtct ccctagcatt agatctttgc gtgcaccccg acgtcgttaa ccgccacaag     240

```
cagacggcat tgatgctcgc ggcgatgcac gggaagaccg actgcgtccg gcggcttctc    300
gacgccggcg ccaatatcgt gatgttcgat tcctcgcatc ggcggacgtg cctgcactac    360
gcggcctact acgggcacgc ggactgcctc cggaccatcc tctcggcggc caagtccgcg    420
ccggtgtcgg aatcctgggg gttcgcgcgc ttcgtgaacg tgcgggacga caccggggcg    480
acgccgctgc acctcgcggc gaggcagggc tggcggcgct gtgtccacgt cctgctcgag    540
aacggcgcca tcgtgtccgc ctccagcggt gccttcggat tccccgggag cacaccgcta    600
catttggccg cgcgcggcgg caacctggac tgcgtccggc aactgctctc ctggggcgcc    660
gaccgcctcc agcgagactc cgtcgggaga attccgtatg aggtcgccgt gaagcgaggg    720
cacgtcgcgt gcgcggcgct gctgaacccg tcatccgcgg agcccctggt ctggccgtcc    780
gctctcaagt tcatcagcga gctggaaccc gacgccaaat ctctcctcga agcagccctg    840
atggaggcca acagagagag ggagaggagg atcctgaaag ggactaagaa tgcgttgccg    900
tcgccaccgc accacgatga cggcgctcat gacaccgcca ttgccgaggc gagcgacgcg    960
gaggtgtgca gcatctgctt cgagcaggcg tgcagcatcg aggtccggga gtgcgggcac   1020
cagatgtgct cggcgtgcac gctggcgctg tgctgccacg ccaagcccaa cccggcgacg   1080
cagtcccagc cgctgccgac ctgcccgttc tgccgcggcg catcgcgcg ctggtggtg    1140 gcgacgcgga cgagggctgg ccacgacgac gagcgggaca agctggagtc gcccaggcac   1200
cgccggtccc gccggtccat gaacctcagc ggcgacgcgg gcagcaccag cagcacactc   1260
atgggcagca tcgcctcgtc catcggcaag atgggccgcc gacgaacaga tagcagcgag   1320
caggtcgacg acaagccgta g                                             1341

<210> SEQ ID NO 73
<211> LENGTH: 446
<212> TYPE: PRT
<213> ORGANISM: Zea mays

<400> SEQUENCE: 73

Met Gly His Gly Ala Ser Cys Ser Arg Pro Ser Glu Glu Val Asp Phe
1               5                   10                  15

Phe Gly Ala Ala Gln Cys Gly Asp Thr Ala Arg Leu Ala Ala Ala Leu
            20                  25                  30

Arg Ser Arg Pro Thr Leu Leu Ala Arg Thr Thr Leu Phe Asp Arg Leu
        35                  40                  45

Ser Ala Leu His Ile Ala Ala Ala His Gly His Leu Gln Val Val Ser
    50                  55                  60

Leu Ala Leu Asp Leu Cys Val His Pro Asp Val Val Asn Arg His Lys
65                  70                  75                  80

Gln Thr Ala Leu Met Leu Ala Ala Met His Gly Lys Thr Asp Cys Val
                85                  90                  95

Arg Arg Leu Leu Asp Ala Gly Ala Asn Ile Val Met Phe Asp Ser Ser
            100                 105                 110

His Arg Arg Thr Cys Leu His Tyr Ala Ala Tyr Tyr Gly His Ala Asp
        115                 120                 125

Cys Leu Arg Thr Ile Leu Ser Ala Ala Lys Ser Ala Pro Val Ser Glu
    130                 135                 140

Ser Trp Gly Phe Ala Arg Phe Val Asn Val Arg Asp Asp Thr Gly Ala
145                 150                 155                 160

Thr Pro Leu His Leu Ala Ala Arg Gln Gly Trp Arg Arg Cys Val His
                165                 170                 175
```

```
Val Leu Leu Glu Asn Gly Ala Ile Val Ser Ala Ser Gly Ala Phe
            180                 185                 190

Gly Phe Pro Gly Ser Thr Pro Leu His Leu Ala Ala Arg Gly Gly Asn
            195                 200                 205

Leu Asp Cys Val Arg Gln Leu Leu Ser Trp Gly Ala Asp Arg Leu Gln
210                 215                 220

Arg Asp Ser Val Gly Arg Ile Pro Tyr Glu Val Ala Lys Arg Gly
225                 230                 235                 240

His Val Ala Cys Ala Leu Leu Asn Pro Ser Ala Glu Pro Leu
                245                 250                 255

Val Trp Pro Ser Ala Leu Lys Phe Ile Ser Glu Leu Glu Pro Asp Ala
            260                 265                 270

Lys Ser Leu Leu Glu Ala Ala Leu Met Glu Ala Asn Arg Glu Arg Glu
            275                 280                 285

Arg Arg Ile Leu Lys Gly Thr Lys Asn Ala Leu Pro Ser Pro Pro His
            290                 295                 300

His Asp Asp Gly Ala His Asp Thr Ala Ile Ala Glu Ala Ser Asp Ala
305                 310                 315                 320

Glu Val Cys Ser Ile Cys Phe Glu Gln Ala Cys Ser Ile Glu Val Arg
                325                 330                 335

Glu Cys Gly His Gln Met Cys Ser Ala Cys Thr Leu Ala Leu Cys Cys
            340                 345                 350

His Ala Lys Pro Asn Pro Ala Thr Gln Ser Gln Pro Leu Pro Thr Cys
            355                 360                 365

Pro Phe Cys Arg Gly Ile Ala Arg Leu Val Val Ala Thr Arg Thr
            370                 375                 380

Arg Ala Gly His Asp Asp Glu Arg Asp Lys Leu Glu Ser Pro Arg His
385                 390                 395                 400

Arg Arg Ser Arg Arg Ser Met Asn Leu Ser Gly Asp Ala Gly Ser Thr
                405                 410                 415

Ser Ser Thr Leu Met Gly Ser Ile Ala Ser Ser Ile Gly Lys Met Gly
            420                 425                 430

Arg Arg Arg Thr Asp Ser Ser Glu Gln Val Asp Asp Lys Pro
            435                 440                 445

<210> SEQ ID NO 74
<211> LENGTH: 1341
<212> TYPE: DNA
<213> ORGANISM: Oryza sativa

<400> SEQUENCE: 74
atggggcacg gcctgagctg cagccgcgac accgacgagt acgacctgtt ccgcgcggcg    60
cagctgggcg acatccacgc cctctccgcc ctcctcgccg ccgaccccgc gctcgcccgc   120
cgcgccacag tctacgaccg cttcaccgct cttcacatcg ccgccgccaa cggccgcctc   180
caggtactgt ccatgttgct ggatcgcgac ggcgacgtgg acgtcctgag ccgcaagaag   240
cagacgccgc tgatggtggc ggccatgcgt ggcaacaccg agtgcgtggt caggctcctc   300
cgcggcggcg ccaacgtcct gaccttcgac tcgccgcgcg ccaggacgtg cctccaccac   360
gccgcctact acggcacgc cgagtgcctg caggccatcc tcggcgccgc ggcgcaggcg   420
cagggccccg tggccgcctc ctggggtttc gcgcgcttcg tcaacgtgag ggacgagcgg   480
ggcgccacgc cgctgcacct ggctgcgagg cacgcccgcg cgtcctgcgt gcgcctgctg   540
ctcgacaagg gcgccatcgt gtcggcgcca accgccgtct acggattccc cggagcacg   600
```

```
gctctgcacc tggcggcacg cgccggcagc atggagtgca tcaggagct gctggcctgg    660
ggggcggacc ggctccagag ggactcggcg gggcggatcg cgtacgcggt ggcgatgagg    720
cgggggcaca gggcgtgcgc ggcgctgctg aacccggcgg cggcggagcc catagtgtgg    780
ccgtccccgc tcaagttcat cggcgagctg gaggcggacg ccaaggcact tctggaggcg    840
gcgctgatgg aggccaacag ggagagggag aagaggatcc tgcacggcag cgacatcaac    900
atcaagggcg cgacgagga ggaggagagc gaggatgagg aggaggcgtg caacatctgc    960
ttcgagcagg cgtgcagcat ggaggtgaag gagtgcgggc accagatgtg cgcggcgtgc   1020
acgctggcca tctgctgcca cagcaagccc aaccccaaga ccctcctcct ccacccgccc   1080
gcctgcccct tctgccgcac caccatctcc cgcctcgtcg tcgccaccac caactccaac   1140
aagaccaaca gccgccgccg gtcgaggagc agaagcagca gcttcaaggg ggggctctcg   1200
tcggccatgg ggtcgttttc caggatagcc gcggctccg ggagattggt ggtggacggc   1260
agcagcgtag agagctcgc cgacaagcct gaccacgact tctcttctgt cgccgccgct   1320
gctgctattt gtgacacatg a                                             1341
```

<210> SEQ ID NO 75
<211> LENGTH: 446
<212> TYPE: PRT
<213> ORGANISM: Oryza sativa

<400> SEQUENCE: 75

```
Met Gly His Gly Leu Ser Cys Ser Arg Asp Thr Asp Glu Tyr Asp Leu
1               5                   10                  15

Phe Arg Ala Ala Gln Leu Gly Asp Ile His Ala Leu Ser Ala Leu Leu
            20                  25                  30

Ala Ala Asp Pro Ala Leu Ala Arg Arg Ala Thr Val Tyr Asp Arg Phe
        35                  40                  45

Thr Ala Leu His Ile Ala Ala Asn Gly Arg Leu Gln Val Leu Ser
    50                  55                  60

Met Leu Leu Asp Arg Asp Gly Asp Val Asp Val Leu Ser Arg Lys Lys
65                  70                  75                  80

Gln Thr Pro Leu Met Val Ala Ala Met Arg Gly Asn Thr Glu Cys Val
                85                  90                  95

Val Arg Leu Leu Arg Gly Gly Ala Asn Val Leu Thr Phe Asp Ser Pro
            100                 105                 110

Arg Ala Arg Thr Cys Leu His His Ala Ala Tyr Tyr Gly His Ala Glu
        115                 120                 125

Cys Leu Gln Ala Ile Leu Gly Ala Ala Ala Gln Ala Gln Gly Pro Val
    130                 135                 140

Ala Ala Ser Trp Gly Phe Ala Arg Phe Val Asn Val Arg Asp Glu Arg
145                 150                 155                 160

Gly Ala Thr Pro Leu His Leu Ala Ala Arg His Ala Arg Ala Ser Cys
                165                 170                 175

Val Arg Leu Leu Leu Asp Lys Gly Ala Ile Val Ser Ala Pro Thr Ala
            180                 185                 190

Val Tyr Gly Phe Pro Gly Ser Thr Ala Leu His Leu Ala Ala Arg Ala
        195                 200                 205

Gly Ser Met Glu Cys Ile Arg Glu Leu Leu Ala Trp Gly Ala Asp Arg
    210                 215                 220

Leu Gln Arg Asp Ser Ala Gly Arg Ile Ala Tyr Ala Val Ala Met Arg
225                 230                 235                 240
```

```
Arg Gly His Arg Ala Cys Ala Ala Leu Leu Asn Pro Ala Ala Ala Glu
            245                 250                 255

Pro Ile Val Trp Pro Ser Pro Leu Lys Phe Ile Gly Glu Leu Glu Ala
        260                 265                 270

Asp Ala Lys Ala Leu Leu Glu Ala Ala Leu Met Glu Ala Asn Arg Glu
    275                 280                 285

Arg Glu Lys Arg Ile Leu His Gly Ser Asp Ile Asn Ile Lys Gly Gly
290                 295                 300

Asp Glu Glu Glu Ser Glu Asp Glu Glu Ala Cys Asn Ile Cys
305                 310                 315                 320

Phe Glu Gln Ala Cys Ser Met Glu Val Lys Glu Cys Gly His Gln Met
                325                 330                 335

Cys Ala Ala Cys Thr Leu Ala Ile Cys Cys His Ser Lys Pro Asn Pro
            340                 345                 350

Lys Thr Leu Leu Leu His Pro Pro Ala Cys Pro Phe Cys Arg Thr Thr
        355                 360                 365

Ile Ser Arg Leu Val Val Ala Thr Thr Asn Ser Asn Lys Thr Asn Ser
    370                 375                 380

Arg Arg Arg Ser Arg Ser Arg Ser Ser Phe Lys Gly Gly Leu Ser
385                 390                 395                 400

Ser Ala Met Gly Ser Phe Ser Arg Ile Gly Arg Gly Ser Arg Leu
                405                 410                 415

Val Val Asp Gly Ser Ser Val Gly Glu Leu Ala Asp Lys Pro Asp His
            420                 425                 430

Asp Phe Ser Ser Val Ala Ala Ala Ala Ile Cys Asp Thr
        435                 440                 445

<210> SEQ ID NO 76
<211> LENGTH: 1398
<212> TYPE: DNA
<213> ORGANISM: Oryza sativa

<400> SEQUENCE: 76
atggggcagg gcgccagctg cgggcggccc agcgaggagg tggacttctt cggcgcggcg    60
cagtcgggcg acctcgcccg cctcgccgcc gccgtccgct cccgcccttc cctcctcggc   120
cgcaccacgc tcttcgaccg cctctccgcc ctccacatcg ccgccgccca cggccacctc   180
caggtggtgt ccatggcgtt ggatctttgc gtgcacccgg acgtcgttaa ccgccacaag   240
cagacggcgc tgatgctcgc ggcgatgcac gggaggaccg agtgcgtgcg gcggctgctc   300
gacgccggcc caatattgt gatgttcgat tcgtcgcacg gcggacgtg cctgcactac   360 gcggcgtact acggccacgc cgactgccta cgggccatcc tctcggcggc gcagtcggcg   420
ccggtgtcgc aatcctgggg tttcgcgcgg ttcgtgaacg tgagggacga caccggagcg   480
acgccgctgc acctcgcggc gaggcagggc tggcggcgct gcgtccacgt cctgctcgag   540
aacggcgcca tcgtgtcagc ctccagtagc gcctttggat ccccgggag cacgccgctg   600 catttggccg cgcgcggcgg cagcctcgac tgcgtccgcc agctcctctc ctggggcgcc   660
gaccgcctcc agcgagactc cgtcgggagg attccgtacg aggtggcgat gaagcgaggg   720
cacgtcgcgt gcgccgcgct gctgaacccg tcgtcggcgg agcccctggt gtggccgtcc   780
ccgctcaagt tcatcagcga gctcgagccg acgccaaag ccctcctgga ggcggcgctc   840
atggaggcca accgggagag ggagaagagg accctgaaag gggccaggag cgcgtcgccg   900
ttggcgttgc catcgccgtc gcgttcagac gacggcgcgc acgacgccgc catctctgag   960
```

```
gaggcggcgg cggccggcgg cggcgaggtg tgcagcatct gcttcgagca ggcgtgcacg     1020
atcgaggtgc gggagtgtgg gcaccagatg tgcgcggcgt gcacgctggc gctgtgctgc     1080
cacgcgaagc ccagcgcggc ggcggcgacg ccgtgccagc agccgctgcc gacctgcccg     1140
ttctgccgcg gcggcatctc ccggctggtg gtggcgacga ccaagaccag agcaggcggc     1200
gacgacgagg aggacgacga ggaggcgggc agcaggctgg cgtcgccgct gcacaggagg     1260
tctcgccggg cggtgaacca ccccagcggc gacggcggca gcaccagcag catcatgggc     1320
agcattgcgt cgtcgatcgg gaagatgggc agacggcgaa ccgacagcag cgaacacgtc     1380
gacgtcgaca agccctag                                                  1398
```

<210> SEQ ID NO 77
<211> LENGTH: 465
<212> TYPE: PRT
<213> ORGANISM: Oryza sativa

<400> SEQUENCE: 77

```
Met Gly Gln Gly Ala Ser Cys Gly Arg Pro Ser Glu Glu Val Asp Phe
1               5                   10                  15

Phe Gly Ala Ala Gln Ser Gly Asp Leu Ala Arg Leu Ala Ala Ala Val
                20                  25                  30

Arg Ser Arg Pro Ser Leu Leu Gly Arg Thr Thr Leu Phe Asp Arg Leu
            35                  40                  45

Ser Ala Leu His Ile Ala Ala His Gly His Leu Gln Val Val Ser
        50                  55                  60

Met Ala Leu Asp Leu Cys Val His Pro Asp Val Val Asn Arg His Lys
65                  70                  75                  80

Gln Thr Ala Leu Met Leu Ala Ala Met His Gly Arg Thr Glu Cys Val
                85                  90                  95

Arg Arg Leu Leu Asp Ala Gly Ala Asn Ile Val Met Phe Asp Ser Ser
            100                 105                 110

His Gly Arg Thr Cys Leu His Tyr Ala Ala Tyr Tyr Gly His Ala Asp
        115                 120                 125

Cys Leu Arg Ala Ile Leu Ser Ala Ala Gln Ser Ala Pro Val Ser Gln
    130                 135                 140

Ser Trp Gly Phe Ala Arg Phe Val Asn Val Arg Asp Asp Thr Gly Ala
145                 150                 155                 160

Thr Pro Leu His Leu Ala Ala Arg Gln Gly Trp Arg Cys Val His
                165                 170                 175

Val Leu Leu Glu Asn Gly Ala Ile Val Ser Ser Ser Ala Phe
            180                 185                 190

Gly Phe Pro Gly Ser Thr Pro Leu His Leu Ala Ala Arg Gly Gly Ser
        195                 200                 205

Leu Asp Cys Val Arg Gln Leu Leu Ser Trp Gly Ala Asp Arg Leu Gln
    210                 215                 220

Arg Asp Ser Val Gly Arg Ile Pro Tyr Glu Val Ala Met Lys Arg Gly
225                 230                 235                 240

His Val Ala Cys Ala Ala Leu Leu Asn Pro Ser Ser Ala Glu Pro Leu
                245                 250                 255

Val Trp Pro Ser Pro Leu Lys Phe Ile Ser Glu Leu Glu Pro Asp Ala
            260                 265                 270

Lys Ala Leu Leu Glu Ala Ala Leu Met Glu Ala Asn Arg Glu Arg Glu
        275                 280                 285

Lys Arg Thr Leu Lys Gly Ala Arg Ser Ala Ser Pro Leu Ala Leu Pro
```

```
                 290                 295                 300

Ser Pro Ser Arg Ser Asp Asp Gly Ala His Asp Ala Ala Ile Ser Glu
305                 310                 315                 320

Glu Ala Ala Ala Gly Gly Gly Glu Val Cys Ser Ile Cys Phe Glu
            325                 330                 335

Gln Ala Cys Thr Ile Glu Val Arg Glu Cys Gly His Gln Met Cys Ala
            340                 345                 350

Ala Cys Thr Leu Ala Leu Cys Cys His Ala Lys Pro Ser Ala Ala Ala
            355                 360                 365

Ala Thr Pro Cys Gln Gln Pro Leu Pro Thr Cys Pro Phe Cys Arg Gly
    370                 375                 380

Gly Ile Ser Arg Leu Val Val Ala Thr Thr Lys Thr Arg Ala Gly Gly
385                 390                 395                 400

Asp Asp Glu Glu Asp Glu Glu Ala Gly Ser Arg Leu Ala Ser Pro
                405                 410                 415

Leu His Arg Arg Ser Arg Arg Ala Val Asn His Pro Ser Gly Asp Gly
            420                 425                 430

Gly Ser Thr Ser Ser Ile Met Gly Ser Ile Ala Ser Ser Ile Gly Lys
            435                 440                 445

Met Gly Arg Arg Arg Thr Asp Ser Ser Glu His Val Asp Val Asp Lys
450                 455                 460

Pro
465

<210> SEQ ID NO 78
<211> LENGTH: 1350
<212> TYPE: DNA
<213> ORGANISM: Hordeum vulgare

<400> SEQUENCE: 78
atggggcacg gggtgagctg cgcgcgcacc ggcgacgagc acgacttctt ccgcgcggcg     60
cagctcgggg acctcgacgc cctgggcgcg ctcctcgccg ccgacgcctc cctcgcccgc    120
cgcgccaccc tctacgaccg cctctccccg ctccacatcg ccgccgccaa cggccggctc    180
gaggcgctct ccatgttcct ggatcgcggg gcgcagccgg acgcggtgga tcggcacaag    240
cagaccccgc tgatgctcgc cgccatgcac ggcaagatcg gctgcgtgct caagctcctc    300
catgccggcg caaacatctt gatgttcgac tcggtgcacg cgcggacctg cctccaccac    360
gcggcctact acggccacgt cgactgcctg acgccatcc tctccacggc gcggaccacg    420
ccggtggccg actcatgggg gttcgcccgg ttcgtcaacg tcaggacga ccacggcgcg    480 acgccgctgc acctcgccgc caggcagggc cggccgggca gcgtgcaggt gctgctggag    540
aacggcgcca tcgtgtcggc attgaccgga tcgtatggct tccctggcag cacgccgttg    600
catctggccg ctcgcagcgg gagcttggat tgcgtccgca agctgcttgc ctggggagcc    660
gatcggctcc aaagggactc tgctgggaga attgcgtatg tggtggcaca gaagcgccac    720 catgggcat gcgcggcatt gctgaaccct tcatcggcgg agcctatggt ctggccttcc    780
ccgctgaagt tcatcagcga gctcgacccg gaagccaaag ctctgctgga agcggccctg    840
acggaggcca cagggagag ggagaagaag atcttgaagg acgcaaagtg ctcgccgcag    900
tcccctttgc aatacgacga taacgtcgac gacgacatgt tctcggaggt gagcgacacg    960
gagctgtgct gcatctgctt cgaccaggcg tgcaccatcg aggtggagga ctgcgggcac   1020
cagatgtgcg cgccgtgcac gctcgcgctg tgctgccaca caagcccaa cccggcgacg   1080
```

```
ctgacaatgc catcaccggc ctgcccgttc tgccgcggca gcatctcgcg gctggtggtg    1140
gcccagaccc gggcagacaa cgccgacccc gacaggccgg cctccccgca gctcgctcac    1200
cggcgatccc ggcgctctca caacctcagt gagggcagca gcagcttcaa agggctgtcc    1260
tcggccatct cgaagatcac ccgcggctcg agcaggatgg ccgacagcga aagcgctgct    1320
gcgatggaca agcccgagca cgatctgtga                                     1350
```

<210> SEQ ID NO 79
<211> LENGTH: 449
<212> TYPE: PRT
<213> ORGANISM: Hordeum vulgare

<400> SEQUENCE: 79

```
Met Gly His Gly Val Ser Cys Ala Arg Thr Gly Asp Glu His Asp Phe
1               5                   10                  15

Phe Arg Ala Ala Gln Leu Gly Asp Leu Asp Ala Leu Gly Ala Leu Leu
                20                  25                  30

Ala Ala Asp Ala Ser Leu Ala Arg Arg Ala Thr Leu Tyr Asp Arg Leu
            35                  40                  45

Ser Pro Leu His Ile Ala Ala Ala Asn Gly Arg Leu Glu Ala Leu Ser
        50                  55                  60

Met Phe Leu Asp Arg Gly Ala Gln Pro Asp Ala Val Asp Arg His Lys
65                  70                  75                  80

Gln Thr Pro Leu Met Leu Ala Ala Met His Gly Lys Ile Gly Cys Val
                85                  90                  95

Leu Lys Leu Leu His Ala Gly Ala Asn Ile Leu Met Phe Asp Ser Val
            100                 105                 110

His Ala Arg Thr Cys Leu His His Ala Ala Tyr Tyr Gly His Val Asp
        115                 120                 125

Cys Leu Asp Ala Ile Leu Ser Thr Ala Arg Thr Thr Pro Val Ala Asp
130                 135                 140

Ser Trp Gly Phe Ala Arg Phe Val Asn Val Arg Asp Asp His Gly Ala
145                 150                 155                 160

Thr Pro Leu His Leu Ala Ala Arg Gln Gly Arg Pro Gly Ser Val Gln
                165                 170                 175

Val Leu Leu Glu Asn Gly Ala Ile Val Ser Ala Leu Thr Gly Ser Tyr
            180                 185                 190

Gly Phe Pro Gly Ser Thr Pro Leu His Leu Ala Ala Arg Ser Gly Ser
        195                 200                 205

Leu Asp Cys Val Arg Lys Leu Leu Ala Trp Gly Ala Asp Arg Leu Gln
    210                 215                 220

Arg Asp Ser Ala Gly Arg Ile Ala Tyr Val Val Ala Gln Lys Arg His
225                 230                 235                 240

His Gly Ala Cys Ala Ala Leu Leu Asn Pro Ser Ser Ala Glu Pro Met
                245                 250                 255

Val Trp Pro Ser Pro Leu Lys Phe Ile Ser Glu Leu Asp Pro Glu Ala
            260                 265                 270

Lys Ala Leu Leu Glu Ala Ala Leu Thr Glu Ala Asn Arg Glu Arg Glu
        275                 280                 285

Lys Lys Ile Leu Lys Asp Ala Lys Cys Ser Pro Gln Ser Pro Leu Gln
    290                 295                 300

Tyr Asp Asp Asn Val Asp Asp Met Phe Ser Glu Val Ser Asp Thr
305                 310                 315                 320

Glu Leu Cys Cys Ile Cys Phe Asp Gln Ala Cys Thr Ile Glu Val Glu
```

```
                    325                 330                 335
Asp Cys Gly His Gln Met Cys Ala Pro Cys Thr Leu Ala Leu Cys Cys
            340                 345                 350

His Asn Lys Pro Asn Pro Ala Thr Leu Thr Met Pro Ser Pro Ala Cys
            355                 360                 365

Pro Phe Cys Arg Gly Ser Ile Ser Arg Leu Val Val Ala Gln Thr Arg
        370                 375                 380

Ala Asp Asn Ala Asp Pro Asp Arg Pro Ala Ser Pro Gln Leu Ala His
385                 390                 395                 400

Arg Arg Ser Arg Arg Ser His Asn Leu Ser Glu Gly Ser Ser Ser Phe
                405                 410                 415

Lys Gly Leu Ser Ser Ala Ile Ser Lys Ile Thr Arg Gly Ser Ser Arg
            420                 425                 430

Met Ala Asp Ser Glu Ser Ala Ala Ala Met Asp Lys Pro Glu His Asp
            435                 440                 445

Leu
```

<210> SEQ ID NO 80
<211> LENGTH: 1389
<212> TYPE: DNA
<213> ORGANISM: Hordeum vulgare

<400> SEQUENCE: 80

```
atggggcacg ggctcagctg cagccgcgac ggcgacgagc acgacttctt ccgcgccgcg      60
caggccggcg acctcgacgc gctcgacggc ctcctcgccg ccgacccggc gctcgcccgc     120
cgcgccacgc tctacgaccg cctcaccgcg ctccacgtcg ccgccgccaa cggctgcctc     180
ccggccgtcg acatgatcct cgcccgcggc gtccgccccg acgttgtcga ccgccgcaag     240
cgcaccccgc tcatgctcgc cgccacccac ggccacatcg actgcgccct cgccctcctc     300
cgcgccggcg ccaatattct gatgttcgac tcggtgaacg cgcggacgtg cctgcaccac     360
gcggcgtact acgccacgc cgactgcctg cgggccatcc tcgccgcggc cgcaccacg      420
ccggtggccg actcgtgggg cttcgtgcga ttcgtcaacg tccgggacga gcacggcgcc     480
acgccgctgc acgtggccgc caggcagggc cggccggagt gcgtgcacct gctgctcgag     540
agcggcgcca tcgtctccgc ccccaccggc tcctacggct tcccggggag cacggcgctt     600
cacctggcgc gcgcggcgg cagcctggag tgcgtccggg agctgctggc gtggggtgcc     660
gaccgcgtgc accgggactc agcgggccgg atcgcgtact cggtggcgac gaagcgcggc     720
cacggcgcgt gcgctgcgct gctgaacccg tcggcggcgg agcccatggt ctggccgtcg     780
ccgctcaagt tcatcggcga gctggggggcg gacgcgaggg cgctccttga ggcggctctg     840
gccgaggcga accgggagcg ggagaagaag atcctcaagg gcaccaatta cacggacgcc     900
tcgccggcgc tctccgacgc cggtggcgac gacgacgccg acgacgtgga cgaccaggag     960
gacgaggagg tgtgcagcat ctgcttcgag caggcgtgca gcatcgaggt ggaggactgc    1020
gggcaccgga tgtgcgccgc ctgcacgctg gcgctctgct gccacagcaa gcccaacccg    1080
gccacgctca cgctgcagcc gccggcgtgc cccttctgcc gcagctgcat ctcccggctc    1140
gtcgtggccc actccaaggc caaggccgtg gcggtcgtgt gcgccggcga cgaggccgag    1200
gagaagcagc cggcgtcgcc gcggctgagc cggaggcggt gcggaggtc ccgcgagggg    1260
agcagcagct tcaagggcct ctcgtcggcc atggggtcgc tgtccagcaa gatcggccgc    1320
ggctccggcc ggctcgccgg cgacagcgac ggcgtgttac tcgacaagct ggaacaccac    1380
``` ctcccgtga                                                                 1389

<210> SEQ ID NO 81
<211> LENGTH: 462
<212> TYPE: PRT
<213> ORGANISM: Hordeum vulgare

<400> SEQUENCE: 81

```
Met Gly His Gly Leu Ser Cys Ser Arg Asp Gly Asp Glu His Asp Phe
1               5                   10                  15

Phe Arg Ala Ala Gln Ala Gly Asp Leu Asp Ala Leu Asp Gly Leu Leu
                20                  25                  30

Ala Ala Asp Pro Ala Leu Ala Arg Arg Ala Thr Leu Tyr Asp Arg Leu
            35                  40                  45

Thr Ala Leu His Val Ala Ala Asn Gly Cys Leu Pro Ala Val Asp
        50                  55                  60

Met Ile Leu Ala Arg Gly Val Arg Pro Asp Val Val Asp Arg Lys
65                  70                  75                  80

Arg Thr Pro Leu Met Leu Ala Ala Thr His Gly His Ile Asp Cys Ala
                85                  90                  95

Leu Ala Leu Leu Arg Ala Gly Ala Asn Ile Leu Met Phe Asp Ser Val
            100                 105                 110

Asn Ala Arg Thr Cys Leu His His Ala Ala Tyr Tyr Gly His Ala Asp
        115                 120                 125

Cys Leu Arg Ala Ile Leu Ala Ala Arg Thr Thr Pro Val Ala Asp
    130                 135                 140

Ser Trp Gly Phe Val Arg Phe Val Asn Val Arg Asp Glu His Gly Ala
145                 150                 155                 160

Thr Pro Leu His Val Ala Ala Arg Gln Gly Arg Pro Glu Cys Val His
                165                 170                 175

Leu Leu Leu Glu Ser Gly Ala Ile Val Ser Ala Pro Thr Gly Ser Tyr
            180                 185                 190

Gly Phe Pro Gly Ser Thr Ala Leu His Leu Ala Ala Arg Gly Gly Ser
        195                 200                 205

Leu Glu Cys Val Arg Glu Leu Leu Ala Trp Gly Ala Asp Arg Val His
    210                 215                 220

Arg Asp Ser Ala Gly Arg Ile Ala Tyr Ser Val Ala Thr Lys Arg Gly
225                 230                 235                 240

His Gly Ala Cys Ala Ala Leu Leu Asn Pro Ser Ala Ala Glu Pro Met
                245                 250                 255

Val Trp Pro Ser Pro Leu Lys Phe Ile Gly Glu Leu Gly Ala Asp Ala
            260                 265                 270

Arg Ala Leu Leu Glu Ala Ala Leu Ala Glu Ala Asn Arg Glu Arg Glu
        275                 280                 285

Lys Lys Ile Leu Lys Gly Thr Asn Tyr Thr Asp Ala Ser Pro Ala Leu
    290                 295                 300

Ser Asp Ala Gly Gly Asp Asp Ala Asp Asp Val Asp Gln Glu
305                 310                 315                 320

Asp Glu Glu Val Cys Ser Ile Cys Phe Glu Gln Ala Cys Ser Ile Glu
                325                 330                 335

Val Glu Asp Cys Gly His Arg Met Cys Ala Ala Cys Thr Leu Ala Leu
            340                 345                 350

Cys Cys His Ser Lys Pro Asn Pro Ala Thr Leu Thr Leu Gln Pro Pro
        355                 360                 365
```

Ala Cys Pro Phe Cys Arg Ser Cys Ile Ser Arg Leu Val Val Ala Asp
        370                 375                 380

Ser Lys Ala Lys Ala Val Ala Val Val Cys Ala Gly Asp Glu Ala Glu
385                 390                 395                 400

Glu Lys Gln Pro Ala Ser Pro Arg Leu Ser Arg Arg Ser Arg Arg
                405                 410                 415

Ser Arg Glu Gly Ser Ser Ser Phe Lys Gly Leu Ser Ser Ala Met Gly
            420                 425                 430

Ser Leu Ser Ser Lys Ile Gly Arg Gly Ser Gly Arg Leu Ala Gly Asp
        435                 440                 445

Ser Asp Gly Val Leu Leu Asp Lys Leu Glu His His Leu Pro
450                 455                 460

<210> SEQ ID NO 82
<211> LENGTH: 1347
<212> TYPE: DNA
<213> ORGANISM: Hordeum vulgare

<400> SEQUENCE: 82

| | |
|---|---:|
| atggggcacg gagccagctg cggccgcccc agcgaggagg tggacttctt cggcgcggca | 60 |
| cagtccggcg acctcgcccg cctcgccgcc gccgtcagct cccgcccctc cctcctccgt | 120 |
| cgcaccacgc tcttcgaccg cctctccgcg ctccacatcg ccgccgccca cggccacctc | 180 |
| caagttgtgt ccatggcatt ggatctttgc gtgcagccgg acgtcgtgag ccgccataag | 240 |
| cagacggcgc tgatgcttgc ggcgatgcac gggaggaccg agtgcgtgcg acggttgctc | 300 |
| gacgccggcg ccaatatcct gatgttcgat tcgtcgcacg gcggacgtg cctgcactac | 360 |
| gcggcgtact acggccactc agactgcctc cggaccatcc tcacggcggc ccggaccgcg | 420 |
| ccggtgtcgc aatcctgggg atacgcgcgg ttcgtcaatg tgcgggatga cacgggagcg | 480 |
| acgccgctgc acctcgcggc gaggcagggc tggcgccgct gcgtccacgt cctgctggag | 540 |
| aacggcgcca tcgtgtctgc ctccagcggc gccttcggat tccccgggag cacgccgctg | 600 |
| catttggccg cgcgcggcgg gagcctcgac tgcgtccgcc agctgctctc ctggggcgcc | 660 |
| gaccgcctcc agcgcgactc cgttggaaga attccatatg aggtcgcggt gaagcgcggg | 720 |
| catgtggcgt gcgcggcgct gctgaacccc tcatcggcag agccctagt atggcctgct | 780 |
| cctctcaagt tcatcagcga gctggaacct gacgccaagg ctctcctgga ggcagccctg | 840 |
| atggaggcca atagggagag ggagaagagg atcctgaaag gggccaagaa ttcattgcca | 900 |
| tcgccgtcgc attcagatga cgatgccatc gtctccgagg cgccgaggt gtgcagcatc | 960 |
| tgcttcgacc aggcgtgcgc gatcgaggtc cgggagtgcg ggcaccaaat gtgcgcggcg | 1020 |
| tgcacgctgg cgctgtgctg ccacgccaag cccaacccgg ccacgcagag ccagccgctg | 1080 |
| cccacctgcc ccttctgccg cggcggcatc tcccggctgg cggtggccac cagggccaag | 1140 |
| gccggcgacg aggacgagga tgacgaagag ggagaaggca ggctggagtc tccgcggcaa | 1200 |
| cggaggtctc gccggtccgt gaacctcggc gacggcggca gcagcagcag cagcctcatg | 1260 |
| ggcagcatcg cctcgtccat cggcaagatg ggccggcgca aaaccgacag cagcgagctg | 1320 |
| caggtgcagc tcgaggacaa gccatag | 1347 |

<210> SEQ ID NO 83
<211> LENGTH: 448
<212> TYPE: PRT
<213> ORGANISM: Hordeum vulgare

<400> SEQUENCE: 83

```
Met Gly His Gly Ala Ser Cys Gly Arg Pro Ser Glu Val Asp Phe
1               5                   10                  15

Phe Gly Ala Ala Gln Ser Gly Asp Leu Ala Arg Leu Ala Ala Val
            20                  25                  30

Ser Ser Arg Pro Ser Leu Leu Arg Arg Thr Thr Leu Phe Asp Arg Leu
        35                  40                  45

Ser Ala Leu His Ile Ala Ala His Gly His Leu Gln Val Val Ser
    50                  55                  60

Met Ala Leu Asp Leu Cys Val Gln Pro Asp Val Val Ser Arg His Lys
65                  70                  75                  80

Gln Thr Ala Leu Met Leu Ala Ala Met His Gly Arg Thr Glu Cys Val
                85                  90                  95

Arg Arg Leu Leu Asp Ala Gly Ala Asn Ile Leu Met Phe Asp Ser Ser
            100                 105                 110

His Gly Arg Thr Cys Leu His Tyr Ala Ala Tyr Tyr Gly His Ser Asp
        115                 120                 125

Cys Leu Arg Thr Ile Leu Thr Ala Ala Arg Thr Ala Pro Val Ser Gln
    130                 135                 140

Ser Trp Gly Tyr Ala Arg Phe Val Asn Val Arg Asp Asp Thr Gly Ala
145                 150                 155                 160

Thr Pro Leu His Leu Ala Ala Arg Gln Gly Trp Arg Arg Cys Val His
            165                 170                 175

Val Leu Leu Glu Asn Gly Ala Ile Val Ser Ala Ser Ser Gly Ala Phe
        180                 185                 190

Gly Phe Pro Gly Ser Thr Pro Leu His Leu Ala Ala Arg Gly Gly Ser
    195                 200                 205

Leu Asp Cys Val Arg Gln Leu Leu Ser Trp Gly Ala Asp Arg Leu Gln
210                 215                 220

Arg Asp Ser Val Gly Arg Ile Pro Tyr Glu Val Ala Val Lys Arg Gly
225                 230                 235                 240

His Val Ala Cys Ala Ala Leu Leu Asn Pro Ser Ser Ala Glu Pro Leu
            245                 250                 255

Val Trp Pro Ala Pro Leu Lys Phe Ile Ser Glu Leu Glu Pro Asp Ala
        260                 265                 270

Lys Ala Leu Leu Glu Ala Ala Leu Met Glu Ala Asn Arg Glu Arg Glu
    275                 280                 285

Lys Arg Ile Leu Lys Gly Ala Lys Asn Ser Leu Pro Ser Pro Ser His
290                 295                 300

Ser Asp Asp Asp Ala Ile Val Ser Glu Gly Ala Glu Val Cys Ser Ile
305                 310                 315                 320

Cys Phe Asp Gln Ala Cys Ala Ile Glu Val Arg Glu Cys Gly His Gln
            325                 330                 335

Met Cys Ala Ala Cys Thr Leu Ala Leu Cys Cys His Ala Lys Pro Asn
        340                 345                 350

Pro Ala Thr Gln Ser Gln Pro Leu Pro Thr Cys Pro Phe Cys Arg Gly
    355                 360                 365

Gly Ile Ser Arg Leu Ala Val Ala Thr Arg Ala Lys Ala Gly Asp Glu
    370                 375                 380

Asp Glu Asp Asp Glu Glu Gly Glu Gly Arg Leu Glu Ser Pro Arg Gln
385                 390                 395                 400

Arg Arg Ser Arg Arg Ser Val Asn Leu Gly Asp Gly Gly Ser Ser Ser
                405                 410                 415
```

-continued

Ser Ser Leu Met Gly Ser Ile Ala Ser Ser Ile Gly Lys Met Gly Arg
                420                 425                 430

Arg Lys Thr Asp Ser Ser Glu Leu Gln Val Gln Leu Glu Asp Lys Pro
            435                 440                 445

<210> SEQ ID NO 84
<211> LENGTH: 1359
<212> TYPE: DNA
<213> ORGANISM: Brachypodium distachyon

<400> SEQUENCE: 84

```
atggggcacg gcctgagctg cggccgcgac ggcgaggagc acgagttctt ccgggcggcg      60
cagtccggcg acgccgacgc catggacggc ctcctcgccg gcgacccgtc gctggcccgc     120
cgcgccacca tctacgaccg gctgacgccg ctccacgtgg cggccgccaa cgggcacctg     180
gaggcggtgt ccctgctcct ggaccggggg cgggcggcgc ggacgcgct  gagccggacc     240
aagcagacgc cgctcatgct cgccgccatg cacggcaagc tcgactgcgt cctccgcctc     300
ctccacgccg gcgccaatat cttgatgttc gattcggtgc acgccaggag ctgcctgcac     360
cacgcggcgt actacggcca cggggactgc ctggcggcga tcctggcggc ggcgcggacg     420
gcgccggtgg cggcgtcgtg gggcttcgca cgcttcgtca acgtccgcga cgagcacggc     480
gccacgccgc tccacctggc ggcgaggcac gggcgcgccg ggtgcgtgca cgcgctcctc     540
gacgccggcg ccatcgtgtc ggcgccgacg gggtcctacg ggttccccgg agcacggcg      600
ctgcacctgg cggcgcgcgg cgggtccctg gagtgcgtca gggagctgct ggcgtggggc     660
gccgacaggg tgcagcggga ctcggcgggg aggatcgcgt acgcggtggc cgtgaagcgg     720
cggcatggcg ggtgcgcggc ggcgctggac cccggcgcgg cggagcccat ggtgtggccg     780
tccccgctca gctcgtcgc  cgagctcgac gccggcgcca gggcgctcct ccaggccgcg     840
ctcgccgacg ccaacaagaa gatcctcaca cgcctcaagg cctccggcaa cacctccgcc     900
ggccgcgagg aagaagaaga agaggaagaa gaggatgagg aattgtgcag catctgcttc     960
gaacaggcgt gcagcatgga ggtggaggac tgcgggcacc ggatgtgcgc ggcgtgcacg    1020
ctggcgctct gctgccacag caagcctaac ccggccacgt tcaccgcgaa cccgccggcg    1080
tgcccgttct gccgcaccct catctcccgc ctcgttgtcg ccgagtccaa ggccaaggcc    1140
aaggcggtgg cgatcaccgg cgatgagctt gaggagaagg cggcggcgat ggtgggatcg    1200
ccgcggctga gccggaggcg gtccagcagc ttcaaggggc tgtcgtccgc cgtggtgggg    1260
tcgctgtcgt gcaagatcgg ccgcggctcc ggcaggttgg ccggtgacag caacggcggc    1320
gggggcggct tcctcgacaa gcctgagcac gacccatga                           1359
```

<210> SEQ ID NO 85
<211> LENGTH: 452
<212> TYPE: PRT
<213> ORGANISM: Brachypodium distachyon

<400> SEQUENCE: 85

Met Gly His Gly Leu Ser Cys Gly Arg Asp Gly Glu Glu His Glu Phe
1               5                   10                  15

Phe Arg Ala Ala Gln Ser Gly Asp Ala Asp Ala Met Asp Gly Leu Leu
            20                  25                  30

Ala Gly Asp Pro Ser Leu Ala Arg Arg Ala Thr Ile Tyr Asp Arg Leu
        35                  40                  45

Thr Pro Leu His Val Ala Ala Asn Gly His Leu Glu Ala Val Ser
    50                  55                  60

Leu Leu Leu Asp Arg Gly Arg Ala Ala Pro Asp Ala Leu Ser Arg Thr
 65                  70                  75                  80

Lys Gln Thr Pro Leu Met Leu Ala Ala Met His Gly Lys Leu Asp Cys
                 85                  90                  95

Val Leu Arg Leu Leu His Ala Gly Ala Asn Ile Leu Met Phe Asp Ser
            100                 105                 110

Val His Ala Arg Ser Cys Leu His His Ala Ala Tyr Tyr Gly His Gly
            115                 120                 125

Asp Cys Leu Ala Ala Ile Leu Ala Ala Arg Thr Ala Pro Val Ala
130                 135                 140

Ala Ser Trp Gly Phe Ala Arg Phe Val Asn Val Arg Asp Glu His Gly
145                 150                 155                 160

Ala Thr Pro Leu His Leu Ala Ala Arg His Gly Arg Ala Gly Cys Val
                165                 170                 175

His Ala Leu Leu Asp Ala Gly Ala Ile Val Ser Ala Pro Thr Gly Ser
            180                 185                 190

Tyr Gly Phe Pro Gly Ser Thr Ala Leu His Leu Ala Ala Arg Gly Gly
            195                 200                 205

Ser Leu Glu Cys Val Arg Glu Leu Leu Ala Trp Gly Ala Asp Arg Val
210                 215                 220

Gln Arg Asp Ser Ala Gly Arg Ile Ala Tyr Ala Val Ala Val Lys Arg
225                 230                 235                 240

Arg His Gly Gly Cys Ala Ala Leu Asp Pro Gly Ala Ala Glu Pro
                245                 250                 255

Met Val Trp Pro Ser Pro Leu Lys Leu Val Ala Glu Leu Asp Ala Gly
            260                 265                 270

Ala Arg Ala Leu Leu Gln Ala Ala Leu Ala Asp Ala Asn Lys Lys Ile
            275                 280                 285

Leu Thr Arg Leu Lys Ala Ser Gly Asn Thr Ser Ala Gly Arg Glu Glu
290                 295                 300

Glu Glu Glu Glu Glu Glu Glu Asp Glu Glu Leu Cys Ser Ile Cys Phe
305                 310                 315                 320

Glu Gln Ala Cys Ser Met Glu Val Glu Asp Cys Gly His Arg Met Cys
                325                 330                 335

Ala Ala Cys Thr Leu Ala Leu Cys Cys His Ser Lys Pro Asn Pro Ala
            340                 345                 350

Thr Phe Thr Ala Asn Pro Pro Ala Cys Pro Phe Cys Arg Thr Ser Ile
            355                 360                 365

Ser Arg Leu Val Val Ala Glu Ser Lys Ala Lys Ala Lys Ala Val Ala
            370                 375                 380

Ile Thr Gly Asp Glu Leu Glu Glu Lys Ala Ala Ala Met Val Gly Ser
385                 390                 395                 400

Pro Arg Leu Ser Arg Arg Arg Ser Ser Ser Phe Lys Gly Leu Ser Ser
                405                 410                 415

Ala Val Val Gly Ser Leu Ser Cys Lys Ile Gly Arg Gly Ser Gly Arg
            420                 425                 430

Leu Ala Gly Asp Ser Asn Gly Gly Gly Gly Phe Leu Asp Lys Pro
            435                 440                 445

Glu His Asp Pro
450

<210> SEQ ID NO 86
<211> LENGTH: 1356

```
<212> TYPE: DNA
<213> ORGANISM: Brachypodium distachyon

<400> SEQUENCE: 86
atggggcacg gggtgagctg cgcgcgcacc ggcgacgagc acgacttctt ccgcgcggcg      60
cagctcgggg acctcgacgc cctggccgcg ctcctcgacg ccgacgcctc cctcgcccgc     120
cgcgccaccc tctacgaccg cctctctccg ctccacatcg ccgccgccaa tggccacctc     180
gaggtgctct ccatgttctt ggatcgcggg gcgcggccgg acgcggtgga tcggcacaag     240
cagactccgc tgatgctcgc cgccacgcac ggcaacatcg gctgcgcgct caagctcctc     300
caggccggcg caaatatctt gatgtttgat tcggtgaacg cgcggacctg cctccaccac     360
gcggcgtact acggccacgt cgactgcctg gaggccatcc tctccgccgc gcggaccacg     420
ccggtggccg attcgtgggg tttcgcccgg ttcgtcaacg tcagggacga ctatggagcc     480
acgccgctgc atctcgcagc caggcagggg cggccggagt gcttgcaggt gctgctggag     540
aagggcgcca ttgtgtctgc tttgacagga tcatacggct ccctggtag cacttcattg      600
catctggccg ctcgaagtgg gagcttggac tgcatccgga agctgcttgc ctggggagct     660
gatcggctcc aaagggactc ggccgggaga attccctatg ccgttgcgct gaagcgcaac     720
catggggcct gtgcagcttt gctaaaccct tcttcggcag agcccatggt ttggccttcc     780
cctcttaagt tcatcagcga gcttgatccg gaagcaaagg ctctcctgga agcagccctc     840
aaggaagcca acagggagag ggagaaaaat atcttgaagg gcacaaaata ttccatgtca     900
tcccctacac gtcacgatga tatcatcgat gatgaagacg catgctcgga ggtgagcgac     960
accgagctgt gctgcatctg cttcgaccag tcctgcacca tagaggtaca agactgcggg    1020
caccaaatgt gcgccccgtg cacacttgcg ctctgctgcc acaacaagcc caacccgacg    1080
accctgaccc tgccctcacc ggcctgccca ttctgccgtg gcagcatctc ccaactggtg    1140
gtggcccgga ccaggacacc cagcgacccc gacaagccag cctccccgac ctccccgcag    1200
ctcacccaaa ggcagtctcg acgctctcgc aacctcagcg aggggagcgg cagcttcaaa    1260
gggctgtcct cggccatctc gaagatcgcc cgtggctcga gccggatggc cggcagcgac    1320
tgcggtgaca tggacaagcc cgagcatgat ccgtga                              1356

<210> SEQ ID NO 87
<211> LENGTH: 451
<212> TYPE: PRT
<213> ORGANISM: Brachypodium distachyon

<400> SEQUENCE: 87

Met Gly His Gly Val Ser Cys Ala Arg Thr Gly Asp Glu His Asp Phe
1               5                   10                  15

Phe Arg Ala Ala Gln Leu Gly Asp Leu Asp Ala Leu Ala Ala Leu Leu
                20                  25                  30

Asp Ala Asp Ala Ser Leu Ala Arg Arg Ala Thr Leu Tyr Asp Arg Leu
            35                  40                  45

Ser Pro Leu His Ile Ala Ala Ala Asn Gly His Leu Glu Val Leu Ser
        50                  55                  60

Met Phe Leu Asp Arg Gly Ala Arg Pro Asp Ala Val Asp Arg His Lys
65                  70                  75                  80

Gln Thr Pro Leu Met Leu Ala Ala Thr His Gly Asn Ile Gly Cys Ala
                85                  90                  95

Leu Lys Leu Leu Gln Ala Gly Ala Asn Ile Leu Met Phe Asp Ser Val
                100                 105                 110
```

Asn Ala Arg Thr Cys Leu His His Ala Ala Tyr Tyr Gly His Val Asp
            115                 120                 125

Cys Leu Glu Ala Ile Leu Ser Ala Ala Arg Thr Thr Pro Val Ala Asp
    130                 135                 140

Ser Trp Gly Phe Ala Arg Phe Val Asn Val Arg Asp Asp Tyr Gly Ala
145                 150                 155                 160

Thr Pro Leu His Leu Ala Ala Arg Gln Gly Arg Pro Glu Cys Leu Gln
                165                 170                 175

Val Leu Leu Glu Lys Gly Ala Ile Val Ser Ala Leu Thr Gly Ser Tyr
            180                 185                 190

Gly Phe Pro Gly Ser Thr Ser Leu His Leu Ala Ala Arg Ser Gly Ser
        195                 200                 205

Leu Asp Cys Ile Arg Lys Leu Leu Ala Trp Gly Ala Asp Arg Leu Gln
    210                 215                 220

Arg Asp Ser Ala Gly Arg Ile Pro Tyr Ala Val Ala Leu Lys Arg Asn
225                 230                 235                 240

His Gly Ala Cys Ala Ala Leu Leu Asn Pro Ser Ser Ala Glu Pro Met
                245                 250                 255

Val Trp Pro Ser Pro Leu Lys Phe Ile Ser Glu Leu Asp Pro Glu Ala
            260                 265                 270

Lys Ala Leu Leu Glu Ala Ala Leu Lys Glu Ala Asn Arg Glu Arg Glu
        275                 280                 285

Lys Asn Ile Leu Lys Gly Thr Lys Tyr Ser Met Ser Ser Pro Thr Arg
    290                 295                 300

His Asp Asp Ile Ile Asp Glu Asp Ala Cys Ser Glu Val Ser Asp
305                 310                 315                 320

Thr Glu Leu Cys Cys Ile Cys Phe Asp Gln Ser Cys Thr Ile Glu Val
                325                 330                 335

Gln Asp Cys Gly His Gln Met Cys Ala Pro Cys Thr Leu Ala Leu Cys
            340                 345                 350

Cys His Asn Lys Pro Asn Pro Thr Thr Leu Thr Leu Pro Ser Pro Ala
        355                 360                 365

Cys Pro Phe Cys Arg Gly Ser Ile Ser Gln Leu Val Val Ala Arg Thr
    370                 375                 380

Arg Thr Pro Ser Asp Pro Asp Lys Pro Ala Ser Pro Thr Ser Pro Gln
385                 390                 395                 400

Leu Thr Gln Arg Gln Ser Arg Arg Ser Arg Asn Leu Ser Glu Gly Ser
                405                 410                 415

Gly Ser Phe Lys Gly Leu Ser Ser Ala Ile Ser Lys Ile Ala Arg Gly
            420                 425                 430

Ser Ser Arg Met Ala Gly Ser Asp Cys Gly Asp Met Asp Lys Pro Glu
        435                 440                 445

His Asp Pro
    450

<210> SEQ ID NO 88
<211> LENGTH: 1362
<212> TYPE: DNA
<213> ORGANISM: Brachypodium distachyon

<400> SEQUENCE: 88
atggggcacg gtgccagctg cggccgcccc agcgaggagg tggacttctt cggcgcggcg      60
cagtccgggg acctcgcccg gctcgctgcc gccgtccgct cccgcccctc cctcctccgc     120

```
cgcaccacgc tcttcgaccg cctctccgcg ctccacatcg ccgccgccca cggccacctc      180
caagtggtct ccatggcatt ggatctttgc gtgcagccgg acgtcgttaa ccgccacaag      240
cagacggcgc tgatgctggc ggcgatgcac gggcggaccg agtgcgtgcg acggctgctc      300
gacgccggcg ccaatatcct gatgttcgat tcgtcgcacg gcggacgtg cctgcactac       360 gcggcgtact acggccactc cgactgcctc cggaccatcc tctcggcggc ccgcaccgcg      420
cccgtgtcgc agtcctgggg atacgcgcgc ttcgtcaacg tgagggacga caccggggcg      480
acgccgctgc acctcgcggc caggcagggc tggcgccgct gcgtccacgt cctgctcgag      540
aacggcgcca tcgtgtccgc ctccagcggc gcattcggat ccccgggag cacgccgctg        600 catttggccg cgcgcggcgg gagcctggac tgcgtccgcc agctgctctc ctggggcgcc      660
gaccgcctcc agcgagattc cgttgggagg attccgtacg aggtcgcgat gaagcgaggc      720
cacgcggcgt gcgcggcgct gctgaacccg gcatcggcag agccctcgt gtggccttcc       780 cctctcaagt tcatcagcga gctcgaaccg gacgccaaag ctctcctgga ggcagcgctg      840
atggaggcca atcgggagag ggagaagagg gttctcaaag gaccaagag cttgctgcca       900 tcgccgtcgc attcagatga cggtgccacc atctctgagg gtgcggccga ggtgtgcagc      960
atctgcttcg agcaggcgtg cagcatcgag gtccgggatt gcgggcacca gatgtgcgcg     1020
gcgtgcacgc tggcgctcct ctgccacacc aagcccaacc cggcgacgca gagccagcag     1080
ctgcccacct gccccttctg ccgcggcagc atctcccggc tggccgtggc caccaaggcc     1140
aaggccggcg acgacgaaga cgacgacgac gatgacgatg tggaaggaga ggacaggctc     1200
gaggagtctc cgcggcaccg gagaactcgc cggtctatga acctcagcgg cgacggggcg     1260
agcagcagcg gcagcctcat gggcagcatc gcctcgtcca tcggcaagat gggccgacgc     1320
aaaaccgaca gcagcgaaca ggtagtcgac gacaagccgt ag                        1362
```

<210> SEQ ID NO 89
<211> LENGTH: 453
<212> TYPE: PRT
<213> ORGANISM: Brachypodium distachyon

<400> SEQUENCE: 89

Met Gly His Gly Ala Ser Cys Gly Arg Pro Ser Glu Glu Val Asp Phe
1               5                   10                  15

Phe Gly Ala Ala Gln Ser Gly Asp Leu Ala Arg Leu Ala Ala Ala Val
                20                  25                  30

Arg Ser Arg Pro Ser Leu Leu Arg Arg Thr Thr Leu Phe Asp Arg Leu
            35                  40                  45

Ser Ala Leu His Ile Ala Ala Ala His Gly His Leu Gln Val Val Ser
        50                  55                  60

Met Ala Leu Asp Leu Cys Val Gln Pro Asp Val Val Asn Arg His Lys
65                  70                  75                  80

Gln Thr Ala Leu Met Leu Ala Ala Met His Gly Arg Thr Glu Cys Val
                85                  90                  95

Arg Arg Leu Leu Asp Ala Gly Ala Asn Ile Leu Met Phe Asp Ser Ser
            100                 105                 110

His Gly Arg Thr Cys Leu His Tyr Ala Ala Tyr Gly His Ser Asp
            115                 120                 125

Cys Leu Arg Thr Ile Leu Ser Ala Ala Arg Thr Ala Pro Val Ser Gln
        130                 135                 140

Ser Trp Gly Tyr Ala Arg Phe Val Asn Val Arg Asp Asp Thr Gly Ala
145                 150                 155                 160

Thr Pro Leu His Leu Ala Ala Arg Gln Gly Trp Arg Cys Val His
        165                 170                 175

Val Leu Leu Glu Asn Gly Ala Ile Val Ser Ala Ser Ser Gly Ala Phe
        180                 185                 190

Gly Phe Pro Gly Ser Thr Pro Leu His Leu Ala Arg Gly Gly Ser
        195                 200                 205

Leu Asp Cys Val Arg Gln Leu Leu Ser Trp Gly Ala Asp Arg Leu Gln
210                 215                 220

Arg Asp Ser Val Gly Arg Ile Pro Tyr Glu Val Ala Met Lys Arg Gly
225                 230                 235                 240

His Ala Ala Cys Ala Ala Leu Leu Asn Pro Ala Ser Ala Glu Pro Leu
                245                 250                 255

Val Trp Pro Ser Pro Leu Lys Phe Ile Ser Glu Leu Glu Pro Asp Ala
        260                 265                 270

Lys Ala Leu Leu Glu Ala Ala Leu Met Glu Ala Asn Arg Glu Arg Glu
        275                 280                 285

Lys Arg Val Leu Lys Gly Thr Lys Ser Leu Leu Pro Ser Pro Ser His
        290                 295                 300

Ser Asp Asp Gly Ala Thr Ile Ser Glu Gly Ala Ala Glu Val Cys Ser
305                 310                 315                 320

Ile Cys Phe Glu Gln Ala Cys Ser Ile Glu Val Arg Asp Cys Gly His
                325                 330                 335

Gln Met Cys Ala Ala Cys Thr Leu Ala Leu Cys Cys His Thr Lys Pro
                340                 345                 350

Asn Pro Ala Thr Gln Ser Gln Gln Leu Pro Thr Cys Pro Phe Cys Arg
                355                 360                 365

Gly Ser Ile Ser Arg Leu Ala Val Ala Thr Lys Ala Lys Ala Gly Asp
370                 375                 380

Asp Glu Asp Asp Asp Asp Asp Val Glu Gly Glu Asp Arg Leu
385                 390                 395                 400

Glu Glu Ser Pro Arg His Arg Arg Thr Arg Arg Ser Met Asn Leu Ser
                405                 410                 415

Gly Asp Gly Gly Ser Ser Ser Gly Ser Leu Met Gly Ser Ile Ala Ser
                420                 425                 430

Ser Ile Gly Lys Met Gly Arg Arg Lys Thr Asp Ser Ser Glu Gln Val
        435                 440                 445

Val Asp Asp Lys Pro
450

<210> SEQ ID NO 90
<211> LENGTH: 1353
<212> TYPE: DNA
<213> ORGANISM: Triticum aestivum

<400> SEQUENCE: 90
atggggcacg gggtgagctg cgcgcgcacc ggcgacgagc acgacttctt ccgcgcggcc     60
cagctcgggg acctcgacgc cctgggcgcg ctgctcgccg ccgacgcctc cctcgcccgc    120
cgcgccacgc tctacgaccg cctctccccg ctccacatcg ccgccgccaa tggccgcctc    180
gaggcgctcg ccatgttcct ggatcgcggg gcgcagccgg acgccgtgga tcggcacaag    240
cagacccccc tgatgctcgc cgccatgcac ggcaagatcg gctgcgtgct caagctcctc    300
caggccggca caaacatctt gatgttcgac tcggtgcacg cgcggacctg cctccaccac    360
gcggcctact acgccacgt cgactgcctg acgccatcc tctccacggc gcggaccacg    420

-continued

```
ccggtggccg gctcatgggg gttcgcccgg ttcgtcaacg tcagggacga ccacggcgcc    480
acgccgctgc acctcgcggc caggcagggc cggccgggct gcgtgcaggt gctgctggag    540
aacggcgcca tcgtgtcggc attgaccgga tcatatggtt ccctggtag cacgtcgttg    600 catttggcag ctcgcagcgg ggacttggat tgcatccgga agctgcttgc gtggggagct    660
gatcggctcc aaagggactc tgctgggaga atccctatg tggtggcaca taagcgcaac    720 catgggcat gcgcagcatt gctgaaccct tcctcggcag agcctatggt ctggccttcc    780
cctctgaagt tcatcagcga gctcgacccg gaagccaagg ctctgctgga agcggccctg    840
atggaggcca caggagag ggagaagaag atcttgaagg acgcaaagtg ctcgccgcag    900
tcccctttgc aatacgatga tgatcacatc gacgacgaca tgttctcgga ggtgagcgac    960
acggagctgt gctgcatctg cttcgaccag gcgtgcacca tcgaggtgca ggactgcggg    1020
caccagatgt gcgcgccctg cacgctggcg ctgtgctgcc acaacaagcc caacccggcg    1080
accctgaccc tgccctcgcc ggcgtgcccg ttctgccgcg gcagcatctc gcggctggtg    1140
gtggcccaga cccagacagc agacaacggc gaccccgaca ggccagcctc cccgcagctc    1200
gcgcaccggc ggtcccggcg ctctcacaac ctcagtgagg gcagcagcag cttcaagggg    1260
ctgtcctcgg ccatctccaa gatcgcgcgc ggctcgagcc ggatggccga gagcgacggc    1320
gctgcgatgg acaagcccga gcacgatctg tga                                 1353
```

<210> SEQ ID NO 91
<211> LENGTH: 450
<212> TYPE: PRT
<213> ORGANISM: Triticum aestivum

<400> SEQUENCE: 91

```
Met Gly His Gly Val Ser Cys Ala Arg Thr Gly Asp Glu His Asp Phe
1               5                   10                  15

Phe Arg Ala Ala Gln Leu Gly Asp Leu Asp Ala Leu Gly Ala Leu Leu
            20                  25                  30

Ala Ala Asp Ala Ser Leu Ala Arg Arg Ala Thr Leu Tyr Asp Arg Leu
        35                  40                  45

Ser Pro Leu His Ile Ala Ala Asn Gly Arg Leu Glu Ala Leu Ala
    50                  55                  60

Met Phe Leu Asp Arg Gly Ala Gln Pro Asp Ala Val Asp Arg His Lys
65                  70                  75                  80

Gln Thr Pro Leu Met Leu Ala Ala Met His Gly Lys Ile Gly Cys Val
                85                  90                  95

Leu Lys Leu Leu Gln Ala Gly Ala Asn Ile Leu Met Phe Asp Ser Val
            100                 105                 110

His Ala Arg Thr Cys Leu His His Ala Ala Tyr Tyr Gly His Val Asp
        115                 120                 125

Cys Leu Asp Ala Ile Leu Ser Thr Ala Arg Thr Thr Pro Val Ala Gly
    130                 135                 140

Ser Trp Gly Phe Ala Arg Phe Val Asn Val Arg Asp Asp His Gly Ala
145                 150                 155                 160

Thr Pro Leu His Leu Ala Ala Arg Gln Gly Arg Pro Gly Cys Val Gln
                165                 170                 175

Val Leu Leu Glu Asn Gly Ala Ile Val Ser Ala Leu Thr Gly Ser Tyr
            180                 185                 190

Gly Phe Pro Gly Ser Thr Ser Leu His Leu Ala Ala Arg Ser Gly Asp
        195                 200                 205
```

```
Leu Asp Cys Ile Arg Lys Leu Leu Ala Trp Gly Ala Asp Arg Leu Gln
            210                 215                 220

Arg Asp Ser Ala Gly Arg Ile Pro Tyr Val Val Ala His Lys Arg Asn
225                 230                 235                 240

His Gly Ala Cys Ala Ala Leu Leu Asn Pro Ser Ser Ala Glu Pro Met
                245                 250                 255

Val Trp Pro Ser Pro Leu Lys Phe Ile Ser Glu Leu Asp Pro Glu Ala
                260                 265                 270

Lys Ala Leu Leu Glu Ala Ala Leu Met Glu Ala Asn Arg Glu Arg Glu
            275                 280                 285

Lys Lys Ile Leu Lys Asp Ala Lys Cys Ser Pro Gln Ser Pro Leu Gln
            290                 295                 300

Tyr Asp Asp His Ile Asp Asp Met Phe Ser Glu Val Ser Asp
305                 310                 315                 320

Thr Glu Leu Cys Cys Ile Cys Phe Asp Gln Ala Cys Thr Ile Glu Val
                325                 330                 335

Gln Asp Cys Gly His Gln Met Cys Ala Pro Cys Thr Leu Ala Leu Cys
                340                 345                 350

Cys His Asn Lys Pro Asn Pro Ala Thr Leu Thr Leu Pro Ser Pro Ala
            355                 360                 365

Cys Pro Phe Cys Arg Gly Ser Ile Ser Arg Leu Val Val Ala Gln Thr
370                 375                 380

Gln Thr Ala Asp Asn Gly Asp Pro Asp Arg Pro Ala Ser Pro Gln Leu
385                 390                 395                 400

Ala His Arg Arg Ser Arg Arg Ser His Asn Leu Ser Glu Gly Ser Ser
                405                 410                 415

Ser Phe Lys Gly Leu Ser Ser Ala Ile Ser Lys Ile Ala Arg Gly Ser
            420                 425                 430

Ser Arg Met Ala Glu Ser Asp Gly Ala Ala Met Asp Lys Pro Glu His
            435                 440                 445

Asp Leu
    450

<210> SEQ ID NO 92
<211> LENGTH: 1386
<212> TYPE: DNA
<213> ORGANISM: Sugarcane

<400> SEQUENCE: 92
atggggcacg gcgtgagctg cgcccgcacc ggcgacgagc acgactactt ccgcgcggcg     60
caggtcgggg acatcgacgc cctggacgcg ctcctcgccg ccgacccctc cctcgcccac    120
cgggccacgc tctacgaccg cctctccgcg ctccacatag ccgccgcgaa tggccgcctc    180
gaggtgctgt ccatgatctt ggatcacggg gtgccgccgg acgcggtgaa tcggcacaag    240
cagactccgc tgatgctcgc ggcgatgcac ggcaagatcg actgcgtgct caagctcctg    300
caggccggcg ccaatatcct gatgttcgac tccctgcacg gcggagctg cctacaccac    360 gcgtcctact cggccacgt cgactgcctg caggccatcc tcacggcggc gcggaccacg    420
ccggtggccg actcatgggg tttcgcccgg ttcgtcaacg tcaggacga ccacggcgcc    480 acgccgctgc acctcgccgc caggcagggc cgccccggct gcgtgcaggt gctgctggag    540
aacggcgcca ttgtctccgc cctcaccggc tcctacgggt tccccggcag cacgtcgctg    600
catctggccg ctcgcagcgg gaacctggac tgcatccgga agctgctcgc ctggggtgca    660
```

```
gatcgtctcc agagggactc agcagggagg attccttatg ccgttgcgct gaagcgcagc      720
cacgaggcgt gtgcggcgct gctgaaccct tcgtcagctg agcccatggt gtggccttcc      780
ccactgaagt tcatcagcga gctggacccg gaggcgaagg cgctcctgga agcggccctg      840
atggaagcca acagggagag ggagaagaag attctgaagg gcacaaagta ctctccacca      900
tcgccttccc cttgcgagca tgagaatgat gccgatgcca tcgacgatgc gtcctcggag      960
gcgagtgaca cggagctatg ctgcatctgc ttcgaccagg cgtgcacgat cgaggtgcaa     1020
gactgcgggc accagatgtg cgcgccatgc acgctggcgc tgtgctgcca cagcaagccc     1080
aacccgacga cgcttacact accgtcgccg gcgtgcccgt tctgccgcgg cagcatctcg     1140
cggttgctgg tggcccgagc aagcaccgcg ttcagcgacg acgccgacaa ggctgcttct     1200
gcggcggcct cctcaccgca gctcgtccgg cggcggtccc ggcggtctca caacctcagt     1260
gacggcggga gcagcagctt caaggggctg tcgtccgccg tggcagggtc cttctccaag     1320
atcgggcgcg ggtcgagccg gatggccgat agcgacggca tggacaagcc cgagcacgac     1380
ctgtga                                                                1386
```

<210> SEQ ID NO 93
<211> LENGTH: 461
<212> TYPE: PRT
<213> ORGANISM: Sugarcane

<400> SEQUENCE: 93

```
Met Gly His Gly Val Ser Cys Ala Arg Thr Gly Asp Glu His Asp Tyr
1               5                   10                  15

Phe Arg Ala Ala Gln Val Gly Asp Ile Asp Ala Leu Asp Ala Leu Leu
            20                  25                  30

Ala Ala Asp Pro Ser Leu Ala His Arg Ala Thr Leu Tyr Asp Arg Leu
        35                  40                  45

Ser Ala Leu His Ile Ala Ala Asn Gly Arg Leu Glu Val Leu Ser
    50                  55                  60

Met Ile Leu Asp His Gly Val Pro Pro Asp Ala Val Asn Arg His Lys
65                  70                  75                  80

Gln Thr Pro Leu Met Leu Ala Ala Met His Gly Lys Ile Asp Cys Val
                85                  90                  95

Leu Lys Leu Leu Gln Ala Gly Ala Asn Ile Leu Met Phe Asp Ser Leu
            100                 105                 110

His Gly Arg Ser Cys Leu His His Ala Ser Tyr Phe Gly His Val Asp
        115                 120                 125

Cys Leu Gln Ala Ile Leu Thr Ala Ala Arg Thr Thr Pro Val Ala Asp
    130                 135                 140

Ser Trp Gly Phe Ala Arg Phe Val Asn Val Arg Asp Asp His Gly Ala
145                 150                 155                 160

Thr Pro Leu His Leu Ala Ala Arg Gln Gly Arg Pro Gly Cys Val Gln
                165                 170                 175

Val Leu Leu Glu Asn Gly Ala Ile Val Ser Ala Leu Thr Gly Ser Tyr
            180                 185                 190

Gly Phe Pro Gly Ser Thr Ser Leu His Leu Ala Ala Arg Ser Gly Asn
        195                 200                 205

Leu Asp Cys Ile Arg Lys Leu Leu Ala Trp Gly Ala Asp Arg Leu Gln
    210                 215                 220

Arg Asp Ser Ala Gly Arg Ile Pro Tyr Ala Val Ala Leu Lys Arg Ser
225                 230                 235                 240
```

```
His Glu Ala Cys Ala Ala Leu Leu Asn Pro Ser Ser Ala Glu Pro Met
            245                 250                 255

Val Trp Pro Ser Pro Leu Lys Phe Ile Ser Glu Leu Asp Pro Glu Ala
        260                 265                 270

Lys Ala Leu Leu Glu Ala Ala Leu Met Glu Ala Asn Arg Glu Arg Glu
    275                 280                 285

Lys Lys Ile Leu Lys Gly Thr Lys Tyr Ser Pro Pro Ser Pro Ser Pro
290                 295                 300

Cys Glu His Glu Asn Asp Ala Asp Ala Ile Asp Ala Ser Ser Glu
305                 310                 315                 320

Ala Ser Asp Thr Glu Leu Cys Cys Ile Cys Phe Asp Gln Ala Cys Thr
                325                 330                 335

Ile Glu Val Gln Asp Cys Gly His Gln Met Cys Ala Pro Cys Thr Leu
            340                 345                 350

Ala Leu Cys Cys His Ser Lys Pro Asn Pro Thr Thr Leu Thr Leu Pro
        355                 360                 365

Ser Pro Ala Cys Pro Phe Cys Arg Gly Ser Ile Ser Arg Leu Leu Val
    370                 375                 380

Ala Arg Ala Ser Thr Ala Phe Ser Asp Asp Ala Asp Lys Ala Ala Ser
385                 390                 395                 400

Ala Ala Ala Ser Ser Pro Gln Leu Val Arg Arg Ser Arg Arg Ser
                405                 410                 415

His Asn Leu Ser Asp Gly Gly Ser Ser Ser Phe Lys Gly Leu Ser Ser
                420                 425                 430

Ala Val Ala Gly Ser Phe Ser Lys Ile Gly Arg Gly Ser Ser Arg Met
            435                 440                 445

Ala Asp Ser Asp Gly Met Asp Lys Pro Glu His Asp Leu
        450                 455                 460

<210> SEQ ID NO 94
<211> LENGTH: 1359
<212> TYPE: DNA
<213> ORGANISM: Panicum virgatum

<400> SEQUENCE: 94
atggggcacg gcgtcagctg cgcccgcacc ggtgacgagc acgactactt ccgcgcggcg      60
cagctcgggg acctcgacgc cttggccgcg ctcctcgccg ccgacacctc cctcactcgc     120
cgcgccaccc tctacgaccg cctctccgcg ctccacatcg ccgccgccaa tggacgcctc     180
gaggtgctgt ccatgatctt ggatcacggg gtgccgccgg acgtggtgaa tcggcacaag     240
cagactccgc tgatgctcgc ggcgatgcac ggcaagattg actgcgtgct caggctcctc     300
caggccggcg ccaatatctt gatgttcgat tctgtgcacg gcggagctg cctgcaccac      360 gctgcctact tcggccatgt ggactgcctg caggccatcc tctcggcggc gcagacgacg     420
ccggtggctg actcatgggg tttcgcccgg ttcgtcaacg tcagggacga ccacggcgcc     480
acgccgttgc atctcgcggc caggcagggg cggccagggt gcgtgcagat gttgctggag     540
aaaggcgcca ttgtatccgc tttgacaggc tcatacgggt ccctggtag cacatcgttg      600 catctggctc tcgcagtgg gaacctggat tgcatccgga actgcttgc ctggggagca       660 gatcgtctcc aaagggactc ggcagggaga attccctatg ctgttgcact gaagcgcaac     720
tacgaagcat gtcggctt gctaaaccct tcatcagctg agcccatggt gtggccttcc       780
ccacttaagt tcatcagcga gctcgatccg gaagcaaagg ctctcctgga agcagccctg     840
atggaagcca acagggagag ggagaagaag atcttgaagg gcacaaagta ctctctgcca     900
```

```
tcgccttcgc attgcgacgc cgatgttgtg gacgatgcat cctcagaggt gagcgacgca      960
gagctgtgct gcatctgctt cgaccaggca tgcaccatcg aggtgcagga ctgcgggcac     1020
cagatgtgcg cgccgtgcac gctggcgctg tgctgccaca gcaagcccaa cccgacgacc     1080
caaacgctgc cgtcgccagc ctgcccgttc tgccgcggca gcatctcgcg gctgctggtg     1140
gcccggacaa gcacgcccag tgaccccgag aaggcaggct actccccgca gctatcccga     1200
cggcggtctc ggcggtctca caacctcagc gacggggggca gcagcagctt caaggggctc    1260
tcgtccgcca tggggtcctt gtccaagatc gggcgcggct cgagccggat ggtcgacagc     1320
gacagtggca gcctggacaa gcccgagcac gacctgtga                            1359
```

<210> SEQ ID NO 95
<211> LENGTH: 452
<212> TYPE: PRT
<213> ORGANISM: Panicum virgatum

<400> SEQUENCE: 95

```
Met Gly His Gly Val Ser Cys Ala Arg Thr Gly Asp Glu His Asp Tyr
1               5                   10                  15
Phe Arg Ala Ala Gln Leu Gly Asp Leu Asp Ala Leu Ala Ala Leu Leu
            20                  25                  30
Ala Ala Asp Thr Ser Leu Thr Arg Arg Ala Thr Leu Tyr Asp Arg Leu
        35                  40                  45
Ser Ala Leu His Ile Ala Ala Asn Gly Arg Leu Glu Val Leu Ser
    50                  55                  60
Met Ile Leu Asp His Gly Val Pro Pro Asp Val Asn Arg His Lys
65                  70                  75                  80
Gln Thr Pro Leu Met Leu Ala Ala Met His Gly Lys Ile Asp Cys Val
                85                  90                  95
Leu Arg Leu Leu Gln Ala Gly Ala Asn Ile Leu Met Phe Asp Ser Val
            100                 105                 110
His Gly Arg Ser Cys Leu His His Ala Ala Tyr Phe Gly His Val Asp
        115                 120                 125
Cys Leu Gln Ala Ile Leu Ser Ala Ala Gln Thr Thr Pro Val Ala Asp
    130                 135                 140
Ser Trp Gly Phe Ala Arg Phe Val Asn Val Arg Asp Asp His Gly Ala
145                 150                 155                 160
Thr Pro Leu His Leu Ala Ala Arg Gln Gly Arg Pro Gly Cys Val Gln
                165                 170                 175
Met Leu Leu Glu Lys Gly Ala Ile Val Ser Ala Leu Thr Gly Ser Tyr
            180                 185                 190
Gly Phe Pro Gly Ser Thr Ser Leu His Leu Ala Ala Arg Ser Gly Asn
        195                 200                 205
Leu Asp Cys Ile Arg Lys Leu Leu Ala Trp Gly Ala Asp Arg Leu Gln
    210                 215                 220
Arg Asp Ser Ala Gly Arg Ile Pro Tyr Ala Val Ala Leu Lys Arg Asn
225                 230                 235                 240
Tyr Glu Ala Cys Ala Ala Leu Leu Asn Pro Ser Ser Ala Glu Pro Met
                245                 250                 255
Val Trp Pro Ser Pro Leu Lys Phe Ile Ser Glu Leu Asp Pro Glu Ala
            260                 265                 270
Lys Ala Leu Leu Glu Ala Ala Leu Met Glu Ala Asn Arg Glu Arg Glu
        275                 280                 285
```

Lys Lys Ile Leu Lys Gly Thr Lys Tyr Ser Leu Pro Ser Pro Ser His
290                 295                 300

Cys Asp Ala Asp Val Val Asp Ala Ser Ser Glu Val Ser Asp Ala
305                 310                 315                 320

Glu Leu Cys Cys Ile Cys Phe Asp Gln Ala Cys Thr Ile Glu Val Gln
                325                 330                 335

Asp Cys Gly His Gln Met Cys Ala Pro Cys Thr Leu Ala Leu Cys Cys
                340                 345                 350

His Ser Lys Pro Asn Pro Thr Thr Gln Thr Leu Pro Ser Pro Ala Cys
                355                 360                 365

Pro Phe Cys Arg Gly Ser Ile Ser Arg Leu Leu Val Ala Arg Thr Ser
370                 375                 380

Thr Pro Ser Asp Pro Glu Lys Ala Gly Tyr Ser Pro Gln Leu Ser Arg
385                 390                 395                 400

Arg Arg Ser Arg Arg Ser His Asn Leu Ser Asp Gly Gly Ser Ser Ser
                405                 410                 415

Phe Lys Gly Leu Ser Ser Ala Met Gly Ser Leu Ser Lys Ile Gly Arg
                420                 425                 430

Gly Ser Ser Arg Met Val Asp Ser Asp Ser Gly Ser Leu Asp Lys Pro
                435                 440                 445

Glu His Asp Leu
450

<210> SEQ ID NO 96
<211> LENGTH: 1359
<212> TYPE: DNA
<213> ORGANISM: Panicum virgatum

<400> SEQUENCE: 96

```
atggggcacg gcgtcagctg cgcccgcacc ggcgacgagc acgactactt ccgcgcggcg      60
cagctcgggg acctcgacgc cctcgccgcg ctcctcgccg ccgacacctc cctcgcccgc     120
cgcgccacgc tctacgaccg cctctccgcg ctccacatcg ccgccgccaa tggacgcctc     180
gaggtgctgt ccatgatctt ggatcacggg gtgacgccgg acgtagtgaa tcggcacaag     240
cagacgccgc tgatgctcgc ggcgatgcat ggcaagattg actgcgtgct caggctcctc     300
caggccggcg ccaatatctt gatgttcgat tcggtgcacg gcggagctg cctgcaccac     360 gctgcctact tcggccatgt cgactgcctg caggccatcc tctcggcggg gcagacgacg     420
ccggtggccg actcatgggg tttcgcccgg ttcgtcaacg tcagggacga ccacggcgcc     480
acgccgctgc atctcgcggc caggcagggg cggccaggt gcgtgcagat gttgctggag     540
aacggcgcca ttgtatccgc tttgacgggc tcatacggat ccctggtag cacatcgttg     600 catctggctg ctcgcagtgg gaacctggat tgcatccga aactgcttgc ctggggagca     660
gatcgtcttc aaagggactc tgcagggaga attccctatg ctgttgcact gaagcgcaat     720
tatgaagcat gtgcggcttt gctaaaccct tcatcagctg agcccatggt gtggccttcc     780
ccacttaagt tcatcagcga gctcgatccg gaagcaaagg ctctcctgga agcagccctg     840
atggaagcca acagggagag ggagaagaag atcttgaagg gcacaaagta ctctctgcca     900
tcgccttcgc attgcgatgc tgatgtcatg gacgatgcat cttcagaggt gagcgacgcg     960
gagctttgct gcatctgctt cgaccaggca tgcaccatcg aggtgcagga ctgcgggcac    1020
cagatgtgcg cgccgtgcac gctggcgctg tgctgccaca gcaagcccaa cccgacgacc    1080
ctaacgctgc cgtcgccagc ctgccgttc tgccgcggca gcatctcgcg gctgttggtg    1140
```

-continued

```
gcccggacaa gcacgcccag tgaccccgag aaggcagcct actccccgca gctatcccgg   1200
cgtcggtctc ggcggtctca caacctcagc gacgggggca gcagcagctt caagggctc    1260 tcgtccgcca tgggatcctt ctccaagatc gggcgcggct cgagccggat ggtcgacagc   1320
gacagtggca gtctggacaa gcccgagcac gacctgtga                          1359
```

<210> SEQ ID NO 97
<211> LENGTH: 422
<212> TYPE: PRT
<213> ORGANISM: Panicum virgatum

<400> SEQUENCE: 97

| Met | Gly | His | Gly | Val | Ser | Cys | Ala | Arg | Thr | Gly | Asp | Glu | His | Asp | Tyr |
|---|---|---|---|---|---|---|---|---|---|---|---|---|---|---|---|
| 1 | | | | 5 | | | | | 10 | | | | | 15 | |

| Phe | Arg | Ala | Ala | Gln | Leu | Gly | Asp | Leu | Asp | Ala | Leu | Ala | Ala | Leu | Leu |
| | | | 20 | | | | | 25 | | | | | 30 | | |

| Ala | Ala | Asp | Thr | Ser | Leu | Ala | Arg | Arg | Ala | Thr | Leu | Tyr | Asp | Arg | Leu |
| | | 35 | | | | | 40 | | | | | 45 | | | |

| Ser | Ala | Leu | His | Ile | Ala | Ala | Ala | Asn | Gly | Arg | Leu | Glu | Val | Leu | Ser |
| 50 | | | | | 55 | | | | | 60 | | | | | |

| Met | Ile | Leu | Asp | His | Gly | Val | Thr | Pro | Asp | Val | Val | Asn | Arg | His | Lys |
| 65 | | | | 70 | | | | | 75 | | | | | 80 | |

| Gln | Thr | Pro | Leu | Met | Leu | Ala | Ala | Met | His | Gly | Lys | Ile | Asp | Cys | Val |
| | | | | 85 | | | | | 90 | | | | | 95 | |

| Leu | Arg | Leu | Leu | Gln | Ala | Gly | Ala | Asn | Ile | Leu | Met | Phe | Asp | Ser | Val |
| | | | 100 | | | | | 105 | | | | | 110 | | |

| His | Gly | Arg | Ser | Cys | Leu | His | His | Ala | Ala | Tyr | Phe | Gly | His | Val | Asp |
| | | | 115 | | | | | 120 | | | | | 125 | | |

| Cys | Leu | Gln | Ala | Ile | Leu | Ser | Ala | Gly | Gln | Thr | Thr | Pro | Val | Ala | Asp |
| 130 | | | | | 135 | | | | | 140 | | | | | |

| Ser | Trp | Gly | Phe | Ala | Arg | Phe | Val | Asn | Val | Arg | Asp | Asp | His | Gly | Ala |
| 145 | | | | | 150 | | | | | 155 | | | | | 160 |

| Thr | Pro | Leu | His | Leu | Ala | Ala | Arg | Gln | Gly | Arg | Pro | Gly | Cys | Val | Gln |
| | | | | 165 | | | | | 170 | | | | | 175 | |

| Met | Leu | Leu | Glu | Asn | Gly | Ala | Ile | Val | Ser | Ala | Leu | Thr | Gly | Ser | Tyr |
| | | | 180 | | | | | 185 | | | | | 190 | | |

| Gly | Phe | Pro | Gly | Ser | Thr | Ser | Leu | His | Leu | Ala | Ala | Arg | Ser | Gly | Asn |
| | | | | 195 | | | | | 200 | | | | | 205 | |

| Leu | Asp | Cys | Ile | Arg | Lys | Leu | Leu | Ala | Trp | Gly | Ala | Asp | Arg | Leu | Gln |
| | | 210 | | | | | 215 | | | | | 220 | | | |

| Arg | Asp | Ser | Ala | Gly | Arg | Ile | Pro | Tyr | Ala | Val | Ala | Leu | Lys | Arg | Asn |
| 225 | | | | | 230 | | | | | 235 | | | | | 240 |

| Tyr | Glu | Ala | Cys | Ala | Ala | Leu | Leu | Asn | Pro | Ser | Ser | Ala | Glu | Pro | Met |
| | | | | 245 | | | | | 250 | | | | | 255 | |

| Val | Trp | Pro | Ser | Pro | Leu | Lys | Phe | Ile | Ser | Glu | Leu | Asp | Pro | Glu | Ala |
| | | | 260 | | | | | 265 | | | | | 270 | | |

| Lys | Ala | Leu | Leu | Glu | Ala | Ala | Leu | Met | Glu | Ala | Asn | Arg | Glu | Arg | Glu |
| | | | | 275 | | | | | 280 | | | | | 285 | |

| Lys | Lys | Ile | Leu | Lys | Gly | Thr | Lys | Tyr | Ser | Leu | Pro | Ser | Pro | Ser | His |
| | | 290 | | | | | 295 | | | | | 300 | | | |

| Cys | Asp | Ala | Asp | Val | Met | Asp | Asp | Ala | Ser | Ser | Glu | Val | Ser | Asp | Ala |
| 305 | | | | | 310 | | | | | 315 | | | | | 320 |

| Glu | Leu | Cys | Cys | Ile | Cys | Phe | Asp | Gln | Ala | Cys | Thr | Ile | Glu | Val | Gln |
| | | | | 325 | | | | | 330 | | | | | 335 | |

```
Asp Cys Gly His Gln Met Cys Ala Pro Cys Thr Leu Ala Leu Cys Cys
            340                 345                 350

His Ser Lys Pro Asn Pro Thr Thr Leu Thr Leu Pro Ser Pro Ala Cys
            355                 360                 365

Pro Phe Cys Arg Gly Ser Ile Ser Arg Leu Leu Val Ala Arg Thr Ser
        370                 375                 380

Thr Pro Ser Asp Pro Glu Lys Ala Ala Tyr Ser Pro Gln Leu Ser Arg
385                 390                 395                 400

Arg Arg Ser Arg Arg Ser His Asn Leu Ser Asp Gly Gly Ser Ser Ser
                405                 410                 415

Phe Lys Gly Leu Ser Ser
            420

<210> SEQ ID NO 98
<211> LENGTH: 1344
<212> TYPE: DNA
<213> ORGANISM: Panicum virgatum

<400> SEQUENCE: 98
atggggcacg gcgccagctg cggccgcccc agcgaggagg tggacttctt cggcgccgcg      60
cagtcgggcg acctcgcccg cctcgccgcc gtcctgcgct cccgcccac cctgctcagc      120 cggaccacgc tcttcgaccg cctctccgcg ctccacatcg ccgccgccca cggccacctc     180
caggtggtct cgctggcatt ggacctttgc gtgcacccgg atgtcgtcaa ccgccacaag     240
cagacggcgc tgatgctcgc ggcgatgcac gggaagacag actgcgttcg ccggttgctc     300
gacgccggcg ccaatatcgt gatgttcgat tcgtcgcacg gcggacgtg cctgcactac     360 gcggcgtact acgggcacgc ggactgcctc cgggccatcc tctcggcggc caagtccgcg     420
ccggtgtcgg aatcctgggg gttcgcgcgc ttcgtgaacg tgcgggacga cgccggggcg     480
acgccgctgc acctcgcggc gaggcagggc tggcggcgct gcgtccacgt cctgctcgag     540
aacggcgcca tcgtgtcagc ctccagtggc gccttcggat tccccgggag cacgccgctg     600
catttggccg cgcgcggcgg caacctggac tgcgtccggc agctcctctc ctggggcgcc     660
gaccgcctcc agcgagactc cgtcgggaga attccgtacg aggtcgccgt gaagcgaggg     720
cacgtcgcgt gcgcggcgct gctgaacccg tcgtccgcag agcccctggt gtggccgtca     780
gctctcaagt tcatcagcga gctcgagccc aacgccaagt ccctgctcga gcggctctg     840 atggaggcca acaggagag ggagaggagg atcctcaagg ggaccaagaa tgcgtcgccg     900
tcgccgtcgc attccgacga cggtgctcat gacgccgccg ccatagctga ggcaagcgac     960
gcggaggtgt gcagcatctg cttcgagcag gtgtgcagca tcgaggtccg ggagtgcggg     1020
caccagatgt gcgcggcgtg cacgctggcg ctgtgctgcc acgccaagcc caacccggcg     1080
acgcagtccc agccgctgcc gacctgcccg ttctgccgcg gcggcatcgc gcggctcgtg     1140
gtggcgacgc ggacgcgggc cgccgacgag gaggaagagg ggagcaggct ggagtcgcct     1200
aggcaccggc gggcgcgccg gtccatgaac ctaagcggcg acgcgggcag caccagcagc     1260
ctcatgggca gcatcgcctc gtccatcggc aagatgggcc gccggcgaac ggacagcagc     1320
gagcaggtcg acgacaagcc gtag                                             1344

<210> SEQ ID NO 99
<211> LENGTH: 447
<212> TYPE: PRT
<213> ORGANISM: Panicum virgatum

<400> SEQUENCE: 99
```

```
Met Gly His Gly Ala Ser Cys Gly Arg Pro Ser Glu Glu Val Asp Phe
1               5                   10                  15

Phe Gly Ala Ala Gln Ser Gly Asp Leu Ala Arg Leu Ala Ala Val Leu
            20                  25                  30

Arg Ser Arg Pro Thr Leu Leu Ser Arg Thr Thr Leu Phe Asp Arg Leu
        35                  40                  45

Ser Ala Leu His Ile Ala Ala His Gly His Leu Gln Val Val Ser
    50                  55                  60

Leu Ala Leu Asp Leu Cys Val His Pro Asp Val Val Asn Arg His Lys
65                  70                  75                  80

Gln Thr Ala Leu Met Leu Ala Ala Met His Gly Lys Thr Asp Cys Val
                85                  90                  95

Arg Arg Leu Leu Asp Ala Gly Ala Asn Ile Val Met Phe Asp Ser Ser
            100                 105                 110

His Gly Arg Thr Cys Leu His Tyr Ala Ala Tyr Tyr Gly His Ala Asp
        115                 120                 125

Cys Leu Arg Ala Ile Leu Ser Ala Ala Lys Ser Ala Pro Val Ser Glu
    130                 135                 140

Ser Trp Gly Phe Ala Arg Phe Val Asn Val Arg Asp Asp Ala Gly Ala
145                 150                 155                 160

Thr Pro Leu His Leu Ala Ala Arg Gln Gly Trp Arg Arg Cys Val His
            165                 170                 175

Val Leu Leu Glu Asn Gly Ala Ile Val Ser Ala Ser Ser Gly Ala Phe
        180                 185                 190

Gly Phe Pro Gly Ser Thr Pro Leu His Leu Ala Ala Arg Gly Gly Asn
    195                 200                 205

Leu Asp Cys Val Arg Gln Leu Leu Ser Trp Gly Ala Asp Arg Leu Gln
210                 215                 220

Arg Asp Ser Val Gly Arg Ile Pro Tyr Glu Val Ala Val Lys Arg Gly
225                 230                 235                 240

His Val Ala Cys Ala Ala Leu Leu Asn Pro Ser Ser Ala Glu Pro Leu
            245                 250                 255

Val Trp Pro Ser Ala Leu Lys Phe Ile Ser Glu Leu Glu Pro Asn Ala
        260                 265                 270

Lys Ser Leu Leu Glu Ala Ala Leu Met Glu Ala Asn Arg Glu Arg Glu
    275                 280                 285

Arg Arg Ile Leu Lys Gly Thr Lys Asn Ala Ser Pro Ser Pro Ser His
    290                 295                 300

Ser Asp Asp Gly Ala His Asp Ala Ala Ile Ala Glu Ala Ser Asp
305                 310                 315                 320

Ala Glu Val Cys Ser Ile Cys Phe Glu Gln Val Cys Ser Ile Glu Val
            325                 330                 335

Arg Glu Cys Gly His Gln Met Cys Ala Ala Cys Thr Leu Ala Leu Cys
        340                 345                 350

Cys His Ala Lys Pro Asn Pro Ala Thr Gln Ser Gln Pro Leu Pro Thr
    355                 360                 365

Cys Pro Phe Cys Arg Gly Gly Ile Ala Arg Leu Val Val Ala Thr Arg
    370                 375                 380

Thr Arg Ala Ala Asp Glu Glu Glu Gly Ser Arg Leu Glu Ser Pro
385                 390                 395                 400

Arg His Arg Arg Ala Arg Arg Ser Met Asn Leu Ser Gly Asp Ala Gly
            405                 410                 415
```

Ser Thr Ser Ser Leu Met Gly Ser Ile Ala Ser Ser Ile Gly Lys Met
            420                 425                 430

Gly Arg Arg Arg Thr Asp Ser Ser Glu Gln Val Asp Asp Lys Pro
        435                 440                 445

<210> SEQ ID NO 100
<211> LENGTH: 1347
<212> TYPE: DNA
<213> ORGANISM: Panicum virgatum

<400> SEQUENCE: 100

```
atggggcacg gcgccagctg cggccgcccc agcgaggagg tggacttctt cggcgccgcg      60
cagtccggcg acctcgcccg cctcgccgcc gccctccgct cccgcccac cctgctcagc     120
cgcaccacgc tcttcgaccg cctctccgcg ctccacatcg ccgccgccca cggccaccgc     180
caggtggtct cgctggcatt ggatctttgc gtgcaccccg atgtcgttaa ccgccacaag     240
cagacggcgc tgatgctcgc ggcgatgcac gggaagacgg actgcgttcg gcggctgctc     300
gacgccggcg ccaatatcgt gatgttcgat tcgtcgcacg gcggacgtg cctgcactac     360
gcggcgtact acggccacgc ggactgcctc cgggccatcc tctcggcggc caagtccgcg     420
ccggtgtcgg aatcctgggg gttcgcgcgc ttcgtgaacg tgcgggacga cgccggggcg     480
acgccgctgc acctcgcggc gaggcagggc tggcggcgct gcgtccacgt cctgctcgag     540
aacggcgcca tcgtgtcggc ctccagcggc gccttcggat tccccgggag cacgccgctg     600
catttggccg cgcgcggcgg caacctggac tgcgtccggc agctcctctc ctggggcgcc     660
gaccgcctcc agcgagactc cgtcgggaga atcccgtacg aggtcgccgt gaagcgaggg     720
cacgtcgcgt gcgcggcgct gctgaacccg tcgtccgggg agcccctggt gtggccgtcc     780
gcgctcaagt tcatcagcga gctcgagccc gacgccaagt ccctgctcga gcggctctg     840
atggaggcca acagggagag ggagcggagg atcctcaagg ggaccaagaa tgcattgccg     900
tcgccgccgc attccgacga cggtgctcac gacgccgcca tagctgaggc tagcgacgcg     960
gaggtgtgca gcatctgctt cgagcaggcg tgcagcatcg aggtccggga gtgcgggcac    1020
cagatgtgcg cggcgtgcac gctggcgctg tgctgccacg ccaagcccaa cccggcgacg    1080
cagtcccagc cgctgccgac ctgccccttc tgccgcggcg ggatcgcgcg gctggtggtg    1140
gcgacgcggg cgcggccgg cgacgacgag gaggaggagg aggggagcag gctggagtcg    1200
cccaggcacc ggcggtcgcg ccggtcgacg aacctcagcg gcgacgcggg cagcaccagc    1260
agcctcatgg gcagcatcgc ctcgtccatc ggcaagatgg gccgccggcg aacggacagc    1320
agcgagcagg tcgacgacaa gccgtag                                        1347
```

<210> SEQ ID NO 101
<211> LENGTH: 448
<212> TYPE: PRT
<213> ORGANISM: Panicum virgatum

<400> SEQUENCE: 101

Met Gly His Gly Ala Ser Cys Gly Arg Pro Ser Glu Glu Val Asp Phe
1               5                   10                  15

Phe Gly Ala Ala Gln Ser Gly Asp Leu Ala Arg Leu Ala Ala Ala Leu
            20                  25                  30

Arg Ser Arg Pro Thr Leu Leu Ser Arg Thr Thr Leu Phe Asp Arg Leu
        35                  40                  45

Ser Ala Leu His Ile Ala Ala Ala His Gly His Arg Gln Val Val Ser
    50                  55                  60

Leu Ala Leu Asp Leu Cys Val His Pro Asp Val Val Asn Arg His Lys
65                  70                  75                  80

Gln Thr Ala Leu Met Leu Ala Ala Met His Gly Lys Thr Asp Cys Val
                85                  90                  95

Arg Arg Leu Leu Asp Ala Gly Ala Asn Ile Val Met Phe Asp Ser Ser
            100                 105                 110

His Gly Arg Thr Cys Leu His Tyr Ala Ala Tyr Tyr Gly His Ala Asp
        115                 120                 125

Cys Leu Arg Ala Ile Leu Ser Ala Ala Lys Ser Ala Pro Val Ser Glu
130                 135                 140

Ser Trp Gly Phe Ala Arg Phe Val Asn Val Arg Asp Asp Ala Gly Ala
145                 150                 155                 160

Thr Pro Leu His Leu Ala Ala Arg Gln Gly Trp Arg Arg Cys Val His
                165                 170                 175

Val Leu Leu Glu Asn Gly Ala Ile Val Ser Ala Ser Ser Gly Ala Phe
            180                 185                 190

Gly Phe Pro Gly Ser Thr Pro Leu His Leu Ala Ala Arg Gly Gly Asn
        195                 200                 205

Leu Asp Cys Val Arg Gln Leu Leu Ser Trp Gly Ala Asp Arg Leu Gln
210                 215                 220

Arg Asp Ser Val Gly Arg Ile Pro Tyr Glu Val Ala Val Lys Arg Gly
225                 230                 235                 240

His Val Ala Cys Ala Ala Leu Leu Asn Pro Ser Ser Gly Glu Pro Leu
                245                 250                 255

Val Trp Pro Ser Ala Leu Lys Phe Ile Ser Glu Leu Glu Pro Asp Ala
            260                 265                 270

Lys Ser Leu Leu Glu Ala Ala Leu Met Glu Ala Asn Arg Glu Arg Glu
        275                 280                 285

Arg Arg Ile Leu Lys Gly Thr Lys Asn Ala Leu Pro Ser Pro Pro His
290                 295                 300

Ser Asp Asp Gly Ala His Asp Ala Ala Ile Ala Glu Ala Ser Asp Ala
305                 310                 315                 320

Glu Val Cys Ser Ile Cys Phe Glu Gln Ala Cys Ser Ile Glu Val Arg
                325                 330                 335

Glu Cys Gly His Gln Met Cys Ala Ala Cys Thr Leu Ala Leu Cys Cys
            340                 345                 350

His Ala Lys Pro Asn Pro Ala Thr Gln Ser Gln Pro Leu Pro Thr Cys
        355                 360                 365

Pro Phe Cys Arg Gly Gly Ile Ala Arg Leu Val Val Ala Thr Arg Ala
370                 375                 380

Arg Ala Gly Asp Glu Glu Glu Glu Gly Ser Arg Leu Glu Ser
385                 390                 395                 400

Pro Arg His Arg Ser Arg Arg Ser Thr Asn Leu Ser Gly Asp Ala
                405                 410                 415

Gly Ser Thr Ser Ser Leu Met Gly Ile Ala Ser Ser Ile Gly Lys
            420                 425                 430

Met Gly Arg Arg Thr Asp Ser Ser Glu Gln Val Asp Asp Lys Pro
        435                 440                 445

<210> SEQ ID NO 102
<211> LENGTH: 1338
<212> TYPE: DNA
<213> ORGANISM: Artemisia desertorum

<400> SEQUENCE: 102

```
atgggacaga atcttagctg tggagtaaaa gatgacaatg gtttatttac agcaatacaa      60
tatggtgata tagaagtggt gaaacatgtt atggaaaatg atgcaaattt tgttgttaag     120
aaaaaaactg tttatgatcg tcattctgct ttgcatattg ctgctgctaa tggtcagatc     180
gagattgtaa acttgctgtt ggataagtca tctgttaatc ctgatgcttt aaatcgtcga     240
aaacaaactc cattgatgtt ggctgcaatg cacgggaaga ttgcttgtgt tgaaaagcta     300
attgaagctg gtgctaatat tttgatgttt gattcattaa atggaagaac atgtttgcac     360
tatgctgctt attatggtca ctctgattgt cttgaaacca ttctttcgtc tgctagaact     420
tcccacgttg cggcttcttg gggcttttcg cggtttgtga atataagaga tggtaaaggg     480
gcaacaccat tgcatttggc agcccgtcaa agacgtccag aatgtgttca tatacttctt     540
gatagtggag cccttgtttg tgcctcaacc ggtggatatg tcttcctgg cagcacgcca      600
cttcatttgg ctgcaagagg gggttcaatg gattgcgttc gcgaattatt agcatggggt     660
gcggatcgac ttcatagaga tgcatcaggg agaatcccat atgcggttgc tttaaaacac     720
aattatggtg tgtgtgcggc tttgctaaac ccttcgtccg cagagccact agtatggcca     780
tcaccattaa aattcattag tgagcttaat caagatgcaa aagcttttgtt agagcaagct     840
ctaatggaga ttaatagaga aagggagaga agtatcttaa agggtacggg ctactcagtt     900
tcatctccat cacattctga tgccaccggc atggatgata catctctga ggcaagtgac      960
tcacaattat gttgcatatg ctttgaccaa ctatgcgcaa tcgaggttca agattgtggt    1020
caccaaatgt gtgctcaatg cacactcgcg ttatgctgcc acgacaagcc aaacccaaca    1080
acttctgccc tagccgcacc catctgcccc ttttgccgaa gcaatataga acgcttagca    1140
gtgatcaaag tcaaagctag cacagttgac caaggcctcg atgtttttc ctcacctaag     1200
cagcggaaat ctagaaggtc aataaactta agtgaaggaa gcagtagctt tagagggtta    1260
tcgggtgcct catttgggaa aatggtgggc cgtgggtcag gtcgggtctc agctgacctc    1320
gaatgggata aaccgtga                                                  1338
```

<210> SEQ ID NO 103
<211> LENGTH: 445
<212> TYPE: PRT
<213> ORGANISM: Artemisia desertorum

<400> SEQUENCE: 103

```
Met Gly Gln Asn Leu Ser Cys Gly Val Lys Asp Asp Asn Gly Leu Phe
1               5                   10                  15

Thr Ala Ile Gln Tyr Gly Asp Ile Glu Val Val Lys His Val Met Glu
            20                  25                  30

Asn Asp Ala Asn Phe Val Val Lys Lys Thr Val Tyr Asp Arg His
        35                  40                  45

Ser Ala Leu His Ile Ala Ala Ala Asn Gly Gln Ile Glu Ile Val Asn
    50                  55                  60

Leu Leu Leu Asp Lys Ser Ser Val Asn Pro Asp Ala Leu Asn Arg Arg
65                  70                  75                  80

Lys Gln Thr Pro Leu Met Leu Ala Ala Met His Gly Lys Ile Ala Cys
                85                  90                  95

Val Glu Lys Leu Ile Glu Ala Gly Ala Asn Ile Leu Met Phe Asp Ser
            100                 105                 110

Leu Asn Gly Arg Thr Cys Leu His Tyr Ala Ala Tyr Tyr Gly His Ser
        115                 120                 125
```

-continued

```
Asp Cys Leu Glu Thr Ile Leu Ser Ser Ala Arg Thr Ser His Val Ala
130                 135                 140

Ala Ser Trp Gly Phe Ser Arg Phe Val Asn Ile Arg Asp Gly Lys Gly
145                 150                 155                 160

Ala Thr Pro Leu His Leu Ala Ala Arg Gln Arg Arg Pro Glu Cys Val
                165                 170                 175

His Ile Leu Leu Asp Ser Gly Ala Leu Val Cys Ala Ser Thr Gly Gly
                180                 185                 190

Tyr Gly Leu Pro Gly Ser Thr Pro Leu His Leu Ala Ala Arg Gly Gly
            195                 200                 205

Ser Met Asp Cys Val Arg Glu Leu Leu Ala Trp Gly Ala Asp Arg Leu
210                 215                 220

His Arg Asp Ala Ser Gly Arg Ile Pro Tyr Ala Val Ala Leu Lys His
225                 230                 235                 240

Asn Tyr Gly Val Cys Ala Ala Leu Leu Asn Pro Ser Ser Ala Glu Pro
                245                 250                 255

Leu Val Trp Pro Ser Pro Leu Lys Phe Ile Ser Glu Leu Asn Gln Asp
            260                 265                 270

Ala Lys Ala Leu Leu Glu Gln Ala Leu Met Glu Ile Asn Arg Glu Arg
            275                 280                 285

Glu Arg Ser Ile Leu Lys Gly Thr Gly Tyr Ser Val Ser Ser Pro Ser
290                 295                 300

His Ser Asp Ala Thr Gly Met Asp Asp Asn Ile Ser Glu Ala Ser Asp
305                 310                 315                 320

Ser Gln Leu Cys Cys Ile Cys Phe Asp Gln Leu Cys Ala Ile Glu Val
                325                 330                 335

Gln Asp Cys Gly His Gln Met Cys Ala Gln Cys Thr Leu Ala Leu Cys
            340                 345                 350

Cys His Asp Lys Pro Asn Pro Thr Thr Ser Ala Leu Ala Ala Pro Ile
            355                 360                 365

Cys Pro Phe Cys Arg Ser Asn Ile Glu Arg Leu Ala Val Ile Lys Val
    370                 375                 380

Lys Ala Ser Thr Val Asp Gln Gly Leu Asp Val Phe Ser Ser Pro Lys
385                 390                 395                 400

Gln Arg Lys Ser Arg Arg Ser Ile Asn Leu Ser Glu Gly Ser Ser Ser
                405                 410                 415

Phe Arg Gly Leu Ser Gly Ala Ser Phe Gly Lys Met Val Gly Arg Gly
            420                 425                 430

Ser Gly Arg Val Ser Ala Asp Leu Glu Trp Asp Lys Pro
            435                 440                 445
```